United States Patent
Ashworth et al.

(10) Patent No.: US 9,611,223 B2
(45) Date of Patent: Apr. 4, 2017

(54) 3-ARYL-5-SUBSTITUTED-ISOQUINOLIN-1-ONE COMPOUNDS AND THEIR THERAPEUTIC USE

(71) Applicant: INSTITUTE OF CANCER RESEARCH: ROYAL CANCER HOSPITAL (THE), London (GB)

(72) Inventors: Alan Ashworth, London (GB); Christopher James Lord, London (GB); Richard James Rowland Elliott, London (GB); Dan Niculescu-Duvaz, Sutton Surrey (GB); Roderick Alan Porter, London (GB); Rehan Aqil, Cambridge (GB); Raymond John Boffey, Cambridge (GB); Melanie Jayne Bayford, Cambridge (GB); Stuart Firth-Clark, Cambridge (GB); Anna Hopkins, Cambridge (GB); Ashley Nicholas Jarvis, Cambridge (GB); Trevor Robert Perrior, Cambridge (GB); Philip Alan Skone, Cambridge (GB); Rebekah Elisabeth Key, St Helier (GB)

(73) Assignee: INSTITUTE OF CANCER RESEARCH: ROYAL CANCER HOSPITAL (THE), London (GB)

( * ) Notice: Subject to any disclaimer, the term of this patent is extended or adjusted under 35 U.S.C. 154(b) by 0 days.

(21) Appl. No.: 14/917,788

(22) PCT Filed: Sep. 11, 2014

(86) PCT No.: PCT/GB2014/052752
§ 371 (c)(1),
(2) Date: Mar. 9, 2016

(87) PCT Pub. No.: WO2015/036759
PCT Pub. Date: Mar. 19, 2015

(65) Prior Publication Data
US 2016/0221953 A1  Aug. 4, 2016

(30) Foreign Application Priority Data

Sep. 11, 2013 (GB) .................................. 1316173.2
Feb. 27, 2014 (GB) .................................. 1403496.1
Jun. 11, 2014 (GB) .................................. 1410387.3

(51) Int. Cl.
*C07D 217/24* (2006.01)
*C07D 401/14* (2006.01)
(Continued)

(52) U.S. Cl.
CPC ............ *C07D 217/24* (2013.01); *C07C 53/06* (2013.01); *C07C 53/18* (2013.01); *C07D 401/04* (2013.01);
(Continued)

(58) Field of Classification Search
CPC ............................ C07D 217/00; C07D 217/24
(Continued)

(56) References Cited

U.S. PATENT DOCUMENTS 2,851,458 A  9/1958 Warner
4,678,500 A  7/1987 Hay et al.
(Continued)

FOREIGN PATENT DOCUMENTS

CN    101316592 A   12/2008
EP    1396488 A1    3/2004
(Continued)

OTHER PUBLICATIONS

Adaimy et al., "Mutation in WNT10A is associated with an autosomal recessive ectodermal dysplasia: the odonto-onycho-dermal dysplasia." Am J Hum Genet. 81(4):821-8 (2007).
(Continued)

*Primary Examiner* — Niloofar Rahmani
(74) *Attorney, Agent, or Firm* — Clark & Elbing LLP

(57) ABSTRACT

The present invention pertains generally to the field of therapeutic compounds. More specifically the present invention pertains to certain 3-aryl-5-substituted-2/-/-isoquinolin-1-one compounds that, inter alia, inhibit PARP (e.g., PARP1, TNKS1, TNKS2, etc.) and/or Wnt signalling. The present invention also pertains to pharmaceutical compositions comprising such compounds, and the use of such compounds and compositions, both in vitro and in vivo, to inhibit PARP (e.g., PARP1, TNKS1, TNKS2, etc.); to inhibit Wnt signalling; to treat disorders that are ameliorated by the inhibition of PARP (e.g., PARP1, TNKS1, TNKS2, etc.); to treat disorders that are ameliorated by the inhibition of Wnt signalling; to treat proliferative conditions such as cancer, etc.

33 Claims, No Drawings

(51) Int. Cl.

| | | |
|---|---|---|
| *C07D 413/14* | (2006.01) | |
| *C07D 401/10* | (2006.01) | |
| *C07D 413/10* | (2006.01) | |
| *C07D 471/08* | (2006.01) | |
| *C07C 53/06* | (2006.01) | |
| *C07C 53/18* | (2006.01) | |
| *C07D 401/04* | (2006.01) | |
| *C07D 401/12* | (2006.01) | |
| *C07D 413/12* | (2006.01) | |
| *C07D 487/08* | (2006.01) | |
| *C07F 7/18* | (2006.01) | |

(52) U.S. Cl.
CPC ......... *C07D 401/10* (2013.01); *C07D 401/12* (2013.01); *C07D 401/14* (2013.01); *C07D 413/10* (2013.01); *C07D 413/12* (2013.01); *C07D 413/14* (2013.01); *C07D 471/08* (2013.01); *C07D 487/08* (2013.01); *C07F 7/186* (2013.01)

(58) Field of Classification Search
USPC ........................................................ 546/152
See application file for complete search history.

(56) References Cited

U.S. PATENT DOCUMENTS

| | | |
|---|---|---|
| 4,942,163 A | 7/1990 | Behrens |
| 5,177,075 A | 1/1993 | Suto et al. |
| 6,340,759 B1 | 1/2002 | Ueno et al. |
| 9,193,689 B2 | 11/2015 | Ashworth et al. |
| 2003/0225106 A1 | 12/2003 | Askew et al. |
| 2004/0176361 A1 | 9/2004 | Fujio et al. |
| 2006/0173039 A1 | 8/2006 | Shiga et al. |
| 2007/0049555 A1 | 3/2007 | Jagtap et al. |
| 2008/0188467 A1 | 8/2008 | Wong et al. |
| 2009/0054392 A1 | 2/2009 | Pelletier et al. |
| 2009/0076276 A1 | 3/2009 | Fujio et al. |
| 2010/0197706 A1 | 8/2010 | Evers et al. |
| 2010/0226879 A1 | 9/2010 | Abbot et al. |
| 2013/0196967 A1 | 8/2013 | Bartolozzi et al. |
| 2013/0281397 A1 | 10/2013 | McLure et al. |
| 2013/0331375 A1 | 12/2013 | Haynes et al. |
| 2013/0345215 A1 | 12/2013 | Feng et al. |
| 2013/0345226 A1 | 12/2013 | Hermann et al. |

FOREIGN PATENT DOCUMENTS

| | | |
|---|---|---|
| EP | 1544194 A1 | 6/2005 |
| EP | 1557414 A1 | 7/2005 |
| EP | 1724262 A1 | 11/2006 |
| EP | 1854792 A1 | 11/2007 |
| EP | 1864976 A1 | 12/2007 |
| EP | 2090570 A1 | 8/2009 |
| GB | 1221971.3 | 6/2014 |
| WO | WO-99/18077 A1 | 4/1999 |
| WO | WO-02/094790 A1 | 11/2002 |
| WO | WO-03/026652 A1 | 4/2003 |
| WO | WO-03/099274 A1 | 12/2003 |
| WO | WO-2004/031171 A1 | 4/2004 |
| WO | WO-2004/037805 A1 | 5/2004 |
| WO | WO-2004/058717 A1 | 7/2004 |
| WO | WO-2004/094452 A2 | 11/2004 |
| WO | WO-2005/075432 A1 | 8/2005 |
| WO | WO-2005/113540 A1 | 12/2005 |
| WO | WO-2006/045096 A2 | 4/2006 |
| WO | WO-2006/047277 A2 | 5/2006 |
| WO | WO-2006/063718 A1 | 6/2006 |
| WO | WO-2007/016525 A2 | 2/2007 |
| WO | WO-2007/025009 A2 | 3/2007 |
| WO | WO-2008/060927 A2 | 5/2008 |
| WO | WO-2008/092231 A1 | 8/2008 |
| WO | WO-2009/027650 A1 | 3/2009 |
| WO | WO-2009/059994 A2 | 5/2009 |
| WO | WO-2009/127723 A1 | 10/2009 |
| WO | WO-2009/132000 A1 | 10/2009 |
| WO | WO-2010/059658 A1 | 5/2010 |
| WO | WO-2010/106436 A2 | 9/2010 |
| WO | WO-2010/123975 A1 | 10/2010 |
| WO | WO-2010/133647 A1 | 11/2010 |
| WO | WO-2011/045258 A1 | 4/2011 |
| WO | WO-2011/146882 A1 | 11/2011 |
| WO | WO-2011/157787 A1 | 12/2011 |
| WO | WO-2013/008217 A1 | 1/2013 |
| WO | WO-2013/010092 A1 | 1/2013 |
| WO | WO-2013/012723 A1 | 1/2013 |
| WO | WO-2013/076090 A1 | 5/2013 |
| WO | WO-2013/097225 A1 | 7/2013 |
| WO | WO-2013/097226 A1 | 7/2013 |
| WO | WO-2013/110433 A1 | 8/2013 |
| WO | WO-2013/117288 A1 | 8/2013 |
| WO | 2013/132253 * | 9/2013 |
| WO | WO-2013/132253 A1 | 9/2013 |
| WO | WO-2013/134079 A1 | 9/2013 |
| WO | WO-2013/143663 A1 | 10/2013 |
| WO | WO-2013/164061 A1 | 11/2013 |
| WO | WO-2013/177349 A2 | 11/2013 |
| WO | WO-2013/182546 A1 | 12/2013 |
| WO | WO-2013/189904 A1 | 12/2013 |
| WO | WO-2014/023390 A2 | 2/2014 |
| WO | WO-2014/036022 A1 | 3/2014 |
| WO | WO-2014/044356 A1 | 3/2014 |
| WO | WO-2014/045101 A1 | 3/2014 |
| WO | WO-2014/048532 A1 | 4/2014 |
| WO | WO-2014/087165 A1 | 6/2014 |

OTHER PUBLICATIONS

Balemans et al.,"Identification of a 52 kb deletion downstream of the SOST gene in patients with van buchem disease," J Med Genet. 39(2):91-7 (2002).

Balemans et al.,"Increased bone density in sclerosteosis is due to the deficiency of a novel secreted protein (SOST)," Hum Mol Genet., 10(5):537-43 (2001).

Bao et al., "Inhibition of tankyrases induces axin stabilization and blocks wnt signalling in breast cancer cells," PLoS One. 7(11):e48670(9 pages) (2012).

Bergmann et al., "Mutations in the gene encoding the wnt-signaling component R-spondin 4 (RSPO4) cause autosomal recessive anonychia," Am J Hum Genet. 79(6):1105-9 (2006).

Beugelmans et al., "A common and general access to berberine and benzo[c]phenanthridine alkaloids," Tetrahedron, 48(38):8285-94 (1992).

Blaydon et al., "The gene encoding R-spondin 4 (RSPO4), a secreted protein implicated in wnt signaling, is mutated in inherited anonychia," Nat Genet. 38(11):1245-7 (2006).

Bregman et al., "Discovery of a class of novel tankyrase inhibitors that bind to both the nicotinamide pocket and the induced pocket," J Med Chem. 56(3):1341-5 (2013).

British Search Report for British Patent Application No. 1316173.2, dated Mar. 10, 2014 (5 pages).

British Search Report for British Patent Application No. 1403496.1, dated Sep. 3, 2014 (6 pages).

British Search Report for British Patent Application No. 1410387.3, dated Feb. 27, 2015 (4 pages).

Cappelli et al., "Further studies on imidazo[4,5-b]pyridine AT1 angiotensin II receptor antagonists. effects of the transformation of the 4-phenylquinoline backbone into 4 phenylisoquinolinone or 1-phenylindene scaffolds," J Med Chem. 49(22):6451-64 (2006).

Caricasole et al., "The Wnt pathway, cell-cycle activation and beta-amyloid: novel therapeutic strategies in Alzheimer's disease?" Trends Pharmacol Sci. 24(5):233-8 (2003).

"Tankyrase and the canonical Wnt pathway protect lung cancer cells from EGFR inhibition," available in PMC Aug. 15, 2013, published in final edited form as: Cancer Res. 72(16):4154-64 (2012) (18 pages).

Chang et al., "Tankyrase-1 polymerization of poly(ADP-ribose) is required for spindle structure and function," Nat Cell Biol. 7(11):1133-9 (2005).

(56) References Cited

OTHER PUBLICATIONS

Cheon et al., "Structure-activity relationship studies of isoquinolineone type anticancer agent," Arch Pharm Res. 24(4):276-80 (2001).
Cheon et al., "Synthesis and structure-activity relationship studies of 2,3-dihydroimidazo[2,1-a]isoquinoline analogs as antitumour agents," Arch Pharm Res. 20(2):138-43 (1997).
Cho et al., "Molecular modeling of 3-arylisoquinoline antitumor agents active against A-549. a comparative molecular field analysis study," Bioorg Med Chem. 10(9):2953-61 (2002).
Cho et al., "Synthesis and biological evaluation of 3-arylisoquinolines as antitumor agents," Bioorg Med Chem Lett. 8(1):41-6 (1998).
Cho et al., "Synthesis and comparative molecular field analysis (CoMFA) of antitumor 3-arylisoquinoline derivatives," Bioorg Med Chem. 6(12):2449-58 (1998).
"Proteasome regulation by ADP-ribosylation," available in PMC Oct. 25, 2013, published in final edited form as: Cell. 153(3):614-27 (2013) (22 pages).
Christodoulides et al., "WNT10B mutations in human obesity," Diabetologia. 49(4):678-84 (2006).
Costantino et al., "Modeling of Poly(ADP-ribose)polymerase (PARP) Inhibitors. Docking of Ligands and Quantitative Structure—Activity Relationship Analysis," J Med Chem. 44:3786-94 (2001).
Couture et al., "A convenient synthesis of 3-aryl-2-methyl-3,4-dihydro-1(2H)-isoquinolones and—1,2,3,4-tetrahydroisoquinolines," Synth Commun. 30(15):2775-84 (2000).
Couture et al., "Intramolecular peterson olefination of ortho-trimethylsilylmethyl-N-acyl-N-alkylbenzamides. a new route to 2-alkyl-1(2H)isoquinolones," J Organomet Chem. 440(1-2):7-13 (1992).
Daniels, "Abnormal cytokinesis in cells deficient in the breast cancer susceptibility protein BRCA2," Science. 306(5697):876-9 (2004).
Deng et al., "Telomeric proteins regulate episomal maintenance of epstein-barr virus origin of plasmid replication," Mol Cell. 9(3):493-503 (2002).
Distler et al., "Inactivation of tankyrases reduces experimental fibrosis by inhibiting canonical Wnt signalling," Ann Rheum Dis. 72(9):1575-80 (2013).
Fancy et al., "Axin2 as regulatory and therapeutic target in newborn brain injury and remyelination," Nat Neurosci. 14(8):1009-16 (2011) (10 pages).
Gong et al., "LDL receptor-related protein 5 (LRP5) affects bone accrual and eye development," Cell. 107(4):513-23 (2001).
Grzeschik et al., "Deficiency of PORCN, a regulator of Wnt signaling, is associated with focal dermal hypoplasia," Nat Genet. 39(7):833-5 (2007).
Guimond et al., "Rhodium(III)-catalyzed isoquinolone synthesis: The N-O bond as a handle for C-N bond formation and catalyst turnover," J Am Chem Soc. 132(20):6908-9 (2010).
Haikarainen et al., "para-substituted 2-phenyl-3,4-dihydroquinazolin-4-ones as potent and selective tankyrase Inhibitors," ChemMedChem, 8(12):1978-85 (2013) (9 pages).
Harley, "Telomerase and cancer therapeutics," Nat Rev Cancer. 8(3):167-79 (2008).
Hsiao et al.,"Sister telomeres rendered dysfunctional by persistent cohesion are fused by NHEJ," J Cell Biol. 184(4):515-26 (2009).
Hsiao et al.,"Tankyrase function at telomeres, spindle poles, and beyond," Biochimie. (90)1:83-92 (2008).
Huang et al., "New ammonia equivalents for the Pd-catalyzed amination of aryl halides," Org Lett. 3(21):3417-9 (2001).
Huang et al., "Tankyrase inhibition stabilizes axin and antagonizes Wnt signalling," Nature. 461(7264):614-20 (2009).
International Preliminary Report on Patentability for International Patent Application No. PCT/GB2014/052752, dated Mar. 15, 2016 (5 pages).

International Search Report and Written Opinion for International Patent Application No. PCT/GB2014/052752, mailed Oct. 31, 2014 (10 pages).
James et al., "WIKI4, a novel inhibitor of tankyrase and Wnt/β-catenin signaling," PLoS One 7(12):e50457 (10 pages) (2012).
Kaelin, "Synthetic lethality: a framework for the development of wiser cancer therapeutics," Genome Med. 1(10):99 (6 pages) (2009).
Khadka et al., "Synthesis of 12-oxobenzo[c]phenanthridinones and 4-substituted 3-arylisoquinolones via Vilsmeier-Haack reaction," Tetrahedron. 68(1):250-61 (2012).
Kim et al., "Hypothetical drug binding receptor site analysis using CoMFA method for 3-arylisoquinolines active against SK-OV-3 tumor cell line," Yakhak Hoechi. 46(4):219-25 (2002).
Kozlovsky et al., "GSK-3 and the neurodevelopmental hypothesis of schizophrenia," Eur Neuropsychopharmacol. 12(1):13-25 (2002).
"The PARP side of the nucleus: molecular actions, physiological outcomes, and clinical targets," available in PMC Jul. 9, 2011, published in final edited form as: Mol Cell. 39(1):8-24 (2010) (34 pages).
Lammi et al., "Mutations in AXIN2 cause familial tooth agenesis and predispose to colorectal cancer," Am J Hum Genet. 74(5):1043-50 (2004).
Le et al., "A versatile total synthesis of benzo[c]phenanthridine and protoberberine alkaloids using lithiated toluamide-benzonitrile cycloaddition," J Org Chem. 69(8): 2768-72 (2004).
Li et al., "Herpes simplex virus requires poly(ADP-ribose) polymerase activity for efficient replication and induces extracellular signal-related kinase-dependent phosphorylation and ICP0-dependent nuclear localization of tankyrase 1," J Virol., 86(1):492-503 (2011).
Li et al., "Platinum(II)-catalyzed intramolecular cyclization of alkynylbenzonitriles: synthesis of 1-alkoxyisoquinolines and isoquinolones," Tetrahedron Lett. 51(49):6422-5 (2010).
Li et al., "Synthesis and activity of 1-aryl-1'-imidazolyl methyl ethers as non-thiol farnesyltransferase inhibitors," Bioorg Med Chem Lett. 14(21):5371-6 (2004).
Lord et al., "Targeted therapy for cancer using PARP inhibitors," Curr Opin Pharmacol. 8(4):363-9 (2008).
Loughlin et al.,"Functional variants within the secreted frizzled-related protein 3 gene are associated with hip osteoarthritis in females," Proc Natl Acad Sci USA. 101(26):9757-62 (2004).
Marsili, "Conversion of indones to quinoline and isoquinoline derivatives. III. Schmidt reaction with 2,3-diphenylindone and similar compounds," Tetrahedron. 24(14):4981-91 (1968).
McCabe et al., "Targeting Tankyrase 1 as a therapeutic strategy for BRCA-associated cancer," Oncogene. 28(11):1465-70 (2009).
Merchant et al., "Synthesis of Heterocyclic Compounds involving Reactions of Indan-1-ones," Indian J Chem. 23B:863-5 (1984).
Mills et al., "Directed ortho metalation of N,N-diethylbenzamides. Silicon protection of ortho sites and the o-methyl group," J Org Chem. 54(18):4372-85 (1989).
Miyaoka et al., "Increased expression of Wnt-1 in schizophrenic brains," Schizophr Res. 38(1):1-6 (1999).
Moon et al., "WNT and beta-catenin signalling: diseases and therapies," Nat Rev Genet. 5(9):689-699 (2004).
Mudher et al., "Alzheimer's disease-do tauists and baptists finally shake hands?" Trends Neurosci. 25(1):22-6 (2002).
Musso et al., "Indanylidenes. 1. Design and synthesis of (E)-2-(4,6-difluoro-1-indanylidene)acetamide, a potent, centrally acting muscle relaxant with anti-inflammatory and analgesic activity," J Med Chem. 46(3):399-408 (2003).
Narwal et al., "Discovery of tankyrase inhibiting flavones with increased potency and isoenzyme selectivity," J Med Chem. 56(20):(33 pages) (2013).
Nathubhai et al., "Design and Discovery of 2-arylquinazolin-4-ones as Potent and Selective Inhibitors of Tankyrases," ACS Med Chem Lett. 4(12):(8 pages) (2013).
Oda et al., "2-Pyridone ring formation through the photo-reaction of arenecarbothioamides with unsaturated carboxylic acids," Heterocycles. 56:69-72 (2002).

(56) References Cited

OTHER PUBLICATIONS

Okano et al., "Synthesis of secondary arylamines through copper-mediated intermolecular aryl amination," Org Lett. 5(26):4987-90 (2003).
Olbrich et al., "CNDO/S-CI Calculations of some Carbonyl-containing Organic Luminophores with a Stilbene Subchromophore," Z Naturforsch. 40a:859-63 (1985).
Oresmaa et al., "Synthesis, ocular effects, and nitric oxide donation of imidazole amidoximes," Eur J Med Chem. 41(9):1073-9 (2006).
Ouchi et al., "Regioselective aromatic substitution of 6,8-dihydroxy-4-ethoxycarbonyl-2H-isoquinolin-1-one derivatives using the Stille coupling reaction," Heterocycles. 62:491-501 (2004).
Paine, "Towards Selective Inhibition of the Tankyrases," Biological & Medicinal Chemistry (BMCS) 6th Postgraduate Symposium, University of Cambridge, United Kingdom. 2 pages (2012).
Parma et al., "R-spondin1 is essential in sex determination, skin differentiation and malignancy," Nat Genet. 38(11):1304-9 (2006).
Riffell et al., "Tankyrase-targeted therapeutics: expanding opportunities in the PARP family," Nat Rev Drug Discov. 11(12):923-36 (2012).
Robitaille et al., "Mutant frizzled-4 disrupts retinal angiogenesis in familial exudative vitreoretinopathy," Nat Genet. 32(2):326-30 (2002).
Roy et al.,"Solution-phase synthesis of a diverse isocoumarin library," available in PMC Nov. 1, 2010, pubished in final edited form as: J Comb Chem. 11(6):1128-35 (2009) (26 pages).
Sarkhel et al., "Synthesis of some 3-aryl-5-methoxy-7-methylisocoumarins," Indian J Chem. 16B(11):1034-7 (1978).
Savarin et al., "Novel intramolecular reactivity of oximes: synthesis of cyclic and spiro-fused imines," Org Lett. 9(6):981-3 (2007).
Sharma et al., "Cytotoxicity and TOP1-targeting activity of 8- and 9-amino derivatives of 5-butyl-and 5-(2-N,N,dimethylamino)ethyl-5H-dibenzo[c,h][1,6]naphthyridin-6-ones," Eur J Med Chem 44(4):1471-6 (2009).
Shenglof et al., "Lanthanide assisted cross-coupling of aryl bromides with triethylaluminum," Tetrahedron Lett. 44:8593-5 (2003).
"Reversible cell-cycle entry in adult kidney podocytes through regulated control of telomerase and Wnt signaling," available in PMC Jul. 1, 2012, published in final edited form as: Nat Med. 18(1):111-9 (2011) (22 pages).
Shuler et al., "Preparation and X-Ray Crystal Structure of 3-(4-(Dimethylamino)phenyl)-2-(phenylamino)isoquinolin-1(2H)-one, 3-(4-Methoxyphenyl)-2-(phenylamino)isoquinolin-1(2H)-one, and 2-Methyl-N'-(4-methylbenzoyl)-N'-phenylbenzohydrazide from Polylithiated 2-methylbenzoic Acid Phenylhydrazide and Methyl 4-dimethylaminobenzoate, Methyl 4-methoxybenzoate, or Methyl 4-methylbenzoate," J Chem Crystallogr. 42(9):952-9 (2012).
Simchem and Krämer, 1969, "Reaktionen mit Halogenwasserstoffaddukten der Nitrile, I. Eine neue Isochinolinsynthese", Chemische Berichte., vol. 102 pp. 3656-3665 (1969).
Sinha et al., "Synthesis of some new 3-ethyl and 3-phenylisocoumarins," Indian J Heterocyclic Chem. 1(5):235-40 (1992).
Sunderland et al., "Synthesis of 4-alkyl, 4-aryl and 4-arylamino-5-aminoisoquinolin-1-ones and identification of a new PARP-2 selective inhibitor," Org Biomol Chem. 9(3):881-91 (2011).
Threadgill, "Design and discovery of potent inhibitors of the tankyrases, triple-function targets in the cancer cell," 19th ISCB International Conference (ISCBC-2013), Book of Abstracts, p. 12 (2013).
Threadgill, "Potency and selectivity in the design and development of new tankyrase inhibitors," 20th ISCB International Conference (ISCBC-2014), Delhi, India, Book of Abstracts, p. 38 (2014) (2 pages).
Tocris Webpage for XAV939 (http://www.tocris.com/dispprod.php?ItemId=243282) retrieved on Jun. 24, 2011 (1 page).
Treus et al., "(Z)-Ethyl 2-phenyl-1-(2-vinylphenyl)vinylcarbamates. Part 1: Synthesis and preliminary studies on their divergent transformation into benzo[c]phenanthridines and 2-phenyl-1,4-naphthoquinones," Tetrahedron. 66(52):9986-95 (2010).
Tropsha et al., "Development of kNN QSAR models for 3-arylisoquinoline antitumor agents," Bull Korean Chem Soc. 32(7):2397-404 (2011).
Turner et al., "Hallmarks of 'BRCAness' in sporadic cancers," Nat Rev Cancer. 4(10):(6 pages) (2004).
Varallo et al., "Beta-catenin expression in Dupuytren's disease: potential role for cell-matrix interactions in modulating beta-catenin levels in vivo and in vitro," Oncogene. 22(24):3680-4 (2003).
Waaler et al., "A novel tankyrase inhibitor decreases canonical Wnt signaling in colon carcinoma cells and reduces tumor growth in conditional APC mutant mice," Cancer Res. 72(11):2822-32 (2012).
Wang et al., "Cardiac induction of embryonic stem cells by a small molecule inhibitor of Wnt/?-catenin signaling," available in PMC Feb. 18, 2012, published in final edited form as: ACS Chem Biol. 6(2):192-7 (2011) (12 pages).
Wolfe et al., "Simple, efficient catalyst system for the palladium-catalyzed amination of aryl chlorides, bromides, and triflates," J. Org. Chem. 65(4):1158-74 (2000).
Woods et al., "Mutations in WNT7A cause a range of limb malformations, including Fuhrmann syndrome and Al-Awadi/Raas-Rothschild/Schinzel phocomelia syndrome," Am J Hum Genet. 79(2):402-8 (2006).
Xu et al., "Vascular development in the retina and inner ear: control by Norrin and Frizzled-4, a high-affinity ligand-receptor pair," Cell. 116(6):883-95 (2004).
Yeh et al., "Insulin-stimulated exocytosis of GLUT4 is enhanced by IRAP and its partner tankyrase," Biochem J. 402(2):279-90 (2007).
Zanon et al., "Copper-catalyzed domino halide exchange-cyanation of aryl bromides," J Am Chem Soc. 125(10):2890-1 (2003).
Zhou et al., "Short and Efficient Total Synthesis of Luotonin A and 22-Hydroxyacuminatine using a common cascade strategy," J Org Chem. 72(16):6270-2 (2007).

* cited by examiner

3-ARYL-5-SUBSTITUTED-ISOQUINOLIN-1-ONE COMPOUNDS AND THEIR THERAPEUTIC USE

RELATED APPLICATIONS

This application is related to: United Kingdom patent application number 1316173.2 filed 11 Sep. 2013; United Kingdom patent application number 1403496.1 filed 27 Feb. 2014; and United Kingdom patent application number 1410387.3 filed 11 Jun. 2014; the contents of each of which are incorporated herein by reference in their entirety.

TECHNICAL FIELD

The present invention pertains generally to the field of therapeutic compounds.

More specifically the present invention pertains to certain 3-aryl-5-substituted-2H-isoquinolin-1-one compounds that, inter alia, inhibit PARP (e.g., PARP1, TNKS1, TNKS2, etc.) and/or Wnt signalling. The present invention also pertains to pharmaceutical compositions comprising such compounds, and the use of such compounds and compositions, both in vitro and in vivo, to inhibit PARP (e.g., PARP1, TNKS1, TNKS2, etc.); to inhibit Wnt signalling; to treat disorders that are ameliorated by the inhibition of PARP (e.g., PARP1, TNKS1, TNKS2, etc.); to treat disorders that are ameliorated by the inhibition of Wnt signalling; to treat proliferative conditions such as cancer, etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cancer

Cancer is the second largest cause of death worldwide. Cancer accounts for 13% of global mortality with more than 70% of cancer deaths occurring in low and middle-income countries where the prevalence of cancer is expected to increase as mortality from other diseases decreases. In the UK alone, a disease such as breast cancer kills over 12,000 women each year.

One approach to this problem has been to identify novel targets for cancer therapies and to use these to tailor the treatment of each patient according to the molecular make-up of their particular disease, rather than their overt clinical characteristics. While this has been in part successful, there are still a significant number of tumour types for which there are no targeted therapies and few treatment options other than surgery and cytotoxic chemotherapy.

PARP

There is now a significant body of evidence to suggest that inhibition of poly ADP ribose polymerase (PARP) super-family proteins, such as PARP1, PARP2, tankyrase 1 (also known as TNKS1, PARP5a) and tankyrase 2 (also known as TNKS2, PARP5B) could have clinical utility. See, e.g., Krishnakumar et al., 2010. PARP superfamily members use beta-NAD$^+$ as a substrate to generate ADP-ribose polymers on amino acid residues of protein acceptors. The result is a dramatic post-translational modification that can significantly alter the properties of the protein acceptor. See, e.g., Krishnakumar et al., 2010.

Although much of the focus has been on PARP1, studies over the past decade have identified a family of as many as 17 proteins that share homology to the catalytic domain of PARP1. In addition to the PARP-like domain, the PARP family members are "functionalized" with a wide variety of other structural and functional domains (e.g., DBDs, RNA-binding domains, subcellular localization signals, macrodomains, BRCT motifs, ankyrin repeats, zinc fingers) that determine their overall biological activities. Recently, a unified nomenclature referring to this family of proteins as ADP-ribosyl transferases (ARTs) has been proposed to recognize that fact that (1) PARPs catalyze a transferase reaction, not a template-dependent polymerization reaction; and (2) not all family members have PARP activity; some are likely to function as mono(ADP-ribosyl) transferases (mARTs). This new nomenclature is reflected in a recent structure-based classification of PARP family members into three groups based on their catalytic domains: (1) PARPs 1-5, which are bona fide PARPs containing a conserved glutamate (Glu 988 in PARP1) that defines the PARP catalytic activity; (2) PARPs 6-8, 10-12, and 14-16, which are confirmed or putative mARTs; and (3) PARPs 9 and 13, which lack key NAD-binding residues and the catalytic glutamate, and are likely inactive. See, e.g., Krishnakumar et al., 2010.

PARP family members localize to various cellular compartments, including the nucleus, cytoplasm, mitochondria, and vault particles, although the subcellular localization and function of many of the PARPs are unknown. The known functions of the PARP family members span a wide range of cellular processes, including DNA repair, transcription, cellular signalling, cell-cycle regulation, and mitosis. This diverse array of processes plays key roles in a wide variety of biological outcomes, including differentiation, development, stress responses, inflammation, and cancer. See, e.g., Krishnakumar et al., 2010.

The primary nuclear PARPs are PARP1, PARP2 (the closest paralog to PARP1), PARP3, and tankyrases 1 and 2. PARP1 is a very well studied protein and has a well-established role in DNA repair. See, e.g., Lord et al., 2008.

Tankyrase 1 encompasses four distinct domains; the N terminal HPS domain (homopolymeric stretches of His, Pro and Ser); the ankyrin domain, containing 24 ANK repeats; a SAM (sterile alpha module) domain; and a C terminal PARP catalytic domain. See, e.g., Hsiao et al., 2008.

The best characterised function of tankyrase 1 is in telomere maintenance. The cellular machinery that normally replicates genomic DNA is unable to synthesise DNA at the telomere, the structure that caps the end of each chromosome. DNA synthesis at the telomere is instead carried out by telomerase. This enzyme complex consists of a RNA template and a DNA polymerase catalytic subunit. However, the activity of telomerase in most human somatic cells is relatively low and as such, attrition of the DNA at the telomere gradually occurs. This attrition of telomeric DNA is one of the factors that can lead to replicative senescence in somatic cells and this shortening of telomeres is often referred to as a "mitotic clock" that predetermines the replicative capacity of most cells. However, the situation in cancer cells is considerably different from that in somatic cells; up to 90% of all human cancer cells have a high level of telomerase activity. This increased level of telomere maintenance is one of the factors that enables tumour cells to avoid senescence and perpetually replicate. See, e.g., Harley, 2008.

The length of telomeric DNA is determined by a "protein counting" mechanism in which a series of telomere-bound proteins negatively regulate the access of telomerase to the telomere. For example, longer telomeres bind a larger number of DNA double strand-binding Telomeric Repeat Binding Factor (TRF1) proteins. Together with the TIN2-TPP1-POT1 protein complex, TRF1 blocks the access of telomerase to the 3' DNA overhang at the end of chromosomes, thus limiting further extension of the telomere. Regulation of this process is controlled by tankyrase 1 which promotes telomeric extension by poly(ADP-ribosyl)ating TRF1, causing its release from the telomere and eventual proteasomal destruction. This release and degradation of TRF1 allows an enhanced level of telomerase access to the chromosome end and extension of the telomere. See, e.g., Harley, 2008.

Tankyrase 1 is also required after DNA replication in the $S/G_2$ phase of the cell cycle to resolve sister chromatid cohesion before mitosis ensues. Depletion of tankyrase 1 in HeLa cells results in mitotic arrest. Persistent sister chromatid cohesion in tankyrase 1 depleted cells results in sister chromatid fusion. See, e.g., Hsiao et al., 2009. The mitotic defect in tankyrase-depleted cells may, in part, be determined by the tankyrase 1-mediated poly(ADP ribosyl)ation of the protein NuMA, which plays an essential role in organising microtubules at spindle pores. See, e.g., Chang et al., 2005.

Recent work has also suggested a role for tankyrase 1 in the control of oncogenic Wnt signalling, most likely via a mechanism that involves the stabilisation of the Wnt signalling component, Axin. See, e.g., Huang et al., 2009. In this latter work and subsequent work (see, e.g., James et al., 2012; Bao et al., 2012; Casás-Selves et al., 2012; Waaler et al., 2012; Riffell et al., 2012) a number of investigators have shown that toolbox, non-drug like small molecule inhibitors of tankyrase can inhibit oncogenic Wnt signalling and can inhibit tumour cells that are addicted to Wnt signalling.

Wnt Signalling

Wnt signalling is an intracellular protein signalling network that transduces signals from cell surface bound receptors to a series of gene transcription events. In canonical Wnt signalling, Wnt ligands bind to cell-surface receptors of the Frizzled family; Frizzled bound receptors activate Dishevelled family proteins. In turn, activated Dishevelled proteins inhibit the function of a complex of proteins including Axin 1 and 2, GSK-3, and the protein APC. This Axin/GSK-3/APC complex normally promotes the proteolytic degradation of the β-catenin intracellular signalling molecule. When Wnt signalling is stimulated and Dishevelled proteins are active, the "β-catenin destruction complex" is inhibited, β-catenin degradation is reduced and β-catenin is able to enter the nucleus and interact with TCF/LEF family transcription factors. This latter act drives a series of specific gene expression events that ultimately mediate Wnt signalling.

The association of dysregulated Wnt/β-catenin signalling with cancer has been well documented. Constitutively activated β-catenin signalling, caused either by APC deficiency or activating β-catenin mutations can lead to tumourigenesis. Furthermore, tankyrase is directly involved in the Wnt signalling cascade. Tankyrase PARylates both Axin 1 and Axin 2 and causes their degradation, driving β-catenin stabilisation/nuclear translocation and TCF/LEF mediated transcription. See, e.g., Huang et al., 2009. When tankyrase is inhibited, either genetically or with small molecules, Axin1 and 2 levels are stabilized and β-catenin degradation is enhanced, ultimately suppressing Wnt signalling, even in situations where Wnt signalling is usually constitutively elevated, such as APC deficiency and castration resistant prostate cancer. See, e.g., Huang et al., 2009. These data suggest that tankyrase inhibition could be used in order to modulate Wnt signalling, both in cancer, but also in other, non-cancer, pathologies where Wnt signalling is aberrant.

In addition to its effects on Wnt signally, it has also recently been demonstrated that silencing of tankyrase 1 by RNA interference is lethal in tumour cells with deficiencies in either of the breast cancer susceptibility proteins, BRCA1 and BRCA2, but not in wild type cells. BRCA mutation carriers with cancer still retain functional BRCA protein function in their normal cells, whilst it is lacking in tumour cells, suggesting that a tankyrase 1 inhibitor could be used to selectively target tumour cells in BRCA patients. See, e.g., McCabe et al., 2009b. This approach of combining tumour-specific genetic deficiencies with inhibition of a drug target to elicit a therapeutic window is an example of a "synthetic lethal" approach to the design of cancer therapies. See, e.g., Kaelin, 2009. This BRCA selective effect of tankyrase 1 inhibition may be caused by telomere attrition (caused by tankyrase 1 inhibition) and stalled replication forks (caused by BRCA deficiency) acting in concert to cause a threshold of DNA damage that is inconsistent with cell viability. Alternatively, synergistic defects in cytokinesis and sister chromatid segregation caused by BRCA deficiency and tankyrase 1 inhibition may also underlie the BRCA selective effect. See, e.g., Daniels, 2004. The use of tankyrase 1 inhibition in this context is described in McCabe et al., 2009a and McCabe et al., 2009b.

It has been shown that a proportion of patients without BRCA mutations have clinical characteristics, tumour morphologies and tumour molecular profiles that are reminiscent of BRCA mutation-associated cancer, a property termed BRCAness. See, e.g., Turner et al., 2004. This BRCAness phenotype is most well described in a significant number of patients with triple negative breast tumours. See, e.g., Turner et al., 2004. It has been shown that BRCA1 deficient, triple-negative breast cancer cell lines such as HCC1937 are particularly sensitive to tankyrase 1 inhibition. See, e.g., McCabe et al., 2009a and McCabe et al., 2009b. Inhibiting tankyrase 1 therefore, may be very effective in patients with germ-line BRCA mutations as well as patients whose tumours exhibit a BRCAness phenotype.

Recently tankyrase has been demonstrated to modulate the activity of the proteasome and tankyrase inhibitors act as proteasome inhibitors (see, e.g., Cho-Park et al., 2013) suggesting that tankyrase inhibitors could be used as therapeutic proteasome inhibitors in the treatment of cancer.

Non-Tumourigenic Mechanisms Modulated by Tankyrase

In addition to tankyrase inhibitors having potential as cancer therapeutics, a number of other studies suggest tankyrase inhibitors could be used in a number of other non-cancer related pathologies, the majority of which are driven by aberrant Wnt signalling, of which tankyrase activity is a rate limiting step (see, e.g., Riffell et al., 2012).

For example:

Recent work has indicated that inhibition of tankyrase can stabilize Axin2 levels in immature oligodendrocyte progenitor cells (OLPs) (see, e.g., Fancy et al., 2011). On the basis that Axin2 function is essential for normal kinetics of remyelination, tankyrase inhibition has been shown to accelerate OLP myelination after hypoxic and demyelinating injury (see, e.g., Fancy et al., 2011). This data suggest that small molecule tankyrase inhibitors might serve as pharmacological agents that could aid remyelination in neuropathies such as multiple sclerosis, neonatal hypoxic ischemic encephalopathy (HIE), and neonatal periventricular leukomalacia (PVL) (see, e.g., Fancy et al., 2011).

Other studies have also shown that tankyrase is essential for Herpes Simplex Virus replication (HSV). Efficient HSV-1 replication requires tankyrase PARP activity (see, e.g., Li et al., 2011). Further support for this hypothesis comes from the observation that HSV did not replicate efficiently in cells depleted of tankyrase 1. Moreover, tankyrase and the tankyrase substrate TRF2 (telomeric repeat binding factor 2) control the degradation of Ebstein-Barr Virus (EBV) DNA (see, e.g., Deng et al., 2002), suggesting tankyrase inhibitors could have utility as antiviral agents.

In addition, tankyrase inhibition is known to modulate glucose uptake (see, e.g., Yeh et al., 2007), suggesting that a small molecule tankyrase inhibitor could have utility in the treatment of metabolic diseases such as type 2 diabetes. In this case, tankyrase inhibition is thought to modulate glucose uptake by altering the function and cellular localisation of the glucose transporter type 4 (GLUT4) and the aminopeptidase IRAP (insulin-responsive aminopeptidase).

In addition, tankyrase inhibition is known to induce cardiomyocyte differentiation (see, e.g., Wang et al., 2011), suggesting that small molecule tankyrase inhibitors could have some ability in the treatment of cardiac disorders, such as cardiac repair after cardiac infarction.

In addition, tankyrase inhibition is know to minimise the pathological effects of lung fibrosis and tankyrase inhibitors can improve the survival of mice with bleomycin-induced lung fibrosis (see, e.g., Distler et al., 2012) suggesting that small molecule tankyrase inhibitors could have some usefulness in the treatment of lung disorders and fibrotic disorders such as pulmonary fibrosis, cystic fibrosis, cirrhosis, endomyocardial fibrosis, mediastinal fibrosis, myelofibrosis, retroperitoneal fibrosis, progressive massive fibrosis, nephrogenic systemic fibrosis, Crohn's disease, keloid, scleroderma/systemic sclerosis and arthrofibrosis.

In addition to these pathologies, Wnt signalling and its modulation are also involved in a number of other pathogenic conditions suggesting that small molecules tankyrase inhibitors could have utility in these other Wnt related diseases, including:

Alzheimer's disease, where the Wnt mediator B-catenin activity is aberrant (see, e.g., Caricasole et al., 2003; Moon et al., 2004; Mudher and Lovestone, 2002); Dupuytren skin disease, where the Wnt mediator B-catenin activity is also aberrant (see, e.g., Varallo et al., 2003);

tooth agenesis, where the Wnt mediator Axin2 activity is aberrant (see, e.g., Lammi et al., 2004);

osteoarthritis, where the Wnt mediator secreted frizzled-related protein 3 (FRP3) activity is aberrant (see, e.g., Loughlin et al., 2004);

exudative vitreoretinopathy, where the Wnt mediators frizzled family receptor 4 (FZD4) (see, e.g., Robitaille et al., 2002) and Norrie disease protein (see, e.g., Xu et al., 2004) activities are aberrant;

schizophrenia, where the Wnt mediators glycogen synthase kinase 3 beta (GSK3b) and wingless-type MMTV integration site family member 1 (Wnt1) are aberrant (see, e.g., Kozlovsky et al., 2002; Miyaoka et al., 1999);

osteoporosis, where the Wnt mediator low density lipoprotein receptor-related protein 5 (LRP5) activity is aberrant (see, e.g., Gong et al., 2001);

dermal hypoplasia, where the Wnt mediator porcupine homolog (PORCN) activity is aberrant (see, e.g., Grzeschik et al., 2007);

XX sex reversal, where the Wnt mediator R-spondin 1 (RSPO1) activity is aberrant (see, e.g., Parma et al., 2006);

anonychia and hyponychia, were the Wnt mediator R-spondin 4 (RSPO4) is aberrant (see, e.g., Bergmann et al., 2006; Blaydon et al., 2006);

sclerosteosis and Van Buchem disease, where the Wnt mediator sclerostin (SOST) activity is aberrant (see, e.g., Balemans et al., 2001; Balemans et al., 2002);

Fuhrmann syndrome, were the Wnt mediator wingless-related MMTV integration site 7A (Wnt7a) activity is aberrant (see, e.g., Woods et al., 2006);

Odonto-onchyo-dermal hypoplasia, where Wnt mediator wingless related MMTV integration site 10a (Wnt10a) activity is aberrant (see, e.g., Adaimy et al., 2007); and early onset obesity, where the Wnt mediator wingless related MMTV integration site 10b (Wnt10b) activity is aberrant (see, e.g., Christodoulides et al., 2006).

Moreover, aberrant telomerase protein component TERT expression and aberrant Wnt signalling are implicated in nephropathy, including HIV-associated nephropathy (see, e.g., Shkreli et al., 2011). Given the strong link between tankyrase inhibitors and modulation of both Wnt signalling and TERT function, it is likely that small molecule tankyrase inhibitors could be used in the treatment of these pathologies.

The inventors have identified a class of small molecule inhibitors of PARP superfamily members including PARP1 and Tankyrase 1 which are useful in the treatment of conditions, including proliferative conditions such as cancer. In some cases, these inhibitors are able to elicit biochemical inhibition of these targets as well as eliciting cellular activity including one or more or all of: (i) inhibition of Wnt signalling; (ii) inhibition of cell survival/proliferation; (iii) stabilisation of Axin and tankyrase levels; and (iv) formation of markers of DNA damage such as γH2AX foci.

It appears that the following 3-aryl-5-substituted-2H-isoquinolin-1-ones are known.

| # | Structure | Registry No. |
|---|---|---|
| P01 | 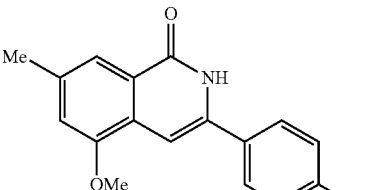 | 70351-69-8 |
| P02 | 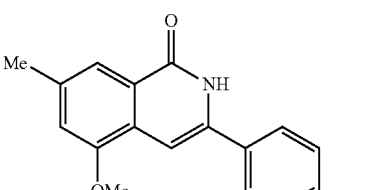 | 70351-70-1 |
| P03 | 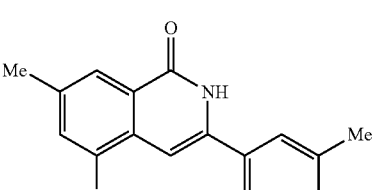 | 70351-71-2 |
| P04 | 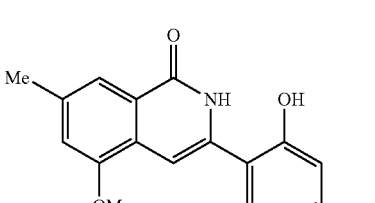 | 70351-72-3 |
| P05 | 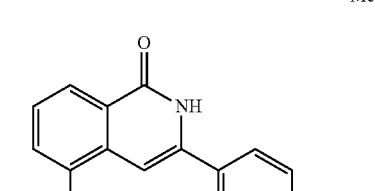 | 203628-15-3 |
| P06 | 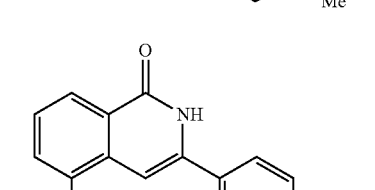 | 203628-17-5 |
| P07 | 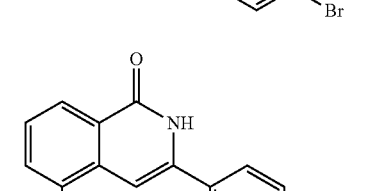 | 203628-19-7 |
-continued
| # | Structure | Registry No. |
|---|---|---|
| P08 | 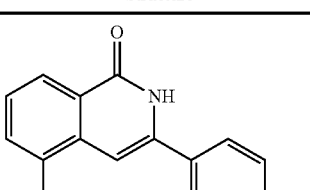 | 220630-92-2 |
| P09 | 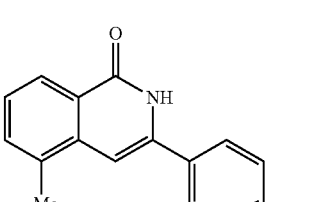 | 223553-35-3 |
| P10 | 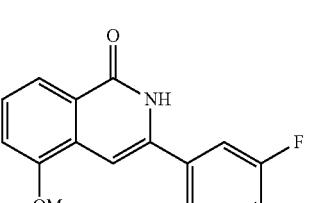 | 884500-93-0 |
| P11 | 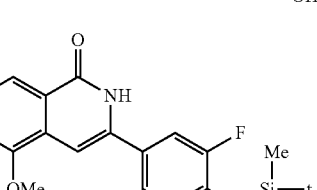 | 884501-99-9 |
| P12 | 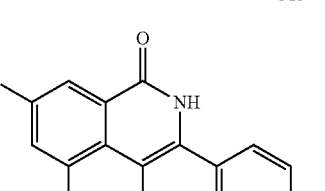 | 1256940-02-9 |
| P13 | 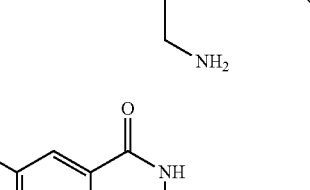 | 1256940-03-0 |

| # | Structure | Registry No. |
|---|---|---|
| P14 | 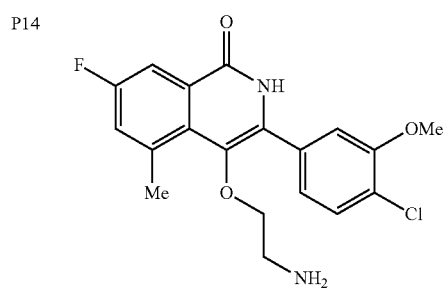 | 1256940-06-3 |
| P15 | 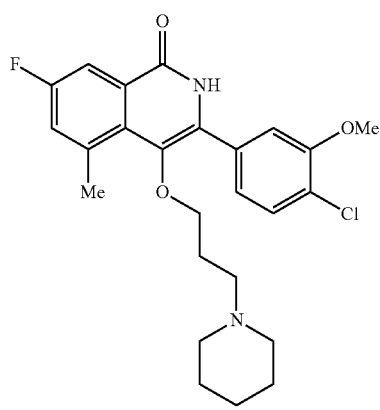 [SMILES: COc1cc(-c2[nH]c(=O)c3cc(F)cc(C)c3c2OCCCN2CCCCC2)ccc1Cl] | 1256940-07-4 |
| P16 | 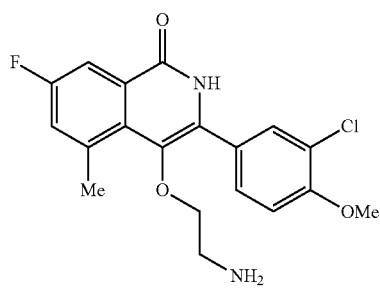 [SMILES: COc1ccc(-c2[nH]c(=O)c3cc(F)cc(C)c3c2OCCN)cc1Cl] | 1256940-08-5 |
| P17 | 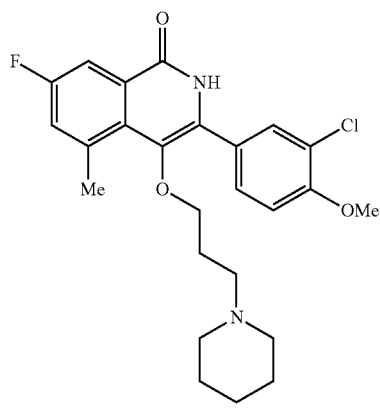 [SMILES: COc1ccc(-c2[nH]c(=O)c3cc(F)cc(C)c3c2OCCCN2CCCCC2)cc1Cl] | 1256940-09-6 |
| # | Structure | Registry No. |
|---|---|---|
| P18 | 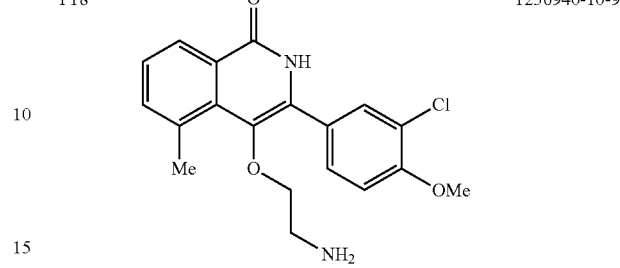 | 1256940-10-9 |
| P19 | | 1256940-11-0 |
| P20 | 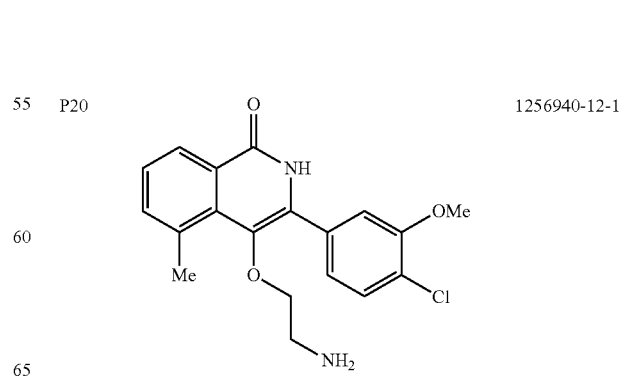 | 1256940-12-1 |

| # | Structure | Registry No. |
|---|---|---|
| P21 | 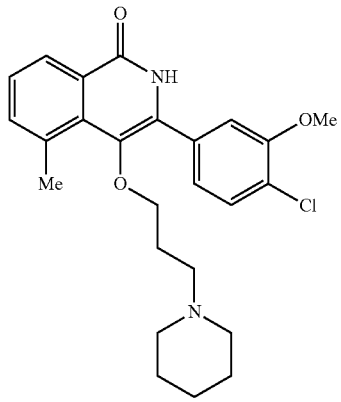 [SMILES: COc1cc(-c2[nH]c(=O)c3cccc(C)c3c2OCCCN2CCCCC2)ccc1Cl] | 1256940-13-2 |
| P22 | 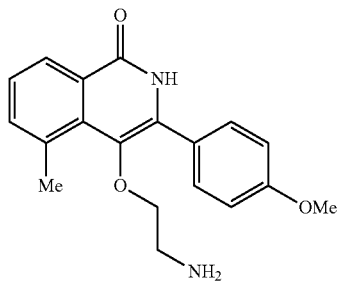 [SMILES: COc1ccc(-c2[nH]c(=O)c3cccc(C)c3c2OCCN)cc1] | 1256940-16-5 |
| # | Structure | Registry No. |
|---|---|---|
| P23 | 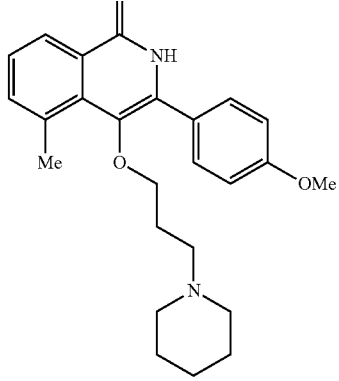 | 1256940-17-6 |
| P24 | 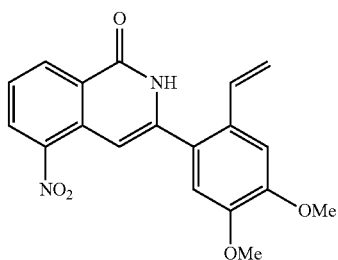 [SMILES: C=Cc1cc(OC)c(OC)cc1-c1cc2c([N+](=O)[O-])cccc2c(=O)[nH]1] | 1262335-24-9 |
It appears that the following 3-aryl-5-unsubstituted-2H-isoquinolin-1-ones are known.
| # | Structure | Registry No. |
|---|---|---|
| P25 | 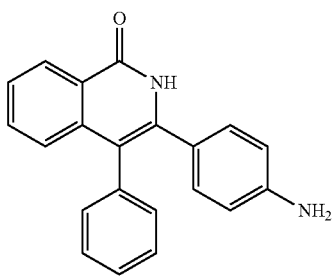 [SMILES: Nc1ccc(-c2[nH]c(=O)c3ccccc3c2-c2ccccc2)cc1] | 19069-81-9 |
| P26 | 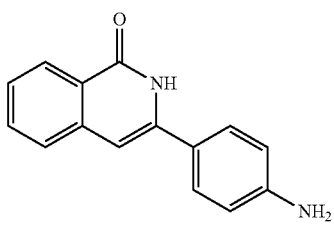 [SMILES: Nc1ccc(-c2cc3ccccc3c(=O)[nH]2)cc1] | 98659-53-1 |
| P27 | 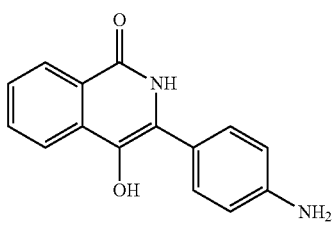 [SMILES: Nc1ccc(-c2[nH]c(=O)c3ccccc3c2O)cc1] | 98659-55-3 |

-continued

| # | Structure | Registry No. |
|---|---|---|
| P28 | 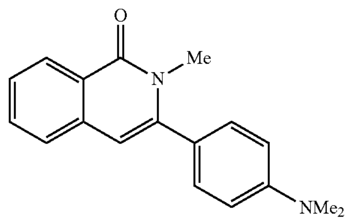 [SMILES: CN(C)c1ccc(-c2cc3ccccc3c(=O)n2C)cc1] | 145104-33-2 |
| P29 | 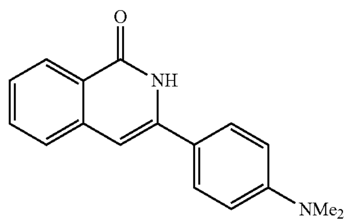 [SMILES: CN(C)c1ccc(-c2cc3ccccc3c(=O)[nH]2)cc1] | 223552-86-1 |
| P30 | 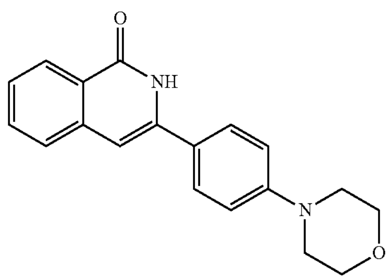 [SMILES: O=c1[nH]c(-c2ccc(N3CCOCC3)cc2)cc2ccccc12] | 223553-20-6 |
| P31 | 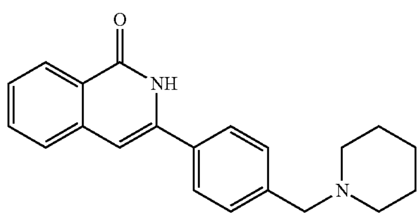 [SMILES: O=c1[nH]c(-c2ccc(CN3CCCCC3)cc2)cc2ccccc12] | 376354-94-8 |
| P32 | 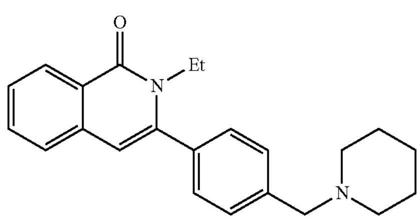 [SMILES: CCn1c(-c2ccc(CN3CCCCC3)cc2)cc2ccccc2c1=O] | 376354-97-1 |
| P33 | 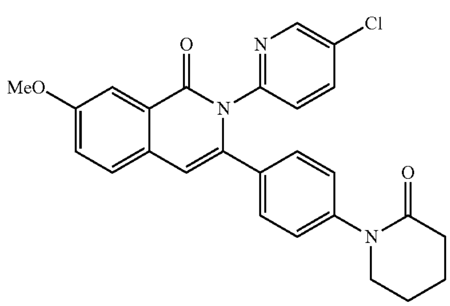 [SMILES: COc1ccc2cc(-c3ccc(N4CCCCC4=O)cc3)n(-c3ccc(Cl)cn3)c(=O)c2c1] | 503613-43-2 |

| # | Structure | Registry No. |
|---|-----------|--------------|
| P34 | 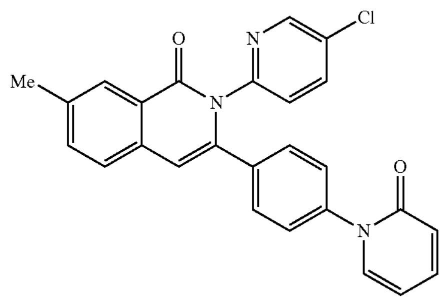 [SMILES: Cc1ccc2cc(-c3ccc(-n4ccccc4=O)cc3)n(-c3ccc(Cl)cn3)c(=O)c2c1] | 503613-44-3 |
| P35 | 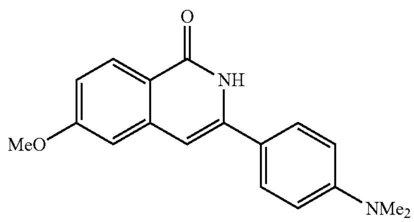 [SMILES: COc1ccc2c(=O)[nH]c(-c3ccc(N(C)C)cc3)cc2c1] | 630423-61-9 |
| P36 | 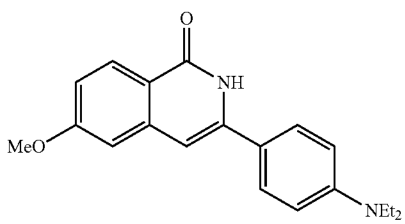 | 630423-64-2 |
| P37 | 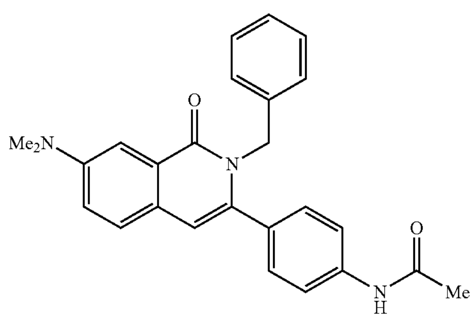 [SMILES: CC(=O)Nc1ccc(-c2cc3ccc(N(C)C)cc3c(=O)n2Cc2ccccc2)cc1] | 721960-58-3 |
| P38 | 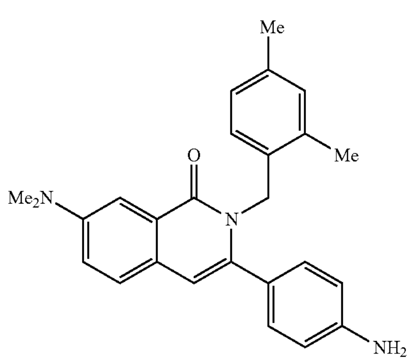 [SMILES: Cc1ccc(Cn2c(-c3ccc(N)cc3)cc3ccc(N(C)C)cc3c2=O)c(C)c1] | 721960-60-7 |

| # | Structure | Registry No. |
|---|---|---|
| P39 | 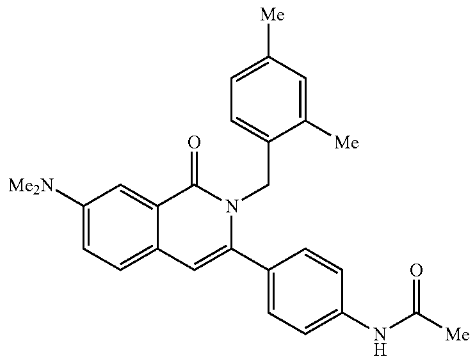 [SMILES: CC(=O)Nc1ccc(-c2cc3ccc(N(C)C)cc3c(=O)n2Cc2ccc(C)cc2C)cc1] | 721960-73-2 |
| P40 | 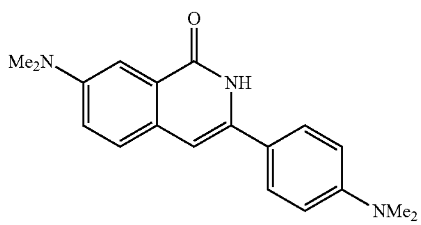 [SMILES: CN(C)c1ccc(-c2cc3ccc(N(C)C)cc3c(=O)[nH]2)cc1] | 862469-72-5 |
| P41 | 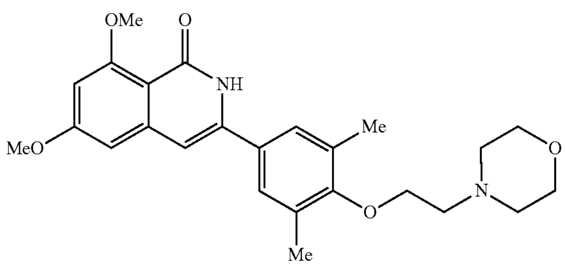 [SMILES: COc1cc(OC)c2c(=O)[nH]c(-c3cc(C)c(OCCN4CCOCC4)c(C)c3)cc2c1] | 924299-93-4 |
| P42 | 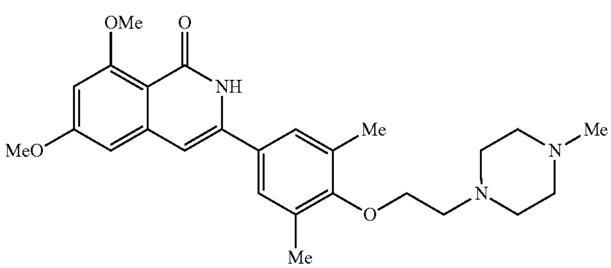 [SMILES: COc1cc(OC)c2c(=O)[nH]c(-c3cc(C)c(OCCN4CCN(C)CC4)c(C)c3)cc2c1] | 1044871-80-8 |
| P43 | 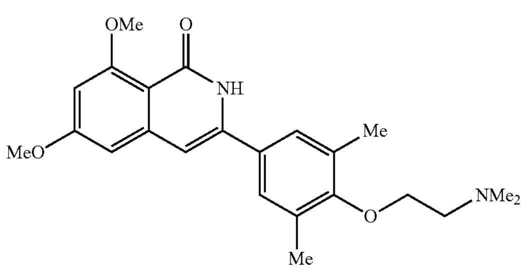 [SMILES: COc1cc(OC)c2c(=O)[nH]c(-c3cc(C)c(OCCN(C)C)c(C)c3)cc2c1] | 1044871-83-1 |
| P44 | 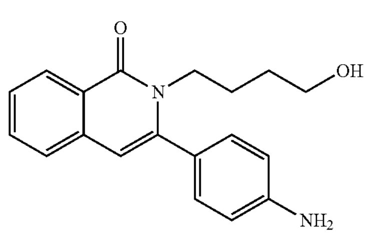 [SMILES: Nc1ccc(-c2cc3ccccc3c(=O)n2CCCCO)cc1] | 1193268-39-1 |

-continued

| # | Structure | Registry No. |
|---|---|---|
| P45 | 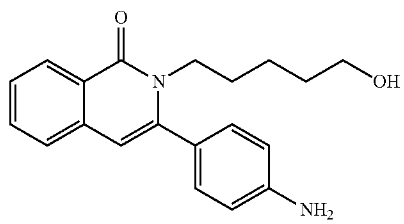 [SMILES: Nc1ccc(-c2cc3ccccc3c(=O)n2CCCCCO)cc1] | 1193268-40-4 |
| P46 | 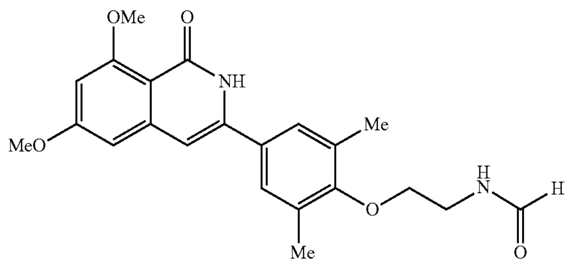 [SMILES: COc1cc(OC)c2c(=O)[nH]c(-c3cc(C)c(OCCNC=O)c(C)c3)cc2c1] | 1253733-07-1 |
| P47 | 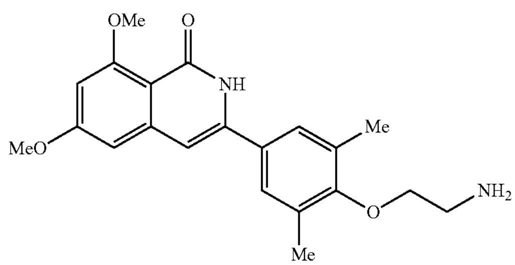 [SMILES: COc1cc(OC)c2c(=O)[nH]c(-c3cc(C)c(OCCN)c(C)c3)cc2c1] | 1253733-10-6 |
| P48 | 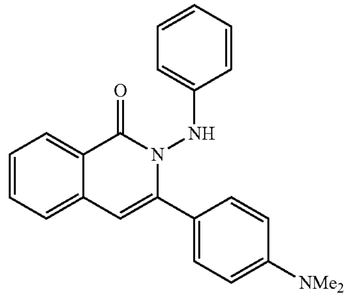 [SMILES: CN(C)c1ccc(-c2cc3ccccc3c(=O)n2Nc2ccccc2)cc1] | 1417652-57-3 |

SUMMARY OF THE INVENTION

One aspect of the invention pertains to certain 3-aryl-5-substituted-2H-isoquinolin-1-one compounds (referred to herein as IQ compounds), as described herein.

Another aspect of the invention pertains to a composition (e.g., a pharmaceutical composition) comprising an IQ compound, as described herein, and a pharmaceutically acceptable carrier or diluent.

Another aspect of the invention pertains to a method of preparing a composition (e.g., a pharmaceutical composition) comprising the step of mixing an IQ compound, as described herein, and a pharmaceutically acceptable carrier or diluent.

Another aspect of the present invention pertains to a method of inhibiting PARP (e.g., PARP1, TNKS1, TNKS2, etc.) function (e.g., in a cell), in vitro or in vivo, comprising contacting the cell with an effective amount of an IQ compound, as described herein.

Another aspect of the present invention pertains to a method of inhibiting Wnt signalling (e.g., in a cell), in vitro or in vivo, comprising contacting the cell with an effective amount of an IQ compound, as described herein.

Another aspect of the present invention pertains to an IQ compound as described herein for use in a method of treatment of the human or animal body by therapy, for example, for use in a method of treatment of a disorder (e.g., a disease) as described herein.

Another aspect of the present invention pertains to use of an IQ compound, as described herein, in the manufacture of a medicament, for example, for use in a method of treatment, for example, for use in a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of an IQ compound, as described herein, preferably in the form of a pharmaceutical composition.

In one embodiment, the treatment is treatment of a disorder of the human or animal body that is ameliorated by the inhibition of PARP.

In one embodiment, the treatment is treatment of a disorder of the human or animal body that is ameliorated by the inhibition of TNKS1 and/or TNKS2.

In one embodiment, the treatment is treatment of a disorder of the human or animal body that is ameliorated by the inhibition of Wnt signalling.

In one embodiment, the treatment is treatment of a proliferative condition.

In one embodiment, the treatment is treatment of cancer.

In one embodiment, the treatment is treatment of head cancer; neck cancer; nervous system cancer; lung/mediastinum cancer; breast cancer; oesophagus cancer; stomach cancer; liver cancer; biliary tract cancer; pancreatic cancer; small bowel cancer; large bowel cancer; gynaecological cancer; genito-urinary cancer; thyroid gland cancer; adrenal gland cancer; skin cancer; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of: a neurodegenerative disorder, such as multiple sclerosis (MS); a neurological disorder associated with demyelination; neonatal hypoxic ischemic encephalopathy (HIE); neonatal periventricular leukomalacia (PVL); a cardiac related pathology, such as myocardial infarction; cardiac damage (e.g., to repair cardiac damage); an infectious disease, such as a pathology related to Herpes Simplex Virus (HSV); a pathology related to Epstein-Barr Virus (EBV); a metabolic disease, such as a metabolic disease where glucose uptake is dysfunctional, such as diabetes, such as type 2 diabetes; or fibrosis (e.g., lung fibrosis).

In one embodiment, the treatment is treatment of: Alzheimer's disease; late onset Alzheimer's disease; Dupuytren skin disease; tooth agenesis; vascular defects in the eye; Osteoperosis-pseudoglioma Syndrome (OPPG); exudative vitreoretinopathy; familial exudative vitreoretinopathy; retinal angiogenesis; schizophrenia; osteoporosis; dermal hypoplasia; XX sex reversal; Mullerian-duct regression and virilization; SERKAL syndrome; anonychia; hyponychia; sclerosteosis; van Buchem disease; Fuhrmann syndrome; odonto-onchyo-dermal hypoplasia; Type 2 diabetes; obesity; early onset obesity; a nephropathy, such as HIV-associated nephropathy; early coronary disease; bone density defects; tetra-amelia syndrome; split-hand/foot malformation; caudal duplication; Fuhrmann syndrome; odonto-onycho-dermal dysplasia; skeletal dysplasia; focal dermal hypoplasia; autosomal recessive anonychia; or neural tube defects.

Another aspect of the present invention pertains to a kit comprising (a) an IQ compound, as described herein, preferably provided as a pharmaceutical composition and in a suitable container and/or with suitable packaging; and (b) instructions for use, for example, written instructions on how to administer the compound.

Another aspect of the present invention pertains to an IQ compound obtainable by a method of synthesis as described herein, or a method comprising a method of synthesis as described herein.

Another aspect of the present invention pertains to an IQ compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which are structurally related to 2H-isoquinolin-1-one.

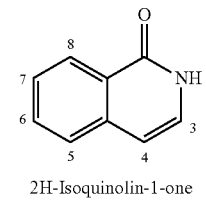 [SMILES: O=c1[nH]ccc2ccccc12]

2H-Isoquinolin-1-one

More particularly, the present invention relates to certain 3-aryl-5-substituted-2H-isoquinolin-1-one compounds, as defined herein.

Yet more particularly, the present invention relates to certain 2H-isoquinolin-1-one compounds which have both:

(a) a particular substituent (denoted herein as $R^5$) at the 5-position; and (b) a particular six-membered carboaryl or heteroaryl substituent (denoted herein as the ring containing W, X, Y, and Z) at the 3-position having a particular para-substituent (denoted herein as $-L^{3P}-R^{3N}$).

Thus, one aspect of the present invention pertains to compounds selected from compounds of the following formula, and pharmaceutically acceptable salts, N-oxides, hydrates, and solvates thereof, wherein $—R^{3N}$, $-L^{3P}-$, W, X, Y, Z, $—R^4$, $—R^5$, $—R^6$, $—R^7$, and $—R^8$ are as defined herein (for convenience, collectively referred to herein as "3-aryl-5-substituted-2H-isoquinolin-1-one compounds" or "IQ compounds"):

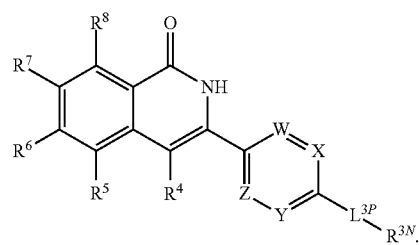

Some embodiments of the invention include the following:

(1) A compound selected from compounds of the following formula, and pharmaceutically acceptable salts, N-oxides, hydrates, and solvates thereof:

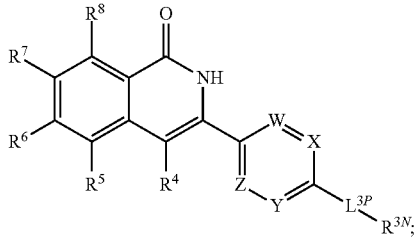

wherein:
W is $CR^W$, X is $CR^X$, Y is $CR^Y$, and Z is $CR^Z$ ("phenyl"); or
W is N, X is $CR^X$, Y is $CR^Y$, and Z is $CR^Z$ ("pyrid-2-yl"); or
W is $CR^W$, X is N, Y is $CR^Y$, and Z is $CR^Z$ ("pyrid-3-yl"); or
W is N, X is $CR^X$, Y is $CR^Y$, and Z is N ("pyrimidin-2-yl"); or
W is $CR^W$, X is N, Y is N, and Z is $CR^Z$ ("pyrimidin-5-yl"); or
W is N, X is $CR^X$, Y is N, and Z is $CR^Z$ ("pyrazin-2-yl"); or
W is N, X is N, Y is $CR^Y$, and Z is $CR^Z$ ("pyridazin-3-yl");
wherein:
—$R^W$ is independently —H or —F;
—$R^X$ is independently —H or —F;
—$R^Y$ is independently —H or —F; and
—$R^Z$ is independently —H or —F;
and wherein:
-$L^{3P}$- is independently a single covalent bond or -$L^{3PL}$-;
wherein:
-$L^{3PL}$- is independently -$L^{3PR1}$-, —C(=O)—, -$L^{3PR2}$-C(=O)—, —S(=O)$_2$—, -$L^{3PR3}$-S(=O)$_2$—, or —O-$L^{3PR4}$-;
wherein:
each -$L^{3PR1}$- is linear or branched saturated $C_{1-4}$alkylene;
each -$L^{3PR2}$- is linear or branched saturated $C_{1-4}$alkylene;
each -$L^{3PR3}$- is linear or branched saturated $C_{1-4}$alkylene;
each -$L^{3PR4}$- is linear or branched saturated $C_{1-4}$alkylene;
and wherein:
—$R^{3N}$ is independently —NH$_2$, —NHR$^A$, —NR$^A$R$^B$, or —NR$^C$R$^D$;
wherein:
each —$R^A$ is independently:
—$R^{A1}$, —$R^{A2}$, —$R^{A3}$, —$R^{A4}$, —$R^{A5}$, -$L^A$-$R^{A2}$, -$L^A$-$R^{A3}$, -$L^A$-$R^{A4}$, or -$L^A$-$R^{A5}$;
each —$R^{A1}$ is linear or branched saturated $C_{1-6}$alkyl,
and is optionally substituted with one or more groups —$R^{S1}$;
each —$R^{A2}$ is saturated $C_{3-6}$cycloalkyl,
and is optionally substituted with one or more groups —$R^{S2C}$;
each —$R^{A3}$ is non-aromatic $C_{3-7}$heterocyclyl,
and is optionally substituted on carbon with one or more groups —$R^{S2C}$,
and is optionally substituted on secondary nitrogen, if present, with a group —$R^{SN}$;
each —$R^{A4}$ is independently phenyl or naphthyl,
and is optionally substituted with one or more groups —$R^{S3C}$;
each —$R^{A5}$ is $C_{5-10}$heteroaryl,
and is optionally substituted on carbon with one or more groups —$R^{S3C}$,
and is optionally substituted on secondary nitrogen, if present, with a group —$R^{SN}$;
each -$L^A$- is linear or branched saturated $C_{1-4}$alkylene;
and wherein:
each —$R^{S1}$ is independently:
—F, —Cl, —Br, —I,
—OH, —OR$^{TT}$,
—OCF$_3$,
—NH$_2$, —NHR$^{TT}$, —NR$^{TT}_2$, —R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$, —C(=O)R$^{TM}$,
—NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, —NHC(=O)R$^{TM}$,
—NR$^{TN}$C(=O)NH$_2$, —NR$^{TN}$C(=O)NHR$^{TT}$, —NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$,
—S(=O)$_2$NH$_2$, —S(=O)$_2$NHR$^{TT}$, —S(=O)$_2$NR$^{TT}_2$, —S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, —SR$^{TT}$, or =O;
each —$R^{S2C}$ is independently:
—R$^{TT}$,
—F, —Cl, —Br, —I,
—OH, —OR$^{TT}$,
-$L^T$-OH, -$L^T$-OR$^{TT}$,
—CF$_3$, —OCF$_3$,
—NH$_2$, —NHR$^{TT}$, —NR$^{TT}_2$, —R$^{TM}$,
-$L^T$-NH$_2$, -$L^T$-NHR$^{TT}$, -$L^T$-NR$^{TT}_2$, -$L^T$-R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$, —C(=O)R$^{TM}$,
—NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, —NHC(=O)R$^{TM}$,
—NR$^{TN}$C(=O)NH$_2$, —NR$^{TN}$C(=O)NHR$^{TT}$, —NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$,
—S(=O)$_2$NH$_2$, —S(=O)$_2$NHR$^{TT}$, —S(=O)$_2$NR$^{TT}_2$, —S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, —SR$^{TT}$, or =O;
each —$R^{S3C}$ is independently:
—R$^{TT}$,
—F, —Cl, —Br, —I,
—OH, —OR$^{TT}$,
-$L^T$-OH, -$L^T$-OR$^{TT}$,
—CF$_3$, —OCF$_3$,
—NH$_2$, —NHR$^{TT}$, —NR$^{TT}_2$, —R$^{TM}$,
-$L^T$-NH$_2$, -$L^T$-NHR$^{TT}$, -$L^T$-NR$^{TT}_2$, -$L^T$-R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$,
—C(=O)R$^{TM}$, —NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, —NHC(=O)R$^{TM}$,
—NR$^{TN}$C(=O)NH$_2$, —NR$^{TN}$C(=O)NHR$^{TT}$,
—NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$,
—S(=O)$_2$NH$_2$, —S(=O)$_2$NHR$^{TT}$, —S(=O)$_2$NR$^{TT}_2$, —S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, or —SR$^{TT}$;
and additionally, two adjacent groups —R$^{S3C}$, if present, may together form:
—O—CH$_2$—O— or —O—CH$_2$CH$_2$—O—;
each —R$^{SN}$ is independently:
—R$^{TT}$,
-L$^T$-OH, -L$^T$-OR$^{TT}$,
-L$^T$-NH$_2$, -L$^T$-NHR$^{TT}$, -L$^T$-NR$^{TT}_2$, -L$^T$-R$^{TM}$,
—C(=O)R$^{TT}$,
—C(=O)OR$^{TT}$,
—C(=O)NH$_2$, —C(=O)NHR$^{TT}$, —C(=O)NR$^{TT}_2$,
—C(=O)R$^{TM}$, or
—S(=O)$_2$R$^{TT}$;
wherein:
each -L$^T$- is linear or branched saturated C$_{1-4}$alkylene;
each —R$^{TT}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{TTT}$, wherein —R$^{TTT}$ is linear or branched saturated C$_{1-4}$alkyl;
each —R$^{TN}$ is linear or branched saturated C$_{1-4}$alkyl;
each —R$^{TM}$ is independently azetidino, pyrrolidino, piperidino, piperazino, morpholino, azepano, or diazepano, and is:
optionally substituted on carbon with one or more groups selected from: —R$^{TMM}$, —C(=O)R$^{TMM}$, —S(=O)$_2$R$^{TMM}$, —F, —NH$_2$, —NHR$^{TMM}$, —NR$^{TMM}_2$, —OH, and —OR$^{TMM}$; and
optionally substituted on secondary nitrogen, if present, with a group selected from: —R$^{TMM}$, —C(=O)R$^{TMM}$, —C(=O)OR$^{TMM}$, and —S(=O)$_2$R$^{TMM}$;
wherein each —R$^{TMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—R$^B$ is independently —R$^{B1}$, —R$^{B2}$, or -L$^B$-R$^{B2}$;
—R$^{B1}$ is linear or branched saturated C$_{1-6}$alkyl, and is optionally substituted with —OH or —OR$^{BB}$, wherein —R$^{BB}$ is linear or branched saturated C$_{1-4}$alkyl;
—R$^{B2}$ is saturated C$_{3-6}$cycloalkyl; and
-L$^B$- is linear or branched saturated C$_{1-4}$alkylene;
and wherein:
—NR$^C$R$^D$ is independently —NR$^{C1}$R$^{D1}$, —NR$^{C2}$R$^{D2}$, —NR$^{C3}$R$^{D3}$, —NR$^{C4}$R$^{D4}$, or —NR$^{C5}$R$^{D5}$;
wherein:
—NR$^{C1}$R$^{D1}$ is a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;
and wherein said monocyclic non-aromatic heterocyclyl group is:
optionally substituted on carbon with one or more groups —R$^{NC}$, and
optionally substituted on secondary nitrogen, if present, with a group —R$^{NN}$;
—NR$^{C2}$R$^{D2}$ is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;
and wherein said fused bicyclic non-aromatic heterocyclyl group is:
optionally substituted on carbon with one or more groups —R$^{NC}$, and
optionally substituted on secondary nitrogen, if present, with a group —R$^{NN}$;
—NR$^{C3}$R$^{D3}$ is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;
and wherein said bridged non-aromatic heterocyclyl group is:
optionally substituted on carbon with one or more groups —R$^{NC}$, and
optionally substituted on secondary nitrogen, if present, with a group —R$^{NN}$;
—NR$^{C4}$R$^{D4}$ is a spiro non-aromatic heterocyclyl group having from 6 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, wherein said S is optionally in the form of S(=O) or S(=O)$_2$;
and wherein said spiro non-aromatic heterocyclyl group is:
optionally substituted on carbon with one or more groups —R$^{NC}$, and
optionally substituted on secondary nitrogen, if present, with a group —R$^{NN}$;
wherein:
each —R$^{NC}$ is independently:
—R$^{QQ}$,
—F, —Cl, —Br, —I,
—OH, —OR$^{QQ}$,
-L$^Q$-OH, -L$^Q$-OR$^{QQ}$,
—CF$_3$, —OCF$_3$,
—NH$_2$, —NHR$^{QQ}$, —NR$^{QQ}_2$, —R$^{QM}$, -L$^Q$-NH$_2$, -L$^Q$-NHR$^{QQ}$, -L$^Q$-NR$^{QQ}$$_2$, -L$^Q$-R$^{QM}$,
—C(=O)OH, —C(=O)OR$^{QQ}$, —OC(=O)R$^{QQ}$,
—C(=O)NH$_2$, —C(=O)NHR$^{QQ}$, —C(=O)NR$^{QQ}$$_2$,
—C(=O)R$^{QM}$,
—NHC(=O)R$^{QQ}$, —NR$^{QN}$C(=O)R$^{QQ}$,
—NHC(=O)NH$_2$, —NHC(=O)NHR$^{QQ}$, —NHC(=O)NR$^{QQ}$$_2$, —NHC(=O)R$^{QM}$,
—NR$^{QN}$C(=O)NH$_2$, —NR$^{QN}$C(=O)NHR$^{QQ}$,
—NR$^{QN}$C(=O)NR$^{QQ}$$_2$, —NR$^{QN}$C(=O)R$^{QM}$,
—NHC(=O)OR$^{QQ}$, —NR$^{QN}$C(=O)OR$^{QQ}$,
—OC(=O)NH$_2$, —OC(=O)NHR$^{QQ}$, —OC(=O)NR$^{QQ}$$_2$, —OC(=O)R$^{QM}$,
—C(=O)R$^{QQ}$,
—S(=O)$_2$NH$_2$, —S(=O)$_2$NHR$^{QQ}$, —S(=O)$_2$NR$^{QQ}$$_2$, —S(=O)$_2$R$^{QM}$,
—NHS(=O)$_2$R$^{QQ}$, —NR$^{QN}$S(=O)$_2$R$^{QQ}$,
—S(=O)$_2$R$^{QQ}$,
—CN, —NO$_2$, —SR$^{QQ}$, or =O;

each —R$^{NN}$ is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}$$_2$, -L$^Q$-R$^{QM}$,
—C(=O)R$^{QQ}$,
—C(=O)OR$^{QQ}$,
—C(=O)NH$_2$, —C(=O)NHR$^{QQ}$, —C(=O)NR$^{QQ}$$_2$,
—C(=O)R$^{QM}$, or
—S(=O)$_2$R$^{QQ}$;

wherein:
each -L$^Q$- is linear or branched saturated C$_{1-4}$alkylene;
each —R$^{QQ}$ is independently —R$^{QQ1}$, —R$^{QQ2}$, or —R$^{QQ3}$;
each —R$^{QQ1}$ is independently linear or branched saturated C$_{1-4}$alkyl, saturated C$_{3-6}$cycloalkyl, or saturated C$_{3-6}$cycloalkyl-methyl; and is optionally substituted with —OH or —OR$^{QQQ}$;
each —R$^{QQ2}$ is independently phenyl or benzyl; and is optionally substituted with —R$^{QQQ}$;
each —R$^{QQ3}$ is independently C$_{5-6}$heteroaryl; and is optionally substituted with —R$^{QQQ}$;
each —R$^{QQQ}$ is linear or branched saturated C$_{1-4}$alkyl or saturated C$_{3-6}$cycloalkyl;
each —R$^{QN}$ is linear or branched saturated C$_{1-4}$alkyl;
each —R$^{QM}$ is independently azetidino, pyrrolidino, piperidino, piperazino, morpholino, azepano, or diazepano, and is:
optionally substituted on carbon with one or more groups selected from: —R$^{QMM}$, —C(=O)R$^{QMM}$, —S(=O)$_2$R$^{QMM}$, —F, —NH$_2$, —NHR$^{QMM}$, —NR$^{QMM}$$_2$, —OH, and —OR$^{QMM}$; and
optionally substituted on secondary nitrogen, if present, with a group selected from: —R$^{QMM}$, —C(=O)R$^{QMM}$, —C(=O)OR$^{QMM}$, and —S(=O)$_2$R$^{QMM}$;
wherein each —R$^{QMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—NR$^{C5}$R$^{D5}$ is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 2H-[1,2,3]triazol-2-yl; 1H-[1,2,4]triazol-1-yl; 1H-benzotriazol-1-yl; or 1H-tetrazol-1-yl; and is optionally substituted with one or more groups —R$^H$;
wherein each —R$^H$ is independently:
—R$^{HH}$,
—F, —Cl, —Br, —I,
—OH, —OR$^{HH}$,
-L$^H$-OH, -L$^H$-OR$^{HH}$
—CF$_3$, —OCF$_3$,
—NH$_2$, —NHR$^{HH}$, —NR$^{HH}$$_2$, —R$^{HM}$,
-L$^H$-NH$_2$, -L$^H$-NHR$^{HH}$, -L$^H$-NR$^{HH}$$_2$, -L$^H$-R$^{HM}$,
—C(=O)OH, —C(=O)OR$^{HH}$, —OC(=O)R$^{HH}$
—C(=O)NH$_2$, —C(=O)NHR$^{HH}$, —C(=O)NR$^{HH}$$_2$, —C(=O)R$^{HM}$,
—NHC(=O)R$^{HH}$, —NR$^{HN}$C(=O)R$^{HH}$,
—NHC(=O)NH$_2$, —NHC(=O)NHR$^{HH}$, —NHC(=O)NR$^{HH}$$_2$, —NHC(=O)R$^{HM}$,
—NR$^{HN}$C(=O)NH$_2$, —NR$^{HN}$C(=O)NHR$^{HH}$, —NR$^{HN}$C(=O)NR$^{HH}$$_2$, —NR$^{HN}$C(=O)R$^{HM}$,
—NHC(=O)OR$^{HH}$, —NR$^{HN}$C(=O)OR$^{HH}$
—OC(=O)NH$_2$, —OC(=O)NHR$^{HH}$, —OC(=O)NR$^{HH}$$_2$, —OC(=O)R$^{HM}$,
—C(=O)R$^{HH}$,
—S(=O)$_2$NH$_2$, —S(=O)$_2$NHR$^{HH}$, —S(=O)$_2$NR$^{HH}$$_2$, —S(=O)$_2$R$^{HM}$
—NHS(=O)$_2$R$^{HH}$, —NR$^{HN}$S(=O)$_2$R$^{HH}$,
—S(=O)$_2$R$^{HH}$,
—CN, —NO$_2$, or —SR$^{HH}$;

wherein:
each -L$^H$- is linear or branched saturated C$_{1-4}$alkylene;
each —R$^{HH}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{HHH}$, wherein —R$^{HHH}$ is linear or branched saturated C$_{1-4}$alkyl;
each —R$^{HN}$ is linear or branched saturated C$_{1-4}$alkyl;
each —R$^{HM}$ is independently azetidino, pyrrolidino, piperidino, piperazino, morpholino, azepano, or diazepano, and is:
optionally substituted on carbon with one or more groups selected from: —R$^{HMM}$, —C(=O)R$^{HMM}$, —S(=O)$_2$R$^{HMM}$, —F, —NH$_2$, —NHR$^{HMM}$, —NR$^{HMM}$$_2$, —OH, and —OR$^{HMM}$; and
optionally substituted on secondary nitrogen, if present, with a group selected from: —R$^{HMM}$, —C(=O)R$^{HMM}$, —C(=O)OR$^{HMM}$, and —S(=O)$_2$R$^{HMM}$;
wherein each —R$^{HMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—R$^5$ is independently —R$^{5A}$, —R$^{5B}$, —R$^{5C}$, or —R$^{5D}$;
—R$^{5A}$ is —CN;
—R$^{5B}$ is independently —CH$_2$NH$_2$, —CH$_2$NHR$^{5B1}$, or —CH$_2$NR$^{5B1}$R$^{5B2}$;
—R$^{5C}$ is independently —CH$_2$NHC(=O)R$^{5C1}$ or —CH$_2$NR$^{5C2}$C(=O)R$^{5C1}$; and
—R$^{5D}$ is independently —CH$_2$NHS(=O)$_2$R$^{5D1}$ or —CH$_2$NR$^{5D2}$S(=O)$_2$R$^{5D1}$;
wherein:
each —R$^{5B1}$ is independently linear or branched saturated C$_{1-4}$alkyl;
each —R$^{5B2}$ is independently linear or branched saturated C$_{1-4}$alkyl;
each —R$^{5C1}$ is independently linear or branched saturated C$_{1-4}$alkyl;
each —R$^{5C2}$ is independently linear or branched saturated C$_{1-4}$alkyl;
each —R$^{5D1}$ is independently linear or branched saturated C$_{1-4}$alkyl; and
each —R$^{5D2}$ is independently linear or branched saturated C$_{1-4}$alkyl;

and wherein:
—$R^4$ is —H;
—$R^6$ is independently —H or —F; and
—$R^7$ is independently —H or —F; and
—$R^8$ is independently —H or —F.

For the avoidance of doubt, it is not intended that any two or more of —$R^{3N}$, -$L^{3P}$, W, X, Y, Z, —$R^4$, —$R^5$, —$R^6$, —$R^7$, and —$R^8$ together form a ring fused to the ring(s) to which they are attached. For example, it is not intended that —$R^4$ and —$R^5$ together form a ring fused to the ring to which they are attached. Similarly, it is not intended that —$R^4$ and Z together form a ring fused to the rings to which they are attached. Similarly, it is not intended that —$R^4$ and W together form a ring fused to the rings to which they are attached.

For the avoidance of doubt, the phrase "substituent on carbon" is intended to refer to a substituent which is attached to a carbon ring atom. Similarly, the phrase "substituent on secondary nitrogen" is intended to refer to a substituent which is attached to a nitrogen ring atom which, in the absence of the substituent, would be a secondary nitrogen ring atom (i.e., —NH—). Consequently, a pyridyl group may only have "substituents on carbon", whereas 1H-pyrrole may have both "substituents on carbon" and a "substituent on secondary nitrogen", as illustrated below.

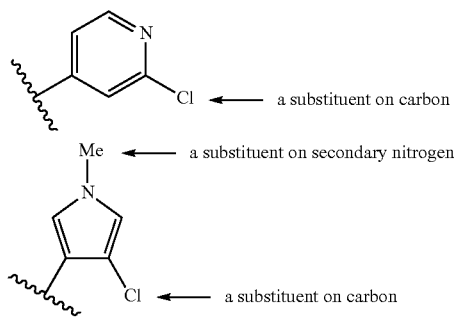

Similarly, a piperidino group may only have "substituents on carbon", whereas piperizino may have both "substituents on carbon" and a "substituent on secondary nitrogen", as illustrated below.

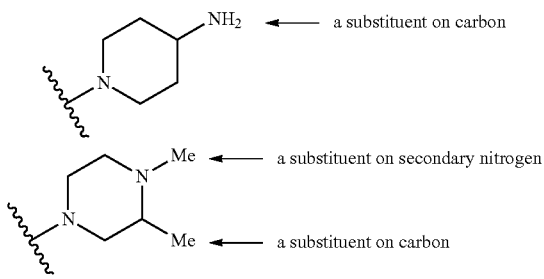

The Groups W, X, Y, and Z
(2) A compound according to (1), wherein:
W is $CR^W$, X is $CR^X$, Y is $CR^Y$, and Z is $CR^Z$ ("phenyl");
or
W is N, X is $CR^X$, Y is $CR^Y$, and Z is $CR^Z$ ("pyrid-2-yl");
or
W is $CR^W$, X is N, Y is $CR^Y$, and Z is $CR^Z$ ("pyrid-3-yl");
or
W is N, X is $CR^X$, Y is $CR^Y$, and Z is N ("pyrimidin-2-yl"); or
W is $CR^W$, X is N, Y is N, and Z is $CR^Z$ ("pyrimidin-5-yl").

(3) A compound according to any (1), wherein:
W is $CR^W$, X is $CR^X$, Y is $CR^Y$, and Z is $CR^Z$ ("phenyl"); or
W is $CR^W$, X is N, Y is $CR^Y$, and Z is $CR^Z$ ("pyrid-3-yl"); or
W is $CR^W$, X is N, Y is N, and Z is $CR^Z$ ("pyrimidin-5-yl").

(4) A compound according to (1), wherein:
W is $CR^W$, X is $CR^X$, Y is $CR^Y$, and Z is $CR^Z$ ("phenyl").

(5) A compound according to (1), wherein:
W is $CR^W$, X is N, Y is $CR^Y$, and Z is $CR^Z$ ("pyrid-3-yl").

(6) A compound according to (1), wherein:
W is $CR^W$, X is N, Y is N, and Z is $CR^Z$ ("pyrimidin-5-yl").

The Group —$R^W$
(7) A compound according to any one of (1) to (6), wherein —$R^W$, if present, is —H.
(8) A compound according to any one of (1) to (6), wherein —$R^W$, if present, is —F.

The Group —$R^X$
(9) A compound according to any one of (1) to (8), wherein —$R^X$, if present, is —H.
(10) A compound according to any one of (1) to (8), wherein —$R^X$, if present, is —F.

The Group —$R^Y$
(11) A compound according to any one of (1) to (10), wherein —$R^Y$, if present, is —H.
(12) A compound according to any one of (1) to (10), wherein —$R^Y$, if present, is —F.

The Group —$R^Z$
(13) A compound according to any one of (1) to (12), wherein —$R^Z$, if present, is —H.
(14) A compound according to any one of (1) to (12), wherein —$R^Z$, if present, is —F.

The Group -$L^{3P}$-
(15) A compound according to any one of (1) to (14), wherein -$L^{3P}$- is a single covalent bond.
(16) A compound according to any one of (1) to (14), wherein -$L^{3P}$- is -$L^{3PL}$-.

The Group -$L^{3PL}$-
(17) A compound according to any one of (1) to (16), wherein -$L^{3PL}$-, if present, is independently -$L^{3PR1}$-, —C(=O)—, -$L^{3PR2}$-C(=O)—, —O-$L^{3PR4}$-, or —S(=O)$_2$—.
(18) A compound according to any one of (1) to (16), wherein -$L^{3PL}$-, if present, is independently -$L^{3PR1}$-, —C(=O)—, —O-$L^{3PR4}$-, or —S(=O)$_2$—.
(19) A compound according to any one of (1) to (16), wherein -$L^{3PL}$-, if present, is -$L^{3PR1}$-.
(20) A compound according to any one of (1) to (16), wherein -$L^{3PL}$-, if present, is —C(=O)—.
(21) A compound according to any one of (1) to (16), wherein -$L^{3PL}$-, if present, is -$L^{3PR2}$-C(=O)—.
(22) A compound according to any one of (1) to (16), wherein -$L^{3PL}$-, if present, is —S(=O)$_2$—.
(23) A compound according to any one of (1) to (16), wherein -$L^{3PL}$-, if present, is -$L^{3PR3}$-S(=O)$_2$—.
(24) A compound according to any one of (1) to (16), wherein -$L^{3PL}$-, if present, is —O-$L^{3PR4}$-.

The Group -$L^{3PR1}$-
(25) A compound according to any one of (1) to (24), wherein each -$L^{3PR1}$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(26) A compound according to any one of (1) to (24), wherein each -L$^{3PR1}$-, if present, is independently —CH$_2$—, —CH(Me)-, —C(Me)$_2$-, —CH(Et)-, or —CH$_2$CH$_2$—.

(27) A compound according to any one of (1) to (24), wherein each -L$^{3PR1}$-, if present, is independently —CH$_2$—, —CH(Me)-, or —C(Me)$_2$-.

(28) A compound according to any one of (1) to (24), wherein each -L$^{3PR1}$-, if present, is independently —CH$_2$—, —CH$_2$CH$_2$—, —CH$_2$CH$_2$CH$_2$—, or —CH$_2$CH$_2$CH$_2$CH$_2$—.

(29) A compound according to any one of (1) to (24), wherein each -L$^{3PR1}$-, if present, is independently —CH$_2$CH$_2$—, —CH$_2$CH$_2$CH$_2$—, or —CH$_2$CH$_2$CH$_2$CH$_2$—.

(30) A compound according to any one of (1) to (24), wherein each -L$^{3PR1}$-, if present, is independently —CH$_2$— or —CH$_2$CH$_2$—.

(31) A compound according to any one of (1) to (24), wherein each -L$^{3PR1}$-, if present, is —CH$_2$—.

(32) A compound according to any one of (1) to (24), wherein each -L$^{3PR1}$-, if present, is independently —CH(Me)-.

(33) A compound according to any one of (1) to (24), wherein each -L$^{3PR1}$-, if present, is independently —C(Me)$_2$-.

(34) A compound according to any one of (1) to (24), wherein each -L$^{3PR1}$-, if present, is —CH$_2$CH$_2$—.

The Group -L$^{3PR2}$-

(35) A compound according to any one of (1) to (34), wherein each -L$^{3PR2}$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(36) A compound according to any one of (1) to (34), wherein each -L$^{3PR2}$-, if present, is independently —CH$_2$—, —CH(Me)-, —C(Me)$_2$-, —CH(Et)-, or —CH$_2$CH$_2$—.

(37) A compound according to any one of (1) to (34), wherein each -L$^{3PR2}$-, if present, is independently —CH$_2$—, —CH(Me)-, or —C(Me)$_2$-.

(38) A compound according to any one of (1) to (34), wherein each -L$^{3PR2}$-, if present, is independently —CH$_2$—, —CH$_2$CH$_2$—, —CH$_2$CH$_2$CH$_2$—, or —CH$_2$CH$_2$CH$_2$CH$_2$—.

(39) A compound according to any one of (1) to (34), wherein each -L$^{3PR2}$-, if present, is independently —CH$_2$CH$_2$—, —CH$_2$CH$_2$CH$_2$—, or —CH$_2$CH$_2$CH$_2$CH$_2$—.

(40) A compound according to any one of (1) to (34), wherein each -L$^{3PR2}$-, if present, is independently —CH$_2$— or —CH$_2$CH$_2$—.

(41) A compound according to any one of (1) to (34), wherein each -L$^{3PR2}$-, if present, is —CH$_2$—.

(42) A compound according to any one of (1) to (34), wherein each -L$^{3PR2}$-, if present, is independently —CH(Me)-.

(43) A compound according to any one of (1) to (34), wherein each -L$^{3PR2}$-, if present, is independently —C(Me)$_2$-.

(44) A compound according to any one of (1) to (34), wherein each -L$^{3PR2}$-, if present, is —CH$_2$CH$_2$—.

The Group -L$^{3PR3}$-

(45) A compound according to any one of (1) to (44), wherein each -L$^{3PR3}$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(46) A compound according to any one of (1) to (44), wherein each -L$^{3PR3}$-, if present, is independently —CH$_2$—, —CH(Me)-, —C(Me)$_2$-, —CH(Et)-, or —CH$_2$CH$_2$—.

(47) A compound according to any one of (1) to (44), wherein each -L$^{3PR3}$-, if present, is independently —CH$_2$—, —CH(Me)-, or —C(Me)$_2$-.

(48) A compound according to any one of (1) to (44), wherein each -L$^{3PR3}$-, if present, is independently —CH$_2$—, —CH$_2$CH$_2$—, —CH$_2$CH$_2$CH$_2$—, or —CH$_2$CH$_2$CH$_2$CH$_2$—.

(49) A compound according to any one of (1) to (44), wherein each -L$^{3PR3}$-, if present, is independently —CH$_2$CH$_2$—, —CH$_2$CH$_2$CH$_2$—, or —CH$_2$CH$_2$CH$_2$CH$_2$—.

(50) A compound according to any one of (1) to (44), wherein each -L$^{3PR3}$-, if present, is independently —CH$_2$— or —CH$_2$CH$_2$—.

(51) A compound according to any one of (1) to (44), wherein each -L$^{3PR3}$-, if present, is —CH$_2$—.

(52) A compound according to any one of (1) to (44), wherein each -L$^{3PR3}$-, if present, is —CH$_2$CH$_2$—.

The Group -L$^{3PR4}$-

(53) A compound according to any one of (1) to (52), wherein each -L$^{3PR4}$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(54) A compound according to any one of (1) to (52), wherein each -L$^{3PR4}$-, if present, is independently —CH$_2$—, —CH(Me)-, —C(Me)$_2$-, —CH(Et)-, or —CH$_2$CH$_2$—.

(55) A compound according to any one of (1) to (52), wherein each -L$^{3PR4}$-, if present, is independently —CH$_2$—, —CH(Me)-, or —C(Me)$_2$-.

(56) A compound according to any one of (1) to (52), wherein each -L$^{3PR4}$-, if present, is independently —CH$_2$—, —CH$_2$CH$_2$—, —CH$_2$CH$_2$CH$_2$—, or —CH$_2$CH$_2$CH$_2$CH$_2$—.

(57) A compound according to any one of (1) to (52), wherein each -L$^{3PR4}$-, if present, is independently —CH$_2$CH$_2$—, —CH$_2$CH$_2$CH$_2$—, or —CH$_2$CH$_2$CH$_2$CH$_2$—.

(58) A compound according to any one of (1) to (52), wherein each -L$^{3PR4}$-, if present, is independently —CH$_2$— or —CH$_2$CH$_2$—.

(59) A compound according to any one of (1) to (52), wherein each -L$^{3PR4}$-, if present, is —CH$_2$—.

(60) A compound according to any one of (1) to (52), wherein each -L$^{3PR4}$-, if present, is —CH$_2$CH$_2$—.

The Group —R$^{3N}$

(61) A compound according to any one of (1) to (60), wherein —R$^{3N}$ is independently —NHR$^A$, —NR$^A$R$^B$, or —NR$^C$R$^D$.

(62) A compound according to any one of (1) to (60), wherein —R$^{3N}$ is independently —NR$^A$R$^B$ or —NR$^C$R$^D$.

(63) A compound according to any one of (1) to (60), wherein —R$^{3N}$ is —NH$_2$.

(64) A compound according to any one of (1) to (60), wherein —R$^{3N}$ is —NHR$^A$.

(65) A compound according to any one of (1) to (60), wherein —R$^{3N}$ is —NR$^A$R$^B$.

(66) A compound according to any one of (1) to (60), wherein —R$^{3N}$ is —NR$^C$R$^D$.

The Group —$R^A$

(67) A compound according to any one of (1) to (66), wherein each —$R^A$, if present, is independently: —$R^{A1}$, —$R^{A2}$, —$R^{A3}$, -$L^A$-$R^{A2}$, or -$L^A$-$R^{A3}$.

(68) A compound according to any one of (1) to (66), wherein each —$R^A$, if present, is independently: —$R^{A1}$, —$R^{A3}$, or -$L^A$-$R^{A3}$.

(69) A compound according to any one of (1) to (66), wherein each —$R^A$, if present, is —$R^{A1}$.

(70) A compound according to any one of (1) to (66), wherein each —$R^A$, if present, is —$R^{A2}$.

(71) A compound according to any one of (1) to (66), wherein each —$R^A$, if present, is —$R^{A3}$.

(72) A compound according to any one of (1) to (66), wherein each —$R^A$, if present, is —$R^{A4}$.

(73) A compound according to any one of (1) to (66), wherein each —$R^A$, if present, is —$R^{A5}$.

(74) A compound according to any one of (1) to (66), wherein each —$R^A$, if present, is -$L^A$-$R^{A2}$.

(75) A compound according to any one of (1) to (66), wherein each —$R^A$, if present, is -$L^A$-$R^{A3}$.

(76) A compound according to any one of (1) to (66), wherein each —$R^A$, if present, is -$L^A$-$R^{A4}$.

(77) A compound according to any one of (1) to (66), wherein each —$R^A$, if present, is -$L^A$-$R^{A5}$.

The Group —$R^{A1}$

(78) A compound according to any one of (1) to (77), wherein each —$R^{A1}$, if present, is independently linear or branched saturated $C_{1-4}$alkyl, and is optionally substituted with one or more groups —$R^{S1}$.

(79) A compound according to any one of (1) to (77), wherein each —$R^{A1}$, if present, is independently linear or branched saturated $C_{1-4}$alkyl, and is optionally substituted with one or more groups selected from: —OH, —$OR^{TT}$, —$NH_2$, —$NHR^{TT}$, and —$NR^{TT}_2$.

(80) A compound according to any one of (1) to (77), wherein each —$R^{A1}$, if present, is independently linear or branched saturated $C_{1-4}$alkyl, and is optionally substituted with one or more groups selected from: —OH and —$OR^{TT}$.

(81) A compound according to any one of (1) to (77), wherein each —$R^{A1}$, if present, is independently -Me, -Et, -nPr, -iPr, -nBu, -iBu, or -tBu, and is optionally substituted with one or more groups —$R^{S1}$.

(82) A compound according to any one of (1) to (77), wherein each —$R^{A1}$, if present, is independently -Me, -Et, -nPr, -iPr, -nBu, -iBu, or -tBu, and is optionally substituted with one or more groups selected from: —OH, —$OR^{TT}$, —$NH_2$, —$NHR^{TT}$, and —$NR^{TT}_2$.

(83) A compound according to any one of (1) to (77), wherein each —$R^{A1}$, if present, is independently -Me, -Et, -nPr, or -iPr, and is optionally substituted with one or more groups —$R^{S1}$.

(84) A compound according to any one of (1) to (77), wherein each —$R^{A1}$, if present, is independently -Me, -Et, -nPr, or -iPr, and is optionally substituted with one or more groups selected from: —OH, —$OR^{TT}$, —$NH_2$, —$NHR^{TT}$, and —$NR^{TT}_2$.

(85) A compound according to any one of (1) to (77), wherein each —$R^{A1}$, if present, is independently -Me or -Et, and is optionally substituted with one or more groups —$R^{S1}$.

(86) A compound according to any one of (1) to (77), wherein each —$R^{A1}$, if present, is independently linear or branched saturated $C_{1-4}$alkyl.

(87) A compound according to any one of (1) to (77), wherein each —$R^{A1}$, if present, is independently -Me, -Et, -nPr, -iPr, -nBu, -iBu, or -tBu.

(88) A compound according to any one of (1) to (77), wherein each —$R^{A1}$, if present, is independently -Me, -Et, -nPr, or -iPr.

(89) A compound according to any one of (1) to (77), wherein each —$R^{A1}$, if present, is independently -Me or -Et.

(90) A compound according to any one of (1) to (77), wherein each —$R^{A1}$, if present, is -Me.

The Group —$R^{A2}$

(91) A compound according to any one of (1) to (90), wherein each —$R^{A2}$, if present, is independently cyclopropyl, cyclobutyl, cyclopentyl, or cyclohexyl, and is optionally substituted with one or more groups —$R^{S2C}$.

(92) A compound according to any one of (1) to (90), wherein each —$R^{A2}$, if present, is independently cyclopropyl, cyclobutyl, or cyclopentyl, and is optionally substituted with one or more groups —$R^{S2C}$.

(93) A compound according to any one of (1) to (90), wherein each —$R^{A2}$, if present, is independently cyclopropyl or cyclobutyl, and is optionally substituted with one or more groups —$R^{S2C}$.

The Group —$R^{A3}$

(94) A compound according to any one of (1) to (93), wherein each —$R^{A3}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl,
and is optionally substituted on carbon with one or more groups —$R^{S2C}$,
and is optionally substituted on secondary nitrogen, if present, with a group —$R^{SN}$.

(95) A compound according to any one of (1) to (93), wherein each —$R^{A3}$, if present, is independently tetrahydrofuranyl, tetrahydropyranyl, dioxanyl, pyrrolidinyl, piperidinyl, piperazinyl, morpholinyl,
and is optionally substituted on carbon with one or more groups —$R^{S2C}$,
and is optionally substituted on secondary nitrogen, if present, with a group —$R^{SN}$.

(96) A compound according to any one of (1) to (93), wherein each —$R^{A3}$, if present, is independently tetrahydropyranyl or piperidinyl,
and is optionally substituted on carbon with one or more groups —$R^{S2C}$,
and is optionally substituted on secondary nitrogen, if present, with a group —$R^{SN}$.

(97) A compound according to any one of (1) to (93), wherein each —$R^{A3}$, if present, is tetrahydropyranyl, and is optionally substituted on carbon with one or more groups —$R^{S2C}$.

(98) A compound according to any one of (1) to (93), wherein each —$R^{A3}$, if present, is piperidinyl,
and is optionally substituted on carbon with one or more groups —$R^{S2C}$,
and is optionally substituted on secondary nitrogen with a group —$R^{SN}$.

(99) A compound according to any one of (1) to (93), wherein each —$R^{A3}$, if present, is pyrrolidinyl,
and is optionally substituted on carbon with one or more groups —$R^{S2C}$,
and is optionally substituted on secondary nitrogen with a group —$R^{SN}$.

(100) A compound according to any one of (1) to (93), wherein each —$R^{A3}$, if present, is azetidinyl,
and is optionally substituted on carbon with one or more groups —$R^{S2C}$,
and is optionally substituted on secondary nitrogen with a group —$R^{SN}$.

The Group —$R^{A4}$ (101) A compound according to any one of (1) to (100), wherein each —$R^{A4}$, if present, is phenyl, and is optionally substituted with one or more groups —$R^{S3C}$.

(102) A compound according to any one of (1) to (100), wherein each —$R^{A4}$, if present, is naphthyl, and is optionally substituted with one or more groups —$R^{S3C}$.

The Group —$R^{A5}$ (103) A compound according to any one of (1) to (102), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl,
  and is optionally substituted on carbon with one or more groups —$R^{S3C}$,
  and is optionally substituted on secondary nitrogen, if present, with a group —$R^{SN}$.

(104) A compound according to any one of (1) to (102), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl,
  and is optionally substituted on carbon with one or more groups —$R^{S3C}$,
  and is optionally substituted on secondary nitrogen, if present, with a group —$R^{SN}$.

(105) A compound according to any one of (1) to (102), wherein each —$R^{A5}$, if present, is independently furanyl, thienyl, pyrrolyl, imidazolyl, oxazolyl, thiazolyl, pyrazolyl, isoxazolyl, or isothiazolyl,
  and is optionally substituted on carbon with one or more groups —$R^{S3C}$,
  and is optionally substituted on secondary nitrogen, if present, with a group —$R^{SN}$.

(106) A compound according to any one of (1) to (102), wherein each —$R^{A5}$, if present, is imidazolyl,
  and is optionally substituted on carbon with one or more groups —$R^{S3C}$,
  and is optionally substituted on secondary nitrogen with a group —$R^{SN}$.

(107) A compound according to any one of (1) to (102), wherein each —$R^{A5}$, if present, is independently pyridyl, pyridazinyl, pyrimidinyl, or pyrazinyl,
  and is optionally substituted on carbon with one or more groups —$R^{S3C}$.

The Group -$L^A$-

(108) A compound according to any one of (1) to (107), wherein each -$L^A$-, if present, is independently —$CH_2$—, —CH(Me)-, —$C(Me)_2$-, —$CH_2CH_2$—, —$CH(Me)CH_2$—, —$CH_2CH(Me)$-, —$C(Me)_2CH_2$—, —$CH_2C(Me)_2$-, —$CH_2CH_2CH_2$—, or —$CH_2CH_2CH_2CH_2$—.

(109) A compound according to any one of (1) to (107), wherein each -$L^A$-, if present, is independently —$CH_2$—, —CH(Me)-, —$C(Me)_2$-, —CH(Et)-, or —$CH_2CH_2$—.

(110) A compound according to any one of (1) to (107), wherein each -$L^A$-, if present, is independently —$CH_2$—, —CH(Me)-, or —$C(Me)_2$-.

(111) A compound according to any one of (1) to (107), wherein each -$L^A$-, if present, is independently —$CH_2$—, —$CH_2CH_2$—, —$CH_2CH_2CH_2$—, or —$CH_2CH_2CH_2CH_2$—.

(112) A compound according to any one of (1) to (107), wherein each -$L^A$-, if present, is independently —$CH_2CH_2$—, —$CH_2CH_2CH_2$—, or —$CH_2CH_2CH_2CH_2$—.

(113) A compound according to any one of (1) to (107), wherein each -$L^A$-, if present, is independently —$CH_2$— or —$CH_2CH_2$—.

(114) A compound according to any one of (1) to (107), wherein each -$L^A$-, if present, is —$CH_2$—.

(115) A compound according to any one of (1) to (107), wherein each -$L^A$-, if present, is —$CH_2CH_2$—.

The Group —$R^{S1}$ (116) A compound according to any one of (1) to (115), wherein each —$R^{S1}$, if present, is independently:
  —F, —Cl, —Br, —I,
  —OH, —$OR^{TT}$,
  —$OCF_3$,
  —$NH_2$, —$NHR^{TT}$, —$NR^{TT}_2$, —$R^{TM}$,
  —C(=O)OH, —C(=O)$OR^{TT}$, —OC(=O)$R^{TT}$,
  —C(=O)$NH_2$, —C(=O)$NHR^{TT}$, —C(=O)$NR^{TT}_2$,
  —C(=O)$R^{TM}$,
  —C(=O) $R^{TT}$,
  —S(=O)$_2NH_2$, —S(=O)$_2NHR^{TT}$, —S(=O)$_2NR^{TT}_2$,
  —S(=O)$_2R^{TM}$,
  —NHS(=O)$_2R^{TT}$, —$NR^{TN}$S(=O)$_2R^{TT}$,
  —S(=O)$_2R^{TT}$,
  —CN, —$NO_2$, —$SR^{TT}$, or =O.

(117) A compound according to any one of (1) to (115), wherein each —$R^{S1}$, if present, is independently:
  —F, —Cl, —Br, —I,
  —OH, —$OR^{TT}$,
  —$OCF_3$,
  —$NH_2$, —$NHR^{TT}$, —$NR^{TT}_2$, —$R^{TM}$,
  —C(=O)OH, —C(=O)$OR^{TT}$, —OC(=O)$R^{TT}$
  —C(=O)$NH_2$, —C(=O)$NHR^{TT}$, —C(=O)$NR^{TT}_2$,
  —C(=O)$R^{TM}$,
  —NHC(=O)$R^{TT}$, —$NR^{TN}$C(=O)$R^{TT}$,
  —C(=O) $R^{TT}$,
  —S(=O)$_2NH_2$, —S(=O)$_2NHR^{TT}$, —S(=O)$_2NR^{T2}$,
  —S(=O)$_2R^{TM}$,
  —NHS(=O)$_2R^{TT}$, —$NR^{TN}$S(=O)$_2R^{TT}$, or
  —S(=O)$_2R^{TT}$.

(118) A compound according to any one of (1) to (115), wherein each —$R^{S1}$, if present, is independently:
  —F, —Cl, —Br, —I,
  —OH, —$OR^{TT}$,
  —$OCF_3$,
  —$NH_2$, —$NHR^{TT}$, —$NR^{TT}_2$, —$R^{TM}$,
  —C(=O)OH, —C(=O)$OR^{TT}$, —OC(=O)$R^{TT}$,
  —C(=O)$NH_2$, —C(=O)$NHR^{TT}$, —C(=O)$NR^{TT}_2$,
  —C(=O)$R^{TM}$,
  —NHC(=O)R', —$NR^{TN}$C(=O)$R^{TT}$, or
  —C(=O) $R^{TT}$.

(119) A compound according to any one of (1) to (115), wherein each —$R^{S1}$, if present, is independently:
  —F,
  —OH, —$OR^{TT}$,
  —$NH_2$, —$NHR^{TT}$, —$NR^{TT}_2$, or —$R^{TM}$.

(120) A compound according to any one of (1) to (115), wherein each —$R^{S1}$, if present, is independently:
  —OH, —$OR^{TT}$,
  —$NH_2$, —$NHR^{TT}$, —$NR^{TT}_2$, or —$R^{TM}$.

(121) A compound according to any one of (1) to (115), wherein each —$R^{S1}$, if present, is independently —OH or —$OR^{TT}$.

The Group —$R^{S2C}$ (122) A compound according to any one of (1) to (121), wherein each —$R^{S2C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
  —C(=O)$R^{TM}$,
—NHC(=O)$R^{TT}$, —$NR^{TN}$C(=O)$R^{TT}$,
—C(=O) $R^{TT}$,
—S(=O)$_2NH_2$, —S(=O)$_2NHR^{TT}$, —S(=O)$_2NR^{T2}$,
  —S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, —$SR^{TT}$, or =O.

(123) A compound according to any one of (1) to (121), wherein each —$R^{S2C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
  —C(=O)$R^{TM}$,
—NHC(=O)$R^{TT}$, —$NR^{TN}$C(=O)$R^{TT}$,
—C(=O) $R^{TT}$,
—S(=O)$_2NH_2$, —S(=O)$_2NHR^{TT}$, —S(=O)$_2NR^{T2}$,
  —S(=O)$_2R^{TM}$,
—NHS(=O)$_2R^{TT}$, —$NR^{TN}$S(=O)$_2R^{TT}$,
—S(=O)$_2R^{TT}$, or
=O.

(124) A compound according to any one of (1) to (121), wherein each —$R^{S2C}$, if present, is independently:
—$R^{TT}$,
—F, —Cl, —Br, —I,
—OH, —$OR^{TT}$,
-$L^T$-OH, -$L^T$-$OR^{TT}$,
—$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(125) A compound according to any one of (1) to (121), wherein each —$R^{S2C}$, if present, is independently:
—$R^{TT}$,
—F,
—OH, —$OR^{TT}$,
-$L^T$-OH, -$L^T$-$OR^{TT}$,
—$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(126) A compound according to any one of (1) to (121), wherein each —$R^{S2C}$, if present, is independently:
—$R^{TT}$,
—F,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(127) A compound according to any one of (1) to (121), wherein each —$R^{S2C}$, if present, is independently:
—$R^{TT}$,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(128) A compound according to any one of (1) to (121), wherein each —$R^{S2C}$, if present, is independently:
—$R^{TT}$,
—OH, —$OR^{TT}$,
—$NH_2$, —$NHR^{TT}$, —$NR^{TT}_2$, —$R^{TM}$, or
=O.

The Group —$R^{S3C}$ (129) A compound according to any one of (1) to (128), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
  —C(=O)$R^{TM}$,
—NHC(=O) $R^n$, —$NR^{TN}$C(=O)$R^{TT}$,
—C(=O)$R^{TT}$,
—S(=O)$_2NH_2$, —S(=O)$_2NHR^{TT}$, —S(=O)$_2NR^{TT}_2$,
  —S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, or —$SR^{TT}$.

(130) A compound according to any one of (1) to (128), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
  —C(=O)$R^{TM}$,
—NHC(=O)$R^n$, —$NR^{TN}$C(=O)$R^{TT}$, or
—C(=O) $R^{TT}$.

(131) A compound according to any one of (1) to (128), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, or -$L^T$-$R^{TM}$.

(132) A compound according to any one of (1) to (128), wherein each —$R^{S3C}$, if present, is independently:
—$R^{TT}$,
—F, —Cl, —Br, —I,
—OH, —$OR^{TT}$,
—$NH_2$, —$NHR^{TT}$, —$NR^{TT}_2$, or —$R^{TM}$.

The Group —$R^{SN}$ (133) A compound according to any one of (1) to (132), wherein each —$R^{SN}$, if present, is independently:
—$R^{TT}$,
-$L^T$-OH, -$L^T$-O$R^{TT}$,
-$L^T$-NH$_2$, -$L^T$-NHR$^{TT}$, -$L^T$-N$R^{TT}{}_2$, -$L^T$-$R^{TM}$,
—C(=O) $R^{TT}$,
—C(=O)O$R^{TT}$,
—C(=O)NH$_2$, —C(=O)NHR$^{TT}$, —C(=O)N$R^{TT}{}_2$, or
—C(=O)$R^{TM}$.

(134) A compound according to any one of (1) to (132), wherein each —$R^{SN}$, if present, is independently:
—$R^{TT}$,
-$L^T$-OH, -$L^T$-O$R^{TT}$,
-$L^T$-NH$_2$, -$L^T$-NHR$^{TT}$, -$L^T$-N$R^{TT}{}_2$, -$L^T$-$R^{TM}$,
—C(=O)$R^{TT}$, or
—C(=O)O$R^{TT}$.

(135) A compound according to any one of (1) to (132), wherein each —$R^{SN}$, if present, is independently:
—$R^{TT}$,
-$L^T$-OH, -$L^T$-O$R^{TT}$,
-$L^T$-NH$_2$, -$L^T$-NHR$^{TT}$, -$L^T$-N$R^{TT}{}_2$, -$L^T$-$R^{TM}$, or
—C(=O)$R^{TT}$.

(136) A compound according to any one of (1) to (132), wherein each —$R^{SN}$, if present, is independently:
—$R^{TT}$,
-$L^T$-OH, -$L^T$-O$R^{TT}$,
-$L^T$-NH$_2$, -$L^T$-NHR$^{TT}$, -$L^T$-N$R^{TT}{}_2$, or
—C(=O) $R^{TT}$.

(137) A compound according to any one of (1) to (132), wherein each —$R^{SN}$, if present, is independently:
—$R^{TT}$,
—C(=O)$R^{TT}$, or
—C(=O)O$R^{TT}$.

(138) A compound according to any one of (1) to (132), wherein each —$R^{SN}$, if present, is independently —$R^{TT}$ or —C(=O)$R^{TT}$.

(139) A compound according to any one of (1) to (132), wherein each —$R^{SN}$, if present, is independently —$R^{TT}$.

The Group -$L^T$-

(140) A compound according to any one of (1) to (139), wherein each -$L^T$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(141) A compound according to any one of (1) to (139), wherein each -$L^T$-, if present, is independently —CH$_2$—, —CH(Me)-, —C(Me)$_2$-, —CH(Et)-, or —CH$_2$CH$_2$—.

(142) A compound according to any one of (1) to (139), wherein each -$L^T$-, if present, is independently —CH$_2$—, —CH(Me)-, or —C(Me)$_2$-.

(143) A compound according to any one of (1) to (139), wherein each -$L^T$-, if present, is independently —CH$_2$—, —CH$_2$CH$_2$—, —CH$_2$CH$_2$CH$_2$—, or —CH$_2$CH$_2$CH$_2$CH$_2$—.

(144) A compound according to any one of (1) to (139), wherein each -$L^T$-, if present, is independently —CH$_2$CH$_2$—, —CH$_2$CH$_2$CH$_2$—, or —CH$_2$CH$_2$CH$_2$CH$_2$—.

(145) A compound according to any one of (1) to (139), wherein each -$L^T$-, if present, is independently —CH$_2$— or —CH$_2$CH$_2$—.

(146) A compound according to any one of (1) to (139), wherein each -$L^T$-, if present, is —CH$_2$—.

(147) A compound according to any one of (1) to (139), wherein each -$L^T$-, if present, is —CH$_2$CH$_2$—.

The Group —$R^{TT}$ (148) A compound according to any one of (1) to (147), wherein each —$R^{TT}$, if present, is independently linear or branched saturated C$_{1-4}$alkyl, saturated C$_{3-6}$cycloalkyl, saturated C$_{3-6}$cycloalkyl-methyl, phenyl, or benzyl.

(149) A compound according to any one of (1) to (147), wherein each —$R^{TT}$, if present, is independently linear or branched saturated C$_{1-4}$alkyl, saturated C$_{3-6}$cycloalkyl, phenyl, or benzyl.

(150) A compound according to any one of (1) to (147), wherein each —$R^{TT}$, if present, is independently linear or branched saturated C$_{1-4}$alkyl, phenyl, or benzyl.

(151) A compound according to any one of (1) to (147), wherein each —$R^{TT}$, if present, is independently linear or branched saturated C$_{1-4}$alkyl, saturated C$_{3-6}$cycloalkyl, or saturated C$_{3-6}$cycloalkyl-methyl; wherein said linear or branched saturated C$_{1-4}$alkyl is optionally substituted with —OH or —OR$^{TTT}$, wherein —$R^{TTT}$ is linear or branched saturated C$_{1-4}$alkyl.

(152) A compound according to any one of (1) to (147), wherein each —$R^{TT}$, if present, is independently linear or branched saturated C$_{1-4}$alkyl, saturated C$_{3-6}$cycloalkyl, or saturated C$_{3-6}$cycloalkyl-methyl.

(153) A compound according to any one of (1) to (147), wherein each —$R^{TT}$, if present, is independently linear or branched saturated C$_{1-4}$alkyl or saturated C$_{3-6}$cycloalkyl; wherein said linear or branched saturated C$_{1-4}$alkyl is optionally substituted with —OH or —OR$^{TTT}$, wherein —$R^{TTT}$ is linear or branched saturated C$_{1-4}$alkyl.

(154) A compound according to any one of (1) to (147), wherein each —$R^{TT}$, if present, is independently linear or branched saturated C$_{1-4}$alkyl or saturated C$_{3-6}$cycloalkyl.

(155) A compound according to any one of (1) to (147), wherein each —$R^{TT}$, if present, is linear or branched saturated C$_{1-4}$alkyl, and is optionally substituted with —OH or —OR$^{TTT}$ wherein —$R^{TTT}$ is linear or branched saturated C$_{1-4}$alkyl.

(156) A compound according to any one of (1) to (147), wherein each —$R^{TT}$, if present, is linear or branched saturated C$_{1-4}$alkyl.

(157) A compound according to any one of (1) to (147), wherein each —$R^{TT}$, if present, is independently -Me, -Et, -nPr, -iPr, -nBu, -iBu, or -tBu.

(158) A compound according to any one of (1) to (147), wherein each —$R^{TT}$, if present, is independently -Me or -tBu.

(159) A compound according to any one of (1) to (147), wherein each —$R^{TT}$, if present, is -Me.

(160) A compound according to any one of (1) to (147), wherein each —$R^{TT}$, if present, is -tBu.

The Group —$R^{TTT}$ (161) A compound according to any one of (1) to (160), wherein each —$R^{TTT}$, if present, is independently -Me, -Et, -nPr, -iPr, -nBu, -iBu, or -tBu.

(162) A compound according to any one of (1) to (160), wherein each —$R^{TTT}$, if present, is independently -Me or -Et.

(163) A compound according to any one of (1) to (160), wherein each —$R^{TTT}$, if present, is -Me.

The Group —$R^{TN}$ (164) A compound according to any one of (1) to (163), wherein each —$R^{TN}$, if present, is independently -Me, -Et, -nPr, -iPr, -nBu, -iBu, or -tBu.

(165) A compound according to any one of (1) to (163), wherein each —$R^{TN}$, if present, is independently -Me or -Et.

(166) A compound according to any one of (1) to (163), wherein each —$R^{TN}$, if present, is -Me.

The Group —R$^{TM}$ (167) A compound according to any one of (1) to (166), wherein each —R$^{TM}$, if present, is independently pyrrolidino, piperidino, piperazino, or morpholino, and is:
optionally substituted on carbon with one or more groups selected from: —R$^{TMM}$, —C(=O)R$^{TMM}$, —S(=O)$_2$R$^{TMM}$, —F, —NH$_2$, —NHR$^{TMM}$, —NR$^{TMM}_2$, —OH, and —OR$^{TMM}$; and
optionally substituted on secondary nitrogen, if present, with a group selected from: —R$^{TMM}$, —C(=O)R$^{TMM}$, —C(=O)OR$^{TMM}$, and —S(=O)$_2$R$^{TMM}$;
wherein each —R$^{TMM}$ is independently linear or branched saturated C$_{1-4}$alkyl, saturated C$_{3-6}$cycloalkyl, saturated C$_{3-6}$cycloalkyl-methyl, phenyl, or benzyl.

The Group —R$^{TMM}$ (168) A compound according to any one of (1) to (167), wherein each —R$^{TMM}$, if present, is independently linear or branched saturated C$_{1-4}$alkyl, saturated C$_{3-6}$cycloalkyl, phenyl, or benzyl.

(169) A compound according to any one of (1) to (167), wherein each —R$^{TMM}$, if present, is independently linear or branched saturated C$_{1-4}$alkyl, phenyl, or benzyl.

(170) A compound according to any one of (1) to (167), wherein each —R$^{TMM}$, if present, is independently linear or branched saturated C$_{1-4}$alkyl, saturated C$_{3-6}$cycloalkyl, or saturated C$_{3-6}$cycloalkyl-methyl.

(171) A compound according to any one of (1) to (167), wherein each —R$^{TMM}$, if present, is independently linear or branched saturated C$_{1-4}$alkyl or saturated C$_{3-6}$cycloalkyl.

(172) A compound according to any one of (1) to (167), wherein each —R$^{TMM}$, if present, is linear or branched saturated C$_{1-4}$alkyl.

(173) A compound according to any one of (1) to (167), wherein each —R$^{TMM}$, if present, is independently -Me, -Et, -nPr, -iPr, -nBu, -iBu, or -tBu.

(174) A compound according to any one of (1) to (167), wherein each —R$^{TMM}$, if present, is independently -Me or -Et.

(175) A compound according to any one of (1) to (167), wherein each —R$^{TMM}$, if present, is -Me.

(176) A compound according to any one of (1) to (167), wherein each —R$^{TMM}$, if present, is independently saturated C$_{3-6}$cycloalkyl.

(177) A compound according to any one of (1) to (167), wherein each —R$^{TMM}$, if present, is independently cyclopropyl, cyclobutyl, cyclopentyl, or cyclohexyl.

(178) A compound according to any one of (1) to (167), wherein each —R$^{TMM}$, if present, is cyclopropyl.

The Group —R$^B$ (179) A compound according to any one of (1) to (178), wherein —R$^B$, if present, is —R$^{B1}$.

(180) A compound according to any one of (1) to (178), wherein —R$^B$, if present, is —R$^{B2}$.

(181) A compound according to any one of (1) to (178), wherein —R$^B$, if present, is -L$^B$-R$^{B2}$.

The Group —R$^{B1}$ (182) A compound according to any one of (1) to (181), wherein —R$^{B1}$, if present, is linear or branched saturated C$_{1-6}$alkyl.

(183) A compound according to any one of (1) to (181), wherein —R$^{B1}$, if present, is independently -Me, -Et, -nPr, -iPr, -nBu, -iBu, or -tBu, and is optionally substituted with —OH or —OR$^{BB}$, wherein —R$^{BB}$ is linear or branched saturated C$_{1-4}$alkyl.

(184) A compound according to any one of (1) to (181), wherein —R$^{B1}$, if present, is independently -Me, -Et, -nPr, -iPr, -nBu, -iBu, or -tBu.

(185) A compound according to any one of (1) to (181), wherein —R$^{B1}$, if present, is independently -Me, -Et, -nPr, or -iPr.

(186) A compound according to any one of (1) to (181), wherein —R$^{B1}$, if present, is independently: -Me; or -Et that is optionally substituted with —OH or —OR$^{BB}$, wherein —R$^{BB}$ is linear or branched saturated C$_{1-4}$alkyl.

(187) A compound according to any one of (1) to (181), wherein —R$^{B1}$, if present, is independently -Me, -Et, —CH$_2$CH$_2$OH, or —CH$_2$CH$_2$OMe.

(188) A compound according to any one of (1) to (181), wherein —R$^{B1}$, if present, is independently -Me, -Et, or —CH$_2$CH$_2$OH.

(189) A compound according to any one of (1) to (181), wherein —R$^{B1}$, if present, is independently -Me or -Et.

(190) A compound according to any one of (1) to (181), wherein —R$^{B1}$, if present, is -Me.

The Group —R$^{BB}$ (191) A compound according to any one of (1) to (190), wherein —R$^{BB}$, if present, is independently -Me or -Et.

(192) A compound according to any one of (1) to (190), wherein —R$^{BB}$, if present, is -Me.

The Group —R$^{B2}$ (193) A compound according to any one of (1) to (192), wherein —R$^{B2}$, if present, is independently cyclopropyl, cyclobutyl, cyclopentyl, or cyclohexyl.

(194) A compound according to any one of (1) to (192), wherein —R$^{B2}$, if present, is independently cyclopropyl, cyclobutyl, or cyclopentyl.

(195) A compound according to any one of (1) to (192), wherein —R$^{B2}$, if present, is independently cyclopropyl or cyclobutyl.

(196) A compound according to any one of (1) to (192), wherein —R$^{B2}$, if present, is cyclopropyl.

The Group -L$^B$-

(197) A compound according to any one of (1) to (196), wherein each -L$^B$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(198) A compound according to any one of (1) to (196), wherein each -L$^B$-, if present, is independently —CH$_2$—, —CH(Me)-, —C(Me)$_2$-, —CH(Et), or —CH$_2$CH$_2$—.

(199) A compound according to any one of (1) to (196), wherein each -L$^B$-, if present, is independently —CH$_2$—, —CH(Me)-, or —C(Me)$_2$-.

(200) A compound according to any one of (1) to (196), wherein each -L$^B$-, if present, is independently —CH$_2$—, —CH$_2$CH$_2$—, —CH$_2$CH$_2$CH$_2$—, or —CH$_2$CH$_2$CH$_2$CH$_2$—.

(201) A compound according to any one of (1) to (196), wherein each -L$^B$-, if present, is independently —CH$_2$CH$_2$—, —CH$_2$CH$_2$CH$_2$—, or —CH$_2$CH$_2$CH$_2$CH$_2$—.

(202) A compound according to any one of (1) to (196), wherein each -L$^B$-, if present, is independently —CH$_2$— or —CH$_2$CH$_2$—.

(203) A compound according to any one of (1) to (196), wherein each -L$^B$-, if present, is —CH$_2$—.

(204) A compound according to any one of (1) to (196), wherein each -L$^B$-, if present, is —CH$_2$CH$_2$—.

The Group —NR$^C$R$^D$ (205) A compound according to any one of (1) to (204), wherein —NR$^C$R$^D$, if present, is —NR$^{C1}$R$^{D1}$.

(206) A compound according to any one of (1) to (204), wherein —NR$^C$R$^D$, if present, is —NR$^{C2}$R$^{D2}$.

(207) A compound according to any one of (1) to (204), wherein —NR$^C$R$^D$, if present, is —NR$^{C3}$R$^{D3}$.

(208) A compound according to any one of (1) to (204), wherein —NR$^C$R$^D$, if present, is —NR$^{C4}$R$^{D4}$.

(209) A compound according to any one of (1) to (204), wherein —NR$^C$R$^D$, if present, is —NR$^{C5}$R$^{D5}$.

The Group —NR$^{C1}$R$^{D1}$ (210) A compound according to any one of (1) to (209), wherein —NR$^{C1}$R$^{D1}$, if present, is a monocyclic non-aromatic heterocyclyl group having from 4 to 7 ring atoms.

(211) A compound according to any one of (1) to (209), wherein —NR$^{C1}$R$^{D1}$, if present, is a monocyclic non-aromatic heterocyclyl group having from 5 to 7 ring atoms.

(212) A compound according to any one of (1) to (209), wherein —NR$^{C1}$R$^{D1}$, if present, is a monocyclic non-aromatic heterocyclyl group having 5 ring atoms.

(213) A compound according to any one of (1) to (209), wherein —NR$^{C1}$R$^{D1}$, if present, is a monocyclic non-aromatic heterocyclyl group having 6 ring atoms.

(214) A compound according to any one of (1) to (209), wherein —NR$^{C1}$R$^{D1}$, if present, is a monocyclic non-aromatic heterocyclyl group having 7 ring atoms.

(215) A compound according to any one of (1) to (209), wherein, in —NR$^{C1}$R$^{D1}$, if present, exactly 1 of said ring atoms is a ring heteroatom, and is N.

(216) A compound according to any one of (1) to (209), wherein, in —NR$^{C1}$R$^{D1}$, if present, exactly 2 of said ring atoms are ring heteroatoms, and are both N.

(217) A compound according to any one of (1) to (209), wherein, in —NR$^{C1}$R$^{D1}$, if present, exactly 2 of said ring atoms are ring heteroatoms, and are N and O.

(218) A compound according to any one of (1) to (209), wherein, in —NR$^{C1}$R$^{D1}$, if present, exactly 2 of said ring atoms are ring heteroatoms, and are N and S, wherein said S is optionally in the form of S(=O) or S(=O)$_2$.

(219) A compound according to any one of (1) to (209), wherein, in —NR$^{C1}$R$^{D1}$, if present, exactly 2 of said ring atoms are ring heteroatoms, and are N and S.

(220) A compound according to any one of (1) to (209), wherein, —NR$^{C1}$R$^{D1}$, if present, is independently selected from the following groups, wherein S, if present, is optionally in the form of S(=O) or S(=O)$_2$, and is:

optionally substituted on carbon with one or more groups —R$^{NC}$, and optionally substituted on secondary nitrogen, if present, with a group —R$^{NN}$:

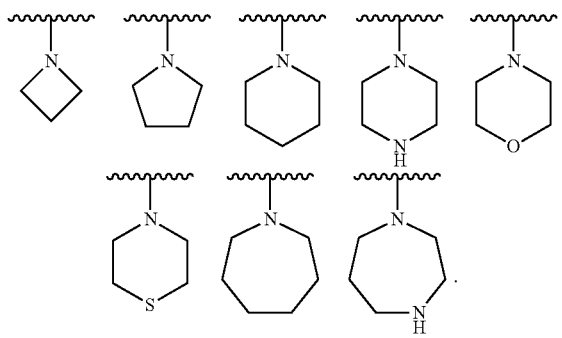

(221) A compound according to any one of (1) to (209), wherein, —NR$^{C1}$R$^{D1}$, if present, is independently selected from the following groups, and is:

optionally substituted on carbon with one or more groups —R$^{NC}$, and optionally substituted on secondary nitrogen, if present, with a group —R$^{NN}$:

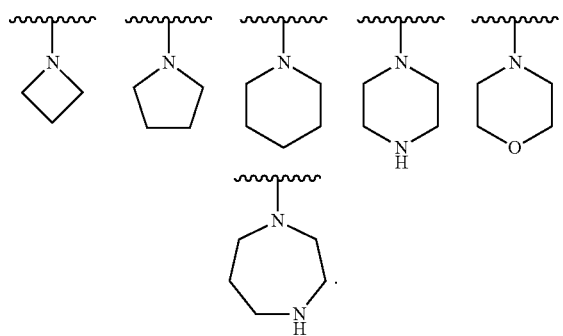

(222) A compound according to any one of (1) to (209), wherein, —NR$^{C1}$R$^{D1}$, if present, is independently selected from the following groups, and is:

optionally substituted on carbon with one or more groups —R$^{NC}$, and optionally substituted on secondary nitrogen, if present, with a group —R$^{NN}$:

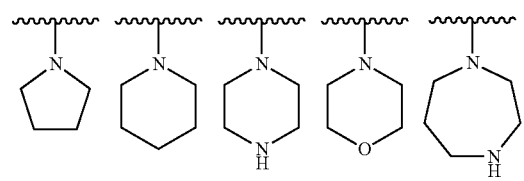

(223) A compound according to any one of (1) to (209), wherein, —NR$^{C1}$R$^{D1}$, if present, is the following group, and is optionally substituted on carbon with one or more groups —R$^{NC}$:

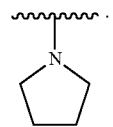

(224) A compound according to any one of (1) to (209), wherein, —NR$^{C1}$R$^{D1}$, if present, is the following group, and is optionally substituted on carbon with one or more groups —R$^{NC}$:

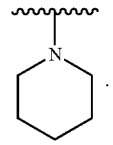

(225) A compound according to any one of (1) to (209), wherein, —NR$^{C1}$R$^{D1}$, if present, is the following group, and is:

optionally substituted on carbon with one or more groups —R$^{NC}$, and optionally substituted on secondary nitrogen with a group —R$^{NN}$:

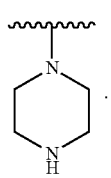

(226) A compound according to any one of (1) to (209), wherein, —NR$^{C1}$R$^{D1}$, if present, is the following group, and is optionally substituted on carbon with one or more groups —R$^{NC}$:

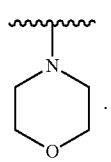

(227) A compound according to any one of (1) to (209), wherein, —NR$^{C1}$R$^{D1}$, if present, is the following group, and is:
optionally substituted on carbon with one or more groups —R$^{NC}$, and
optionally substituted on secondary nitrogen with a group —R$^{NN}$:

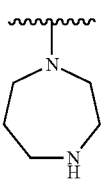

The Group —NR$^{C2}$R$^{D2}$ (228) A compound according to any one of (1) to (227), wherein —NR$^{C2}$R$^{D2}$, if present, is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;
and wherein said fused bicyclic non-aromatic heterocyclyl group is:
optionally substituted on carbon with one or more groups —R$^{NC}$, and
optionally substituted on secondary nitrogen, if present, with a group —R$^{NN}$.

(229) A compound according to any one of (1) to (227), wherein —NR$^{C2}$R$^{D2}$, if present, is a fused bicyclic non-aromatic heterocyclyl group having from 8 to 10 ring atoms.

(230) A compound according to any one of (1) to (227), wherein —NR$^{C2}$R$^{D2}$, if present, is a fused bicyclic non-aromatic heterocyclyl group having 8 ring atoms.

(231) A compound according to any one of (1) to (227), wherein —NR$^{C2}$R$^{D2}$, if present, is a fused bicyclic non-aromatic heterocyclyl group having 9 ring atoms.

(232) A compound according to any one of (1) to (227), wherein —NR$^{C2}$R$^{D2}$, if present, is a fused bicyclic non-aromatic heterocyclyl group having 10 ring atoms.

(233) A compound according to any one of (1) to (227), wherein, in —NR$^{C2}$R$^{D2}$, if present, exactly 1 of said ring atoms is a ring heteroatom, and is N.

(234) A compound according to any one of (1) to (227), wherein, in —NR$^{C2}$R$^{D2}$, if present, exactly 2 of said ring atoms are ring heteroatoms, and are both N.

(235) A compound according to any one of (1) to (227), wherein, in —NR$^{C2}$R$^{D2}$, if present, exactly 2 of said ring atoms are ring heteroatoms, and are N and O.

(236) A compound according to any one of (1) to (227), wherein, in —NR$^{C2}$R$^{D2}$, if present, exactly 2 of said ring atoms are ring heteroatoms, and are N and S, wherein said S is optionally in the form of S(=O) or S(=O)$_2$.

(237) A compound according to any one of (1) to (227), wherein, in —NR$^{C2}$R$^{D2}$, if present, exactly 2 of said ring atoms are ring heteroatoms, and are N and S.

(238) A compound according to any one of (1) to (227), wherein, —NR$^{C2}$R$^{D2}$, if present, is independently selected from the following groups, and is:
optionally substituted on carbon with one or more groups —R$^{NC}$, and
optionally substituted on secondary nitrogen, if present, with a group —R$^{NN}$:

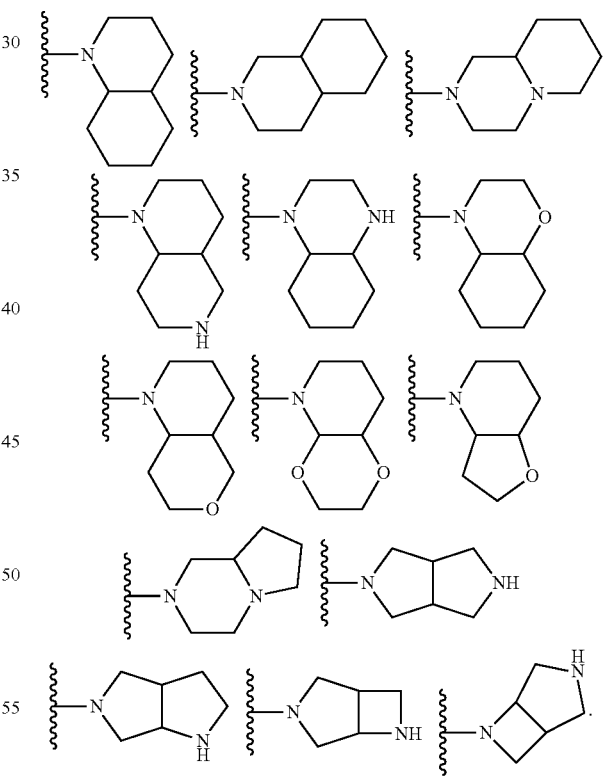

(239) A compound according to any one of (1) to (227), wherein, —NR$^{C2}$R$^{D2}$, if present, is independently selected from the following groups, and is:
optionally substituted on carbon with one or more groups —R$^{NC}$, and
optionally substituted on secondary nitrogen, if present, with a group —R$^{NN}$:

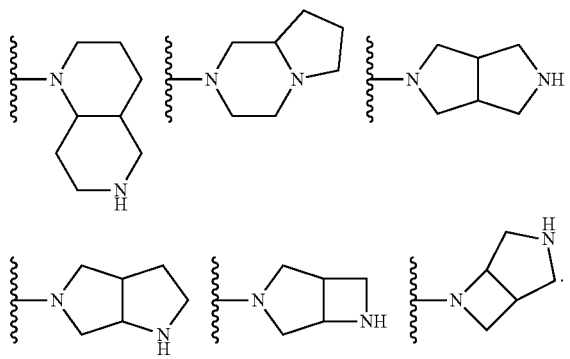

(240) A compound according to any one of (1) to (227), wherein, —NR$^{C2}$R$^{D2}$, if present, is the following group, and is optionally substituted on carbon with one or more groups —R$^{NC}$:

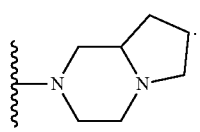 [SMILES: *N1CCN2CCCC2C1]

(241) A compound according to any one of (1) to (227), wherein, —NR$^{C2}$R$^{D2}$, if present, is the following group, and is:
  optionally substituted on carbon with one or more groups —R$^{NC}$, and
  optionally substituted on secondary nitrogen with a group —R$^{NN}$:

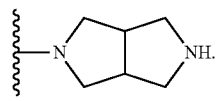 [SMILES: *N1CC2CNCC2C1]

The Group —NR$^{C3}$R$^{D3}$ (242) A compound according to any one of (1) to (241), wherein —NR$^{C3}$R$^{D3}$, if present, is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O;
  and wherein said bridged non-aromatic heterocyclyl group is:
  optionally substituted on carbon with one or more groups —R$^{NC}$, and
  optionally substituted on secondary nitrogen, if present, with a group —R$^{NN}$.

(243) A compound according to any one of (1) to (241), wherein —NR$^{C3}$R$^{D3}$, if present, is a bridged non-aromatic heterocyclyl group having 7 ring atoms.

(244) A compound according to any one of (1) to (241), wherein —NR$^{C3}$R$^{D3}$, if present, is a bridged non-aromatic heterocyclyl group having 8 ring atoms.

(245) A compound according to any one of (1) to (241), wherein —NR$^{C3}$R$^{D3}$, if present, is a bridged non-aromatic heterocyclyl group having 9 ring atoms.

(246) A compound according to any one of (1) to (241), wherein —NR$^{C3}$R$^{D3}$, if present, is a bridged non-aromatic heterocyclyl group having 11 ring atoms.

(247) A compound according to any one of (1) to (241), wherein, in —NR$^{C3}$R$^{D3}$, if present, exactly 1 of said ring atoms is a ring heteroatom, and is N.

(248) A compound according to any one of (1) to (241), wherein, in —NR$^{C3}$R$^{D3}$, if present, exactly 2 of said ring atoms are ring heteroatoms, and are both N.

(249) A compound according to any one of (1) to (241), wherein, in —NR$^{C3}$R$^{D3}$, if present, exactly 2 of said ring atoms are ring heteroatoms, and are N and O.

(250) A compound according to any one of (1) to (241), wherein, in —NR$^{C3}$R$^{D3}$, if present, exactly 2 of said ring atoms are ring heteroatoms, and are N and S, wherein said S is optionally in the form of S(=O) or S(=O)$_2$.

(251) A compound according to any one of (1) to (241), wherein, in —NR$^{C3}$R$^{D3}$, if present, exactly 2 of said ring atoms are ring heteroatoms, and are N and S.

(252) A compound according to any one of (1) to (241), wherein, in —NR$^{C3}$R$^{D3}$, if present, exactly 3 of said ring atoms are ring heteroatoms, one of which is N, and each of the other two is independently N, O, or S, wherein said S is optionally in the form of S(=O) or S(=O)$_2$.

(253) A compound according to any one of (1) to (241), wherein, in —NR$^{C3}$R$^{D3}$, if present, exactly 3 of said ring atoms are ring heteroatoms, one of which is N, and each of the other two is independently N, O, or S.

(254) A compound according to any one of (1) to (241), wherein, —NR$^{C3}$R$^{D3}$, if present, is independently selected from the following groups, and is:
  optionally substituted on carbon with one or more groups —R$^{NC}$, and
  optionally substituted on secondary nitrogen, if present, with groups —R$^{NN}$:

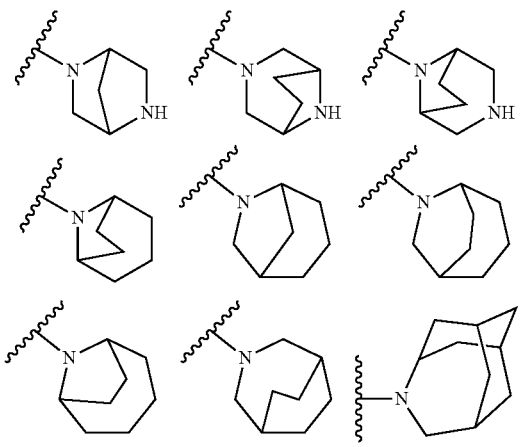

(255) A compound according to any one of (1) to (241), wherein, —NR$^{C3}$R$^{D3}$, if present, is independently selected from the following groups, and is:
  optionally substituted on carbon with one or more groups —R$^{NC}$, and
  optionally substituted on secondary nitrogen, if present, with groups —R$^{NN}$:

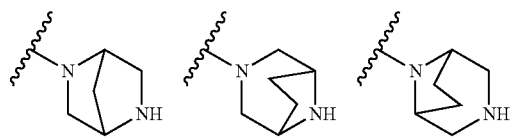

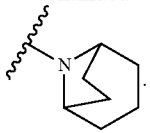

(256) A compound according to any one of (1) to (241), wherein, —NR$^{C3}$R$^{D3}$, if present, is independently selected from the following groups, and is:
  optionally substituted on carbon with one or more groups —R$^{NC}$, and
  optionally substituted on secondary nitrogen, if present, with groups —R$^{NN}$:

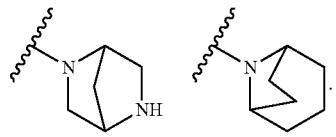 [SMILES: *N1CC2CC1CN2 ; *N1C2CCCC1CC2]

(257) A compound according to any one of (1) to (241), wherein, —NR$^{C3}$R$^{D3}$, if present, is the following group, and is:
  optionally substituted on carbon with one or more groups —R$^{NC}$, and
  optionally substituted on secondary nitrogen with a group —R$^{NN}$:

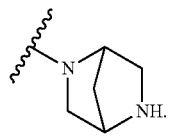 [SMILES: *N1CC2CC1CN2]

(258) A compound according to any one of (1) to (241), wherein, —NR$^{C3}$R$^{D3}$, if present, is the following group, and is:
  optionally substituted on carbon with one or more groups —R$^{NC}$, and
  optionally substituted on secondary nitrogen with groups —R$^{NN}$:

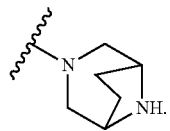 [SMILES: *N1CC2CCC(C1)N2]

The Group —NR$^{C4}$R$^{D4}$ (259) A compound according to any one of (1) to (258), wherein —NR$^{C4}$R$^{D4}$, if present, is a spiro non-aromatic heterocyclyl group having 7 ring atoms.

(260) A compound according to any one of (1) to (258), wherein —NR$^{C4}$R$^{D4}$, if present, is a spiro non-aromatic heterocyclyl group having 8 ring atoms.

(261) A compound according to any one of (1) to (258), wherein —NR$^{C4}$R$^{D4}$, if present, is a spiro non-aromatic heterocyclyl group having 9 ring atoms.

(262) A compound according to any one of (1) to (258), wherein —NR$^{C4}$R$^{D4}$, if present, is a spiro non-aromatic heterocyclyl group having 10 ring atoms.

(263) A compound according to any one of (1) to (258), wherein —NR$^{C4}$R$^{D4}$, if present, is a spiro non-aromatic heterocyclyl group having 11 ring atoms.

(264) A compound according to any one of (1) to (258), wherein —NR$^{C4}$R$^{D4}$, if present, is a spiro non-aromatic heterocyclyl group having 12 ring atoms.

(265) A compound according to any one of (1) to (258), wherein, in —NR$^{C4}$R$^{D4}$, if present, exactly 1 of said ring atoms is a ring heteroatom, and is N.

(266) A compound according to any one of (1) to (258), wherein, in —NR$^{C4}$R$^{D4}$, if present, exactly 2 of said ring atoms are ring heteroatoms, and are both N.

(267) A compound according to any one of (1) to (258), wherein, in —NR$^{C4}$R$^{D4}$, if present, exactly 2 of said ring atoms are ring heteroatoms, and are N and O.

(268) A compound according to any one of (1) to (258), wherein, in —NR$^{C4}$R$^{D4}$, if present, exactly 2 of said ring atoms are ring heteroatoms, and are N and S, wherein said S is optionally in the form of S(=O) or S(=O)$_2$.

(269) A compound according to any one of (1) to (258), wherein, in —NR$^{C4}$R$^{D4}$, if present, exactly 2 of said ring atoms are ring heteroatoms, and are N and S.

(270) A compound according to any one of (1) to (258), wherein, in —NR$^{C4}$R$^{D4}$, if present, exactly 3 of said ring atoms are ring heteroatoms, one of which is N, and each of the other two is independently N, O, or S, wherein said S is optionally in the form of S(=O) or S(=O)$_2$.

(271) A compound according to any one of (1) to (258), wherein, in —NR$^{C4}$R$^{D4}$, if present, exactly 3 of said ring atoms are ring heteroatoms, one of which is N, and each of the other two is independently N, O, or S.

(272) A compound according to any one of (1) to (258), wherein, —NR$^{C4}$R$^{D4}$, if present, is independently selected from the following groups, and is:
  optionally substituted on carbon with one or more groups —R$^{NC}$, and
  optionally substituted on secondary nitrogen, if present, with a group —R$^{NN}$:

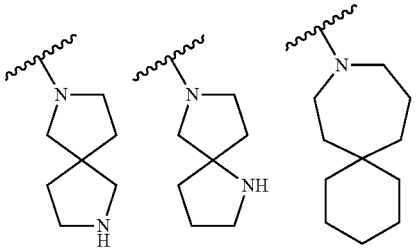

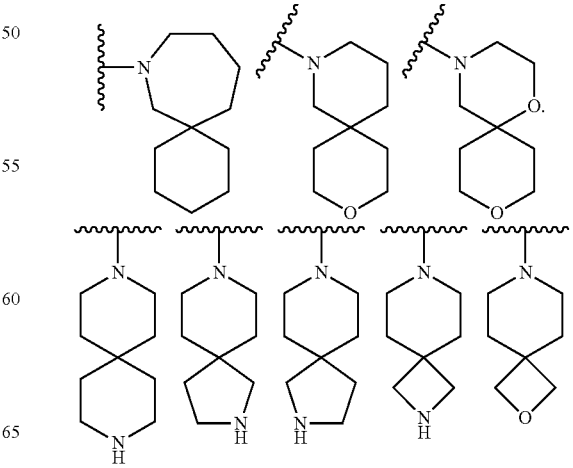

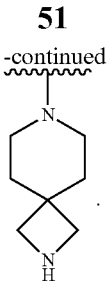

(273) A compound according to any one of (1) to (258), wherein, —NR$^{C4}$R$^{D4}$, if present, is independently selected from the following groups, and is:

optionally substituted on carbon with one or more groups —R$^{NC}$, and optionally substituted on secondary nitrogen, if present, with a group —R$^{NN}$:

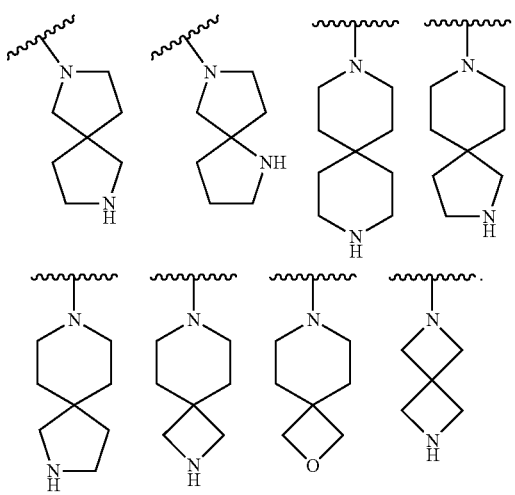

(274) A compound according to any one of (1) to (258), wherein, —NR$^{C4}$R$^{D4}$, if present, is independently selected from the following groups, and is:

optionally substituted on carbon with one or more groups —R$^{NC}$, and optionally substituted on secondary nitrogen with a group —R$^{NN}$:

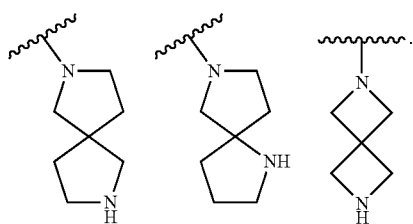 [SMILES: *N1CCC2(CCNC2)C1 ; *N1CCC2(CCCN2)C1 ; *N1CC2(CNC2)C1]

(275) A compound according to any one of (1) to (258), wherein, —NR$^{C4}$R$^{D4}$, if present, is the following group, and is:

optionally substituted on carbon with one or more groups —R$^{NC}$, and optionally substituted on secondary nitrogen with a group —R$^{NN}$:

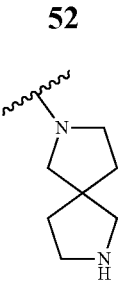

The Group —R$^{NC}$ (276) A compound according to any one of (1) to (275), wherein each —R$^{NC}$, if present, is independently:
—R$^{QQ}$,
—F, —Cl, —Br, —I,
—OH, —OR$^{QQ}$,
-L$^Q$-OH, -L$^Q$-OR$^{QQ}$,
—NH$_2$, —NHR$^{QQ}$, —NR$^{QQ}$$_2$, —R$^{QM}$,
-L$^Q$-NH$_2$, -L$^Q$-NHR$^{QQ}$, -L$^Q$-NR$^{QQ}$$_2$, -L$^Q$-R$^{QM}$, or
=O.

(277) A compound according to any one of (1) to (275), wherein each —R$^{NC}$, if present, is independently:
—R$^{QQ}$,
—OH, —OR$^{QQ}$,
—NH$_2$, —NHR$^{QQ}$, —NR$^{QQ2}$, —R$^{QM}$, or
=O.

(278) A compound according to any one of (1) to (275), wherein each —R$^{NC}$, if present, is independently —R$^{QQ}$.

The Group —R$^{NN}$ (279) A compound according to any one of (1) to (278), wherein each —R$^{NN}$, if present, is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}$$_2$, -L$^Q$-R$^{QM}$,
—C(=O)R$^{QQ}$,
—C(=O)OR$^{QQ}$,
—C(=O)NH$_2$, —C(=O)NHR$^{QQ}$, —C(=O)NR$^{QQ}$$_2$, or
—C(=O)R$^{QM}$.

(280) A compound according to any one of (1) to (278), wherein each —R$^{NN}$, if present, is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}$$_2$, -L$^Q$-R$^{QM}$,
—C(=O)R$^{QQ}$, or
—C(=O)OR$^{QQ}$.

(281) A compound according to any one of (1) to (278), wherein each —R$^{NN}$, if present, is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}$$_2$, -L$^Q$-R$^{QM}$, or
—C(=O)R$^{QQ}$.

(282) A compound according to any one of (1) to (278), wherein each —R$^{NN}$, if present, is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}$$_2$, or
—C(=O)R$^{QQ}$.

(283) A compound according to any one of (1) to (278), wherein each —R$^{NN}$, if present, is independently:
—R$^{QQ}$,
—C(=O)R$^{QQ}$, or
—C(=O)OR$^{QQ}$.

(284) A compound according to any one of (1) to (278), wherein each —R$^{NN}$, if present, is independently —R$^{QQ}$ or —C(=O)R$^{QQ}$.

(285) A compound according to any one of (1) to (278), wherein each —$R^{NN}$, if present, is independently —$R^{QQ}$.

(286) A compound according to any one of (1) to (278), wherein each —$R^{NN}$, if present, is independently: —$R^{QQ}$, -$L^Q$-OH, or -$L^Q$-OR$^{QQ}$.

(287) A compound according to any one of (1) to (278), wherein each —$R^{NN}$, if present, is independently: -$L^Q$-OH or -$L^Q$-OR$^{QQ}$.

(288) A compound according to any one of (1) to (278), wherein each —$R^{NN}$, if present, is independently: -$L^Q$-OH.

The Group -$L^Q$-

(289) A compound according to any one of (1) to (288), wherein each -$L^Q$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(290) A compound according to any one of (1) to (288), wherein each -$L^Q$-, if present, is independently —CH$_2$—, —CH(Me)-, —C(Me)$_2$-, —CH(Et)-, or —CH$_2$CH$_2$—.

(291) A compound according to any one of (1) to (288), wherein each -$L^Q$-, if present, is independently —CH$_2$—, —CH(Me)-, or —C(Me)$_2$-.

(292) A compound according to any one of (1) to (288), wherein each -$L^Q$-, if present, is independently —CH$_2$—, —CH$_2$CH$_2$—, —CH$_2$CH$_2$CH$_2$—, or —CH$_2$CH$_2$CH$_2$CH$_2$—.

(293) A compound according to any one of (1) to (288), wherein each -$L^Q$-, if present, is independently —CH$_2$CH$_2$—, —CH$_2$CH$_2$CH$_2$—, or —CH$_2$CH$_2$CH$_2$CH$_2$—.

(294) A compound according to any one of (1) to (288), wherein each -$L^Q$-, if present, is independently —CH$_2$— or —CH$_2$CH$_2$—.

(295) A compound according to any one of (1) to (288), wherein each -$L^Q$-, if present, is —CH$_2$—.

(296) A compound according to any one of (1) to (288), wherein each -$L^Q$-, if present, is —CH$_2$CH$_2$—.

The Group —$R^{QQ}$ (297) A compound according to any one of (1) to (296), wherein each —$R^{QQ}$, if present, is independently —$R^{QQ1}$ or —$R^{QQ2}$.

(298) A compound according to any one of (1) to (296), wherein each —$R^{QQ}$, if present, is —$R^{QQ1}$.

(299) A compound according to any one of (1) to (296), wherein each —$R^{QQ}$, if present, is —$R^{QQ2}$.

(300) A compound according to any one of (1) to (296), wherein each —$R^{QQ}$, if present, is —$R^{QQ3}$.

The Group —$R^{QQ1}$ (301) A compound according to any one of (1) to (300), wherein each —$R^{QQ1}$, if present, is independently linear or branched saturated C$_{1-4}$alkyl, saturated C$_{3-6}$cycloalkyl, or saturated C$_{3-6}$cycloalkyl-methyl; wherein said linear or branched saturated C$_{1-4}$alkyl is optionally substituted with —OH or —OR$^{QQQ}$, wherein —$R^{QQQ}$ is linear or branched saturated C$_{1-4}$alkyl.

(302) A compound according to any one of (1) to (300), wherein each —$R^{QQ1}$, if present, is independently linear or branched saturated C$_{1-4}$alkyl, saturated C$_{3-6}$cycloalkyl, or saturated C$_{3-6}$cycloalkyl-methyl.

(303) A compound according to any one of (1) to (300), wherein each —$R^{QQ1}$, if present, is independently linear or branched saturated C$_{1-4}$alkyl or saturated C$_{3-6}$cycloalkyl; wherein said linear or branched saturated C$_{1-4}$alkyl is optionally substituted with —OH or —OR$^{QQQ}$, wherein —$R^{QQQ}$ is linear or branched saturated C$_{1-4}$alkyl.

(304) A compound according to any one of (1) to (300), wherein each —$R^{QQ1}$, if present, is independently linear or branched saturated C$_{1-4}$alkyl or saturated C$_{3-6}$cycloalkyl.

(305) A compound according to any one of (1) to (300), wherein each —$R^{QQ1}$, if present, is linear or branched saturated C$_{1-4}$alkyl, and is optionally substituted with —OH or —OR$^{QQQ}$ wherein —$R^{QQQ}$ is linear or branched saturated C$_{1-4}$alkyl.

(306) A compound according to any one of (1) to (300), wherein each —$R^{QQ1}$, if present, is linear or branched saturated C$_{1-4}$alkyl.

(307) A compound according to any one of (1) to (300), wherein each —$R^{QQ1}$, if present, is independently -Me, -Et, -nPr, -iPr, -nBu, -iBu, or -tBu.

(308) A compound according to any one of (1) to (300), wherein each —$R^{QQ1}$, if present, is independently -Me or -tBu.

(309) A compound according to any one of (1) to (300), wherein each —$R^{QQ1}$, if present, is -Me.

(310) A compound according to any one of (1) to (300), wherein each —$R^{QQ1}$, if present, is -tBu.

(311) A compound according to any one of (1) to (300), wherein each —$R^{QQ1}$, if present, is saturated C$_{3-6}$cycloalkyl.

(312) A compound according to any one of (1) to (300), wherein each —$R^{QQ1}$, if present, is independently cyclopropyl, cyclobutyl, cyclopentyl, or cyclohexyl.

(313) A compound according to any one of (1) to (300), wherein each —$R^{QQ1}$, if present, is cyclopropyl.

(314) A compound according to any one of (1) to (300), wherein each —$R^{QQ1}$, if present, is saturated C$_{3-6}$cycloalkyl-methyl.

(315) A compound according to any one of (1) to (300), wherein each —$R^{QQ1}$, if present, is independently cyclopropyl-methyl, cyclobutyl-methyl, cyclopentyl-methyl, or cyclohexyl-methyl.

(316) A compound according to any one of (1) to (300), wherein each —$R^{QQ1}$, if present, is cyclopropyl-methyl.

The Group —$R^{QQ2}$ (317) A compound according to any one of (1) to (316), wherein each —$R^{QQ2}$, if present, is independently phenyl, and is optionally substituted with —$R^{QQQ}$.

(318) A compound according to any one of (1) to (316), wherein each —$R^{QQ2}$, if present, is independently phenyl.

(319) A compound according to any one of (1) to (316), wherein each —$R^{QQ2}$, if present, is independently benzyl, and is optionally substituted with —$R^{QQQ}$.

(320) A compound according to any one of (1) to (316), wherein each —$R^{QQ2}$, if present, is independently benzyl.

The Group —$R^{QQ3}$ (321) A compound according to any one of (1) to (320), wherein each —$R^{QQ3}$, if present, is independently C$_{5-6}$heteroaryl; and is optionally substituted with —$R^{QQQ}$.

(322) A compound according to any one of (1) to (320), wherein each —$R^{QQ3}$, if present, is independently C$_{5-6}$heteroaryl.

(323) A compound according to any one of (1) to (320), wherein each —$R^{QQ3}$, if present, is independently C$_5$heteroaryl; and is optionally substituted with —$R^{QQQ}$.

(324) A compound according to any one of (1) to (320), wherein each —$R^{QQ3}$, if present, is independently furanyl, thienyl, pyrrolyl, imidazolyl, pyrazolyl, triazolyl (e.g., [1,2,3]triazolyl), [1,2,4]triazolyl), oxazolyl, isoxazolyl, thiazolyl, isothiazolyl, oxadiazolyl (e.g., [1,2,3]oxadiazolyl, [1,2,4]oxadiazolyl, [1,2,5]oxadiazolyl, [1,3,4]oxadiazolyl), thiadiazolyl (e.g. [1,2,3]thiadiazolyl, [1,2,4]thiadiazolyl, [1,2,5]thiadiazolyl, [1,3,4]thiadiazolyl); and is optionally substituted with —$R^{QQQ}$.

(325) A compound according to any one of (1) to (320), wherein each —$R^{QQ3}$, if present, is independently oxadiazolyl (e.g., [1,2,3]oxadiazolyl, [1,2,4]oxadiazolyl, [1,2,5]oxadiazolyl, [1,3,4]oxadiazolyl); and is optionally substituted with —$R^{QQQ}$.

(326) A compound according to any one of (1) to (320), wherein each —$R^{QQ3}$, if present, is independently [1,2,4]oxadiazol-5-yl or [1,3,4]oxadiazol-2-yl; and is optionally substituted with —$R^{QQQ}$.

(327) A compound according to any one of (1) to (320), wherein each —$R^{QQ3}$, if present, is independently [1,3,4]oxadiazol-2-yl; and is optionally substituted with —$R^{QQQ}$.

(328) A compound according to any one of (1) to (320), wherein each —$R^{QQ3}$, if present, is independently $C_6$heteroaryl; and is optionally substituted with —$R^{QQQ}$.

(329) A compound according to any one of (1) to (320), wherein each —$R^{QQ3}$, if present, is independently $C_6$heteroaryl.

(330) A compound according to any one of (1) to (320), wherein each —$R^{QQ3}$, if present, is independently pyridyl, pyridazinyl, pyrimidinyl, or pyrazinyl; and is optionally substituted with —$R^{QQQ}$.

The Group —$R^{QQQ}$.

(331) A compound according to any one of (1) to (330), wherein each —$R^{QQQ}$, if present, is linear or branched saturated $C_{1-4}$alkyl.

(332) A compound according to any one of (1) to (330), wherein each —$R^{QQQ}$, if present, is independently -Me, -Et, -nPr, -iPr, -nBu, -iBu, or -tBu.

(333) A compound according to any one of (1) to (330), wherein each —$R^{QQQ}$, if present, is independently -Me or -iPr.

(334) A compound according to any one of (1) to (330), wherein each —$R^{QQQ}$, if present, is independently -Me or -Et.

(335) A compound according to any one of (1) to (330), wherein each —$R^{QQQ}$, if present, is independently -iPr.

(336) A compound according to any one of (1) to (330), wherein each —$R^{QQQ}$, if present, is independently -Me.

(337) A compound according to any one of (1) to (330), wherein each —$R^{QQQ}$, if present, is saturated $C_{3-6}$cycloalkyl.

(338) A compound according to any one of (1) to (330), wherein each —$R^{QQQ}$, if present, is independently cyclopropyl, cyclobutyl, cyclopentyl, or cyclohexyl.

(339) A compound according to any one of (1) to (330), wherein each —$R^{QQQ}$, if present, is independently cyclopropyl or cyclobutyl.

(340) A compound according to any one of (1) to (330), wherein each —$R^{QQQ}$, if present, is independently cyclopropyl.

The Group —$R^{QN}$ (341) A compound according to any one of (1) to (340), wherein each —$R^{QN}$, if present, is independently -Me, -Et, -nPr, -iPr, -nBu, -iBu, or -tBu.

(342) A compound according to any one of (1) to (340), wherein each —$R^{QN}$, if present, is independently -Me or -Et.

(343) A compound according to any one of (1) to (340), wherein each —$R^{QN}$, if present, is independently -Me.

The Group —$R^{QM}$ (344) A compound according to any one of (1) to (343), wherein each —$R^{QM}$, if present, is independently pyrrolidino, piperidino, piperazino, or morpholino, and is:

optionally substituted on carbon with one or more groups selected from: —$R^{QMM}$, —C(=O)$R^{QMM}$, —S(=O)$_2$$R^{QMM}$, —F, —NH$_2$, —NHR$^{QMM}$, —NR$^{QMM}$$_2$, —OH, and —OR$^{QMM}$; and optionally substituted on secondary nitrogen, if present, with a group selected from: —$R^{QMM}$, —C(=O)$R^{QMM}$, —C(=O)OR$^{QMM}$, and —S(=O)$_2$$R^{QMM}$;

wherein each —$R^{QMM}$ is independently linear or branched saturated $C_{1-4}$alkyl, saturated $C_{3-6}$cycloalkyl, saturated $C_{3-6}$cycloalkyl-methyl, phenyl, or benzyl.

The Group —$R^{QMM}$ (345) A compound according to any one of (1) to (344), wherein each —$R^{QMM}$, if present, is independently linear or branched saturated $C_{1-4}$alkyl, saturated $C_{3-6}$cycloalkyl, phenyl, or benzyl.

(346) A compound according to any one of (1) to (344), wherein each —$R^{QMM}$, if present, is independently linear or branched saturated $C_{1-4}$alkyl, phenyl, or benzyl.

(347) A compound according to any one of (1) to (344), wherein each —$R^{QMM}$, if present, is independently linear or branched saturated $C_{1-4}$alkyl, saturated $C_{3-6}$cycloalkyl, or saturated $C_{3-6}$cycloalkyl-methyl.

(348) A compound according to any one of (1) to (344), wherein each —$R^{QMM}$, if present, is independently linear or branched saturated $C_{1-4}$alkyl or saturated $C_{3-6}$cycloalkyl.

(349) A compound according to any one of (1) to (344), wherein each —$R^{QMM}$, if present, is linear or branched saturated $C_{1-4}$alkyl.

(350) A compound according to any one of (1) to (344), wherein each —$R^{QMM}$, if present, is independently -Me, -Et, -nPr, -iPr, -nBu, -iBu, or -tBu.

(351) A compound according to any one of (1) to (344), wherein each —$R^{QMM}$, if present, is independently -Me or -Et.

(352) A compound according to any one of (1) to (344), wherein each —$R^{QMM}$, if present, is -Me.

(353) A compound according to any one of (1) to (344), wherein each —$R^{QMM}$, if present, is independently saturated $C_{3-6}$cycloalkyl.

(354) A compound according to any one of (1) to (344), wherein each —$R^{QMM}$, if present, is independently cyclopropyl, cyclobutyl, cyclopentyl, or cyclohexyl.

(355) A compound according to any one of (1) to (344), wherein each —$R^{QMM}$, if present, is cyclopropyl.

The Group —NR$^{C5}$R$^{D5}$ (356) A compound according to any one of (1) to (355), wherein —NR$^{C5}$R$^{D5}$, if present, is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 2H-[1,2,3]triazol-2-yl; 1H-[1,2,4]triazol-1-yl; 1H-benzotriazol-1-yl; or 1H-tetrazol-1-yl; and is optionally substituted with one or more groups —$R^H$.

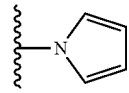

1H-pyrrol-1-yl

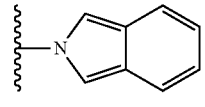

2H-isoindol-2-yl

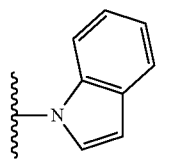

1H-indol-1-yl

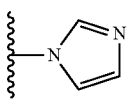

1H-imidazol-1-yl

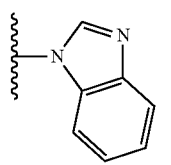

1H-benzoimidazol-1-yl

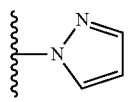

1H-pyrazol-1-yl

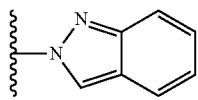

2H-indazol-2-yl

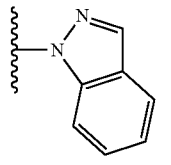

1H-indazol-1-yl

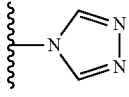

4H-[1,2,4]triazol-4-yl

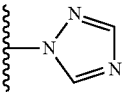

1H-[1,2,4]triazol-1-yl

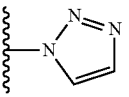

1H-[1,2,3]triazol-1-yl

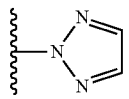

2H-[1,2,3]triazol-2-yl

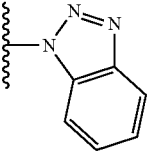

1H-benzotriazol-1-yl

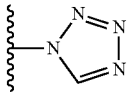

1H-tetrazol-1-yl (357) A compound according to any one of (1) to (355), wherein $-NR^{C5}R^{D5}$, if present, is independently: 1H-pyrrol-1-yl; 1H-pyrazol-1-yl; 1H-imidazol-1-yl; 4H-[1,2,4]triazol-4-yl; 1H-[1,2,3]triazol-1-yl; 2H-[1,2,3]triazol-2-yl; 1H-[1,2,4]triazol-1-yl; or 1H-tetrazol-1-yl; and is optionally substituted with one or more groups $-R^H$.

(358) A compound according to any one of (1) to (355), wherein $-NR^{C5}R^{D5}$, if present, is independently: 1H-pyrrol-1-yl; 1H-pyrazol-1-yl; or 1H-imidazol-1-yl; and is optionally substituted with one or more groups $-R^H$.

(359) A compound according to any one of (1) to (355), wherein $-NR^{C5}R^{D5}$, if present, is 1H-pyrrol-1-yl; and is optionally substituted with one or more groups $-R^H$.

(360) A compound according to any one of (1) to (355), wherein $-NR^{C5}R^{D5}$, if present, is 1H-pyrazol-1-yl; and is optionally substituted with one or more groups $-R^H$.

(361) A compound according to any one of (1) to (355), wherein $-NR^{C5}R^{D5}$, if present, is 1H-imidazol-1-yl; and is optionally substituted with one or more groups $-R^H$.

(362) A compound according to any one of (1) to (355), wherein $-NR^{C5}R^{D5}$, if present, is 1H-[1,2,4]triazol-1-yl; and is optionally substituted with one or more groups $-R^H$.

(363) A compound according to any one of (1) to (355), wherein $-NR^{C5}R^{D5}$, if present, is 2H-[1,2,3]triazol-2-yl; and is optionally substituted with one or more groups $-R^H$ (364) A compound according to any one of (1) to (355), wherein $-NR^{C5}R^{D5}$, if present, is 1H-benzoimidazol-1-yl; and is optionally substituted with one or more groups $-R^H$.

(365) A compound according to any one of (1) to (355), wherein $-NR^{C5}R^{D5}$, if present, is 1H-indol-1-yl; and is optionally substituted with one or more groups $-R^H$.

The Group $-R^H$ (366) A compound according to any one of (1) to (365), wherein each $-R^H$, if present, is independently:
—$R^{HH}$,
—F, —Cl, —Br, —I,
—OH, —$OR^{HH}$,
-$L^H$-OH, -$L^H$-$OR^{HH}$
—$CF_3$, —$OCF_3$,
—$NH_2$, —$NHR^{HH}$, —$NR^{HH}_2$, —$R^{HM}$,
-$L^H$-$NH_2$, -$L^H$-$NHR^{HH}$, -$L^H$-$NR^{HH}_2$, -$L^H$-$R^{HM}$,
—C(=O)OH, —C(=O)$OR^{HH}$, —OC(=O)$R^{HH}$
—C(=O)$NH_2$, —C(=O)$NHR^{HH}$, —C(=O)$NR^{HH}_2$,
—C(=O)$R^{HM}$, —NHC(=O)R$^{HH}$, —NR$^{HN}$C(=O)R$^{HH}$, or
—C(=O)R$^{HH}$ (367) A compound according to any one of (1) to (365), wherein each —R$^H$, if present, is independently:
—R$^{HH}$,
—F, —Cl, —Br, —I,
—OH, —OR$^{HH}$,
-L$^H$-OH, -L$^{HH}$-OR$^{HH}$,
—NH$_2$, —NHR$^{HH}$, —NR$^{HH}{}_2$, —R$^{HM}$,
-L$^H$-NH$_2$, -L$^H$-NHR$^{HH}$, -L$^H$-NR$^{HH}{}_2$, or -L$^H$-R$^{HM}$.

(368) A compound according to any one of (1) to (365), wherein each —R$^H$, if present, is independently:
—R$^{HH}$,
-L$^H$-OH, -L$^{HH}$-OR$^{HH}$,
—NH$_2$, —NHR$^{HH}$, —NR$^{HH}{}_2$, —R$^{HM}$,
-L$^H$-NH$_2$, -L$^H$-NHR$^{HH}$, -L$^H$-NR$^{HH}{}_2$, or -L$^H$-R$^{HM}$.

(369) A compound according to any one of (1) to (365), wherein each —R$^H$, if present, is independently:
—R$^{HH}$,
—OH, —OR$^{HH}$,
—NH$_2$, —NHR$^{HH}$, —NR$^{HH}{}_2$, or —R$^{HM}$.

(370) A compound according to any one of (1) to (365), wherein each —R$^H$, if present, is independently:
-L$^H$-OH, -L$^{HH}$-OR$^{HH}$,
—NH$_2$, —NHR$^{HH}$, —NR$^{HH}{}_2$, —R$^{HM}$,
-L$^H$-NH$_2$, -L$^H$-NHR$^{HH}$, -L$^H$-NR$^{HH}{}_2$, or -L$^H$-R$^{HM}$.

(371) A compound according to any one of (1) to (365), wherein each —R$^H$, if present, is independently:
-L$^H$-OH or -L$^{HH}$-OR$^{HH}$.

(372) A compound according to any one of (1) to (365), wherein each —R$^H$, if present, is independently:
—NH$_2$, —NHR$^{HH}$, —NR$^{HH}{}_2$, —R$^{HM}$,
-L$^H$-NH$_2$, -L$^H$-NHR$^{HH}$, -L$^H$-NR$^{HH}{}_2$, or -L$^H$-R$^{HM}$.

(373) A compound according to any one of (1) to (365), wherein each —R$^H$, if present, is independently:
—NH$_2$, —NHR$^{HH}$, —NR$^{HH}{}_2$, or —R$^{HM}$.

(374) A compound according to any one of (1) to (365), wherein each —R$^H$, if present, is independently:
-L$^H$-NH$_2$, -L$^H$-NHR$^{HH}$, -L$^H$-NR$^{HH}{}_2$, or -L$^H$-R$^{HM}$.

(375) A compound according to any one of (1) to (365), wherein each —R$^H$, if present, is independently —R$^{HH}$.

The Group -L$^H$-

(376) A compound according to any one of (1) to (375), wherein each -L$^H$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(377) A compound according to any one of (1) to (375), wherein each -L$^H$-, if present, is independently —CH$_2$—, —CH(Me)-, —C(Me)$_2$-, —CH(Et)-, or —CH$_2$CH$_2$—.

(378) A compound according to any one of (1) to (375), wherein each -L$^H$-, if present, is independently —CH$_2$—, —CH(Me)-, or —C(Me)$_2$-.

(379) A compound according to any one of (1) to (375), wherein each -L$^H$-, if present, is independently —CH$_2$—, —CH$_2$CH$_2$—, —CH$_2$CH$_2$CH$_2$—, or —CH$_2$CH$_2$CH$_2$CH$_2$—.

(380) A compound according to any one of (1) to (375), wherein each -L$^H$-, if present, is independently —CH$_2$CH$_2$—, —CH$_2$CH$_2$CH$_2$—, or —CH$_2$CH$_2$CH$_2$CH$_2$—.

(381) A compound according to any one of (1) to (375), wherein each -L$^H$-, if present, is independently —CH$_2$— or —CH$_2$CH$_2$—.

(382) A compound according to any one of (1) to (375), wherein each -L$^H$-, if present, is —CH$_2$—.

(383) A compound according to any one of (1) to (375), wherein each -L$^H$-, if present, is —CH$_2$CH$_2$—.

The Group —R$^{HH}$ (384) A compound according to any one of (1) to (383), wherein each —R$^{HH}$, if present, is independently linear or branched saturated C$_{1-4}$alkyl, saturated C$_{3-6}$cycloalkyl, saturated C$_{3-6}$cycloalkyl-methyl, phenyl, or benzyl.

(385) A compound according to any one of (1) to (383), wherein each —R$^{HH}$, if present, is independently linear or branched saturated C$_{1-4}$alkyl, saturated C$_{3-6}$cycloalkyl, phenyl, or benzyl.

(386) A compound according to any one of (1) to (383), wherein each —R$^{HH}$, if present, is independently linear or branched saturated C$_{1-4}$alkyl, phenyl, or benzyl.

(387) A compound according to any one of (1) to (383), wherein each —R$^{HH}$, if present, is independently linear or branched saturated C$_{1-4}$alkyl, saturated C$_{3-6}$cycloalkyl, or saturated C$_{3-6}$cycloalkyl-methyl; wherein said linear or branched saturated C$_{1-4}$alkyl is optionally substituted with —OH or —OR$^{HHH}$, wherein —R$^{HHH}$ is linear or branched saturated C$_{1-4}$alkyl.

(388) A compound according to any one of (1) to (383), wherein each —R$^{HH}$, if present, is independently linear or branched saturated C$_{1-4}$alkyl, saturated C$_{3-6}$cycloalkyl, or saturated C$_{3-6}$cycloalkyl-methyl.

(389) A compound according to any one of (1) to (383), wherein each —R$^{HH}$, if present, is independently linear or branched saturated C$_{1-4}$alkyl or saturated C$_{3-6}$cycloalkyl; wherein said linear or branched saturated C$_{1-4}$alkyl is optionally substituted with —OH or —OR$^{HHH}$, wherein —R$^{QQ}$ is linear or branched saturated C$_{1-4}$alkyl.

(390) A compound according to any one of (1) to (383), wherein each —R$^{HH}$, if present, is independently linear or branched saturated C$_{1-4}$alkyl or saturated C$_{3-6}$cycloalkyl.

(391) A compound according to any one of (1) to (383), wherein each —R$^{HH}$, if present, is linear or branched saturated C$_{1-4}$alkyl, and is optionally substituted with —OH or —OR$^{HHH}$ wherein —R$^{HHH}$ is linear or branched saturated C$_{1-4}$alkyl.

(392) A compound according to any one of (1) to (383), wherein each —R$^{HH}$, if present, is linear or branched saturated C$_{1-4}$alkyl.

(393) A compound according to any one of (1) to (383), wherein each —R$^{HH}$, if present, is independently -Me, -Et, -nPr, -iPr, -nBu, -iBu, or -tBu.

(394) A compound according to any one of (1) to (383), wherein each —R$^{HH}$, if present, is independently -Me or -tBu.

(395) A compound according to any one of (1) to (383), wherein each —R$^{HH}$, if present, is -Me.

(396) A compound according to any one of (1) to (383), wherein each —R$^{HH}$, if present, is -tBu.

(397) A compound according to any one of (1) to (383), wherein each —R$^{HH}$, if present, is saturated C$_{3-6}$cycloalkyl.

(398) A compound according to any one of (1) to (383), wherein each —R$^{HH}$, if present, is independently cyclopropyl, cyclobutyl, cyclopentyl, or cyclohexyl.

(399) A compound according to any one of (1) to (383), wherein each —R$^{HH}$, if present, is cyclopropyl.

The Group —R$^{HHH}$ (400) A compound according to any one of (1) to (399), wherein each —R$^{HHH}$, if present, is independently -Me, -Et, -nPr, -iPr, -nBu, -iBu, or -tBu.

(401) A compound according to any one of (1) to (399), wherein each —R$^{HHH}$, if present, is independently -Me or -Et.

(402) A compound according to any one of (1) to (399), wherein each —$R^{HHH}$, if present, is independently -Me.

The Group —$R^{HN}$ (403) A compound according to any one of (1) to (402), wherein each —$R^{HN}$, if present, is independently -Me, -Et, -nPr, -iPr, -nBu, -iBu, or -tBu.

(404) A compound according to any one of (1) to (402), wherein each —$R^{HN}$, if present, is independently -Me or -Et.

(405) A compound according to any one of (1) to (402), wherein each —$R^{HN}$, if present, is independently -Me.

The Group —$R^{HM}$ (406) A compound according to any one of (1) to (405), wherein each —$R^{HM}$, if present, is independently pyrrolidino, piperidino, piperazino, or morpholino, and is:

optionally substituted on carbon with one or more groups selected from: —$R^{HMM}$, —C(=O)$R^{HMM}$, —S(=O)$_2$$R^{HMM}$, —F, —NH$_2$, —NHR$^{HMM}$, —NR$^{HMM}$$_2$, —OH, and —OR$^{HMM}$; and optionally substituted on secondary nitrogen, if present, with a group selected from: —$R^{HMM}$, —C(=O)$R^{HMM}$, —C(=O)OR$^{HMM}$, and —S(=O)$_2$$R^{HMM}$;

wherein each —$R^{HMM}$ is independently linear or branched saturated $C_{1-4}$alkyl, saturated $C_{3-6}$cycloalkyl, saturated $C_{3-6}$cycloalkyl-methyl, phenyl, or benzyl.

The Group —$R^{HMM}$ (407) A compound according to any one of (1) to (406), wherein each —$R^{HMM}$, if present, is independently linear or branched saturated $C_{1-4}$alkyl, saturated $C_{3-6}$cycloalkyl, phenyl, or benzyl.

(408) A compound according to any one of (1) to (406), wherein each —$R^{HMM}$, if present, is independently linear or branched saturated $C_{1-4}$alkyl, phenyl, or benzyl.

(409) A compound according to any one of (1) to (406), wherein each —$R^{HMM}$, if present, is independently linear or branched saturated $C_{1-4}$alkyl, saturated $C_{3-6}$cycloalkyl, or saturated $C_{3-6}$cycloalkyl-methyl.

(410) A compound according to any one of (1) to (406), wherein each —$R^{HMM}$, if present, is independently linear or branched saturated $C_{1-4}$alkyl or saturated $C_{3-6}$cycloalkyl.

(411) A compound according to any one of (1) to (406), wherein each —$R^{HMM}$, if present, is linear or branched saturated $C_{1-4}$alkyl.

(412) A compound according to any one of (1) to (406), wherein each —$R^{HMM}$, if present, is independently -Me, -Et, -nPr, -iPr, -nBu, -iBu, or -tBu.

(413) A compound according to any one of (1) to (406), wherein each —$R^{HMM}$, if present, is independently -Me or -Et.

(414) A compound according to any one of (1) to (406), wherein each —$R^{HMM}$, if present, is -Me.

(415) A compound according to any one of (1) to (406), wherein each —$R^{HMM}$, if present, is independently saturated $C_{3-6}$cycloalkyl.

(416) A compound according to any one of (1) to (406), wherein each —$R^{HMM}$, if present, is independently cyclopropyl, cyclobutyl, cyclopentyl, or cyclohexyl.

(417) A compound according to any one of (1) to (406), wherein each —$R^{HMM}$, if present, is cyclopropyl.

The Group —$R^5$ (418) A compound according to any one of (1) to (417), wherein —$R^5$ is —$R^{5A}$.

(419) A compound according to any one of (1) to (417), wherein —$R^5$ is —$R^{5B}$.

(420) A compound according to any one of (1) to (417), wherein —$R^5$ is —$R^{5C}$.

(421) A compound according to any one of (1) to (417), wherein —$R^5$ is —$R^{5D}$.

The Group —$R^{5B}$ (422) A compound according to any one of (1) to (421), wherein —$R^{5B}$, if present, is —CH$_2$NH$_2$.

(423) A compound according to any one of (1) to (421), wherein —$R^{5B}$, if present, is independently —CH$_2$NHR$^{5B1}$ or —CH$_2$NR$^{5B1}$R$^{5B2}$.

(424) A compound according to any one of (1) to (421), wherein —$R^{5B}$, if present, is —CH$_2$NHR$^{5B1}$.

(425) A compound according to any one of (1) to (421), wherein —$R^{5B}$, if present, is —CH$_2$NR$^{5B1}$R$^{5B2}$.

The Group —$R^{5C}$ (426) A compound according to any one of (1) to (425), wherein —$R^{5C}$, if present, is —CH$_2$NHC(=O)R$^{5C1}$.

(427) A compound according to any one of (1) to (425), wherein —$R^{5C}$, if present, is —CH$_2$NR$^{5C2}$C(=O)R$^{5C1}$.

The Group —$R^{5D}$ (428) A compound according to any one of (1) to (427), wherein —$R^{5D}$, if present, is —CH$_2$NHS(=O)$_2$R$^{5D1}$.

(429) A compound according to any one of (1) to (427), wherein —$R^{5D}$, if present, is —CH$_2$NR$^{5D2}$S(=O)$_2$R$^{5D1}$.

The Group —$R^{5B1}$ (430) A compound according to any one of (1) to (429), wherein each —$R^{5B1}$, if present, is independently -Me, -Et, -nPr, -iPr, -nBu, -iBu, or -tBu.

(431) A compound according to any one of (1) to (429), wherein each —$R^{5B1}$, if present, is independently -Me, -Et, -nPr, or -iPr.

(432) A compound according to any one of (1) to (429), wherein each —$R^{5B1}$, if present, is independently -Me or -Et.

(433) A compound according to any one of (1) to (429), wherein each —$R^{5B1}$, if present, is -Me.

The Group —$R^{5B2}$ (434) A compound according to any one of (1) to (433), wherein each —$R^{5B2}$, if present, is independently -Me, -Et, -nPr, -iPr, -nBu, -iBu, or -tBu.

(435) A compound according to any one of (1) to (433), wherein each —$R^{5B2}$, if present, is independently -Me, -Et, -nPr, or -iPr.

(436) A compound according to any one of (1) to (433), wherein each —$R^{5B2}$, if present, is independently -Me or -Et.

(437) A compound according to any one of (1) to (433), wherein each —$R^{5B2}$, if present, is -Me.

The Group —$R^{5C1}$ (438) A compound according to any one of (1) to (437), wherein each —$R^{5C1}$, if present, is independently -Me, -Et, -nPr, -iPr, -nBu, -iBu, or -tBu.

(439) A compound according to any one of (1) to (437), wherein each —$R^{5C1}$, if present, is independently -Me, -Et, -nPr, or -iPr.

(440) A compound according to any one of (1) to (437), wherein each —$R^{5C1}$, if present, is independently -Me or -Et.

(441) A compound according to any one of (1) to (437), wherein each —$R^{5C1}$, if present, is -Me.

The Group —$R^{5C2}$ (442) A compound according to any one of (1) to (441), wherein each —$R^{5C2}$, if present, is independently -Me, -Et, -nPr, -iPr, -nBu, -iBu, or -tBu.

(443) A compound according to any one of (1) to (441), wherein each —$R^{5C2}$, if present, is independently -Me, -Et, -nPr, or -iPr.

(444) A compound according to any one of (1) to (441), wherein each —$R^{5C2}$, if present, is independently -Me or -Et.

(445) A compound according to any one of (1) to (441), wherein each —R$^{5C2}$, if present, is -Me.

The Group —R$^{5D1}$ (446) A compound according to any one of (1) to (445), wherein each —R$^{5D1}$, if present, is independently -Me, -Et, -nPr, -iPr, -nBu, -iBu, or -tBu.

(447) A compound according to any one of (1) to (445), wherein each —R$^{5D1}$, if present, is independently -Me, -Et, -nPr, or -iPr.

(448) A compound according to any one of (1) to (445), wherein each —R$^{5D1}$, if present, is independently -Me or -Et.

(449) A compound according to any one of (1) to (445), wherein each —R$^{5D1}$, if present, is -Me.

The Group —R$^{5D2}$ (450) A compound according to any one of (1) to (449), wherein each —R$^{5D2}$, if present, is independently -Me, -Et, -nPr, -iPr, -nBu, -iBu, or -tBu.

(451) A compound according to any one of (1) to (449), wherein each —R$^{5D2}$, if present, is independently -Me, -Et, -nPr, or -iPr.

(452) A compound according to any one of (1) to (449), wherein each —R$^{5D2}$, if present, is independently -Me or -Et.

(453) A compound according to any one of (1) to (449), wherein each —R$^{5D2}$, if present, is -Me.

The Group —R$^6$ (454) A compound according to any one of (1) to (453), wherein —R$^6$ is —H.

(455) A compound according to any one of (1) to (453), wherein —R$^6$ is —F.

The Group —R$^7$ (456) A compound according to any one of (1) to (455), wherein —R$^7$ is —H.

(457) A compound according to any one of (1) to (455), wherein —R$^7$ is —F.

The Group —R$^8$ (458) A compound according to any one of (1) to (457), wherein —R$^8$ is —H.

(459) A compound according to any one of (1) to (457), wherein —R$^8$ is —F.

Specific Compounds (460) A compound according to (1), selected from compounds of the following formulae and pharmaceutically acceptable salts, N-oxides, hydrates, and solvates thereof:

| Code | Structure |
| --- | --- |
| IQ-001 | 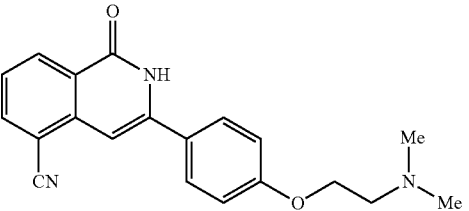 [SMILES: CN(C)CCOc1ccc(-c2cc3c(C#N)cccc3c(=O)[nH]2)cc1] |
| IQ-002 | 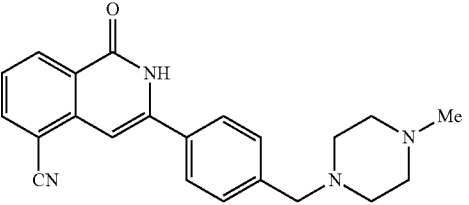 [SMILES: CN1CCN(Cc2ccc(-c3cc4c(C#N)cccc4c(=O)[nH]3)cc2)CC1] |
| IQ-003 | 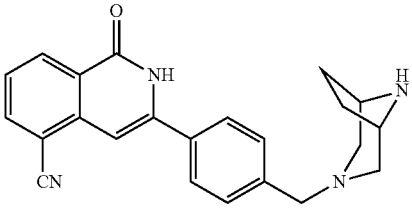 [SMILES: N#Cc1cccc2c(=O)[nH]c(-c3ccc(CN4CC5CCC(C4)N5)cc3)cc12] |
| IQ-004 | 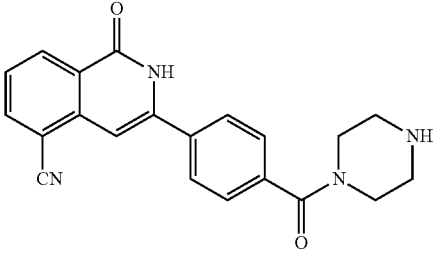 [SMILES: N#Cc1cccc2c(=O)[nH]c(-c3ccc(C(=O)N4CCNCC4)cc3)cc12] |

-continued
| Code | Structure |
|------|-----------|
| IQ-005 | 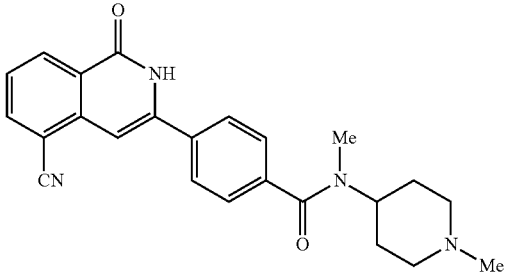 [SMILES: CN1CCC(N(C)C(=O)c2ccc(-c3cc4c(C#N)cccc4c(=O)[nH]3)cc2)CC1] |
| IQ-006 | 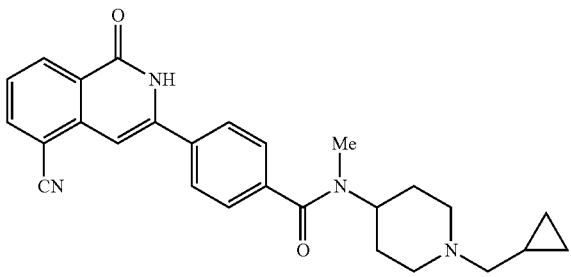 [SMILES: CN(C(=O)c1ccc(-c2cc3c(C#N)cccc3c(=O)[nH]2)cc1)C1CCN(CC2CC2)CC1] |
| IQ-007 | 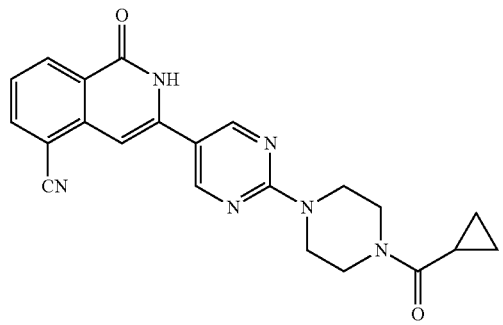 [SMILES: N#Cc1cccc2c(=O)[nH]c(-c3cnc(N4CCN(C(=O)C5CC5)CC4)nc3)cc12] |
| IQ-008 | 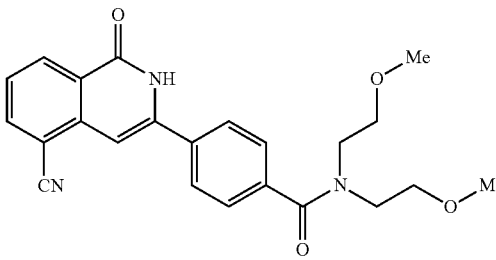 |
| IQ-009 | 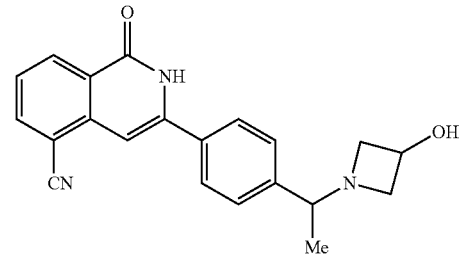 [SMILES: CC(c1ccc(-c2cc3c(C#N)cccc3c(=O)[nH]2)cc1)N1CC(O)C1] |

-continued
| Code | Structure |
|---|---|
| IQ-010 | 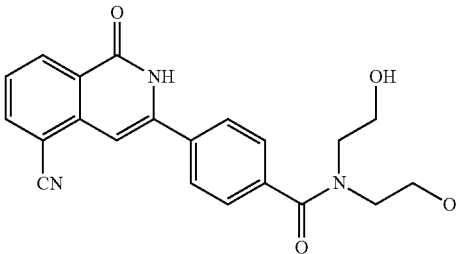 |
| IQ-011 | 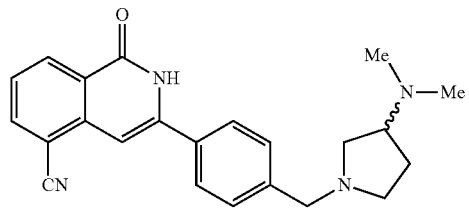 [SMILES: CN(C)C1CCN(Cc2ccc(-c3cc4c(C#N)cccc4c(=O)[nH]3)cc2)C1] |
| IQ-012 | 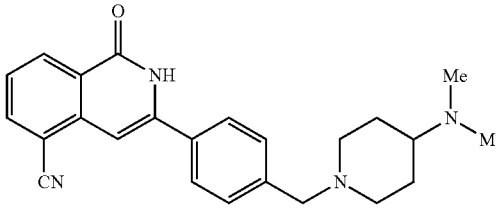 |
| IQ-013 | 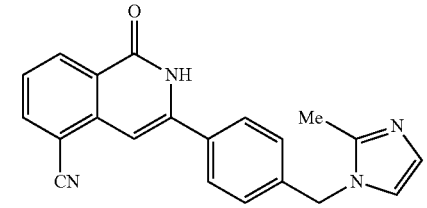 [SMILES: Cc1nccn1Cc1ccc(-c2cc3c(C#N)cccc3c(=O)[nH]2)cc1] |
| IQ-014 | 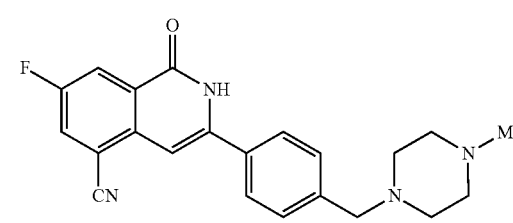 |
| IQ-015 | 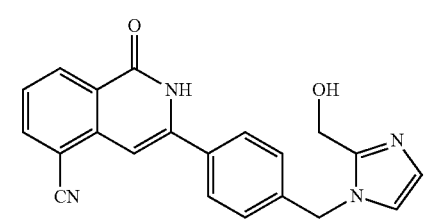 [SMILES: N#Cc1cccc2c(=O)[nH]c(-c3ccc(Cn4ccnc4CO)cc3)cc12] |
| IQ-016 | 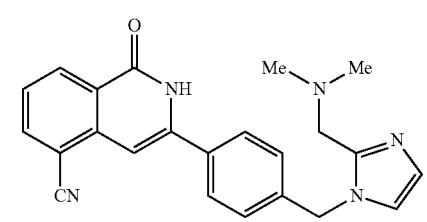 [SMILES: CN(C)Cc1nccn1Cc1ccc(-c2cc3c(C#N)cccc3c(=O)[nH]2)cc1] |

-continued
| Code | Structure |
|---|---|
| IQ-017 | 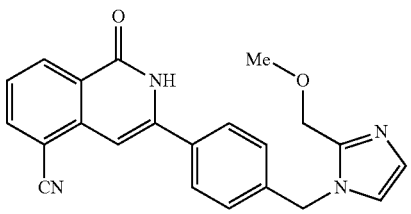 [SMILES: COCc1nccn1Cc1ccc(-c2cc3c(C#N)cccc3c(=O)[nH]2)cc1] |
| IQ-018 | 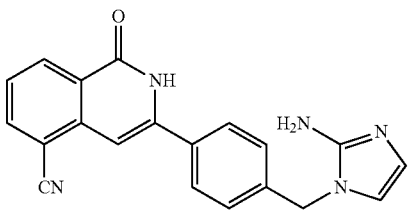 [SMILES: N#Cc1cccc2c(=O)[nH]c(-c3ccc(Cn4ccnc4N)cc3)cc12] |
| IQ-019 | 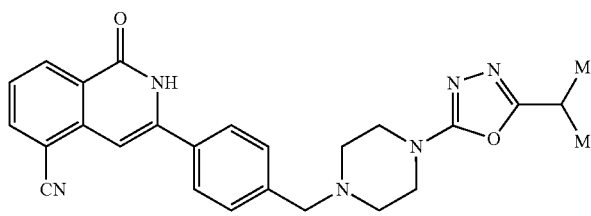 |
| IQ-020 | 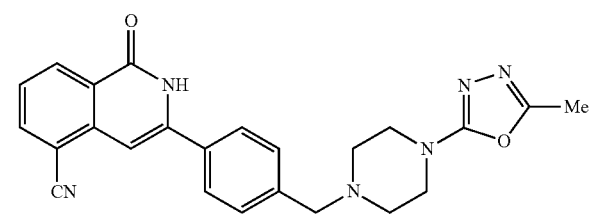 [SMILES: Cc1nnc(N2CCN(Cc3ccc(-c4cc5c(C#N)cccc5c(=O)[nH]4)cc3)CC2)o1] |
| IQ-021 | 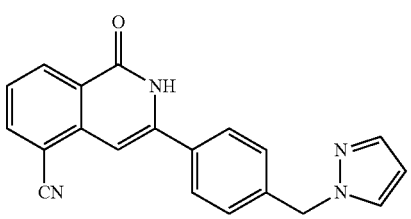 [SMILES: N#Cc1cccc2c(=O)[nH]c(-c3ccc(Cn4cccn4)cc3)cc12] |
| IQ-022 | 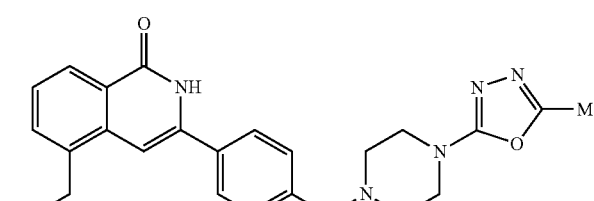 |
| IQ-023 | 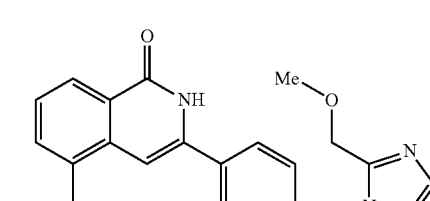 |

-continued

| Code | Structure |
| --- | --- |
| IQ-024 | 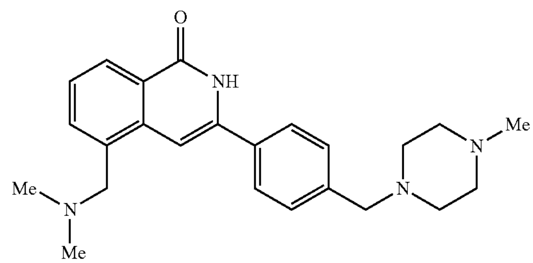 [SMILES: CN(C)Cc1cccc2c(=O)[nH]c(-c3ccc(CN4CCN(C)CC4)cc3)cc12] |
| IQ-025 | 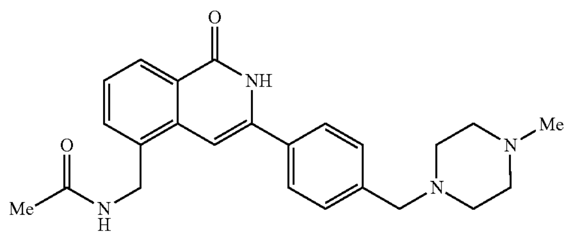 [SMILES: CC(=O)NCc1cccc2c(=O)[nH]c(-c3ccc(CN4CCN(C)CC4)cc3)cc12] |
| IQ-026 | 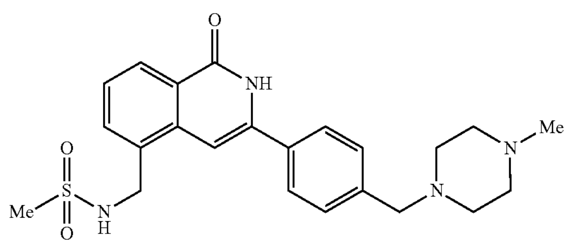 [SMILES: CN1CCN(Cc2ccc(-c3cc4c(CNS(C)(=O)=O)cccc4c(=O)[nH]3)cc2)CC1] |
| IQ-027 | 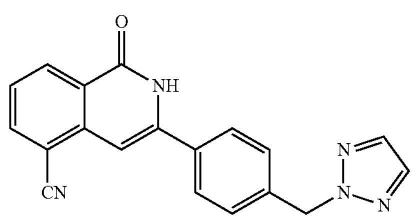 [SMILES: N#Cc1cccc2c(=O)[nH]c(-c3ccc(Cn4nccn4)cc3)cc12] |
| IQ-028 | 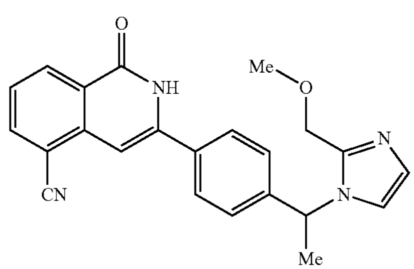 [SMILES: COCc1nccn1C(C)c1ccc(-c2cc3c(C#N)cccc3c(=O)[nH]2)cc1] |
| IQ-029 | 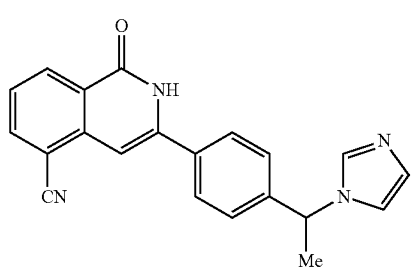 [SMILES: CC(c1ccc(-c2cc3c(C#N)cccc3c(=O)[nH]2)cc1)n1ccnc1] |

| Code | Structure |
|---|---|
| IQ-030 | 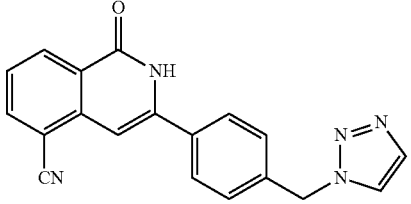 [SMILES: N#Cc1cccc2c(=O)[nH]c(-c3ccc(Cn4ccnn4)cc3)cc12] |
| IQ-031 | 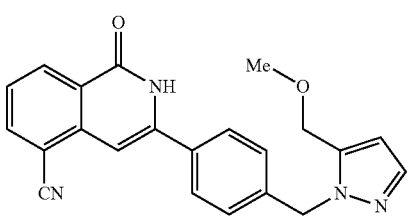 [SMILES: COCc1ccnn1Cc1ccc(-c2cc3c(C#N)cccc3c(=O)[nH]2)cc1] |
| IQ-032 | 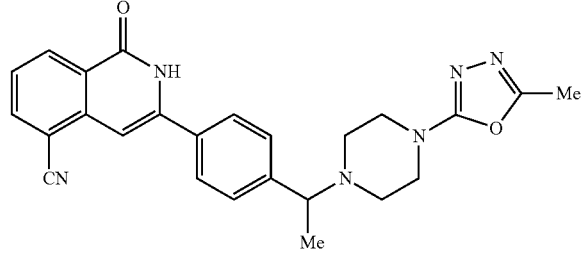 [SMILES: Cc1nnc(N2CCN(C(C)c3ccc(-c4cc5c(C#N)cccc5c(=O)[nH]4)cc3)CC2)o1] |
| IQ-033 | 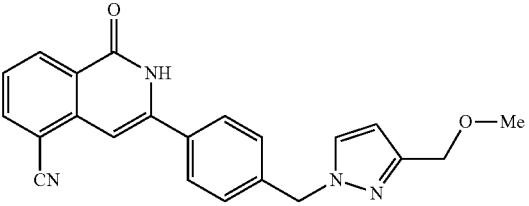 [SMILES: COCc1ccn(Cc2ccc(-c3cc4c(C#N)cccc4c(=O)[nH]3)cc2)n1] |
| IQ-034 | 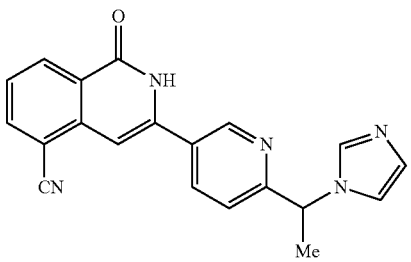 [SMILES: CC(c1ccc(-c2cc3c(C#N)cccc3c(=O)[nH]2)cn1)n1ccnc1] |
| IQ-035 | 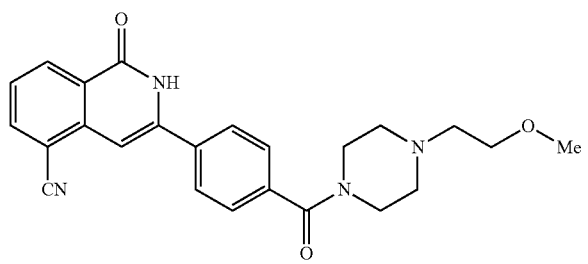 [SMILES: COCCN1CCN(C(=O)c2ccc(-c3cc4c(C#N)cccc4c(=O)[nH]3)cc2)CC1] |

| Code | Structure |
|---|---|
| IQ-036 | (structure) |
| IQ-037 | (structure) |
| IQ-038 | (structure) |
| IQ-039 | (structure) |
| IQ-040 | (structure) |
| IQ-041 | (structure) |

| Code | Structure |
|------|-----------|
| IQ-042 | 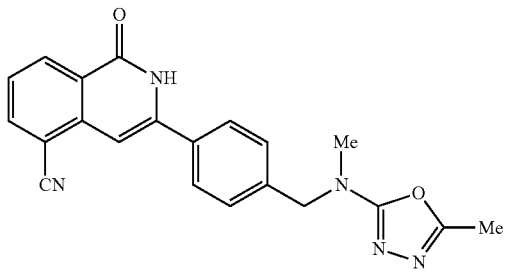 [SMILES: Cc1nnc(N(C)Cc2ccc(-c3cc4c(C#N)cccc4c(=O)[nH]3)cc2)o1] |
| IQ-043 | 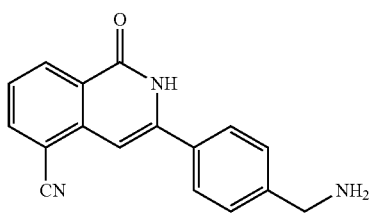 [SMILES: N#Cc1cccc2c(=O)[nH]c(-c3ccc(CN)cc3)cc12] |
| IQ-044 | 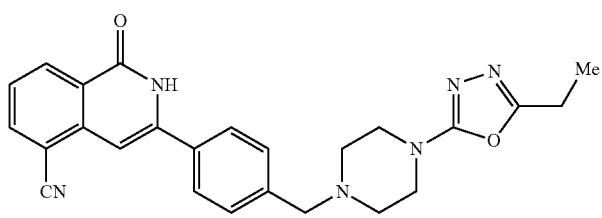 [SMILES: CCc1nnc(N2CCN(Cc3ccc(-c4cc5c(C#N)cccc5c(=O)[nH]4)cc3)CC2)o1] |
| IQ-045 | 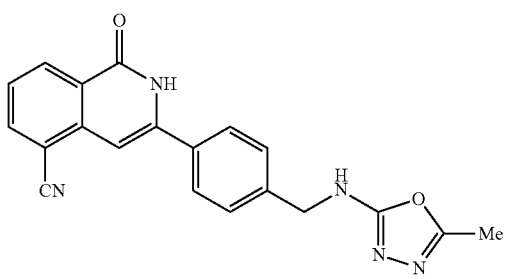 [SMILES: Cc1nnc(NCc2ccc(-c3cc4c(C#N)cccc4c(=O)[nH]3)cc2)o1] |
| IQ-046 | 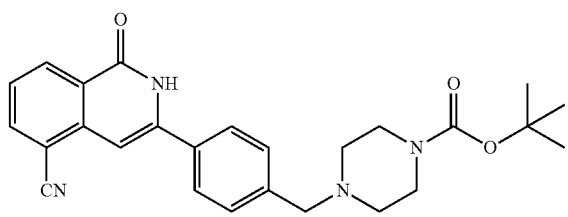 [SMILES: CC(C)(C)OC(=O)N1CCN(Cc2ccc(-c3cc4c(C#N)cccc4c(=O)[nH]3)cc2)CC1] |
| IQ-047 | 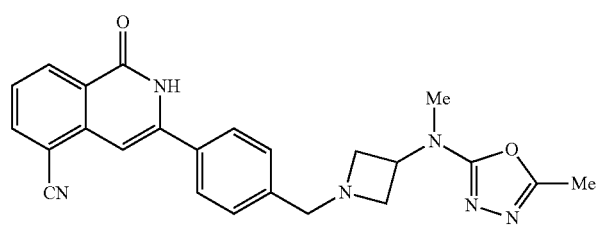 [SMILES: Cc1nnc(N(C)C2CN(Cc3ccc(-c4cc5c(C#N)cccc5c(=O)[nH]4)cc3)C2)o1] |

| Code | Structure |
|---|---|
| IQ-048 | 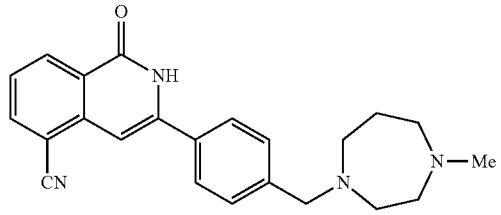 [SMILES: CN1CCCN(Cc2ccc(-c3cc4c(C#N)cccc4c(=O)[nH]3)cc2)CC1] |
| IQ-049 | 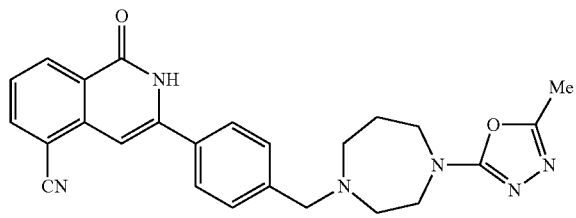 [SMILES: Cc1nnc(N2CCCN(Cc3ccc(-c4cc5c(C#N)cccc5c(=O)[nH]4)cc3)CC2)o1] |
| IQ-050 | 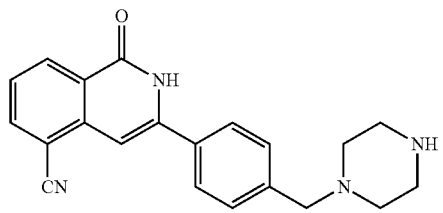 [SMILES: N#Cc1cccc2c(=O)[nH]c(-c3ccc(CN4CCNCC4)cc3)cc12] |
| IQ-051 | 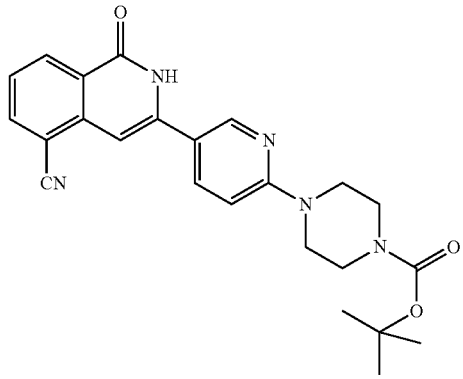 [SMILES: CC(C)(C)OC(=O)N1CCN(c2ccc(-c3cc4c(C#N)cccc4c(=O)[nH]3)cn2)CC1] |
| IQ-052 | 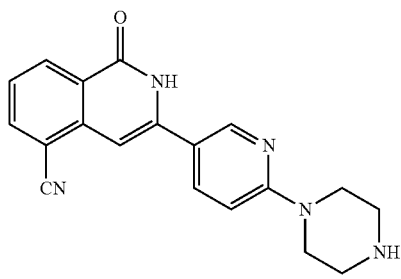 [SMILES: N#Cc1cccc2c(=O)[nH]c(-c3ccc(N4CCNCC4)nc3)cc12] |

| Code | Structure |
|---|---|
| IQ-053 | (structure) |
| IQ-054 | (structure) |
| IQ-055 | (structure) |
| IQ-056 | (structure) |
| IQ-057 | (structure) |

| Code | Structure |
|---|---|
| IQ-058 | 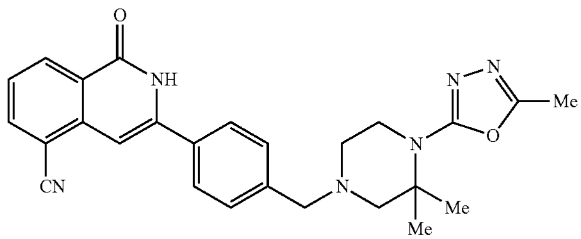 [SMILES: Cc1nnc(N2CCN(Cc3ccc(-c4cc5c(C#N)cccc5c(=O)[nH]4)cc3)CC2(C)C)o1] |
| IQ-059 | 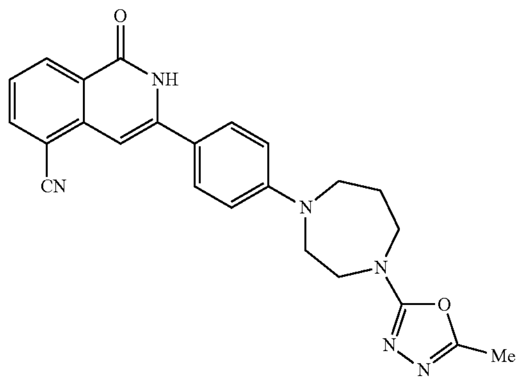 [SMILES: Cc1nnc(N2CCCN(c3ccc(-c4cc5c(C#N)cccc5c(=O)[nH]4)cc3)CC2)o1] |
| IQ-060 | 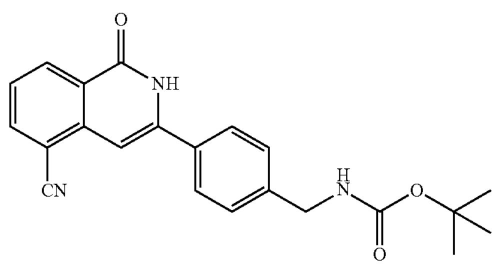 [SMILES: CC(C)(C)OC(=O)NCc1ccc(-c2cc3c(C#N)cccc3c(=O)[nH]2)cc1] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., W, X, Y, Z, —$R^W$, —$R^X$, —$R^Y$, —$R^Z$, -$L^{3P}$-, -$L^{3PL}$-, -$L^{3PR1}$-, -$L^{3PR2}$-, -$L^{3PR3}$-, -$L^{3PR4}$-, —$R^{3N}$, —$R^A$, —$R^{A1}$, —$R^{A2}$, —$R^{A3}$, —$R^{A4}$, —$R^{A5}$, -$L^A$-, —$R^{S1}$, —$R^{S2C}$, —$R^{S3C}$, —$R^{SN}$, -$L^T$-, —$R^{TT}$, —$R^{TTT}$, —$R^{TN}$, —$R^{TM}$, —$R^{TMM}$, —$R^B$, —$R^{B1}$, —$R^{B2}$, -$L^B$-, —$R^{BB}$, —$NR^C R^D$, —$NR^{C1}R^{D1}$, —$NR^{C2}R^{D2}$, —$NR^{C3}R^{D3}$, —$NR^{C4}R^{D4}$, —$NR^{C5}R^{D5}$, —$R^{NC}$, —$R^{NN}$, -$L^Q$-, —$R^{QQ}$, —$R^{QQ1}$, —$R^{QQ2}$, —$R^{QQ3}$, —$R^{QQQ}$, —$R^{QN}$, —$R^{QM}$, —$R^{QMM}$, —$R^H$, -$L^H$-, —$R^{HH}$, —$R^{HN}$, —$R^{HM}$, —$R^{HHH}$, —$R^{HMM}$, —$R^5$, —$R^{5A}$, —$R^{5B}$, —$R^{5C}$, —$R^{5D}$, —$R^{5B1}$, —$R^{5B2}$, —$R^{5C1}$, —$R^{5C2}$, —$R^{5D1}$, —$R^{5D2}$, —$R^4$, —$R^6$, —$R^7$, —$R^8$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to IQ compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

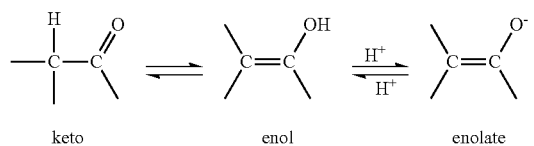

keto       enol       enolate

For example, 1H-pyridin-2-one-5-yl and 2-hydroxyl-pyridin-5-yl (shown below) are tautomers of one another. A reference herein to one is intended to encompass both.

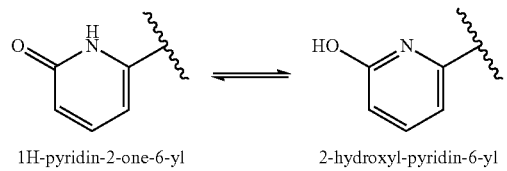 [SMILES: *c1cccc(=O)[nH]1 ; *c1cccc(O)n1]

1H-pyridin-2-one-6-yl       2-hydroxyl-pyridin-6-yl

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric.

Examples of suitable polymeric organic anions include, but are not limited to, those derived from the following polymeric acids: tannic acid, carboxymethyl cellulose.

Unless otherwise specified, a reference to a particular compound also includes salt forms thereof.

N-Oxides

It may be convenient or desirable to prepare, purify, and/or handle a corresponding N-oxide of the compound. For example, a compound having a pyridyl group may be prepared, purified, and/or handled as the corresponding N-oxide.

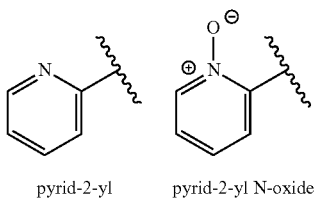 [SMILES: *c1ccccn1 ; *c1cccc[n+]1[O-]]

pyrid-2-yl      pyrid-2-yl N-oxide

Unless otherwise specified, a reference to a particular compound also includes N-oxide forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxycarbonyl amide (—NHCO—OCH$_2$C$_6$H$_5$, —NH-Cbz); as a t-butoxycarbonyl amine (—NHCO—OC(CH$_3$)$_3$, —NH-Boc); a 2-biphenyl-2-propoxycarbonyl amine (—NHCO—OC(CH$_3$)$_2$C$_6$H$_4$C$_6$H$_5$, —NH-Bpoc), as a 9-fluorenylmethoxycarbonyl amine (—NH-Fmoc), as a 6-nitroveratryloxycarbonyl amine (—NH-Nvoc), as a 2-trimethylsilylethyloxycarbonyl amine (—NH-Teoc), as a 2,2,2-trichloroethyloxycarbonyl amine (—NH-Troc), as an allyloxycarbonyl amine (—NH-Alloc), as a 2(-phenylsulfonyl)ethyloxycarbonyl amine (—NH—Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

General Chemical Synthesis Several methods for the chemical synthesis of IQ compounds are described herein.

These and/or other well known methods may be modified and/or adapted in known ways in order to facilitate the synthesis of additional compounds described herein.

All reagents were either purchased from common commercial sources or synthesised in accordance with known literature procedures. Commercial reagents were used without further purification unless otherwise stated. Microwave reactions were conducted using a CEM Discover. Flash column chromatography was conducted using pre-packed silica Biotage® SNAP (KP-Sil) cartridges or loose silica ($SiO_2$ or Florisil®, 100-200 mesh). Ion exchange chromatography was performed using Isolute® Flash SCX-2 cartridges.

Abbreviations

AIBN: 2,2'-Azobis(2-methylpropionitrile).

Ambersep® 900 (OH) resin: Amberlite strong anion exchanger.

APCI: atmospheric pressure chemical ionisation.

$BBr_3$: boron tribromide.

BINAP: 2,2'-bis(diphenylphosphino)-1,1'-binaphthyl.

Boc: tert-butyloxycarbonyl.

$CCl_4$: carbon tetrachloride.

$CH_2Cl_2$: dichloromethane.

DCM: dichloromethane.

CV: column volume.

DEAD: diethylazodicarboxylate.

DIAD: diisopropyl azodicarboxylate.

Dioxane: 1,4-dioxane.

DIPEA: N,N-diisopropylamine.

DMA: dimethyl acetamide.

DMAP: 4-dimethylaminopyridine.

DCE: 1,2-dichloroethane.

DME: dimethoxyethane.

DMF: N,N-dimethylformamide.

Dppf: 1,1'-Bis(diphenylphosphino)ferrocene.

EDCI: 1-ethyl-3-(3-dimethylaminopropyl) carbodiimide.

ES: electrospray.

$Et_2O$: diethyl ether.

EtOAc: ethyl acetate.

h: hour(s).

HATU: 2-(7-aza-1H-benzotriazole-1-yl)-1, 1,3,3-tetramethyluronium.

hexafluorophosphate.

IPA: isopropyl alcohol.

LDA: lithium diisopropylamide.

MCPBA: meta-Chloroperoxybenzoic acid.

min: minute(s).

Ms/mesyl: methane sulfonyl.

NBS: N-bromosuccinimide.

Pet-ether: petroleum ether (b.p. 60-80° C.).

PFPA: perfluorophthalic anhydride.

$PPh_3$: triphenyl phosphine.

PS: polymer supported.

Py: pyridine.

Quant.: quantitative (conversion).

$R_f$: retention factor.

Rt: retention time.

RT: room temperature.

SCX: strong cation exchange.

SEM: 2-(trimethylsilyl)ethoxymethyl.

TBAF: tetra-n-butylammonium fluoride.

TBDMS: tert-butyldimethylsilyl.

TBDPS: tert-butyldiphenylsilyl.

TBTU: O-(benzotriazol-1-yl)-N,N,N',N'-tetramethyluronium tetrafluoroborate.

TFA: trifluoroacetic acid.

OTf: triflate or trifluoromethanesulfonate

THF: tetrahydrofuran.

Ts/tosyl: 4-toluenesulfonyl.

The general synthetic methods for the synthesis of 2H-isoquinolin-1-ones 14 are illustrated below:

Route 1, part 1: Synthesis of 2H-isoquinolin-1-ones 5 via Cyclisation

Scheme 1

A = Cl, Br, I, OMe, OAlkyl

Acid 1 can be reacted with amine 2 (e.g., N,N-diethylamine) to yield amide 3, either by utilising standard amine coupling procedures (e.g., EDCI, HATU, etc.) or converting the acid 1 into the corresponding acid chloride (or mixed anhydride) and reacting with the amine 2 (see, e.g., Le et al., 2004). The 2H-isoquinolin-1-one 5 can be prepared by in situ deprotonation of 2-methyl-benzamide derivative 3 with a suitable base (e.g., n-BuLi, sec-BuLi, t-BuLi, LDA, etc.) in THF (or similar suitable aprotic solvent) at −78° C., then reacting with the required nitrile 4 (see, e.g., Hattori et al., 2006).

Route 2a, part 1: Synthesis of 2H-isoquinolin-1-ones 10 via Organopalladium Cross-Coupling

Scheme 2

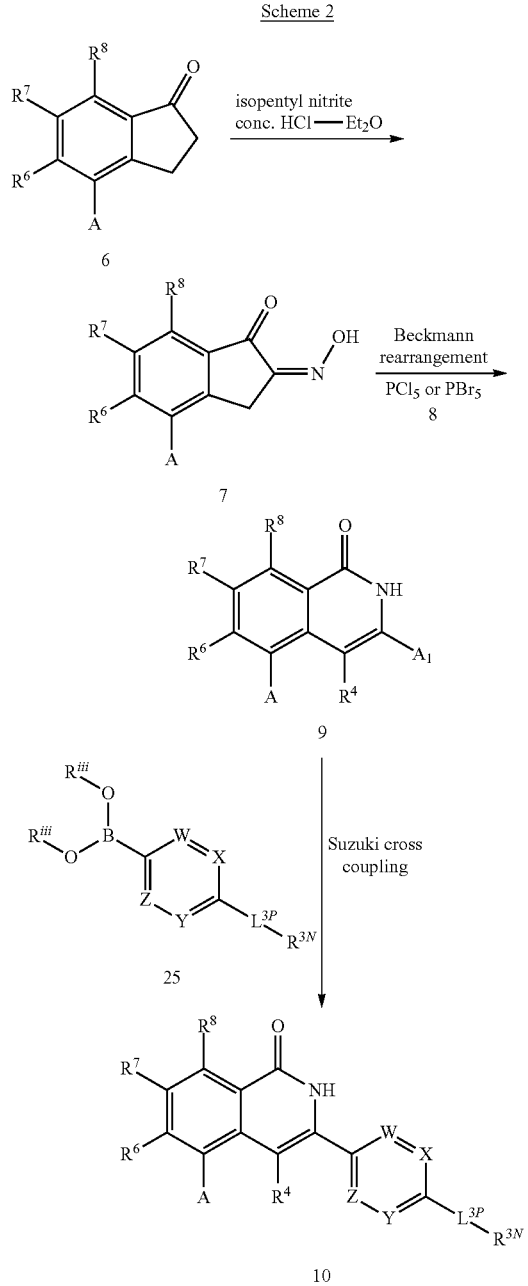

A = OMe, OAlkyl
A₁ = Br or Cl

The 2H-isoquinolin-1-one 10 can be synthesised by a palladium-mediated cross-coupling from the corresponding aryl halide 9 (e.g. chloride) and the corresponding boronic acid or ester (Suzuki cross-coupling) 25 in the presence of a suitable base (e.g., $K_2CO_3$, NaOt-Bu, $K_3PO_4$, etc.), a suitable source of palladium (e.g., $Pd(PPh_3)_4$, $PdCl_2(PPh_3)_2$, etc.) and a ligand (e.g., $P(t-Bu)_3$, BINAP, etc.) in an appropriate solvent (e.g., THF, DME, DCE, toluene, etc.).

The 3-halo-2H-isoquinolin-1-one 9 can be synthesised from indan-1,2-dione 2-oxime 7 (see, e.g., Merchant et al., 1984) via Beckmann rearrangement followed by treatment with $PCl_5$ or $PBr_5$ 8.

Indan-1,2-dione 2-oxime 7 can be accessed from commercial sources or prepared from commercially-available indanones 6 by nitrosation (see, e.g., Musso et al., 2003).

Route 1, part 2 & Route 2a part 2: Synthesis of 2H-isoquinolin-1-ones 12 via OTs or OTf formation

Scheme 3

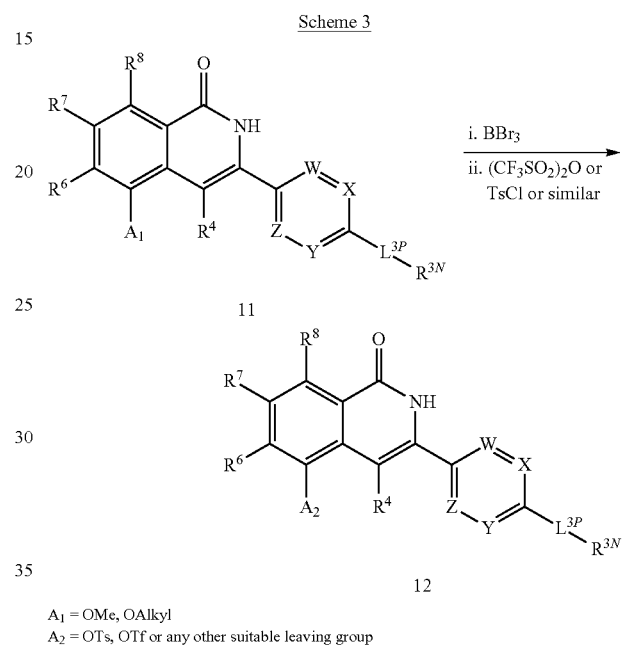

$A_1$ = OMe, OAlkyl
$A_2$ = OTs, OTf or any other suitable leaving group

The 2H-isoquinolin-1-one 12 can be accessed by dealkylation, e.g. demethylation of the corresponding methoxy analogue, using $BBr_3$ or similar (e.g. $AlCl_3$, HBr, HCl etc.) in a suitable solvent ($CH_2Cl_2$, THF etc), followed by conversion to a suitable leaving group (e.g. OTs, OTf) using trifluoromethanesulfonic anhydride, tosyl chloride or similar in a suitable solvent ($CH_2Cl_2$, THF etc.) and with a suitable base (e.g. $NEt_3$, DIPEA etc.).

Routes 1 & 2a part 3: Synthesis of 5-cyano-2H-isoquinolin-1-ones 14 via cyanide insertion

Scheme 4

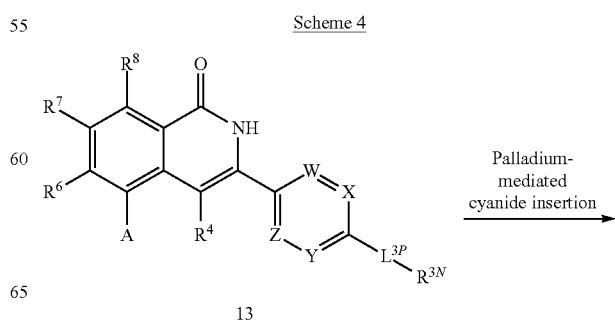

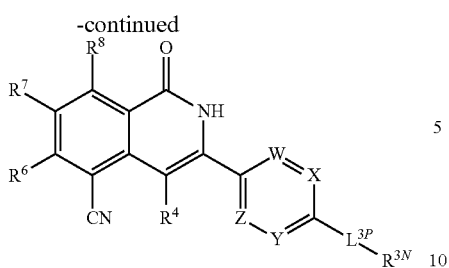

14

A = Cl, Br, I OTs, OTf or any other suitable leaving group

The nitrile 14 can be accessed by a palladium-mediated cyanide insertion from the corresponding aryl halide 13 (e.g., iodide, bromide, chloride) or other suitable leaving group (e.g. tosyl, triflate etc.) with a source of cyanide e.g., $Zn(CN)_2$, $Cu(CN)_2$, and a suitable source of palladium (e.g., $Pd(PPh_3)_4$, $PdCl_2(PPh_3)_2$) in an appropriate solvent (e.g., THF, DMF, DME, DCE, toluene, etc.).

Route 2b: Alternative synthesis of 5-cyano-2H-isoquinolin-1-ones 14 via Organopalladium Cross-Coupling Scheme 5

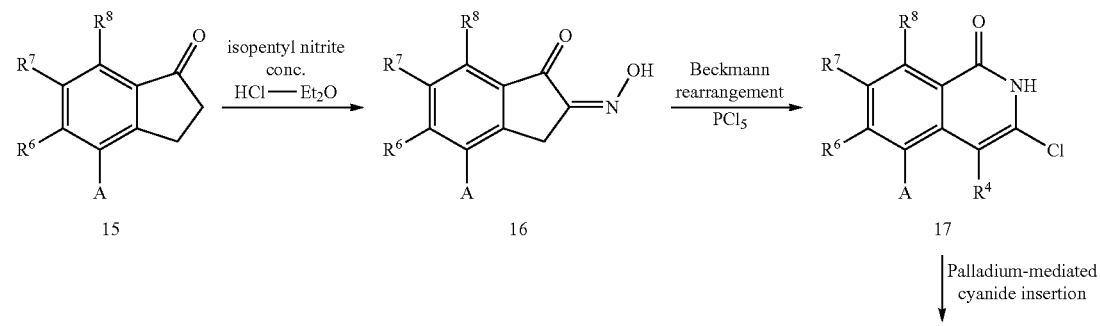

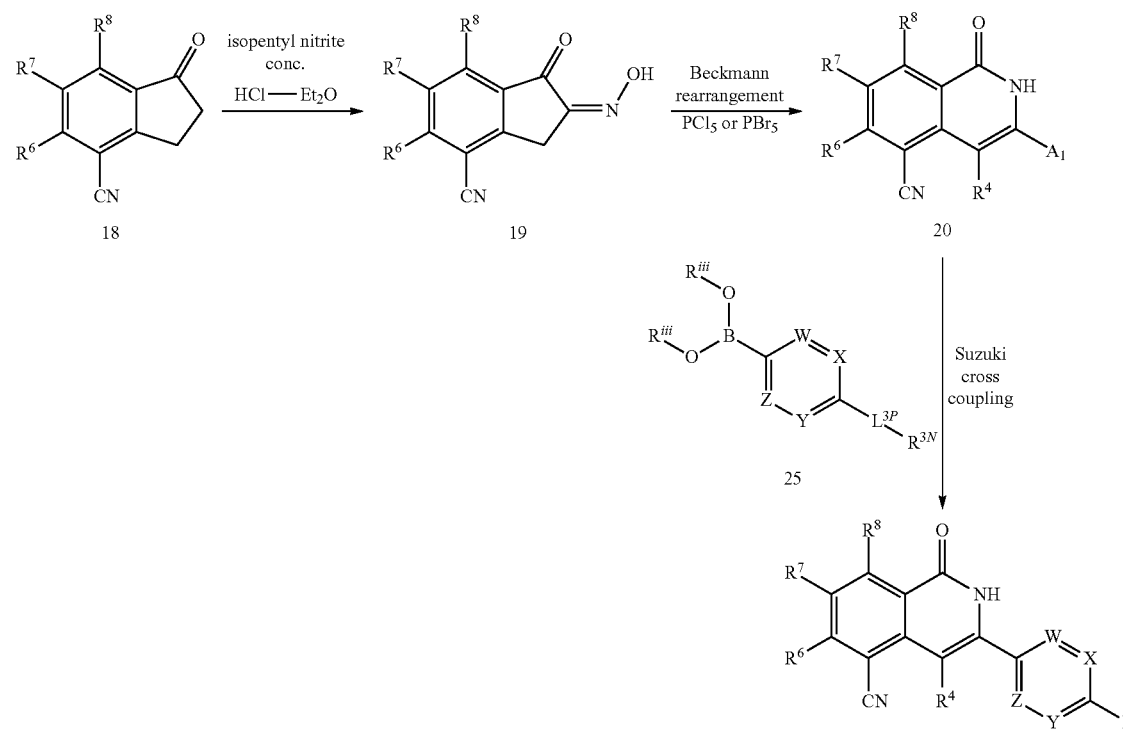

A = Br, I
$A_1$ = Cl or Br

In an alternative route, the 5-cyano-2H-isoquinolin-1-one 14 can be synthesised by palladium-mediated cyanide insertion (as described in Scheme 4) prior to the Suzuki cross-coupling reaction (as described in Scheme 2).

Route 2c: Alternative synthesis of 5-cyano-2H-isoquinolin-1-ones 14 via Organopalladium Cross-Coupling

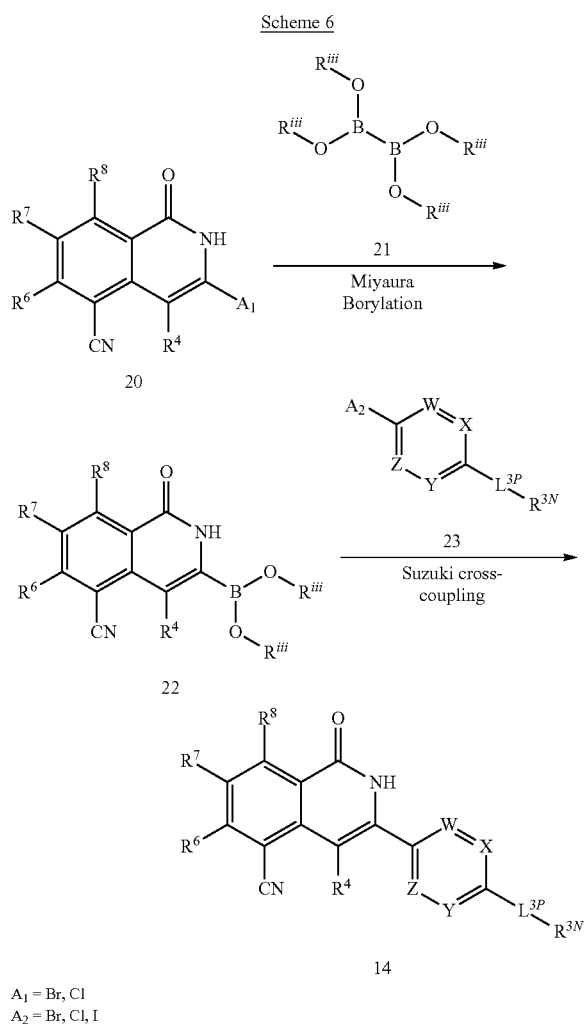

$A_1$ = Br, Cl
$A_2$ = Br, Cl, I

In an alternative route, the 2H-isoquinolin-1-one 14 can be synthesised by a palladium-mediated cross-coupling from the corresponding aryl or heteroaryl halides 23 (e.g., bromide) and the corresponding boronic ester 22 (Suzuki cross-coupling). The boronic ester 22 can be accessed by a palladium-mediated cross-coupling from the corresponding 3-halo-2H-isoquinolin-1-one 20 (e.g., chloride) with a suitable diboron reagent (e.g. bis (pinacolato) diboron), a base (e.g., KOAc) and a suitable source of palladium (e.g., Pd(PPh$_3$)$_4$, PdCl$_2$(PPh$_3$)$_2$) in an appropriate solvent (e.g., THF, DMF, DME, DCE, toluene, dioxane etc.).

The general synthetic methods for the synthesis of nitrile intermediates 4 and boronic acid or boronic ester intermediates 9 are illustrated below:

Synthesis of Boronic Acid or Boronic Ester Intermediate 25 from Aryl Halide 24

Scheme 7

A = Cl, Br, I

The boronic acid or ester 25 can be accessed by a palladium-mediated cross-coupling from the corresponding aryl (heteroaryl) halide 24 (e.g., iodide, bromide, chloride) with bis (pinacolato) diboron, and a suitable source of palladium (e.g., Pd(PPh$_3$)$_4$, PdCl$_2$(PPh$_3$)$_2$) in an appropriate solvent (e.g., THF, DMF, DME, DCE, toluene, etc.).

Synthesis of Amine 28 from Alkyl Halide 26

Scheme 8

A = CN, Br, or B(OR$^{iii}$)$_2$
$A_1$ = Cl, Br, I

The amine 28 can be accessed by halide displacement from the corresponding alkyl halide 26 (e.g., iodide, bromide, chloride) and an appropriate amine 27 in an appropriate solvent (e.g., THF, DMF, CH$_2$Cl$_2$ etc.).

This method is exemplified in Scheme 8 with benzyl or heteroarylmethyl bromides, but it is understood that the same approach can be extended to other examples of A-aryl-L$^{3PR1}$-Cl, Br, I. The same method can be used for any amine 27 as defined in the claims, including aromatic heterocycles (e.g., imidazole, pyrazole, etc.).

Synthesis of Ether 31 from Phenol 29

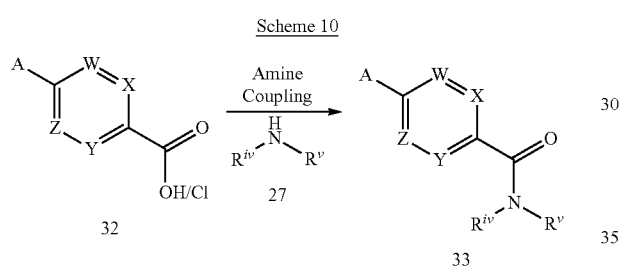

A = CN, Br, or B(OR$^{iii}$)$_2$
A$_1$ = Br, Cl, I

The ether 31 can be accessed by halide displacement from the corresponding halide 30 (e.g., iodide, bromide, chloride) and an appropriate phenol 29 with a suitable base (e.g. K$_2$CO$_3$, NEt$_3$ etc.) in an appropriate solvent (e.g., MeCN, DMF etc.).

Synthesis of Amide 33 from Acid 32

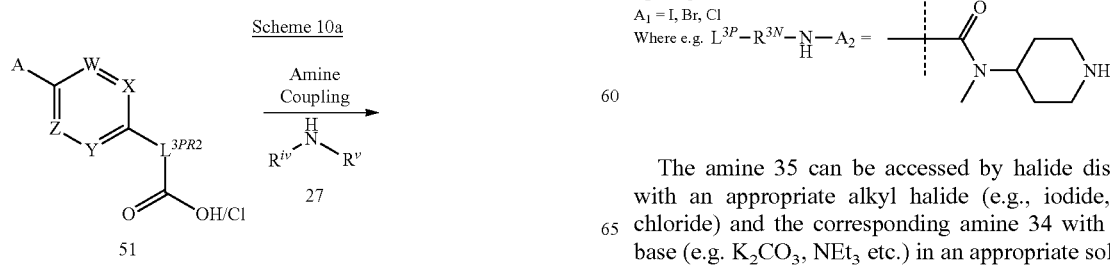

A = CN, Br, or B(OR$^{iii}$)$_2$

The amide 33 can be accessed by standard amine coupling conditions from the corresponding acid (or acid chloride) 32 and an appropriate amine 27 in an appropriate solvent (e.g., THF, DMF, CH$_2$Cl$_2$ etc.), with a suitable base (e.g., DIPEA, Et$_3$N etc.) with the use a standard amine coupling reagent (e.g., HATU, TBTU, EDCI etc.).

Alternatively, the amide 33 can be accessed by standard amine coupling conditions from the corresponding acid chloride 32 and an appropriate amine 27 in an appropriate solvent (e.g., THF, DMF, CH$_2$Cl$_2$ etc.), with a suitable base (e.g., DIPEA, Et$_3$N etc.).

Synthesis of Amide 52 from Acid 51

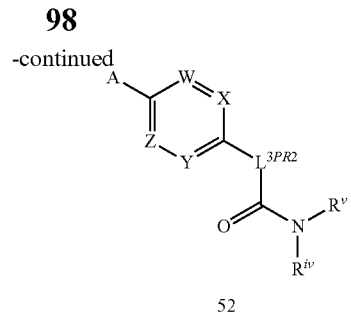

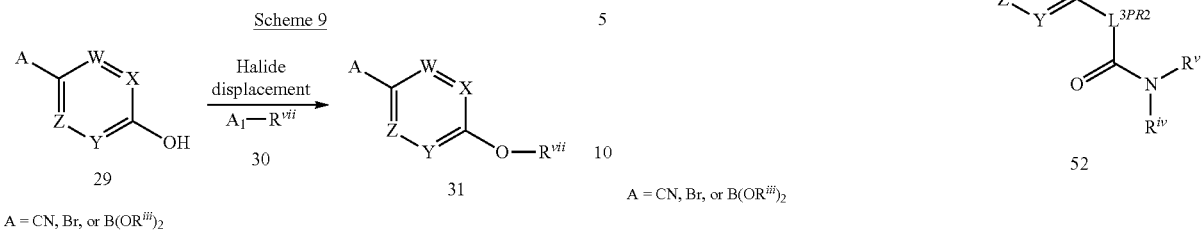

A = CN, Br, or B(OR$^{iii}$)$_2$

The same method from Scheme 10 can be applied using a carboxylic acid (or acid chloride) 51, with an amine 27, to afford amide 52.

Synthesis of Amine 35 from Amine 34

A = CN, Br, or B(OR$^{iii}$)$_2$
A$_2$ = H, part of R$^{3N}$, R$^{viii}$
A$_1$ = I, Br, Cl
Where e.g. L$^{3P}$—R$^{3N}$—N(H)—A$_2$ =

The amine 35 can be accessed by halide displacement with an appropriate alkyl halide (e.g., iodide, bromide, chloride) and the corresponding amine 34 with a suitable base (e.g. K$_2$CO$_3$, NEt$_3$ etc.) in an appropriate solvent (e.g., MeCN, DMF etc.).

Synthesis of Ether 38 from Alcohol 36

Scheme 12

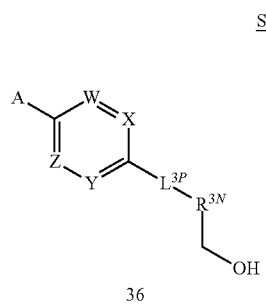

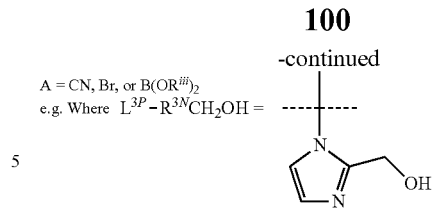

The ether 38 can be accessed by conversion of the alcohol 36 into a suitable leaving group (e.g. chloride, OMs, OTs), followed by treatment with an appropriate alcohol 37 (e.g., MeOH etc) deprotonated with a suitable base (e.g. NaOMe etc) in an appropriate solvent (e.g., MeOH etc.).

Synthesis of Amine 39 from Alcohol 36

Scheme 13

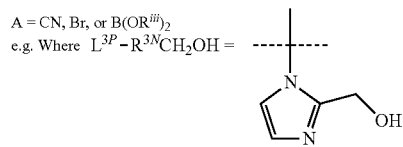

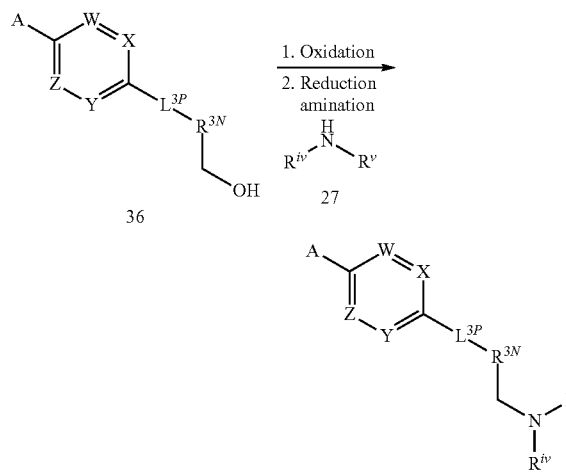

The amine 39 can be accessed by oxidation of the corresponding alcohol 36 to the corresponding aldehyde, using an appropriate oxidising agent (e.g. $MnO_2$ etc.), followed by standard reductive amination conditions with an appropriate amine 27 in an appropriate solvent (e.g., DCE etc.), with the use a standard reducing reagent (e.g., sodium triacetoxy borohydride, sodium borohydride, etc.).

The general synthetic methods for the synthesis of 2H-isoquinolin-1-ones (42-44, 46, 48, 50 and 55) are illustrated below:

Synthesis of 2H-isoquinolin-1-ones 42 via N-Acylation

Scheme 14

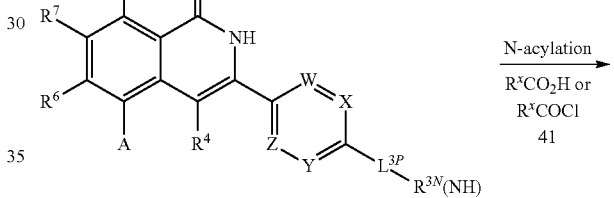

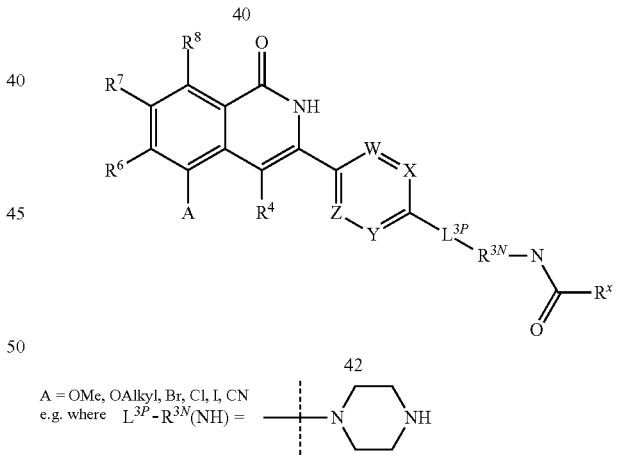

The amide 42 can be accessed by standard amine coupling conditions from the corresponding amine 40 and an appropriate acid 41 in an appropriate solvent (e.g., THF, DMF, $CH_2Cl_2$ etc.), with a suitable base (e.g., DIPEA, $Et_3N$ etc.) with the use a standard amine coupling reagent (e.g., HATU, TBTU, EDCI etc.).

Alternatively, the amide 42 can be accessed by standard amine coupling conditions from the corresponding amine 40 and an appropriate acid chloride 41 in an appropriate solvent (e.g., THF, DMF, $CH_2Cl_2$ etc.), with a suitable base (e.g., DIPEA, $Et_3N$ etc.).

Synthesis of 2H-isoquinolin-1-ones 55 via N-(hetero)arylation

Scheme 14a

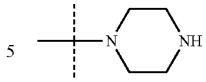

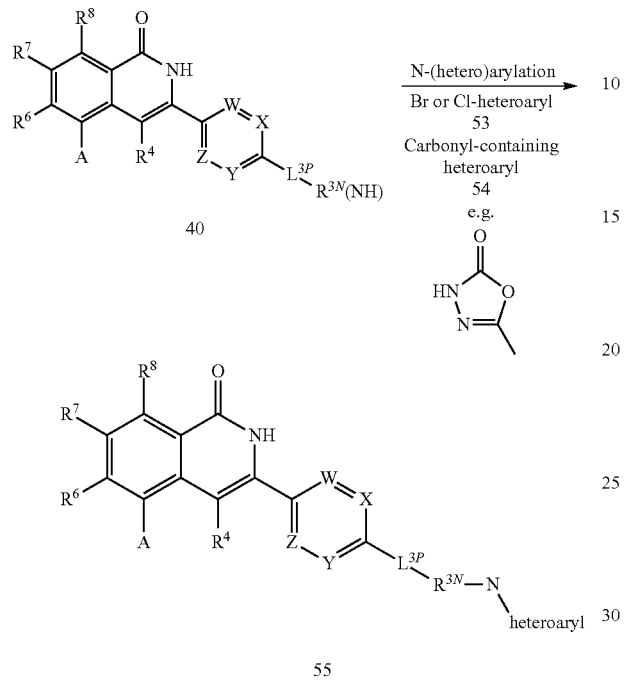

The 2H-isoquinolin-1-one 55 can be accessed by bromide or chloride displacement using an appropriate bromo- or chloro-heteroaryl 53 with the corresponding amine 40 in an appropriate solvent (e.g., DMF etc.).

Alternatively, the 2H-isoquinolin-1-one 55 can be accessed by standard amine coupling conditions from the corresponding carbonyl-containing heteroaryl 54 and an appropriate amine 40 in an appropriate solvent (e.g., THF, DMF, $CH_2Cl_2$ etc.), with a suitable base (e.g., DIPEA, $Et_3N$ etc.) with the use a standard amine coupling reagent (e.g., BOP, HATU, TBTU, EDCI etc.).

Route 2d: Alternative synthesis of 5-cyano-2H-isoquinolin-1-ones 14 via Organopalladium Cross-Coupling using tosylates or triflates

Scheme 14b

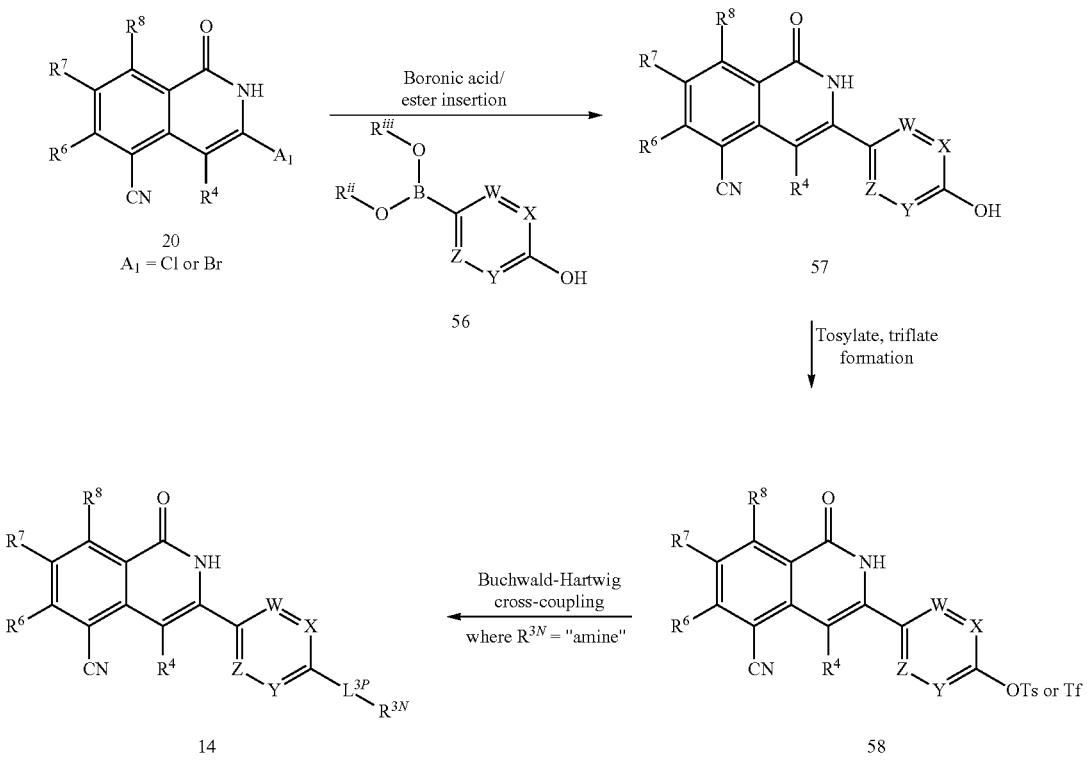

The 2H-isoquinolin-1-one 57 can be accessed can be accessed by a palladium-mediated cross-coupling from the corresponding heteroaryl halide 20 (e.g., bromide, chloride) with a boronic acid or ester 56, and a suitable source of palladium (e.g., Pd(PPh$_3$)$_4$, PdCl$_2$(PPh$_3$)$_2$) in an appropriate solvent (e.g., THF, DMF, DME, DCE, toluene, etc.).

The 2H-isoquinolin-1-one 58 can be accessed by conversion of the phenol 57 to a suitable leaving group (e.g. OTs, OTf) using trifluoromethanesulfonic anhydride, tosyl chloride or similar in a suitable solvent (CH$_2$Cl$_2$, THF etc.) and with a suitable base (e.g. NEt$_3$, DIPEA etc.).

The 2H-isoquinolin-1-one 14 can be accessed by tosylate or triflate displacement using an appropriate tosylate or triflate 58, with an amine, in the presence of a suitable base (e.g., K$_2$CO$_3$, NaOt-Bu, K$_3$PO$_4$, etc.), a suitable source of palladium (e.g., Pd(PPh$_3$)$_4$, PdCl$_2$(dppf), etc.) and a ligand (e.g., P(t-Bu)$_3$, BINAP, etc.) in an appropriate solvent (e.g., THF, 1,4-dioxane, DME, DCE, toluene, etc.).

Synthesis of 2H-isoquinolin-1-ones 43 via Reduction

Scheme 15

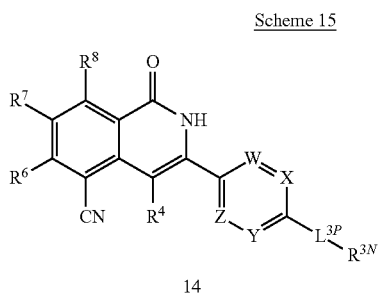

14

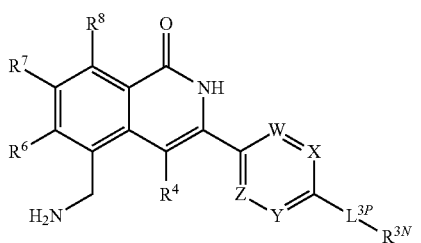

43

The primary amine 43 can be accessed by reduction of the corresponding nitrile 14 with a suitable reducing agent (e.g. H$_2$, NaBH$_4$) and catalyst (e.g. Raney nickel, Pd/C, NiCl$_2$.6H$_2$O, etc.).

Alternatively, the primary amine 43 can be accessed using a 2-step procedure with, firstly, reduction of the corresponding nitrile and in situ protection of the resulting primary amine with a suitable protecting group, e.g. Boc, in an appropriate solvent (e.g., THF, MeOH, etc.), followed by, secondly, protecting group removal via treatment with acid (e.g. TFA, HCl etc.) in a suitable solvent (e.g. DCM, dioxane etc.).

Synthesis of 2H-isoquinolin-1-ones 44 via N-Acylation

Scheme 16

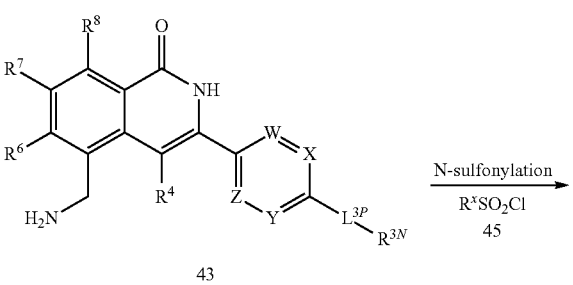

The amide 44 can be accessed by standard amine coupling conditions from the corresponding amine 43 and an appropriate acid 41 in an appropriate solvent (e.g., THF, DMF, CH$_2$Cl$_2$ etc.), with a suitable base (e.g., DIPEA, Et$_3$N etc.) with the use a standard amine coupling reagent (e.g., HATU, TBTU, EDCI etc.).

Alternatively, the amide 44 can be accessed by standard amine coupling conditions from the corresponding amine 43 and an appropriate acid chloride 41 in an appropriate solvent (e.g., THF, DMF, CH$_2$Cl$_2$ etc.), with a suitable base (e.g., DIPEA, Et$_3$N etc.).

Synthesis of 2H-isoquinolin-1-ones 46 via N-Sulfonylation

Scheme 17

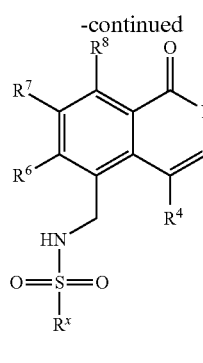

46

The sulfonamide 46 can be prepared from the corresponding amine 43 and an appropriate sulfonyl chloride 45 in an appropriate solvent (e.g., THF, $CH_2Cl_2$ etc.), with a suitable base (e.g., DIPEA, $Et_3N$ etc.).

Synthesis of 2H-isoquinolin-1-ones 48 via N-Alkylation

Scheme 18

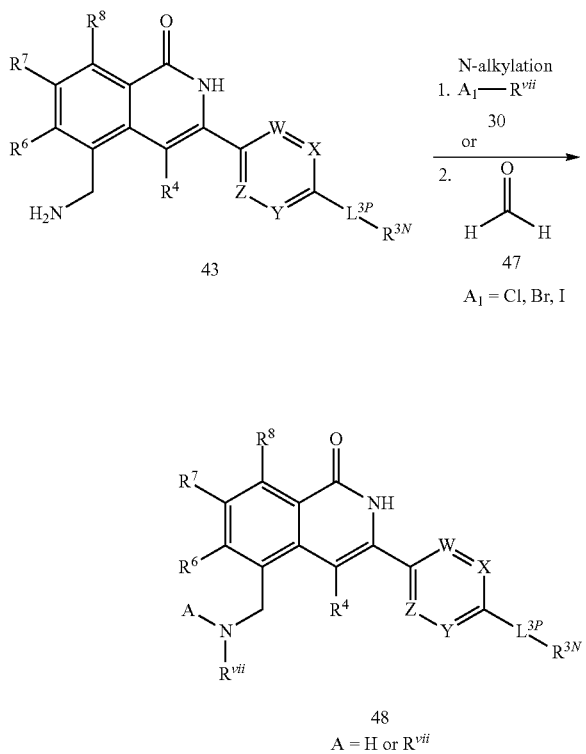

48
A = H or $R^{vii}$

The amine 48 can be accessed by halide displacement from the corresponding alkyl halide 30 (e.g., iodide, bromide, chloride) and an appropriate amine 43 in an appropriate solvent (e.g., THF, DMF, $CH_2Cl_2$ etc.).

Alternatively, the methylated amine 48 (where $R^{vii}$=Me) can be accessed by Eschweiler-Clarke methylation of the corresponding amine 43 with formaldehyde 47 and formic acid using microwave irradiation in DMSO (or other suitable solvent).

Synthesis of 2H-isoquinolin-1-ones 50 via Reductive Amination

Scheme 19

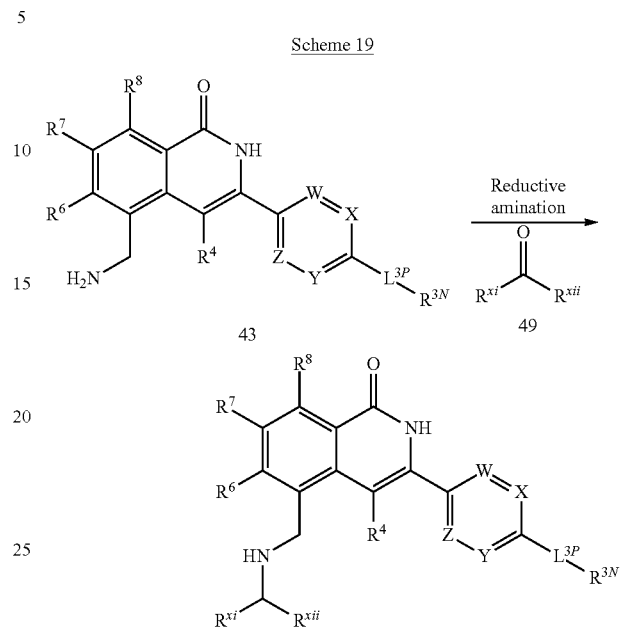

50

The amine 50 can be accessed by standard reductive amination conditions from an appropriate aldehyde or ketone 49 and the corresponding amine 43 in an appropriate solvent (e.g., DCE etc.), with the use a standard reducing reagent (e.g., sodium triacetoxy borohydride, sodium borohydride, etc.).

Compositions

One aspect of the present invention pertains to a composition (e.g., a pharmaceutical composition) comprising an IQ compound, as described herein, and a pharmaceutically acceptable carrier, diluent, or excipient.

Another aspect of the present invention pertains to a method of preparing a composition (e.g., a pharmaceutical composition) comprising mixing an IQ compound, as described herein, and a pharmaceutically acceptable carrier, diluent, or excipient.

Uses

The IQ compounds, as described herein, are useful, for example, in the treatment of disorders (e.g., diseases) that are ameliorated by the inhibition of PARP (e.g., PARP1, TNKS1, TNKS2, etc.) and/or the inhibition of Wnt signalling, as described herein.

Use in Methods of Inhibiting PARP (e.g., PARP1, TNKS1, TNKS2, etc.)

One aspect of the present invention pertains to a method of inhibiting PARP (e.g., PARP1, TNKS1, TNKS2, etc.) in a cell, in vitro or in vivo, comprising contacting the cell with an effective amount of an IQ compound, as described herein.

One aspect of the present invention pertains to a method of inhibiting TNKS1 and/or TNKS2 in a cell, in vitro or in vivo, comprising contacting the cell with an effective amount of an IQ compound, as described herein.

One of ordinary skill in the art is readily able to determine whether or not a candidate compound inhibits PARP (e.g., PARP1, TNKS1, TNKS2, etc.). For example, suitable assays are described herein or are known in the art.

In one embodiment, the method is performed in vitro.

In one embodiment, the method is performed in vivo.

In one embodiment, the IQ compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Wnt Signalling

One aspect of the present invention pertains to a method of inhibiting Wnt signalling in a cell, in vitro or in vivo, comprising contacting the cell with an effective amount of an IQ compound, as described herein.

One of ordinary skill in the art is readily able to determine whether or not a candidate compound inhibits Wnt signalling. For example, suitable assays are described herein or are known in the art.

In one embodiment, the method is performed in vitro.

In one embodiment, the method is performed in vivo.

In one embodiment, the IQ compound is provided in the form of a pharmaceutically acceptable composition.

Use in Methods of Inhibiting Cell Proliferation, Etc.

The IQ compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an IQ compound, as described herein.

In one embodiment, the method is a method of regulating (e.g., inhibiting) cell proliferation (e.g., proliferation of a cell), in vitro or in vivo, comprising contacting a cell with an effective amount of an IQ compound, as described herein.

In one embodiment, the method is performed in vitro.

In one embodiment, the method is performed in vivo.

In one embodiment, the IQ compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an IQ compound, as described herein, for use in a method of treatment of the human or animal body by therapy, for example, for use in a method of treatment of a disorder (e.g., a disease) as described herein.

Use in the Manufacture of Medicaments

Another aspect of the present invention pertains to use of an IQ compound, as described herein, in the manufacture of a medicament, for example, for use in a method of treatment, for example, for use a method of treatment of a disorder (e.g., a disease) as described herein.

In one embodiment, the medicament comprises the IQ compound.

Methods of Treatment

Another aspect of the present invention pertains to a method of treatment, for example, a method of treatment of a disorder (e.g., a disease) as described herein, comprising administering to a subject in need of treatment a therapeutically-effective amount of an IQ compound, as described herein, preferably in the form of a pharmaceutical composition.

Disorders Treated—Disorders Ameliorated by the Inhibition of PARP (e.g., PARP1, TNKS1, TNKS2, etc.)

In one embodiment (e.g., of use in methods of therapy, of use in the manufacture of medicaments, of methods of treatment), the treatment is treatment of a disorder (e.g., a disease) that is ameliorated by the inhibition of PARP.

In one embodiment (e.g., of use in methods of therapy, of use in the manufacture of medicaments, of methods of treatment), the treatment is treatment of a disorder (e.g., a disease) that is ameliorated by the inhibition of TNKS1 and/or TNKS2.

Disorders Treated—Proliferative Conditions

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as neoplastic or hyperplastic growth.

In one embodiment, the treatment is treatment of: a proliferative condition characterised by benign, pre-malignant, or malignant cellular proliferation, including for example: neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer characterised by, or further characterised by, cancer cells which overexpress PARP.

In one embodiment, the treatment is treatment of cancer characterised by, or further characterised by, cancer cells which overexpress TNKS1 and/or TNKS2.

In one embodiment, the treatment is treatment of lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:
- a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
- a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
- a hematopoietic tumour of myeloid lineage, for example acute and chronic myelogenous leukemias, myelodysplastic syndrome, or promyelocytic leukemia;
- a tumour of mesenchymal origin, for example fibrosarcoma or habdomyosarcoma;
- a tumour of the central or peripheral nervous system, for example astrocytoma, neuroblastoma, glioma or schwannoma;
- melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of cancer head and neck cancer; nervous system cancer; lung/mediastinum cancer; breast cancer; oesophagus cancer; stomach cancer; liver cancer; biliary tract cancer; pancreatic cancer; small bowel cancer; large bowel cancer; gynaecological cancer; genito-urinary cancer; thyroid gland cancer; adrenal gland cancer; skin cancer; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of cancer metastasis.

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Disorders Treated—Non-Cancer Indications Related to Tankyrase Inhibition

In one embodiment, the treatment is treatment of: a neurodegenerative disorder, such as multiple sclerosis (MS); a neurological disorder associated with demyelination; neonatal hypoxic ischemic encephalopathy (HIE); neonatal periventricular leukomalacia (PVL); a cardiac related pathology, such as myocardial infarction; cardiac damage (e.g., to repair cardiac damage); an infectious disease, such as a pathology related to Herpes Simplex Virus (HSV); a pathology related to Epstein-Barr Virus (EBV); a metabolic disease, such as a metabolic disease where glucose uptake is dysfunctional, such as diabetes, such as type 2 diabetes; or fibrosis (e.g., lung fibrosis).

Disorder Treated—Non-Cancer Indications Related to Wnt Signalling

In one embodiment (e.g., of use in methods of therapy, of use in the manufacture of medicaments, of methods of treatment), the treatment is treatment of a disorder (e.g., a disease) that is ameliorated by the inhibition of Wnt signalling.

In one embodiment, the treatment is treatment of: Alzheimer's disease; late onset Alzheimer's disease; Dupuytren skin disease; tooth agenesis; vascular defects in the eye; Osteoperosis-pseudoglioma Syndrome (OPPG); exudative vitreoretinopathy; familial exudative vitreoretinopathy; retinal angiogenesis; schizophrenia; osteoporosis; dermal hypoplasia; XX sex reversal; Mullerian-duct regression and virilization; SERKAL syndrome; anonychia; hyponychia; sclerosteosis; van Buchem disease; Fuhrmann syndrome; odonto-onchyo-dermal hypoplasia; Type 2 diabetes; obesity; early onset obesity; a nephropathy, such as HIV-associated nephropathy; early coronary disease; bone density defects; tetra-amelia syndrome; split-hand/foot malformation; caudal duplication; Fuhrmann syndrome; odonto-onycho-dermal dysplasia; skeletal dysplasia; focal dermal hypoplasia; autosomal recessive anonychia; or neural tube defects.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously.

For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the IQ compounds described herein include the following: antimetabolites; alkylating agents; spindle poisons; topoisomerase inhibitors; DNA binding agents; kinase inhibitors; therapeutic antibodies; PARP inhibitors; NAD metabolism inhibitors; metabolic inhibitors; targeted agents; endocrine agents; etc.

Other Uses

The IQ compounds described herein may also be used as cell culture additives to inhibit PARP (e.g., PARP1, TNKS1, TNKS2, etc.), to inhibit Wnt signalling, etc.

The IQ compounds described herein may also be used as part of an in vitro assay, for example, in order to determine whether a candidate host is likely to benefit from treatment with the compound in question.

The IQ compounds described herein may also be used as a standard, for example, in an assay, in order to identify other active compounds, other PARP (e.g., PARP1, TNKS1, TNKS2, etc.) inhibitors, other Wnt signalling inhibitors, etc.

Kits

One aspect of the invention pertains to a kit comprising (a) an IQ compound as described herein, or a composition comprising an IQ compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The IQ compound or pharmaceutical composition comprising the IQ compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for an IQ compound to be administered alone, it is preferable to present it as a pharmaceutical formulation (e.g., composition, preparation, medicament) comprising at least one IQ compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one IQ compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth.

Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the IQ compounds, and compositions comprising the IQ compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular IQ compound, the route of administration, the time of administration, the rate of excretion of the IQ compound, the duration of the treatment, other drugs, compounds, and/or materials used in combination, the severity of the disorder, and the species, sex, age, weight, condition, general health, and prior medical history of the patient. The amount of IQ compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the IQ compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

Analytical Methods

Reverse Phase Preparative HPLC-MS: Mass-directed purification by preparative LC-MS using a preparative C-18 column (Phenomenex Luna C18 (2), 100×21.2 mm, 5 μm).

Analysis of products and intermediates has been carried out using reverse phase analytical HPLC-MS using the parameters set out below.

HPLC Analytical Methods:

AnalpH2_MeOH_4min(1): Phenomenex Luna C18 (2) 3 μm, 50×4.6 mm; A=water+0.1% formic acid; B=MeOH+0.1% formic acid; 45° C.; % B: 0 min 5%, 1 min 37.5%, 3 min 95%, 3.51 min 5%, 4.0 min 5%; 2.25 mL/min.

AnalpH2_MeOH_4min(2): Phenomenex Luna C18 (2) 3 μm, 50×4.6 mm; A=water+0.1% formic acid; B=MeOH; 45° C.; % B: 0 min 5%, 1 min 37.5%, 3 min 95%, 3.51 min 5%, 4.0 min 5%; 2.25 mL/min.

AnalpH9_MeOH_4min(1): Phenomenex Luna C18 (2) 3 μm, 50×4.6 mm; A=water pH9 (Ammonium Bicarbonate 10 mM); B=MeOH+0.1% formic acid; 45° C.; % B: 0 min 5%, 1 min 37.5%, 3 min 95%, 3.51 min 5%, 4.0 min 5%; 2.25 mL/min.

AnalpH9_MeOH_4min(2): Phenomenex Luna C18 (2) 3 μm, 50×4.6 mm; A=water pH9 (Ammonium Bicarbonate 10 mM); B=MeOH; 45° C.; % B: 0 min 5%, 1 min 37.5%, 3 min 95%, 3.51 min 5%, 4.0 min 5%; 2.25 mL/min.

AnalpH2_MeCN_FA_7 min(XTERRA1.m): Xterra C18 2.5 μm, 50×4.6 mm; A=water+0.1% FA; B=Acetonitrile+0.1% FA; % B: 0 min 20%, 4 min 90%, 7 min 90%, 7.1 min 20%; 1.0 mL/min.

AnalpH2_MeCN_FA_5 min(1): Aquity UPLC BEH C18 1.7 μm, 50×2.1 mm; A=water+0.1% FA; B=Acetonitrile+0.1% FA; 35° C.; % B: 0 min 3%, 0.3 min 3%, 3.5 min 98%, 4.8 min 98%, 5 min 3%, 5.01 min 3%; 0.6 mL/min.

AnalpH2_MeOH_QC: Phenomenex Luna C18 (2) 5 μm, 150×4.6 mm; A=water+0.1% formic acid; B=MeOH; 35° C.; % B: 0 min 5%, 7.5 min 95%, 10 min 95%, 10.10 min 5%, 13.0 min 5%; 1.5 mL/min.

AnalpH2_MeOH_QC(1): Phenomenex Luna C18 (2) 3 μm, 150×4.6 mm; A=water+0.1% formic acid; B=MeOH+

0.1% formic acid; 40° C.; % B: 0 min 5%, 7.5 min 95%, 10 min 95%, 10.10 min 5%, 13.0 min 5%; 1.5 mL/min.

AnalpH2_MeOH_QC(2): Phenomenex Gemini C18 5 μm, 150×4.6 mm; A=water+0.1% formic acid; B=MeOH+ 0.1% formic acid; 40° C.; % B: 0 min 5%, 7.5 min 95%, 10 min 95%, 10.10 min 5%, 13.0 min 5%; 1.5 mL/min.

AnalpH2_MeOH_QC(3): Phenomenex Gemini C18 5 μm, 150×4.6 mm; A=water+0.1% formic acid; B=MeOH; 40° C.; % B: 0 min 5%, 7.5 min 95%, 10 min 95%, 10.10 min 5%, 13.0 min 5%; 1.5 mL/min.

AnalpH9_MeOH_QC(1): Phenomenex Luna C18 (2) 5 μm, 150×4.6 mm; A=water+pH9 (Ammonium Bicarbonate 10 mM); B=MeOH; 45° C.; % B: 0 min 5%, 7.5 min 95%, 10 min 95%, 10.10 min 5%, 13.0 min 5%; 1.5 mL/min.

AnalpH9_MeOH_QC(2): Phenomenex Luna C18 5 μm, 150×4.6 mm; A=water+pH9 (Ammonium Bicarbonate 10 mM); B=MeOH; 45° C.; % B: 0 min 5%, 7.5 min 95%, 10 min 95%, 10.10 min 5%, 13.0 min 5%; 1.5 mL/min.

AnalpH2_MeOH_QC(Sunfire1): Waters Sunfire C18 (2) 5 μm, 100×4.6 mm; A=water+0.1% formic acid; B=MeOH+ 0.1% formic acid; 40° C.; % B: 0 min 5%, 7.5 min 95%, 10 min 95%, 10.10 min 5%, 13.0 min 5%; 1.5 mL/min.

AnalpH9_MeOH_QC(Sunfire): Waters Sunfire C18 (2) 5 μm, 100×4.6 mm; A=water+pH9 (Ammonium Bicarbonate 10 mM); B=MeCN; 40° C.; % B: 0 min 5%, 7.5 min 95%, 10 min 95%, 10.10 min 5%, 13.0 min 5%; 1.5 mL/min.

AnalpH9_MeOH_QC(Sunfire1): Waters Sunfire C18 (2) 5 μm, 100×4.6 mm; A=water+pH9 (Ammonium Bicarbonate 10 mM); B=MeOH+0.1% formic acid; 35° C.; % B: 0 min 5%, 7.5 min 95%, 10 min 95%, 10.10 min 5%, 13.0 min 5%; 1.5 mL/min.

Synthesis of 2H-isoquinolin-1-ones of Formula 4-9

Scheme A (via Route 1)

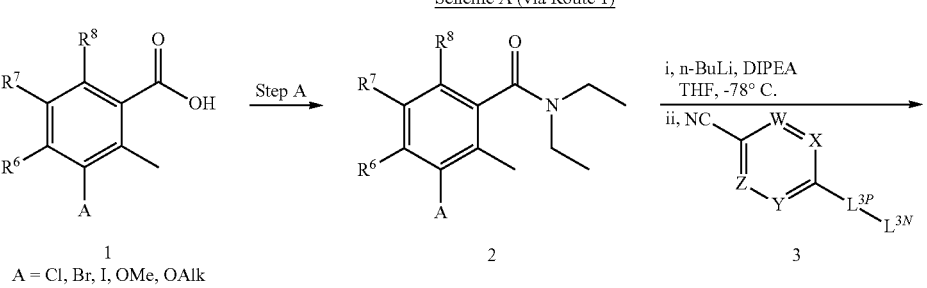

1
A = Cl, Br, I, OMe, OAlk

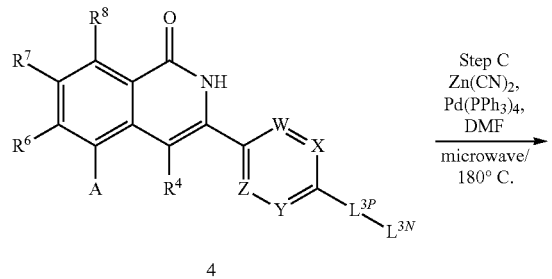

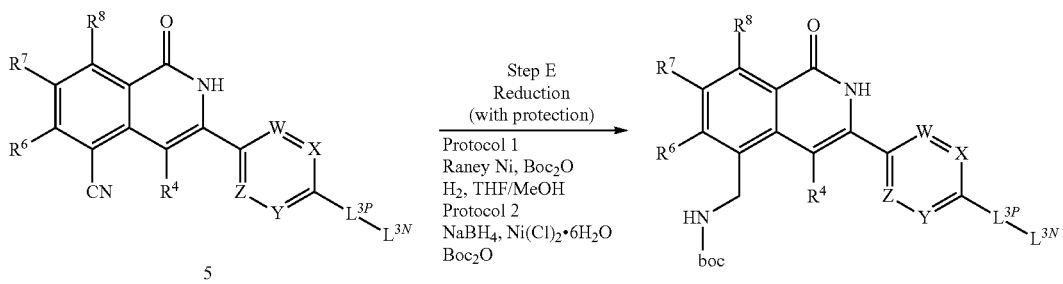

Protocol 1:
4M HCl/dioxane;
NBoc to NH ($R^{3N}$)
Protocol 2:
HCl/dioxane (4M);
OTBDPS to OH ($R^{3N}$)
Protocol 3:
BBr$_3$; OMe to OH ($R^{3N}$)

Step D
Deprotection step

TFA/CH$_2$Cl$_2$
or HCl/dioxane;
NBoc to NH

Step F
Deprotection step

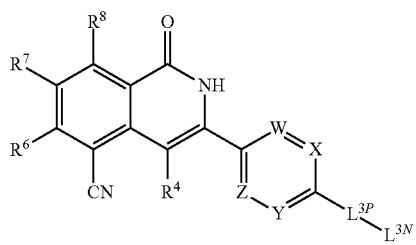

6

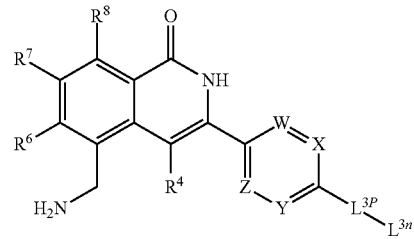

8

Protocol 1:
$R^iCHO$, $HCO_2H$;
N-alkylation
Protocol 2:
$R^iC(O)Cl$, DIPEA,
$CH_2Cl_2$, RT; N-acetylation
Protocol 3:
$R^iSO_2Cl$, DIPEA,
$CH_2Cl_2$, RT; N-sulfonylation Step G
Alkylation/
acylation/
sulfonylation

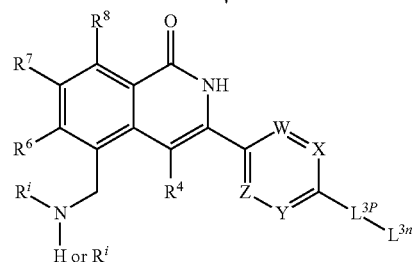

9

Scheme A, Step A: Synthesis of
N,N-Diethyl-benzamide derivatives 2

3-Bromo-N,N-diethyl-2-methyl-benzamide 40

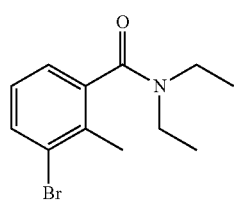

To a stirred solution of 3-bromo-2-methyl-benzoic acid (2.50 g, 11.6 mmol) in DMF (30 mL) was added N,N-diisopropylethylamine (6.20 mL, 34.9 mmol) and TBTU (3.70 g, 11.6 mmol) and the reaction mixture stirred at RT for 10 min. N,N-diethylamine (1.40 mL, 14 mmol) was added and the reaction mixture stirred for 18 h. The reaction mixture was diluted with $NaHCO_3$ (aq., sat.) solution (30 mL) and EtOAc (40 mL). The aqueous layer was separated and washed with EtOAc (2×40 mL). The combined organic extracts were washed with brine (3×50 mL), $H_2O$ (2×50 mL) and dried over $MgSO_4$ before concentrating in vacuo. The crude material was purified by silica gel column chromatography, eluting with isohexane and increasing the polarity to 50% EtOAc/isohexane to obtain 3-bromo-N,N-diethyl-2-methyl-benzamide as a yellow oil (3.00 g, 96%).

AnalpH2_MeOH_4min(1): Rt 2.86 min; m/z 270 [M+1]⁺.

Synthesis of Nitrile Intermediates 3 of Formula 12
(Required for Step B, Scheme A)

Scheme B

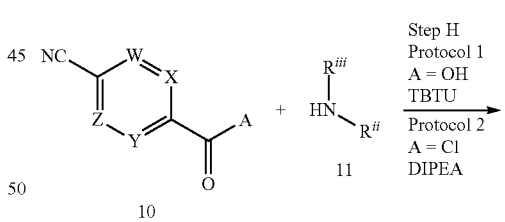

Step H
Protocol 1
A = OH
TBTU
Protocol 2
A = Cl
DIPEA

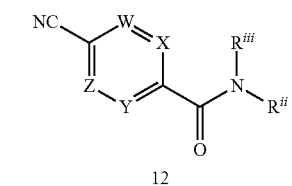

12

Scheme B, Step H (Protocol 1): Synthesis of Amide-Substituted Benzonitriles 12 (Via Acid Coupling)

4-Cyano-N-methyl-N-(1-methyl-piperidin-4-yl)-benzamide

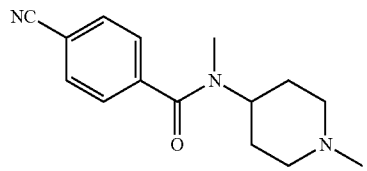 [SMILES: CN1CCC(N(C)C(=O)c2ccc(C#N)cc2)CC1]

To 4-cyanobenzoic acid (150 mg, 1.02 mmol) and TBTU (327 mg, 1.02 mmol) in DMF (11 mL) and CH$_2$Cl$_2$ (2 mL) was added N,N-diisopropylethylamine (178 μL, 1.02 mmol) and the reaction mixture stirred at RT for ~45 min. Methyl-(1-methyl-piperidin-4-yl)-amine (157 mg, 1.22 mmol) in CH$_2$Cl$_2$ (1 mL) was added and the reaction mixture was stirred for 16 h at RT. The crude material was diluted with CH$_2$Cl$_2$ and washed with 10%, aqueous NaHCO$_3$ (×2). The organic phases were combined, passed through a phase separation cartridge and concentrated in vacuo. The crude material was purified by silica gel column chromatography, eluting with CH$_2$Cl$_2$ and increasing the polarity to 15% MeOH/CH$_2$Cl$_2$ to afford 4-cyano-N-methyl-N-(1-methyl-piperidin-4-yl)-benzamide as a pale yellow solid (198 mg, 76%).

AnalpH9_MeOH_4min(2): Rt 1.97 min; m/z 258 [M+1]$^+$.

The following nitrile derivatives are prepared using analogous procedures.

Scheme B, Step H (Protocol 2): Synthesis of Amide-Substituted Benzonitriles 12 (Via Acid Chloride Coupling)

4-(4-Cyano-benzoyl)-piperazine-1-carboxylic acid tert-butyl ester

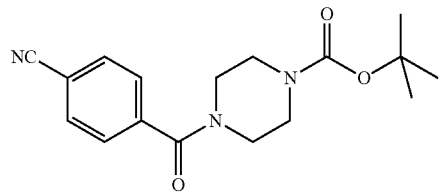 [SMILES: CC(C)(C)OC(=O)N1CCN(C(=O)c2ccc(C#N)cc2)CC1]

N,N-diisopropylethylamine (2.09 mL, 12 mmol) was added to 4-cyanobenzyl chloride (1 g, 6 mmol) and piperazine-1-carboxylic acid tert-butyl ester (1.11 g, 6 mmol) in anhydrous CH$_2$Cl$_2$ (5 mL) under N$_2$ at 0° C. The reaction mixture was allowed to warm to RT and stirred for 16 h. The reaction mixture was concentrated in vacuo, washed with satd., aqueous NaHCO$_3$ (×2), 2M HCl and brine. The organic phase was separated and passed through a phase separation cartridge and concentrated in vacuo. The crude material was purified by silica gel column chromatography, eluting with isohexane and increasing the polarity to 50% EtOAc/isohexane to afford 4-(4-cyano-benzoyl)-piperazine-1-carboxylic acid tert-butyl ester as a white solid (1.50 g, 79%).

AnalpH2_MeOH_4min(1): Rt 2.64 min; m/z 316 [M+1]$^+$.

TABLE 1

Amide-substituted Benzonitrile Intermediates 3 of Formula 12

| Compound | Analytical Data | Mass, % Yield, State |
|---|---|---|
|  | AnalpH2_MeOH_4 min(1): Rt 2.68 min; m/z 366 [M + Na]$^+$ | 693 mg quant., dark gold gum |
|  | AnalpH2_MeOH_4 min(1): Rt 1.95 min; m/z 263 [M + 1]$^+$ | 768 mg 86%, yellow oil |

Synthesis of Nitrile Intermediates 3 of Formula 14
(Required for Step B, Scheme A)

Synthesis of Nitrile Intermediates 3 of Formula 17
(Required for Step B, Scheme A)

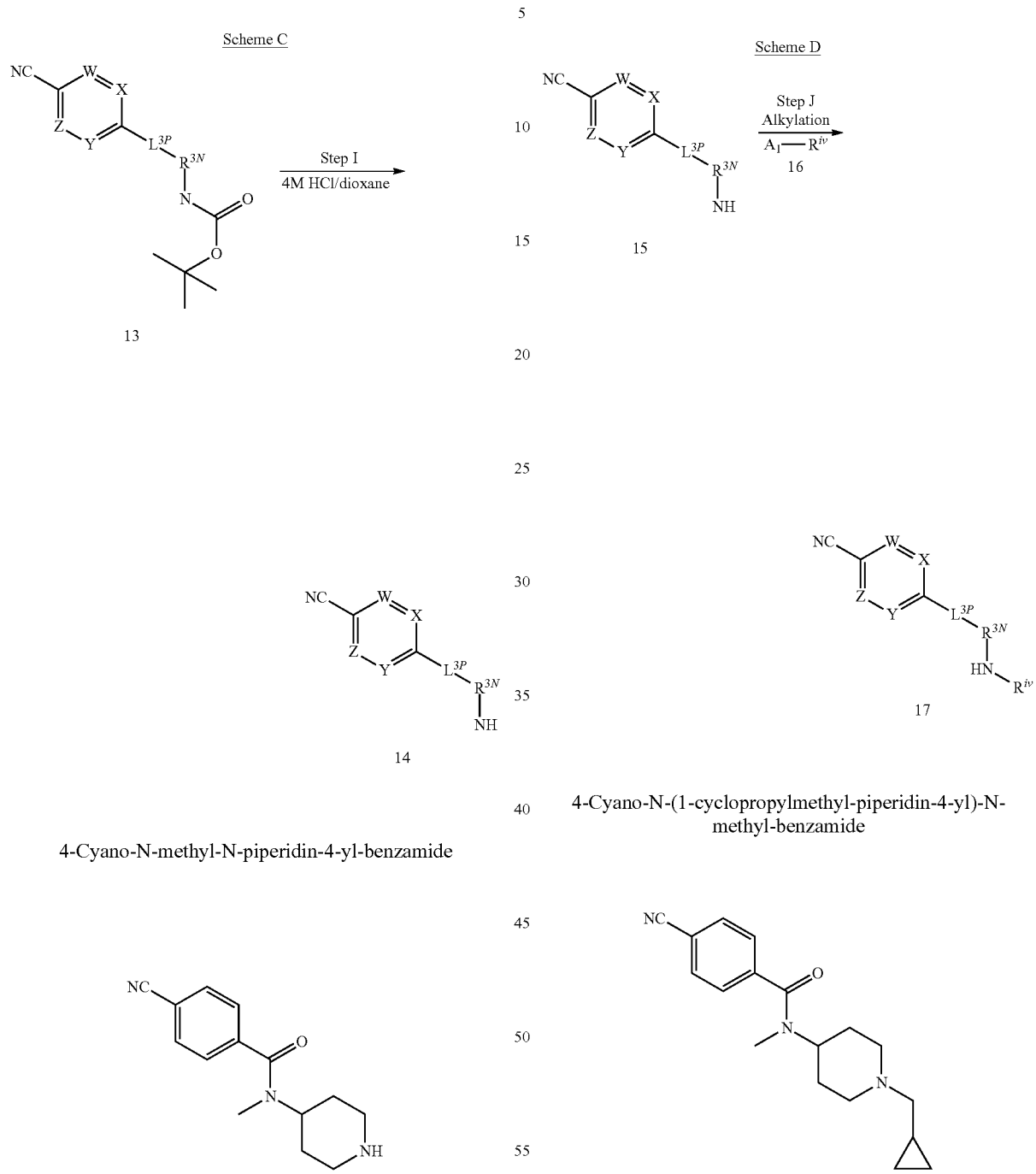

4-Cyano-N-methyl-N-piperidin-4-yl-benzamide

4-Cyano-N-(1-cyclopropylmethyl-piperidin-4-yl)-N-methyl-benzamide

4-[(4-cyano-benzoyl)-methyl-amino]-piperidine-1-carboxylic acid tert-butyl ester (450 mg, 1.31 mmol) was dissolved in CH$_2$Cl$_2$ (10 mL) followed by the addition of 4M HCl in dioxane/H$_2$O (5 mL) and the reaction stirred at RT for 2 h. The solvent was removed in vacuo and the crude product purified by reverse phase preparative HPLC-MS to obtain 4-cyano-N-methyl-N-piperidin-4-yl-benzamide as an orange solid (360 mg, quant.).

AnalpH2_MeOH_4min(1): Rt 0.69 min; m/z 244 [M+1]$^+$.

4-Cyano-N-methyl-N-piperidin-4-yl-benzamide (360 mg, 1.53 mmol), bromomethyl-cyclopropane (298 µL, 3.07 mmol) and K$_2$CO$_3$ (212 mg, 1.53 mmol) were suspended in DMF (3 mL) and the reaction mixture stirred at RT for 4 h. The solvent was removed in vacuo and the crude product purified by reverse phase preparative HPLC-MS to obtain 4-cyano-N-(1-cyclopropylmethyl-piperidin-4-yl)-N-methyl-benzamide as a pale yellow solid (270 mg, 59%).

AnalpH2_MeOH_4min(1): Rt 0.97 min; m/z 298 [M+1]$^+$.

Synthesis of Nitriles 3 of Formula 19 (Required for Step B, Scheme A)

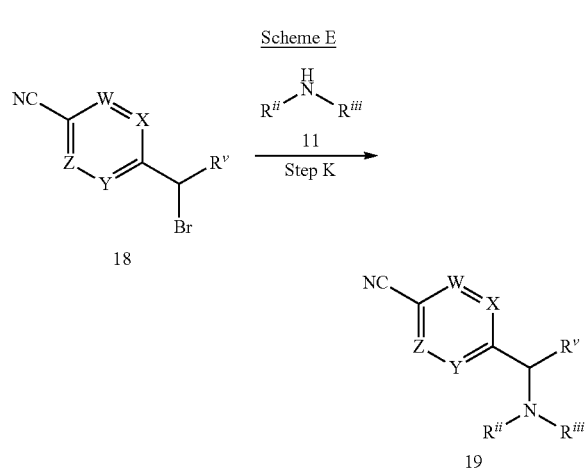

Synthesis of Amine Intermediates 11

3-(tert-Butyl-diphenyl-silanyloxy)-azetidine-1-carboxylic acid tert-butyl ester

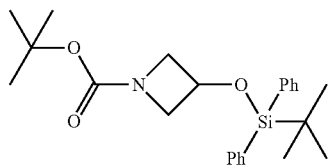 [SMILES: CC(C)(C)OC(=O)N1CC(O[Si](c2ccccc2)(c2ccccc2)C(C)(C)C)C1]

3-Hydroxy-azetidine-1-carboxylic acid tert-butyl ester (5 g, 29 mmol), tert-butyl(chloro)diphenylsilane (10.55 mL, 40 mmol) and imidazole (4.32 g, 63.2 mmol) in DMF (25 mL) were stirred at RT for 16 h. The crude reaction mixture was concentrated in vacuo and purified by silica gel column chromatography, eluting with isohexane and increasing the polarity to 40% EtOAc/isohexane to obtain 3-(tert-butyl-diphenyl-silanyloxy)-azetidine-1-carboxylic acid tert-butyl ester as a colourless oil which solidified on standing to a white solid (13.41 g, quant.).

AnalpH2_MeOH_4min(1): Rt 3.66 min; m/z 412 [M+1]$^+$.

3-(tert-Butyl-diphenyl-silanyloxy)-azetidine

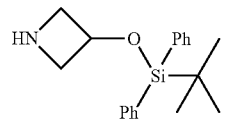 [SMILES: CC(C)(C)[Si](OC1CNC1)(c1ccccc1)c1ccccc1]

3-(tert-Butyl-diphenyl-silanyloxy)-azetidine-1-carboxylic acid tert-butyl ester (13.41 g, 32.6 mmol) was dissolved in CH$_2$Cl$_2$ (100 mL) followed by the addition of 4M HCl/dioxane (80 mL) and stirred at RT for 1 h. The reaction mixture was concentrated in vacuo and the crude material was purified by silica gel column chromatography, eluting with CH$_2$Cl$_2$ and increasing the polarity to 10% MeOH/CH$_2$Cl$_2$ to obtain 3-(tert-butyl-diphenyl-silanyloxy)-azetidine as a white solid (8.75 g, 78.5%).

AnalpH2_MeOH_4min(1): Rt 2.38 min; m/z 312 [M+1]$^+$.

Scheme E, Step K: Synthesis of Nitrile Intermediates 3 of Formula 19 (Via Halide Displacement)

4-(4-Dimethylamino-piperidin-1-ylmethyl)-benzonitrile

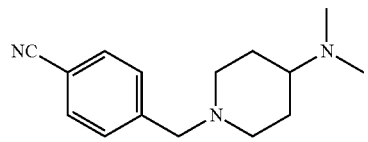 [SMILES: CN(C)C1CCN(Cc2ccc(C#N)cc2)CC1]

4-Bromomethyl benzonitrile (2 g, 10.2 mmol), 4-dimethylamino piperidine (1.56 g, 12.2 mmol) and K$_2$CO$_3$ (1.7 g, 12.2 mmol) in DMF (30 mL) were heated at 40° C. for 18 h. The reaction was diluted with H$_2$O (50 mL) and extracted with EtOAc (3×60 mL). The combined organic extracts were washed with H$_2$O (2×50 mL), brine (3×50 mL) and dried over MgSO$_4$. The reaction mixture was concentrated in vacuo and the crude material was purified by silica gel column chromatography, eluting with CH$_2$Cl$_2$ and increasing the polarity to 30% MeOH/CH$_2$Cl$_2$ to obtain 4-(4-dimethylamino-piperidin-1-ylmethyl)-benzonitrile as a white solid (1.4 g, 56%).

AnalpH2_MeOH_4min(1): Rt 2.40 min; m/z 244 [M+1]$^+$.

The following nitrile derivatives are prepared using analogous procedures.

TABLE 2

| Nitrile Intermediates 3 of formula 19 | | | |
|---|---|---|---|
| Compound | Reference | Analytical Data | Mass, % Yield, State |
| 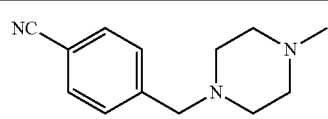 | Commercially available | | N/A |

TABLE 2-continued

Nitrile Intermediates 3 of formula 19

| Compound | Reference | Analytical Data | Mass, % Yield, State |
|---|---|---|---|
| [structure: NC-phenyl-CH2-N-bicyclic-N-Boc] | | AnalpH2_MeOH_ 4 min(1): Rt 2.82 min; m/z 328 [M + 1]+ | 194 mg, 100%, off-white solid |
| [structure: NC-phenyl-CH(CH3)-N-azetidine-O-Si(Ph)2-tBu] | | AnalpH2_MeOH_ 4 min(1): Rt 2.72 min; m/z 441 [M + 1]+ | 317 mg, 75%, colourless oil |
| [structure: NC-phenyl-CH2-N-pyrrolidine-NMe2] | | AnalpH2_MeOH_ 4 min(1): Rt 0.39 min; m/z 230 [M + 1]+ | 414 mg, 51%, orange oil |
| [structure: NC-phenyl-CH2-N-methylimidazole] | Commercially available | | N/A |

Synthesis of Nitriles 3 of Formula 21 (Required for Step B, Scheme A)

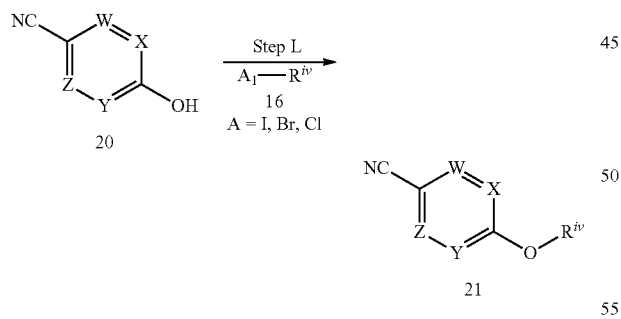

Scheme F

TABLE 3

Nitrile Intermediates 3 of formula 21

| Compound | Reference | Analytical Data | Mass, % Yield, State |
|---|---|---|---|
| [structure: NC-phenyl-O-CH2CH2-N(CH3)2] | Commercially available | | N/A |

Scheme A, Step B: Synthesis of
2H-isoquinolin-1-one derivatives of formula 4

5-Bromo-3-[4-(4-methyl-piperazin-1-ylmethyl)-phenyl]-2H-isoquinolin-1-one

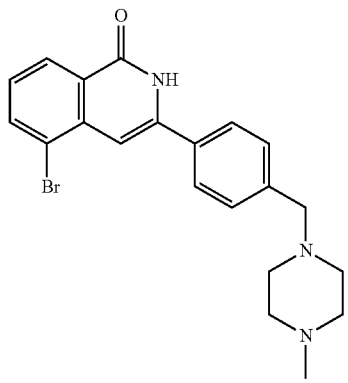 [SMILES: CN1CCN(Cc2ccc(-c3cc4c(Br)cccc4c(=O)[nH]3)cc2)CC1]

To a stirred solution of N,N-diisopropylamine (1.1 mL, 7.78 mmol) in THF (6.55 mL) under $N_2$ at −78° C. was added n-BuLi (2.5M in hexanes) (3.1 mL, 7.78 mmol) drop-wise and the reaction stirred at −78° C. for 20 min, after which time a solution of 3-bromo-N,N-diethyl-2-methyl-benzamide (701 mg, 2.59 mmol) in THF (6.5 mL) was added, and the reaction stirred at −78° C. for 20 minutes. A solution of 4-(4-methyl-piperazin-1-ylmethyl)-benzonitrile (559 mg, 2.59 mmol) in THF (6.5 mL) was added and the reaction stirred at -78° C. for 3 h. The reaction was added drop-wise into ice and extracted with EtOAc (2×50 mL). The organic layers were combined and passed through a phase separation cartridge and concentrated in vacuo. The crude material was triturated with isohexane/EtOAc (2:1), filtered and dried to afford 5-bromo-3-[4-(4-methyl-piperazin-1-ylmethyl)-phenyl]-2H-isoquinolin-1-one as a pale pink solid (845 mg, 79%).

$^1$H NMR (400 MHz, DMSO-$d_6$): δ 11.84-11.76 (brs, 1H), 8.23 (d, J=8.6 Hz, 1H), 8.04 (dd, J=7.6, 1.3 Hz, 1H), 7.74 (d, J=8.3 Hz, 2H), 7.44 (d, J=8.3 Hz, 2H), 7.41 (t, J=7.8 Hz, 1H), 6.87 (s, 1H), 3.52 (s, 2H), 2.46-2.25 (m, 8H), 2.16 (s, 3H).

AnalpH2_MeOH_4min(1): Rt 1.97 min; m/z 412 [M+1]$^+$.

The following 2H-isoquinolin-1-one derivatives are prepared using analogous procedures.

TABLE 4

| 2H-isoquinolin-1-one derivatives of Formula 4 | | |
| --- | --- | --- |
| Compound | Reference Analytical Data | Mass, % Yield, State |
| 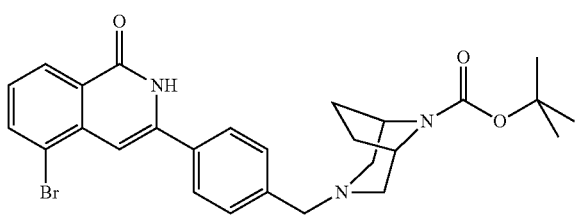 | $^1$H NMR (400 MHz, DMSO-$d_6$): δ 11.81-11.71 (br s, 1H), 8.22 (d, J = 8.1 Hz, 1H), 8.03 (dd, J = 7.6, 1.3 Hz, 1H), 7.73 (d, J = 8.8 Hz, 2H), 7.38 (t, J = 7.8 Hz, 1H), 7.08 (d, J = 8.8 Hz, 2H), 6.80 (s, 1H), 4.12 (t, J = 5.8 Hz, 2H), 2.65 (t, J = 5.8 Hz, 2H), 2.23 (s, 6H). AnalpH2_MeOH_QC: Rt 5.69 min; m/z 387.0 [M + 1]$^+$ | 1.23 g, 86%, off-white solid |
| (structure with Boc-protected bicyclic amine) | AnalpH2_MeOH_4min(1): Rt 3.29 min; m/z 524 [M + 1]$^+$. | 32 mg, 20%, off-white solid |

TABLE 4-continued 2H-isoquinolin-1-one derivatives of Formula 4

| Compound | Reference | Analytical Data | Mass, % Yield, State |
|---|---|---|---|
| | | AnalpH2_MeOH_4min(1): Rt 3.24 min; m/z 512 [M + 1]+. | 187 mg, 19%, yellow solid |
| | | AnalpH2_MeOH_4min(1): Rt 1.85 min; m/z 454 [M + 1]+. | 122 mg, 71%, pale yellow solid |
| | | AnalpH2_MeOH_4min(1): Rt 1.97 min; m/z 494.5 [M + 1]+. | 213 mg, 47%, orange solid |

TABLE 4-continued 2H-isoquinolin-1-one derivatives of Formula 4

| Compound | Reference Analytical Data | Mass, % Yield, State |
|---|---|---|
| 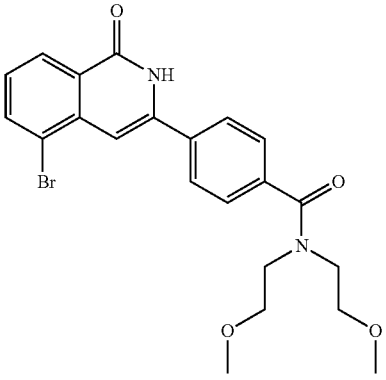 [SMILES: COCCN(CCOC)C(=O)c1ccc(-c2cc3c(Br)cccc3c(=O)[nH]2)cc1] | AnalpH2_MeOH_4min(1): Rt 3.01 min; m/z 460 [M + 1]$^+$. | 118 mg, 13%, yellow solid |
| 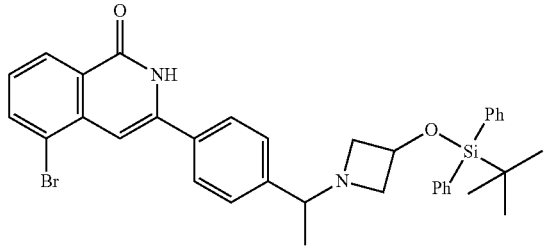 [SMILES: CC(c1ccc(-c2cc3c(Br)cccc3c(=O)[nH]2)cc1)N1CC(O[Si](c2ccccc2)(c2ccccc2)C(C)(C)C)C1] | AnalpH2_MeOH_4min(1): Rt 3.00 min; m/z 637 [M + 1]$^+$. | 918 mg, quant, dark green oil |
| 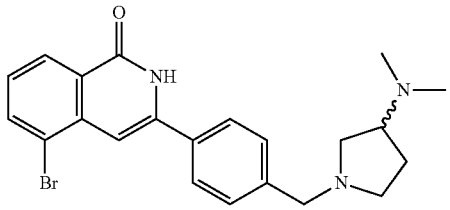 [SMILES: CN(C)C1CCN(Cc2ccc(-c3cc4c(Br)cccc4c(=O)[nH]3)cc2)C1] | AnalpH2_MeOH_4min(1): Rt 1.65 min; m/z 426 [M + 1]$^+$. | 7 mg, 2%, colourless oil |
| 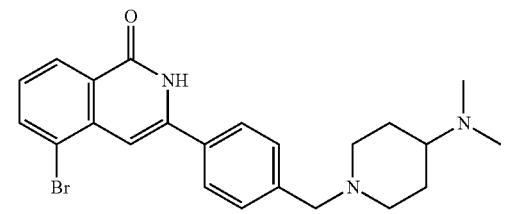 | AnalpH2_MeOH_4min(1): Rt 1.40 min; m/z 444 [M + 1]$^+$. | 1 g, quant., white solid |
| 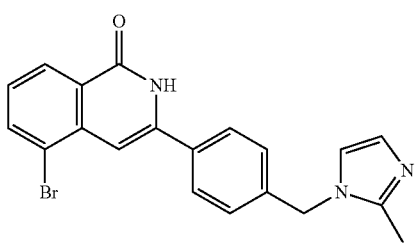 [SMILES: Cc1nccn1Cc1ccc(-c2cc3c(Br)cccc3c(=O)[nH]2)cc1] | AnalpH2_MeOH_4min(1): Rt 1.92 min; m/z 394 [M + 1]$^+$. | 41 mg, 14%, white solid |

TABLE 4-continued 2H-isoquinolin-1-one derivatives of Formula 4

| Compound | Reference | Analytical Data | Mass, % Yield, State |
|---|---|---|---|
| (structure: 7-fluoro-5-bromo-3-[4-(4-methyl-piperazin-1-ylmethyl)-phenyl]-2H-isoquinolin-1-one with formic acid) | | AnalpH2_MeOH_QC(2): Rt 5.78 min; m/z 430.4 [M + 1] | 43 mg, 36%, light brown solid |

Scheme A, Step C: Synthesis of 5-nitrile-2H-isoquinolin-1-one derivatives of formula 5

3-[4-(4-Methyl-piperazin-1-ylmethyl)-phenyl]-1-oxo-1,2-dihydro-isoquinoline-5-carbonitrile (IQ-002)

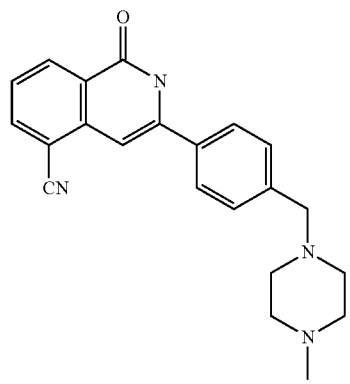 [SMILES: CN1CCN(Cc2ccc(-c3cc4c(C#N)cccc4c(=O)[nH]3)cc2)CC1]

5-Bromo-3-[4-(4-methyl-piperazin-1-ylmethyl)-phenyl]-2H-isoquinolin-1-one (30 mg, 0.073 mmol), zinc cyanide (11 mg, 0.087 mmol) and Pd(PPh$_3$)$_4$ (9 mg, 0.007 mmol) were added to a microwave vial followed by DMF (purged with N$_2$ for 10 min.). The reaction mixture was irradiated using a microwave reactor (300 W, 180° C., 30 min). The reaction mixture was diluted with EtOAc (30 mL), washed with 1M NaHCO$_3$ (30 mL) and filtered to remove solids. The organic phase was separated and passed through a phase separator cartridge and concentrated in vacuo. The crude compound was dissolved in CH$_2$Cl$_2$/MeOH (1:1) and passed through a Si-thiol cartridge, eluting with CH$_2$Cl$_2$/MeOH (1:1) and the solvent removed in vacuo. The crude material was purified by silica gel column chromatography, eluting with CH$_2$Cl$_2$ and increasing the polarity to 10% MeOH/CH$_2$Cl$_2$ to obtain 3-[4-(4-methyl-piperazin-1-ylmethyl)-phenyl]-1-oxo-1,2-dihydro-isoquinoline-5-carbonitrile as a light brown solid (167 mg, 68%).

$^1$H NMR (400 MHz, DMSO-d$_6$): δ 12.04-11.97 (br s, 1H), 8.52 (d, J=7.8 Hz, 1H), 8.30 (dd, J=1.3, 7.3 Hz, 1H), 7.81 (d, J=8.1 Hz, 2H), 7.65 (t, J=7.8 Hz, 1H), 7.49 (d, J=8.1 Hz, 2H), 6.83 (s, 1H), 3.56 (s, 2H), 2.48-2.26 (br, 8H), 2.19 (s, 3H).

AnalpH2_MeOH_QC(Sunfirel): Rt 4.09 min; m/z 359 [M+1]$^+$.

The following 5-cyano-2H-isoquinolin-1-one derivatives are prepared using analogous procedures.

TABLE 5

5-Cyano-2H-isoquinolin-1-one of Formula 5

| Compound | Reference | Analytical Data | Mass, % Yield, State |
|---|---|---|---|
| (structure: 5-cyano-3-[4-(2-dimethylaminoethoxy)phenyl]-2H-isoquinolin-1-one) | IQ-001 | $^1$H NMR (400 MHz, DMSO-d$_6$): δ 11.98-11.86 (br s, 1H), 8.47 (dd, J = 8.1, 0.8 Hz, 1H), 8.25 (dd, J = 7.6, 1.3 Hz, 1H), 7.77 (d, J = 9.1 Hz, 2H), 7.59 (t, J = 7.6 Hz, 1H), 7.10 (d, J = 9.1 Hz, 2H), 6.75 (d, J = 0.8 Hz, 1H), 4.14 (t, J = 5.8 Hz, 2H), 2.66 (t, J = 5.8 Hz, 2H), 2.24 (s, 6H). | 12 mg, 46%, pale yellow solid |

TABLE 5-continued

5-Cyano-2H-isoquinolin-1-one of Formula 5

| Compound | Reference | Analytical Data | Mass, % Yield, State |
|---|---|---|---|
| | | AnalpH2_MeOH_QC: Rt 4.93 min; m/z 334.3 [M + 1]⁺ | |
| (structure) | | AnalpH2_MeOH_4min(1): Rt 2.71 min; m/z 4.71 [M + 1]⁺. | 45 mg, quant., brown solid |
| (structure) | | AnalpH2_MeOH_4min(1): Rt 2.93 min; m/z 459 [M + 1]⁺. | 165 mg, quant., light brown solid |
| (structure) | IQ-005 | ¹H NMR (400 MHz, DMSO-d₆): δ 12.13-12.09 (br s, 1H), 8.50 (br d, J = 7.6 Hz, 1H), 8.30 (dd, J = 7.6, 1.5 Hz, 1H), 7.88 (br d, J = 8.3 Hz, 2H), 7.65 (t, J = 7.8 Hz, 1H), 7.55-7.50 (m, 2H), 6.86 (s, 1H), 4.32-4.26 (br s, 0.4H), 2.91-2.72 (m, 5H), 2.20-2.06 (m, 4H), 1.95-1.88 (m, 2H), 1.67-1.56 (m, 3H). AnalpH2_MeOH_QC(1): Rt 4.85 min; m/z 401.2 [M + 1]⁺. | 48 mg, 34%, off-white solid |

TABLE 5-continued
5-Cyano-2H-isoquinolin-1-one of Formula 5
| Compound | Reference | Analytical Data | Mass, % Yield, State |
|---|---|---|---|
| 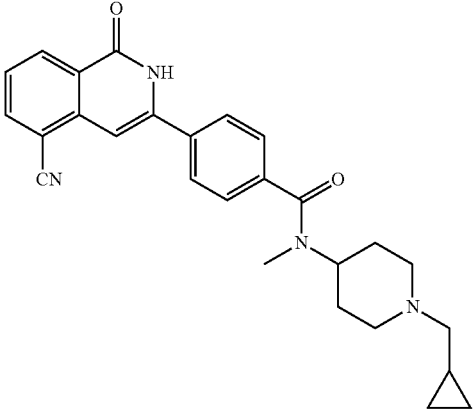 [SMILES: CN(C(=O)c1ccc(-c2cc3c(C#N)cccc3c(=O)[nH]2)cc1)C1CCN(CC2CC2)CC1] | IQ-006 | AnalpH2_MeOH_QC(1): Rt 5.17 min; m/z 441.4 [M + 1]+ | 84.6 mg, 46%, off-white solid |
| 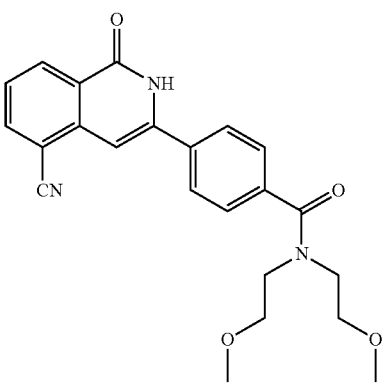 [SMILES: COCCN(CCOC)C(=O)c1ccc(-c2cc3c(C#N)cccc3c(=O)[nH]2)cc1] | IQ-008 | AnalpH2_MeOH_QC(1): Rt 7.33 min; m/z 406.5 [M + 1]+ | 77 mg, 75%, pale yellow solid |
| 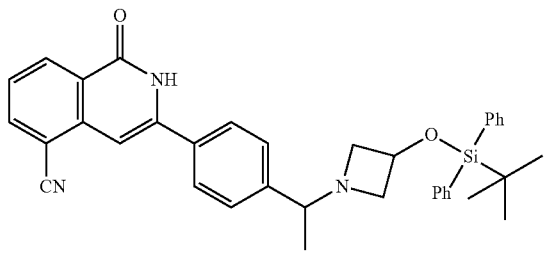 | | AnalpH2_MeOH_4min(1): Rt 2.78 min; m/z 587 [M + 1]+. | 130 mg, 35%, pale orange solid |
| 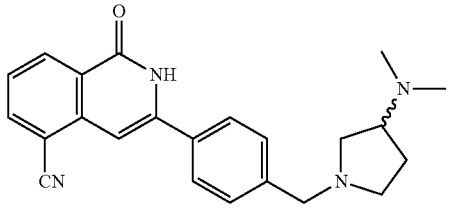 [SMILES: CN(C)C1CCN(Cc2ccc(-c3cc4c(C#N)cccc4c(=O)[nH]3)cc2)C1] | IQ-011 | AnalpH2_MeOH_QC(1): Rt 4.03 min; m/z 373.5 [M + 1]+. | 1.6 mg, 32%, white solid |

TABLE 5-continued

5-Cyano-2H-isoquinolin-1-one of Formula 5

| Compound | Reference | Analytical Data | Mass, % Yield, State |
|---|---|---|---|
| 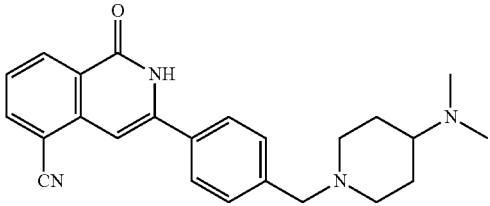 [SMILES: CN(C)C1CCN(Cc2ccc(-c3cc4c(C#N)cccc4c(=O)[nH]3)cc2)CC1] | IQ-012 | $^1$H NMR (400 MHz, DMSO-d$_6$): δ 11.95-11.83 (br s, 1H), 8.48 (br d, J = 8.1 Hz, 1H), 8.27 (dd, J = 7.3, 1.3 Hz, 1H), 7.77 (br d, J = 8.3 Hz, 2H), 7.62 (t, J = 7.6 Hz, 1H), 7.45 (br d, J = 8.3 Hz, 2H), 6.79 (s, 1H), 3.50 (s, 2H), 2.83 (br d, J = 11.6 Hz, 2H), 2.15 (s, 6H), 2.07-1.98 (m, 1H), 1.94 (br t, J = 11.6 Hz, 2H), 1.69 (br d, J = 12.4 Hz, 2H), 1.43-1.33 (m, 2H). AnalpH2_MeOH_QC(1): Rt 3.61 min; m/z 387.5 [M + 1]$^+$. | 100 mg, 11%, white solid |
| 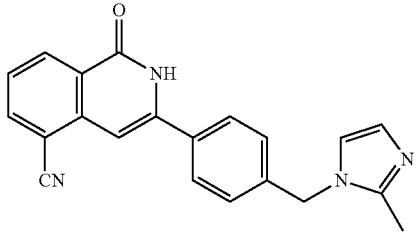 [SMILES: Cc1nccn1Cc1ccc(-c2cc3c(C#N)cccc3c(=O)[nH]2)cc1] | IQ-013 | $^1$H NMR (400 MHz, DMSO-d$_6$): δ 12.06-12.02 (br s, 1H), 8.49 (d, J = 8.1 Hz, 1H), 8.28 (dd, J = 7.3, 1.3 Hz, 1H), 7.81 (d, J = 8.3 Hz, 2H), 7.63 (t, J = 7.8 Hz, 1H), 7.29 (d, J = 8.3 Hz, 2H), 7.19 (d, J = 1.3 Hz, 1H), 6.80 (d, J = 4.0 Hz, 2H), 5.25 (s, 2H), 2.25 (s, 3H). AnalpH2_MeOH_QC(2): Rt 4.39 min; m/z 341.4 [M + 1]$^+$. | 19 mg, 58%, pale pink solid |
| 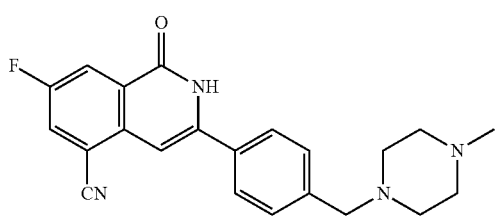 [SMILES: CN1CCN(Cc2ccc(-c3cc4c(C#N)cc(F)cc4c(=O)[nH]3)cc2)CC1] | IQ-014 | AnalpH2_MeOH_QC(2): Rt 4.91 min; m/z 377.5 [M + 1]$^+$. | 23 mg, 71%, pale yellow solid |

Scheme A, Step D (Protocol 1): Synthesis of 5-Cyano-2H-isoquinolin-1-one derivatives of formula 6 (via Boc deprotection)

1-Oxo-3-[4-(piperazine-1-carbonyl)-phenyl]-1,2-dihydro-isoquinoline-5-carbonitrile (IQ-004)

Scheme A, Step D (Protocol 2): Synthesis of 5-cyano-2H-isoquinolin-1-one derivatives of formula 6 (via TBDPS deprotection)

3-{4-[1-(3-Hydroxy-azetidin-1-yl)-ethyl]-phenyl}-1-oxo-1,2-dihydro-isoquinoline-5-carbonitrile (IQ-009)

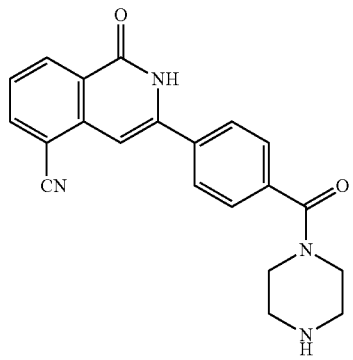 [SMILES: N#Cc1cccc2c(=O)[nH]c(-c3ccc(C(=O)N4CCNCC4)cc3)cc12]

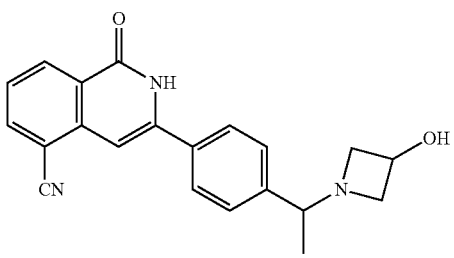 [SMILES: CC(c1ccc(-c2cc3c(C#N)cccc3c(=O)[nH]2)cc1)N1CC(O)C1]

4M HCl/dioxane (5 mL) was added to 4-[4-(5-cyano-1-oxo-1,2-dihydro-isoquinolin-3-yl)-benzoyl]-piperazine-1-carboxylic acid tert-butyl ester and the reaction mixture stirred at RT for 3 h. The solvent was removed in vacuo and the crude product was loaded as a MeOH suspension onto a SCX-2 column (5 g). The column was washed with MeOH, EtOAc, DCM, MeCN, isohexane, Et$_2$O and MeOH/H$_2$O (1:1). The desired product was eluted from the cartridge with 0.4M NH$_3$/MeOH and concentrated in vacuo. The crude product was purified by reverse phase preparative HPLC-MS to obtain 1-oxo-3-[4-(piperazine-1-carbonyl)-phenyl]-1,2-dihydro-isoquinoline-5-carbonitrile as a white solid (10.9 mg, 9%).

$^1$H NMR (400 MHz, DMSO-d$_6$): δ 8.50 (d, J=7.8 Hz, 1H), 8.30 (dd, J=7.6, 1.3 Hz, 1H), 7.88 (d, J=8.3 Hz, 2H), 7.65 (t, J=7.8 Hz, 1H), 7.54 (d, J=8.3 Hz, 2H), 6.84 (s, 1H), 3.57 (m, 2H), 3.27 (m, 2H), 2.75 (m, 2H), 2.65 (m, 2H).

AnalpH9_MeOH_QC(1): Rt 6.37 min; m/z 359.2 [M+1]$^+$.

The following 5-cyano-2H-isoquinolin-1-one derivatives are prepared using analogous procedures.

To 3-(4-{1-[3-(tert-butyl-diphenyl-silanyloxy)-azetidin-1-yl]-ethyl}-phenyl)-1-oxo-1,2-dihydro-isoquinoline-5-carbonitrile (130 mg, 0.22 mmol) in CH$_2$Cl$_2$ (5 mL) was added 4M HCl/dioxane (1 mL) and the reaction stirred at RT for 16 h. A further portion of 4M HCl/dioxane (2 mL) added and the reaction mixture stirred at RT for 21 h. The reaction mixture was concentrated in vacuo and the crude residue purified by reverse phase preparative HPLC-MS to afford 3-{4-[1-(3-hydroxy-azetidin-1-yl)-ethyl]-phenyl}-1-oxo-1,2-dihydro-isoquinoline-5-carbonitrile as a white solid (45 mg, 58%).

AnalpH2_MeOH_QC(1): Rt 4.91 min; m/z 346.4 [M+1]$^+$.

TABLE 6

5-Cyano-2H-isoquinolin-1-one of Formula 6

| Compound | Reference | Analytical Data | Mass, % Yield, State |
|---|---|---|---|
| ![structure] | IQ-003 | AnalpH2_MeOH_QC(1): Rt 5.64 min; m/z 371.2 [M + 1]$^+$ | 0.66 mg, 2%, pale cream solid |

Scheme A, Step D (Protocol 3): Synthesis of 5-cyano-2H-isoquinolin-1-one derivatives of formula 6 (via OMe deprotection)

4-(5-Cyano-1-oxo-1,2-dihydro-isoquinolin-3-yl)-N,N-bis-(2-hydroxy-ethyl)-benzamide (IQ-010)

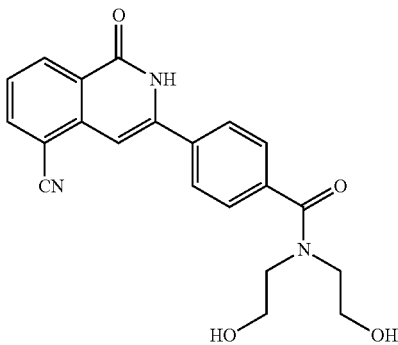 [SMILES: N#Cc1cccc2c(=O)[nH]c(-c3ccc(C(=O)N(CCO)CCO)cc3)cc12]

To a stirred solution of 4-(5-cyano-1-oxo-1,2-dihydro-isoquinolin-3-yl)-N,N-bis-(2-methoxy-ethyl)-benzamide (40 mg, 0.10 mmol) in $CH_2Cl_2$ (2.5 mL) under $N_2$ at −78° C. was added boron tribromide (1M in $CH_2Cl_2$, 2.5 mL, 2.5 mmol). The reaction was allowed to warm to RT and stirred for 6 h. The reaction mixture was concentrated in vacuo and suspended in $CH_2Cl_2/H_2O$ (1:1) resulting in the precipitation of a white solid. The solid was filtered and the crude product was purified by reverse phase preparative HPLC-MS to obtain 4-(5-cyano-1-oxo-1,2-dihydro-isoquinolin-3-yl)-N,N-bis-(2-hydroxy-ethyl)-benzamide as a white solid (10 mg, 27%).
$^1$H NMR (400 MHz, DMSO-$d_6$): δ 12.19-12.11 (brs, 1H), 8.53 (d, J=7.9 Hz, 1H), 8.32 (dd, J=7.6, 1.3 Hz, 1H), 7.90 (d, J=8.3 Hz, 2H), 7.68 (t, J=7.8 Hz, 1H), 7.59 (d, J=8.3 Hz, 2H), 6.79 (s, 1H), 4.91-4.84 (m, 2H), 3.69-3.65 (m, 2H), 3.59-3.56 (m, 2H), 3.52-3.49 (m, 2H).
AnalpH2_MeOH_QC(1): Rt 6.19 min; m/z 378.4 $[M+1]^+$.

Scheme A, Step E (Protocol 1): Synthesis of 2H-isoquinolin-1-one derivatives of formula 7 (via nitrile reduction)

{3-[4-(4-Methyl-piperazin-1-ylmethyl)-phenyl]-1-oxo-1,2-dihydro-isoquinolin-5-ylmethyl}-carbamic acid tert-butyl ester

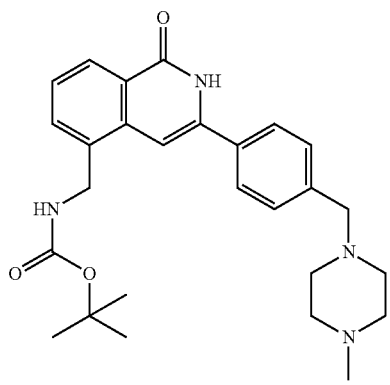 [SMILES: CN1CCN(Cc2ccc(-c3cc4c(CNC(=O)OC(C)(C)C)cccc4c(=O)[nH]3)cc2)CC1]

To a slurry of 3-[4-(4-Methyl-piperazin-1-ylmethyl)-phenyl]-1-oxo-1,2-dihydro-isoquinoline-5-carbonitrile (151 mg, 0.42 mmol) in 1:1 THF/MeOH (10 mL) was added di-tert-butyl dicarbonate (138 mg, 0.63 mmol) in 1:1 THF/MeOH (1 mL) and Raney nickel (50% slurry in $H_2O$, 2 mL). The reaction mixture was evacuated and purged with a $N_2$ balloon (×2) then evacuated and purged with a $H_2$ balloon. The reaction mixture was allowed to stir at RT for 16 h under an atmosphere of $H_2$ (2×balloons). The reaction mixture was filtered through a Celite® pad, washed with MeOH and EtOAc. The combined filtrates were concentrated in vacuo. The crude product was purified by reverse phase preparative HPLC-MS to obtain {3-[4-(4-methyl-piperazin-1-ylmethyl)-phenyl]-1-oxo-1,2-dihydro-isoquinolin-5-ylmethyl}-carbamic acid tert-butyl ester as a white solid (47 mg, 24%).
AnalpH9_MeOH_4min(1): Rt 2.07 min; m/z 463 $[M+1]^+$.

Scheme A, Step E (Protocol 2): Synthesis of 2H-isoquinolin-1-one derivatives of formula 7 (via nitrile reduction)

{3-[4-(2-Methoxymethyl-imidazol-1-ylmethyl)-phenyl]-1-oxo-1,2-dihydro-isoquinolin-5-ylmethyl}-carbamic acid tert-butyl ester

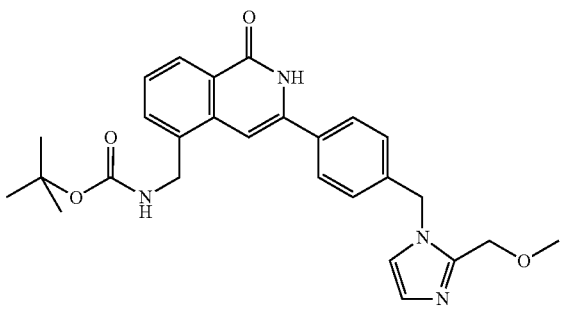 [SMILES: COCc1nccn1Cc1ccc(-c2cc3c(CNC(=O)OC(C)(C)C)cccc3c(=O)[nH]2)cc1]

3-[4-(2-Methoxymethyl-imidazol-1-ylmethyl)-phenyl]-1-oxo-1,2-dihydro-isoquinoline-5-carbonitrile (10 mg, 0.027 mmol), $NiCl_2$ (3.5 mg, 0.027 mmol) and di-tert-butyl dicarbonate (11.8 mg, 0.054 mmol) were suspended in 1:1 THF/MeOH (0.2 mL) and cooled to 0° C. Sodium borohydride (7.15 mg, 0.189 mmol) was added and the reaction was stirred at RT for 15 h. Additional sodium borohydride (7.15 mg, 0.189 mmol) was added and the reaction was stirred at RT for 90 min. Water (2 ml) was added to the reaction mixture and the product was extracted with $CH_2Cl_2$ (3×1 ml). The organic extracts were combined and filtered through a hydrophobic frit and concentrated in vacuo to afford {3-[4-(2-methoxymethyl-imidazol-1-ylmethyl)-phenyl]-1-oxo-1,2-dihydro-isoquinolin-5-ylmethyl}-carbamic acid tert-butyl ester as an off-white solid (10.5 mg, 82%).
AnalpH2_MeOH_4min(2): Rt 2.19 min; m/z 475.5 $[M+1]^+$.

The following 2H-isoquinolin-1-one derivatives are prepared using analogous procedures.

TABLE 7

2H-isoquinolin-1-ones of Formula 7

| Compound | Reference | Analytical Data | Mass, % Yield, State |
|---|---|---|---|
| 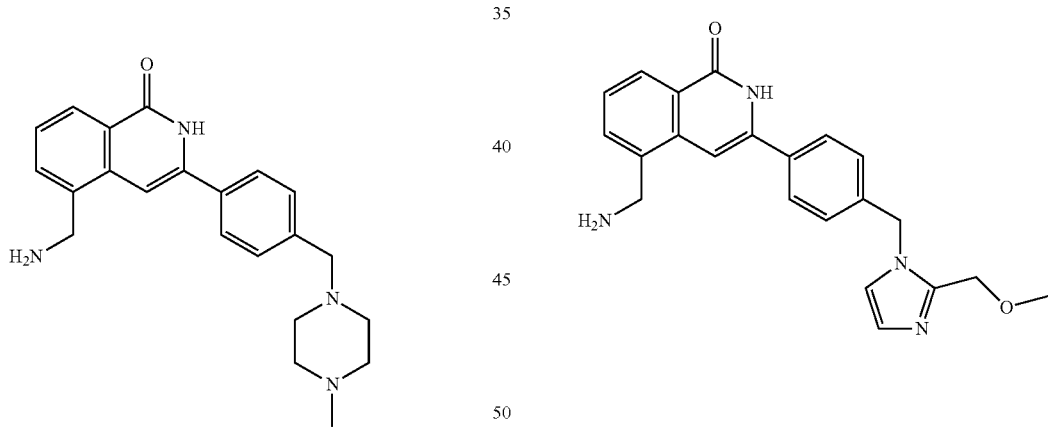 | | AnalpH2_MeOH_4 min(2): Rt 2.27 min; m/z 531.6 [M + 1]⁺. | 27.4 mg, quant., off-white solid. |

Scheme A, Step F: Synthesis of 2H-isoquinolin-1-one derivatives of formula 8 (via Boc-deprotection)

5-Aminomethyl-3-[4-(4-methyl-piperazin-1-ylmethyl)-phenyl]-2H-isoquinolin-1-one

5-Aminomethyl-3-[4-(2-methoxymethyl-imidazol-1-ylmethyl)-phenyl]-2H-isoquinolin-1-one (IQ-023)

To {3-[4-(4-methyl-piperazin-1-ylmethyl)-phenyl]-1-oxo-1,2-dihydro-isoquinolin-5-ylmethyl}-carbamic acid tert-butyl ester (112 mg, 0.24 mmol) was added CH$_2$Cl$_2$/TFA 2:1 (1.5 mL) and the reaction mixture stirred at RT for 1 h. The solvent was removed in vacuo and combined with a previous sample for further purification. The combined sample was passed through a SCX-2 cartridge, washing with MeOH (3×column volumes) and the compound eluted from the cartridge with 0.5M NH$_3$/MeOH (3×column volumes) to afford 5-aminomethyl-3-[4-(4-methyl-piperazin-1-ylmethyl)-phenyl]-2H-isoquinolin-1-one as a pale yellow solid (102 mg, 98%) which was used in the next step without further purification.

AnalpH2_MeOH_4min(1): Rt 1.40 min; m/z 363 [M+1]+

4M HCl in dioxane (0.105 mL, 0.421 mmol) was added to a solution of {3-[4-(2-methoxymethyl-imidazol-1-ylmethyl)-phenyl]-1-oxo-1,2-dihydro-isoquinolin-5-ylmethyl}-carbamic acid tert-butyl ester (10 mg, 0.021 mmol) in methanol (0.2 ml). The reaction was stirred at RT for 90 min. The reaction mixture was concentrated in vacuo and purified by reverse phase preparative HPLC-MS to obtain 5-aminomethyl-3-[4-(2-methoxymethyl-imidazol-1-ylmethyl)-phenyl]-2H-isoquinolin-1-one as a white solid (3.8 mg, 48%).

AnalpH9_MeOH_QC(2): Rt 6.22 min; m/z 375.5 [M+1]⁺.

The following 2H-isoquinolin-1-one derivatives are prepared using analogous procedures.

TABLE 8

2H-isoquinolin-1-ones of Formula 8

| Compound | Reference | Analytical Data | Mass, % Yield, State |
|---|---|---|---|
|  | IQ-022 | AnalpH9_MeOH_QC(2): Rt 6.62 min; m/z 431.5 [M + 1]+. | 8.3 mg, 27% White solid |

Scheme A, Step G (Protocol 1): Synthesis of 2H-isoquinolin-1-one derivatives of formula 9 (via alkylation)

5-Dimethylaminomethyl-3-[4-(4-methyl-piperazin-1-ylmethyl)-phenyl]-2H-isoquinolin-1-one (IQ-024)

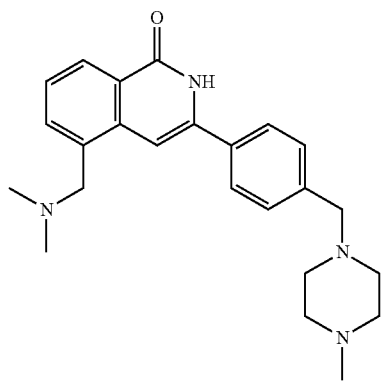 [SMILES: CN(C)Cc1cccc2c(=O)[nH]c(-c3ccc(CN4CCN(C)CC4)cc3)cc12]

5-Aminomethyl-3-[4-(4-methyl-piperazin-1-ylmethyl)-phenyl]-2H-isoquinolin-1-one (35 mg, 0.097 mmol), formaldehyde (7.2 µL, 37% aqueous solution, 0.097 mmol) and formic acid (4.5 mg, 0.097 mmol) in DMSO (0.5 mL) were placed in a microwave vial. The reaction mixture was irradiated using a microwave reactor (300 W, 180° C., 2 min). The crude reaction mixture was purified by reverse phase preparative HPLC-MS to obtain 5-dimethylaminomethyl-3-[4-(4-methyl-piperazin-1-ylmethyl)-phenyl]-2H-isoquinolin-1-one as a yellow solid (13 mg, 36%).

$^1$H NMR (400 MHz, DMSO-$d_6$): δ 11.64-11.54 (brs, 1H), 8.53 (d, J=7.8 Hz, 1H), 7.83 (d, J=8.1 Hz, 2H), 7.70 (d, J=7.1 Hz, 1H), 7.52-7.49 (m, 3H), 7.13 (s, 1H), 3.77 (s, 2H), 3.60 (s, 2H), 2.53-2.36 (m, 8H), 2.28 (s, 6H), 2.25 (s, 3H).

AnalpH9_MeOH_QC(Sunfirel): Rt 7.32 min; m/z 391.4 [M+1]+.

Scheme A, Step G (Protocol 2): Synthesis of 2H-isoquinolin-1-one Derivatives of formula 9 (via acetylation)

N-{3-[4-(4-Methyl-piperazin-1-ylmethyl)-phenyl]-1-oxo-1,2-dihydro-isoquinolin-5-ylmethyl}-acetamide (IQ-025)

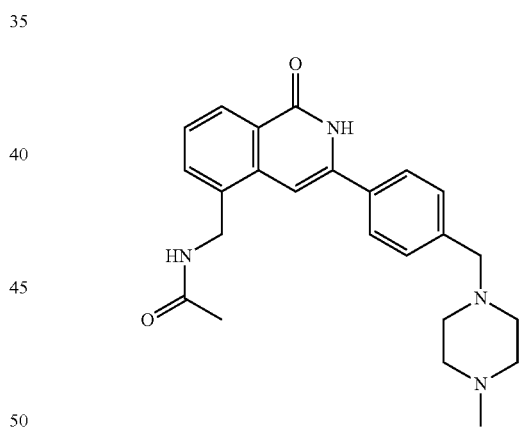

To 5-aminomethyl-3-[4-(4-methyl-piperazin-1-ylmethyl)-phenyl]-2H-isoquinolin-1-one (33 mg, 0.092 mmol) was added acetyl chloride (0.5 mL, 0.24M in $CH_2Cl_2$, 0.12 mmol) followed by DIPEA (0.5 mL, 0.28M in $CH_2Cl_2$, 0.14 mmol). The reaction vessel was purged with $N_2$ and stirred at RT for 5 h. MeOH was added and the reaction mixture was applied to a SCX-2 (1 g) cartridge. The cartridge was washed with MeOH (2×column volumes). The desired product was eluted from the column with 0.5M $NH_3$/MeOH (3×column volumes) and the solvent removed in vacuo. The crude product was purified by reverse phase preparative HPLC-MS to obtain N-{3-[4-(4-methyl-piperazin-1-ylmethyl)-phenyl]-1-oxo-1,2-dihydro-isoquinolin-5-ylmethyl}-acetamide as a white solid (28 mg, 75%).

$^1$H NMR (400 MHz, DMSO-$d_6$): δ 11.57-11.53 (br s, 1H), 8.40 (t, J=6.1 Hz, 1H), 8.16 (d, J=7.6 Hz, 1H), 7.78 (d, J=8.1

Hz, 2H), 7.63 (dd, J=8.3, 1.0 Hz, 1H), 7.45-7.41 (m, 3H), 6.99 (s, 1H), 4.58 (d, J=5.8 Hz, 2H), 3.52 (s, 2H), 2.46-2.30 (m, 8H), 2.16 (s, 3H), 1.89 (s, 3H).

AnalpH9_MeOH_QC(Sunfire): Rt 4.40 min; m/z 405.3 [M+1]$^+$.

Scheme A, Step G (Protocol 3): Synthesis of 2H-isoquinolin-1-one derivatives of formula 9 (via sulfonylation)

N-{3-[4-(4-Methyl-piperazin-1-yl methyl)-phenyl]-1-oxo-1,2-dihydro-isoquinolin-5-ylmethyl}-methanesulfonamide (IQ-026)

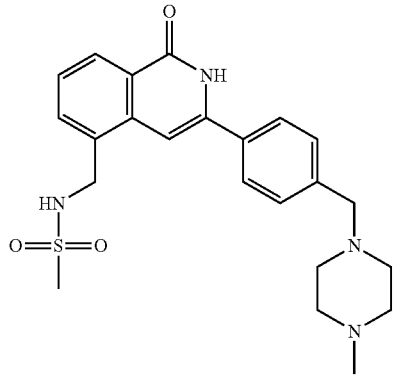 [SMILES: CN1CCN(Cc2ccc(-c3cc4c(CNS(C)(=O)=O)cccc4c(=O)[nH]3)cc2)CC1]

To 5-aminomethyl-3-[4-(4-methyl-piperazin-1-ylmethyl)-phenyl]-2H-isoquinolin-1-one (33 mg, 0.092 mmol) was added methane sulfonyl chloride (0.5 mL, 0.24M in CH$_2$Cl$_2$, 0.12 mmol) followed by DIPEA (0.5 mL, 0.28M in CH$_2$Cl$_2$, 0.14 mmol). The reaction vessel was purged with N$_2$ and stirred at RT for 5 h. MeOH was added and the reaction mixture was applied to a SCX-2 (1 g) cartridge. The cartridge was washed with MeOH (2×column volumes). The desired product was eluted from the column with 0.5M NH$_3$/MeOH (3×column volumes) and the solvent removed in vacuo. The crude product was purified by reverse phase preparative HPLC-MS to obtain N-{3-[4-(4-methyl-piperazin-1-ylmethyl)-phenyl]-1-oxo-1,2-dihydro-isoquinolin-5-ylmethyl}-methanesulfonamide as a white solid (16 mg, 39%).

$^1$H NMR (400 MHz, DMSO-d$_6$): δ 11.63-11.48 (br s, 1H), 8.19 (d, J=7.8 Hz, 1H), 7.80 (d, J=8.3 Hz, 2H), 7.71 (dd, J=8.3, 1.0 Hz, 1H), 7.64 (t, J=6.3 Hz, 1H), 7.46 (t, J=7.8 Hz, 1H), 7.42 (d, J=8.3 Hz, 2H) 7.01 (s, 1H), 4.49 (d, J=6.1 Hz, 2H), 3.52 (s, 2H), 2.96 (s, 3H), 2.45-2.27 (m, 8H), 2.16 (s, 3H).

AnalpH9_MeOH_QC(Sunfire): Rt 4.59 min; m/z 441.2 [M+1]$^+$.

Synthesis of 2H-isoquinolin-1-ones of Formula 4

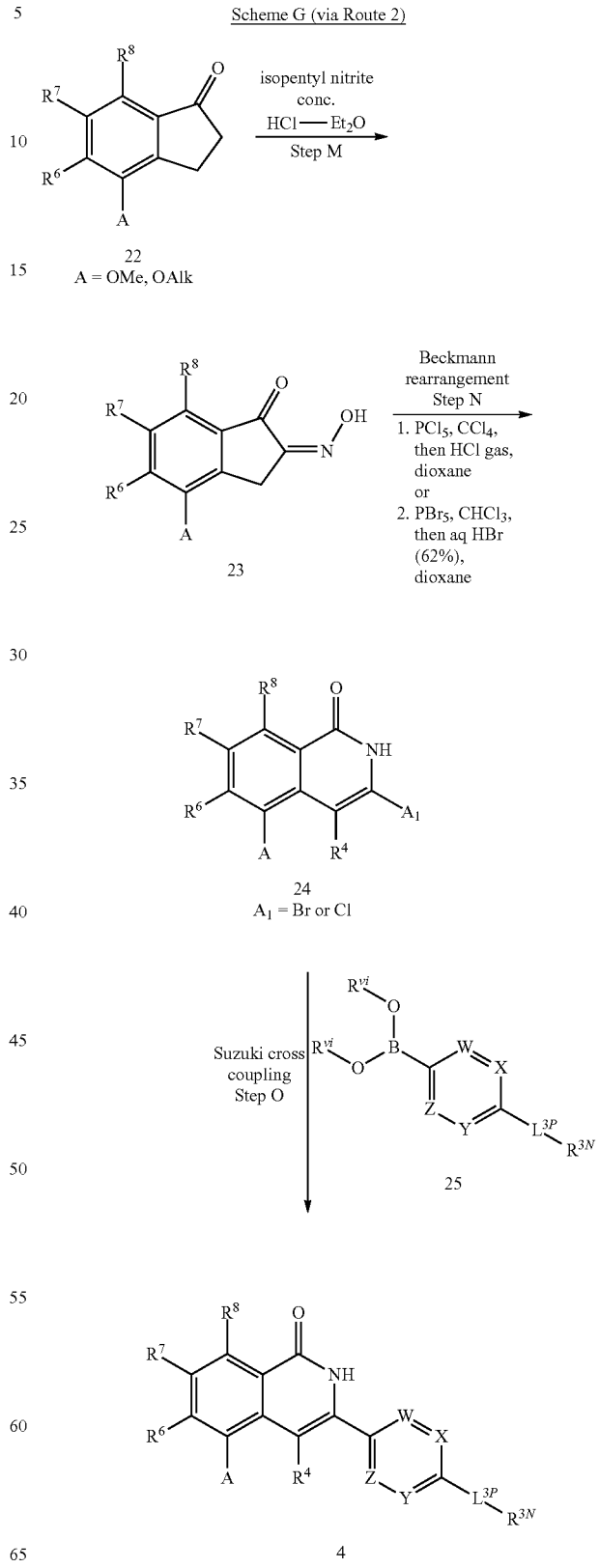

Scheme G, Step M Synthesis 2-(hydroxyimino-2,3-dihydro-1H-inden-1-one derivatives 23

4-Methoxy-indan-1,2-dione 2-oxime

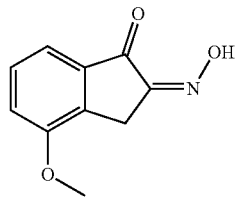

A solution of 4-methoxy-indan-1-one (5 g, 30.86 mmol) in a mixture of diethyl ether (50 mL) and concentrated aq. HCl (50 mL) was treated with isopentyl nitrite (2.88 g, 24.61 mmol) and stirred at room temperature for 2 h. TLC analysis indicated presence of ~10% of unreacted starting material. Isopentyl nitrite (0.72 g, 6.15 mmol) was added and stirred at RT for 1 h. The precipitated solid was collected by filtration to obtain 4 g of the crude product which was further purified by re-crystallization from methanol to obtain 4-methoxy-indan-1,2-dione 2-oxime as a brown solid (2.5 g, 42%).

$^1$H NMR (400 MHz, DMSO-$d_6$): δ 12.68 (s, 1H), 7.45 (m, 1H), 7.32 (m, 2H), 3.89 (s, 3H), 3.60 (s, 2H).

AnalpH2_MeCN_FA_7 min(XTERRA1.m): Rt 2.67 min; m/z 192.2 [M+1]$^+$.

Scheme G, Step N: Synthesis of 3-chloro-isoquinolin-1(2H)-one derivatives of formula 24

3-Chloro-5-methoxy-2H-isoquinolin-1-one

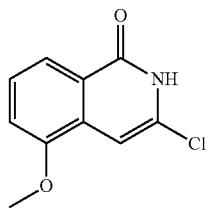

To a solution of compound 4-methoxy-indan-1,2-dione 2-oxime (2.5 g, 13.08 mmol) in dry CCl$_4$ (250 mL) was added PCl$_5$ (4.08 g, 19.63 mmol) and stirred at RT for 16 h. The reaction mixture was concentrated to remove the CCl$_4$ and POCl$_3$ under reduced pressure. The residue was re-dissolved in dry 1,4-dioxane (250 mL), cooled to 0° C. and dry HCl gas was passed through the solution until saturated and the reaction allowed to stir RT for 16 h. The reaction mixture was heated at 60° C. for 2 h, cooled to RT and concentrated. The residue was dissolved in EtOAc (150 mL), washed with H$_2$O (50 mL), saturated NaHCO$_3$ solution (2×50 mL), brine solution (50 mL), dried (Na$_2$SO$_4$) and concentrated. The crude compound was washed with chloroform (2×25 mL), diethyl ether (25 mL) and n-pentane (25 mL) to afford 3-chloro-5-methoxy-2H-isoquinolin-1-one as an off-white solid (900 mg, 33%).

$^1$H NMR (400 MHz, DMSO-$d_6$): δ 12.34 (br s, NH, 1H), 7.71 (d, J=8.0 Hz, 1H), 7.46 (m, 1H), 7.28 (d, J=8.0 Hz, 1H), 6.73 (br s, 1H), 3.91 (s, 3H).

AnalpH2_MeOH_4min(1): Rt 2.62 min; m/z 210.1 [M+1]$^+$.

Scheme G, Step O: Synthesis of 2H-isoquinolin-1-one derivatives of formula 4 (via Suzuki cross-coupling)

4-[5-(5-Methoxy-1-oxo-1,2-dihydro-isoquinolin-3-yl)-pyrimidin-2-yl]-piperazine-1-carboxylic acid tert-butyl ester

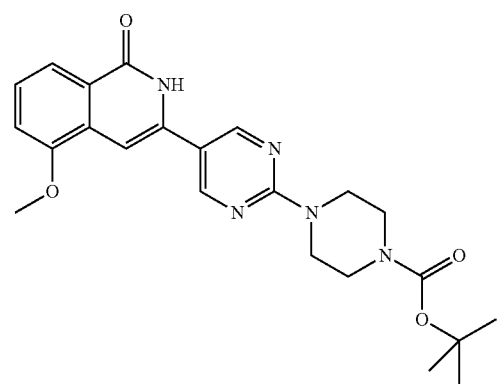 [SMILES: COc1cccc2c(=O)[nH]c(-c3cnc(N4CCN(C(=O)OC(C)(C)C)CC4)nc3)cc12]

3-Chloro-5-methoxy-2H-isoquinolin-1-one (100 mg, 0.48 mmol), 2-(4-Boc-piperazin-1-yl)pyrimidine-5-boronic acid pinacol ester (280 mg, 0.72 mmol), K$_2$CO$_3$ (132 mg, 0.96 mmol) and Pd(dppf)Cl$_2$ (1:1 complex with CH$_2$Cl$_2$) (36 mg, 0.044 mmol) in DME/EtOH/H$_2$O 4:1:1 (2.5 mL) were added to a microwave vial and the reaction mixture purged with N$_2$ for 10 min. The reaction mixture was irradiated using a microwave reactor (300 W, 120° C., 120 min). The reaction mixture was concentrated in vacuo passed through a thiol cartridge (Silylcycle 1 g, 6 mL) eluting with CH$_2$Cl$_2$, followed by MeOH. The organic fractions were concentrated in vacuo to afford 4-[5-(5-methoxy-1-oxo-1,2-dihydro-isoquinolin-3-yl)-pyrimidin-2-yl]-piperazine-1-carboxylic acid tert-butyl ester as a brown solid (210 mg, quant.) which was used in the next step without further purification.

AnalpH2_MeOH_4min(1): Rt 3.28 min; m/z 438 [M+1]$^+$.

Synthesis of 2H-isoquinolin-1-ones of Formula 5
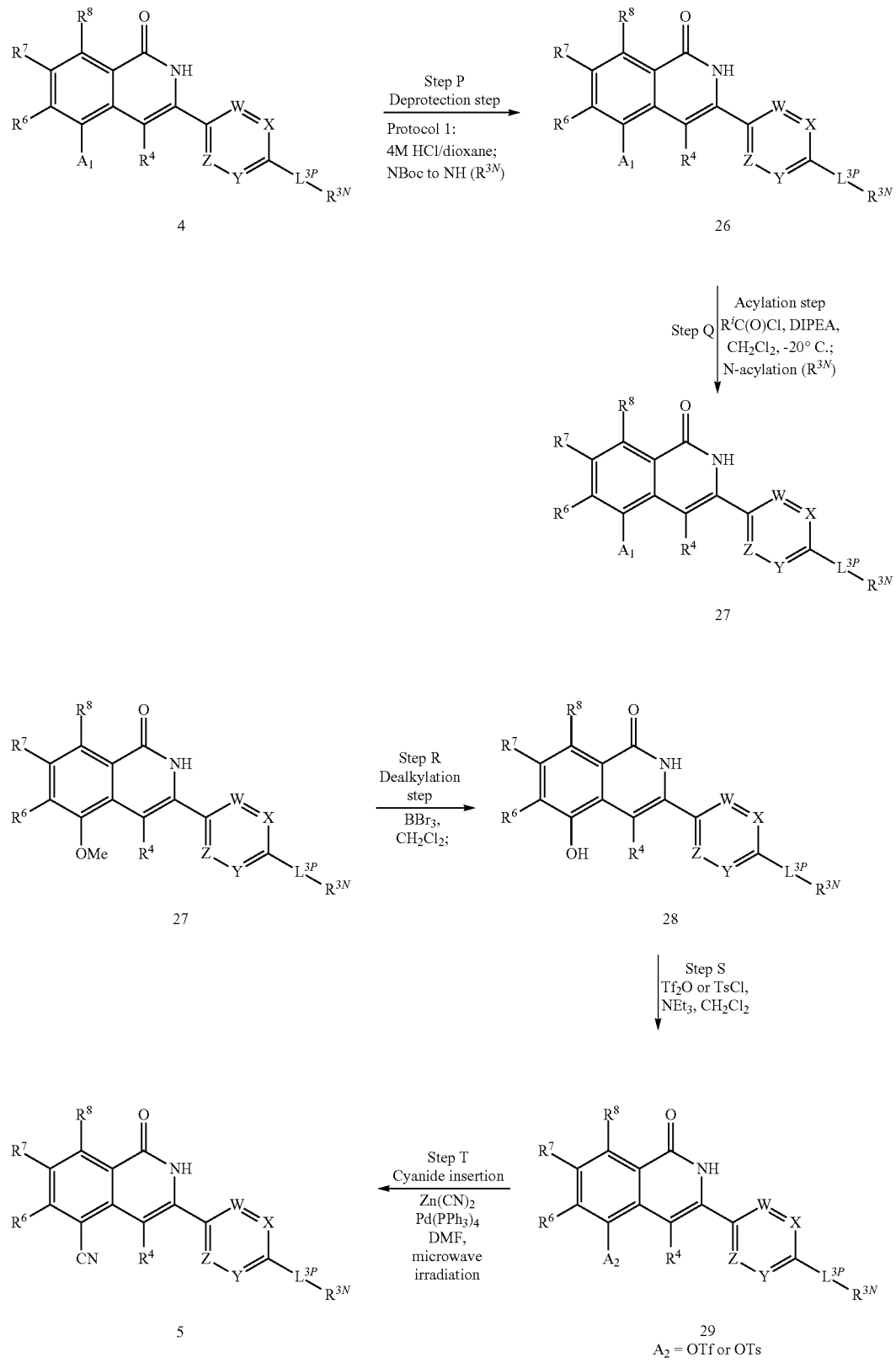

Scheme H, Step P: Synthesis of 2H-isoquinolin-1-one derivatives of formula 26 (via deprotection)

5-Methoxy-3-(2-piperazin-1-yl-pyrimidin-5-yl)-2H-isoquinolin-1-one

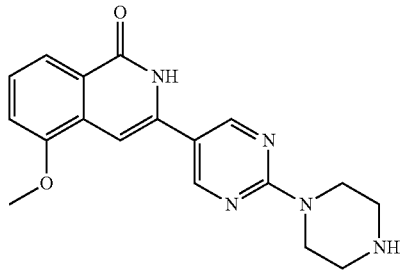 [SMILES: COc1cccc2c(=O)[nH]c(-c3cnc(N4CCNCC4)nc3)cc12]

To 4-[5-(5-methoxy-1-oxo-1,2-dihydro-isoquinolin-3-yl)-pyrimidin-2-yl]-piperazine-1-carboxylic acid tert-butyl ester (210 mg, 0.48 mmol) was added 4M HCl/dioxane (5 mL) and the reaction mixture stirred at RT for 2 h. The solvent was removed in vacuo and the crude material dissolved in MeOH:DMSO (4:1) and passed through an SCX-2 cartridge (2 g), washing the impurities with MeOH, $CH_2Cl_2$ and MeCN then eluting the desired product with 10% $NH_3$/MeOH. The organic fractions were concentrated in vacuo to afford 5-methoxy-3-(2-piperazin-1-yl-pyrimidin-5-yl)-2H-isoquinolin-1-one as an off-white solid (183 mg, quant.) which was used in the next step without further purification.

AnalpH2_MeOH_4min(1): Rt 1.65 min; m/z 338 [M+1]$^+$.

Scheme H, Step Q: Synthesis of 2H-isoquinolin-1-one derivatives of formula 27 (via N-acetylation)

3-[2-(4-Cyclopropanecarbonyl-piperazin-1-yl)-pyrimidin-5-yl]-5-methoxy-2H-isoquinolin-1-one

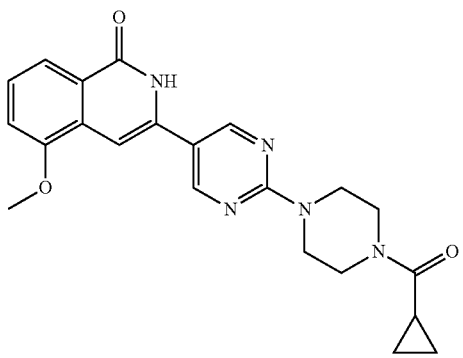 [SMILES: COc1cccc2c(=O)[nH]c(-c3cnc(N4CCN(C(=O)C5CC5)CC4)nc3)cc12]

Cyclopropylcarbonyl chloride (43 μL, 0.48 mmol) was added to a stirred solution of 5-methoxy-3-(2-piperazin-1-yl-pyrimidin-5-yl)-2H-isoquinolin-1-one (183 mg, 0.54 mmol) and N,N-diisopropylethylamine (113 μL, 0.65 mmol) in $CH_2Cl_2$ (10 mL) at −20° C. and allowed to stir for 10 min. The reaction mixture was concentrated in vacuo to afford 3-[2-(4-cyclopropanecarbonyl-piperazin-1-yl)-pyrimidin-5-yl]-5-methoxy-2H-isoquinolin-1-one as a white solid (56 mg, 26%) which was used in the next step without further purification.

AnalpH2_MeOH_QC(1): Rt 8.09 min; m/z 406 [M+1]$^+$.

Scheme H, Step R: Synthesis of 2H-isoquinolin-1-one derivatives of formula 28 (via de-alkylation)

3-[2-(4-Cyclopropanecarbonyl-piperazin-1-yl)-pyrimidin-5-yl]-5-hydroxy-2H-isoquinolin-1-one

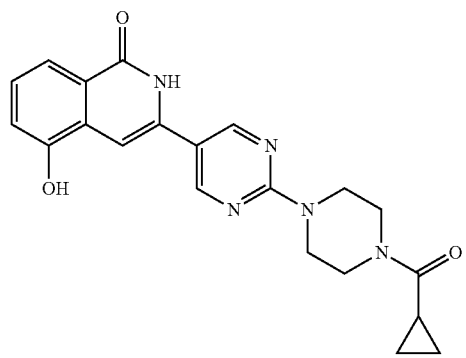 [SMILES: O=C(C1CC1)N1CCN(c2ncc(-c3cc4c(O)cccc4c(=O)[nH]3)cn2)CC1]

To a stirred solution of 3-[2-(4-cyclopropanecarbonyl-piperazin-1-yl)-pyrimidin-5-yl]-5-methoxy-2H-isoquinolin-1-one (56 mg, 0.14 mmol) in $CH_2Cl_2$ (10 mL) under $N_2$ at −78° C. was added boron tribromide (1M in $CH_2Cl_2$, 2.0 mL, 2.0 mmol). The reaction was allowed to warm to RT and stirred for 16 h. The reaction mixture was quenched with $H_2O$ and extracted with $CH_2Cl_2$ (3×50 mL). The combined organics were concentrated in vacuo obtain 3-[2-(4-cyclopropanecarbonyl-piperazin-1-yl)-pyrimidin-5-yl]-5-hydroxy-2H-isoquinolin-1-one as a white solid (60 mg, quantitative) which was used in the next step without further purification.

AnalpH2_MeOH_QC(1): Rt 6.85 min; m/z 392 [M+1]$^+$.

Scheme H, Step S: Synthesis of 2H-isoquinolin-1-one derivatives of formula 29

Trifluoro-methanesulfonic acid 3-[2-(4-cyclopropanecarbonyl-piperazin-1-yl)-pyrimidin-5-yl]-1-oxo-1,2-dihydro-isoquinolin-5-yl ester

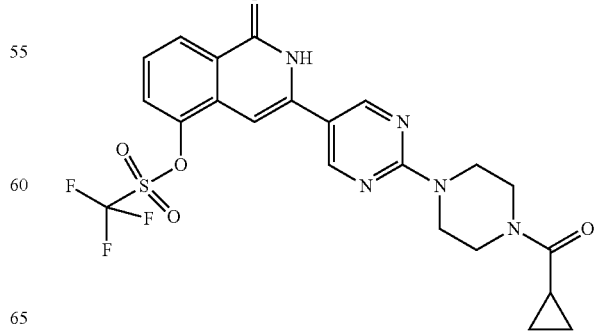

To a stirred solution of 3-[2-(4-cyclopropanecarbonyl-piperazin-1-yl)-pyrimidin-5-yl]-5-hydroxy-2H-isoquinolin-1-one (105 mg, 0.27 mmol) in CH$_2$Cl$_2$ (2 mL) under N$_2$ at 0° C. was added Et$_3$N (74 □L, 0.54 mmol) followed by trifluoromethanesulfonic anhydride (40 □L, 0.24 mmol). The reaction was allowed to warm to RT over 1 h. The reaction mixture was quenched with NaHCO$_3$ (sat, 2 mL) and extracted with CH$_2$Cl$_2$ (3×50 mL). The combined organics were washed with HCl (1M, 20 mL) and the combined organics were concentrated in vacuo to obtain trifluoromethanesulfonic acid 3-[2-(4-cyclopropanecarbonyl-piperazin-1-yl)-pyrimidin-5-yl]-1-oxo-1,2-dihydro-isoquinolin-5-yl ester as an off-white solid (140 mg, quantitative) which was used in the next step without further purification.

AnalpH2_MeOH_4min(1): Rt 3.13 min; m/z 524 [M+1]$^+$.

Scheme H, Step T: Synthesis of 2H-isoquinolin-1-one derivatives of formula 5 (via cyanide insertion)

3-[2-(4-Cyclopropanecarbonyl-piperazin-1-yl)-pyrimidin-5-yl]-1-oxo-1,2-dihydro-isoquinoline-5-carbonitrile (IQ-007)

Trifluoro-methanesulfonic acid 3-[2-(4-cyclopropanecarbonyl-piperazin-1-yl)-pyrimidin-5-yl]-1-oxo-1,2-dihydro-isoquinolin-5-yl ester (140 mg, 0.27 mmol), zinc cyanide (38 mg, 0.32 mmol) and tetrakis(triphenylphosphine)palladium(0) (31 mg, 0.027 mmol) were stirred in DMF (2.5 mL) and degassed with N$_2$ and irradiated using a microwave (300 W, 180° C., 30 min). The reaction mixture was passed through a thiol cartridge (Silycycle 1 g, 6 mL) eluting with MeOH. The organic fractions were concentrated in vacuo and the crude product purified by reverse phase preparative HPLC-MS to obtain 3-[2-(4-cyclopropanecarbonyl-piperazin-1-yl)-pyrimidin-5-yl]-1-oxo-1,2-dihydro-isoquinoline-5-carbonitrile as a white solid (4 mg, 4%).

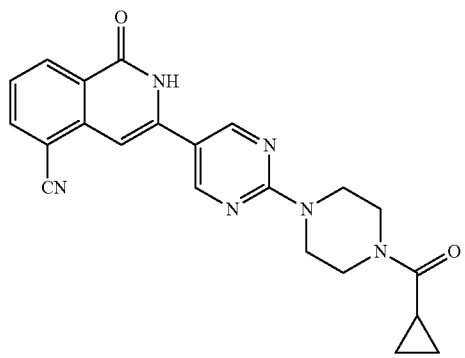 [SMILES: N#Cc1cccc2c(=O)[nH]c(-c3cnc(N4CCN(C(=O)C5CC5)CC4)nc3)cc12]

AnalpH2_MeOH_QC(1): Rt 7.72 min; m/z 401 [M+1]$^+$

Synthesis of 2H-isoquinolin-1-one derivatives of Formula 5, 5a and 5b (via Route 2a)

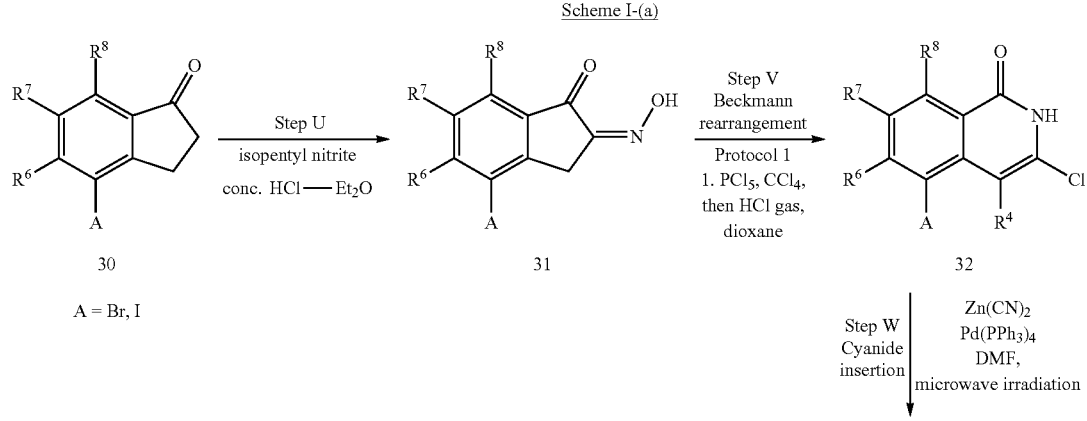

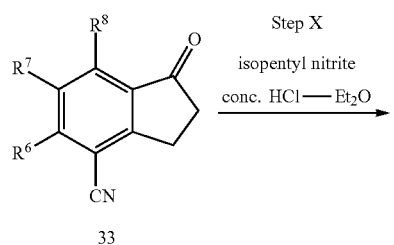
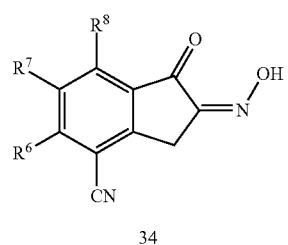
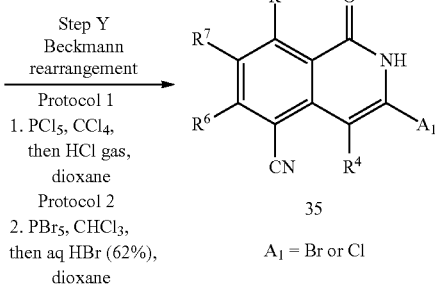
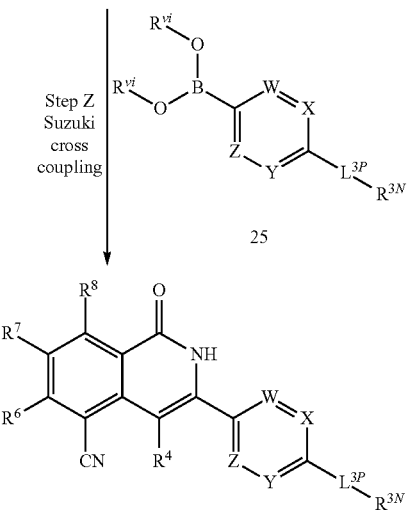
Scheme I-(b)
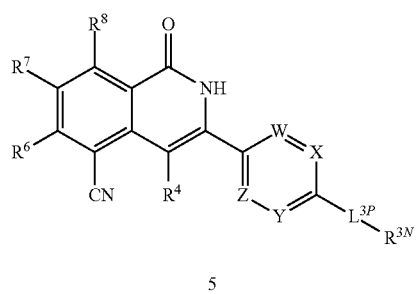
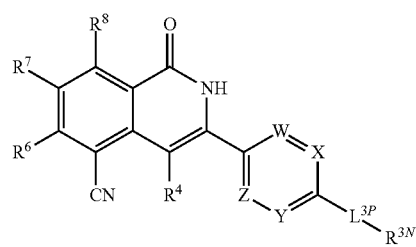
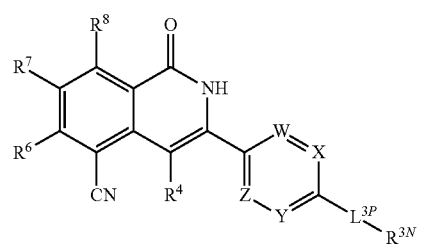

Synthesis of indanone derivatives of Formula 33
(required for Step X, Scheme I)

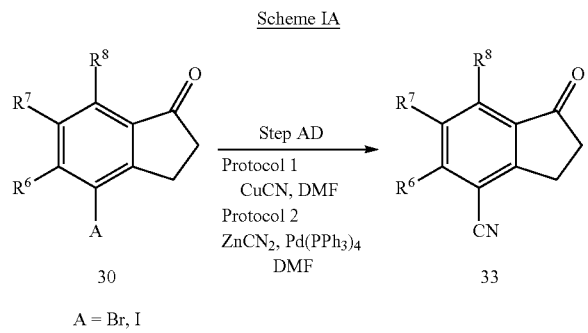

Scheme IA

30 → Step AD
Protocol 1
CuCN, DMF
Protocol 2
ZnCN$_2$, Pd(PPh$_3$)$_4$
DMF
→ 33

A = Br, I

Synthesis of boronic acid/ester derivatives of
Formula 25 (required for Step Z, Scheme I)

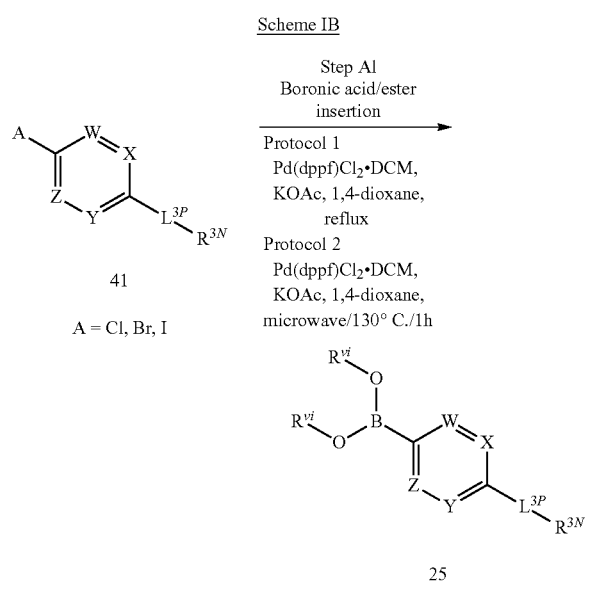

Scheme IB

41 → Step AI
Boronic acid/ester insertion
Protocol 1
Pd(dppf)Cl$_2$·DCM,
KOAc, 1,4-dioxane,
reflux
Protocol 2
Pd(dppf)Cl$_2$·DCM,
KOAc, 1,4-dioxane,
microwave/130° C./1h
→ 25

A = Cl, Br, I

Synthesis of indanone derivatives 30 required for
Step U, Scheme I 2-(2-Bromo-4-fluoro-benzyl)-malonic acid diethyl
ester

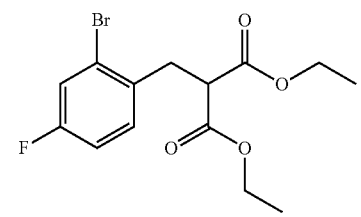 [SMILES: CCOC(=O)C(Cc1ccc(F)cc1Br)C(=O)OCC]

A solution of diethyl malonate (8.49 mL, 55.97 mmol) in dimethoxyethane (20 mL) was added drop-wise to a suspension of sodium hydride (60% dispersion in mineral oil) (2.23 g, 55.97 mmol) in dimethoxyethane (10 mL) at 0° C. The reaction mixture was stirred at RT for 1.5 h, then cooled to 0° C. and a solution of 2-bromo-1-(bromomethyl)-4-fluorobenzene (10 g, 37.31 mmol) in dimethoxyethane (20 mL) was added drop-wise and the reaction mixture was heated under reflux for 1.5 h. The reaction mixture was cooled to RT and concentrated in vacuo. The resulting residue was quenched with ice-water, extracted with EtOAc, dried (Na$_2$SO$_4$) and concentrated in vacuo. The crude compound was purified by silica gel column chromatography, eluting with pet-ether and increasing the polarity to 6% EtOAc/pet-ether to obtain 2-(2-bromo-4-fluoro-benzyl)-malonic acid diethyl ester as a colourless oil (7 g, 54%).

R$_f$: 0.4 (20% EtOAc/pet-ether).

$^1$H NMR (400 MHz, CDCl$_3$): δ 7.30-7.21 (m, 2H), 6.96-6.91 (m, 1H), 4.20-4.10 (m, 4H), 3.79 (t, J=7.8 Hz, 1H), 3.30 (t, J=7.8 Hz, 2H), 1.26-1.20 (m, 6H).

3-(2-Bromo-4-fluoro-phenyl)-propionic acid

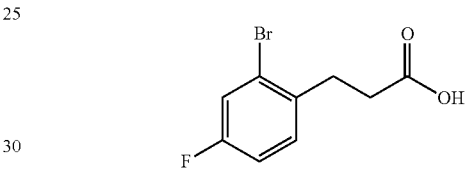

To a mixture of 2-(2-bromo-4-fluoro-benzyl)-malonic acid diethyl ester (2.1 g, 6.07 mmol) and water (14 mL) was added potassium hydroxide (0.68 g, 12.14 mmol) and the reaction mixture was heated under reflux for 4.5 h. The reaction mixture was cooled to RT and the ethanol removed in vacuo. The aqueous residue was cooled to 0° C., acidified with conc. H$_2$SO$_4$, and heated at 120° C. for 16 h. The reaction mixture was cooled to 0° C., the precipitated solid was collected by filtration, washed with water and dried to obtain 3-(2-bromo-4-fluoro-phenyl)-propionic acid as an off-white solid (0.5 g, 33%).

R$_f$: 0.2 (30% EtOAc/pet-ether).

$^1$H NMR (400 MHz, DMSO-d$_6$): δ 12.26 (s, 1H), 7.55-7.52 (m, 1H), 7.42-7.38 (m, 1H), 7.23-7.18 (m, 1H), 2.90 (t, J=7.8 Hz, 2H), 2.52 (t, J=7.8 Hz, 2H).

4-Bromo-6-fluoro-indan-1-one

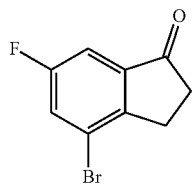

To a solution of 3-(2-bromo-4-fluoro-phenyl)-propionic acid (5.6 g, 22.67 mmol) in CH$_2$Cl$_2$ (56 mL) was added oxalyl chloride (4.13 mL, 48.18 mmol) at 0° C. and allowed to stir at RT for 18 h. Excess oxalyl chloride was removed in vacuo to give the acid chloride as a semi-solid. The acid chloride was dissolved in CH$_2$Cl$_2$ (30 mL) and added to a suspension of anhydrous AlCl$_3$ (3.77 g, 28.340 mmol) in CH$_2$Cl$_2$ (60 mL) at 0° C. and the reaction mixture was heated under reflux for 2 h. The reaction mixture was cooled to RT, poured into ice-water and extracted with CH$_2$Cl$_2$ (1×150 mL). The combined organic layers were washed with 0.1M sodium hydroxide solution and water. The organic layer was dried (Na$_2$SO$_4$) and concentrated in vacuo to afford 4-bromo-6-fluoro-indan-1-one as an off-white solid (4.1 g, 78%).

R$_f$: 0.5 (10% EtOAc/pet-ether).
$^1$H NMR (400 MHz, CDCl$_3$): δ 7.55-7.52 (m, 1H), 7.39-7.37 (m, 1H), 3.06-3.03 (m, 2H), 2.79-2.76 (m, 2H).

Scheme IA, Step AD (Protocol 1): Synthesis 2-(hydroxyimino-2,3-dihydro-1H-inden-1-one derivative 33

1-Oxo-indan-4-carbonitrile

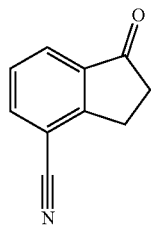 [SMILES: N#Cc1cccc2c1CCC2=O]

To a solution of 4-bromo-1-indanone (10 g, 47.37 mmol) in DMF (100 mL) was added CuCN (12.72 g, 142.11 mmol) and the reaction mixture heated under reflux for 6 h. The reaction mixture was cooled to RT and stirred for 16 h. The reaction mixture was filtered through Celite®, and washed with EtOAc. The combined filtrate was diluted with EtOAc (500 mL) and washed with ice-water (3×300 mL) and the combined organic layers were washed with brine, dried over Na$_2$SO$_4$ and concentrated in vacuo. The crude material was purified by silica gel column chromatography, eluting with 10-20% EtOAc/pet. ether to afford 1-oxo-indan-4-carbonitrile (4.5 g, 60%) as a yellow solid.

R$_f$: 0.6 (30% EtOAc/pet ether).
$^1$H NMR (400 MHz, CDCl$_3$): δ 7.97 (d, J=7.6 Hz, 1H), 7.89 (dd, J=6.0, 1.2 Hz, 1H), 7.52 (dd, J=4.4, 3.6 Hz, 1H), 3.33 (t, J=6.0 Hz, 2H), 2.82-2.79 (m, 2H).

Scheme IA, Step AD (Protocol 2): Synthesis 2-(hydroxyimino-2,3-dihydro-1H-inden-1-one derivative 33

6-Fluoro-1-oxo-indan-4-carbonitrile

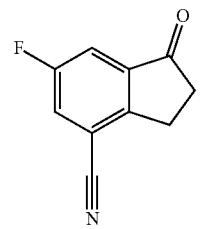 [SMILES: N#Cc1cc(F)cc2c1CCC2=O]

A stirred solution of 4-bromo-6-fluoro-indan-1-one (50 mg, 0.22 mmol) in DMF (1.5 mL) was degassed with argon. Zn(CN)$_2$ (51 mg, 0.44 mmol) and Pd(PPh$_3$)$_4$ (12 mg, 0.010 mmol) were added and the mixture degassed for a further 10 minutes. The reaction mixture was irradiated using a microwave reactor (300 W, 150° C., 30 min) and then diluted with diethyl ether (60 mL) and washed with ice-water (2×30 mL). The organic layer was dried, concentrated in vacuo to obtain the crude compound. The crude compound was purified by silica gel column chromatography, and eluting with pet-ether and increasing the polarity to 10% EtOAc/pet-ether to obtain 6-fluoro-1-oxo-indan-4-carbonitrile as an off-white solid (20 mg, 52%).

R$_f$: 0.4 (20% EtOAc/pet-ether).
$^1$H NMR (400 MHz, CDCl$_3$): δ 7.65-7.60 (m, 2H), 3.31-3.28 (m, 2H), 2.86-2.83 (m, 2H).

Scheme I, Step U & X: Synthesis 2-(hydroxyimino-2,3-dihydro-1H-inden-1-one derivatives 31 & 34

4-Bromo-indan-1,2-dione 2-oxime

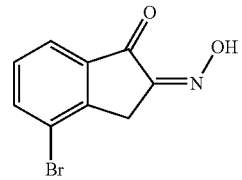 [SMILES: O=C1/C(=N\O)Cc2c(Br)cccc21]

To a stirred solution of 4-bromo-1-indanone (2.0 g, 9.48 mmol) in a mixture of diethyl ether (20 mL) and concentrated HCl (32%, 20 mL) was added isopentyl nitrite (1.16 mL, 8.62 mmol) and stirred at RT for 3 h, after which a further aliquot of isopentyl nitrite (116 µL, 0.862 mmol) was added and the reaction was stirred for a further 2.5 h. The precipitated solid was collected by filtration and washed with ether (4×20 mL) followed by pentane (4×20 mL) to obtain 4-bromoindan-1,2-dione-2-oxime as a yellow solid (1.40 g, 62%).

AnalpH2_MeOH_4min(2): Rt 2.82 min; m/z 240.2 [M+1]$^+$.

The following 2-(hydroxyimino-2,3-dihydro-1H-inden-1-one derivatives 31 & 34 are prepared using analogous procedures.

TABLE 9

2-(Hydroxyimino-2,3-dihydro-1H-inden-1-one Derivatives of formula 31 & 34

| Compound | Reference | Analytical Data | Mass, % Yield, State |
|---|---|---|---|
| (structure: 4-CN indanone oxime) | | AnalpH2_MeOH_4 min(2): Rt 2.07 min; m/z 187.3 [M + 1]$^+$ | 166 mg, 61%, pale pink solid. |

TABLE 9-continued 2-(Hydroxyimino-2,3-dihydro-1H-inden-1-one Derivatives of formula 31 & 34

| Compound | Reference | Analytical Data | Mass, % Yield, State |
|---|---|---|---|
| 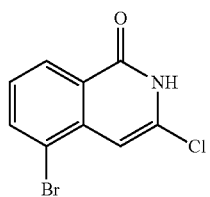 [SMILES: O=c1[nH]c(Cl)cc2c(Br)cccc12] | | ¹H NMR (300 MHz, DMSO-d₆): δ 13.00 (s, 1H), 8.29-8.25 (m, 1H), 7.96-7.93 (m, 1H), 3.09 (s, 2H). AnalpH2_MeCN_FA_5 min(1): Rt 2.01 min; m/z 203.1 [M − 1]⁻ | 1.45 g, 95%, off-white solid. |

Scheme I, Step V & Y (Protocol 1): Synthesis of 3-chloro-isoquinolin-1(2H)-one derivatives of formula 32 & 35

5-Bromo-3-chloro-2H-isoquinolin-1-one

To a solution of 4-bromoindan-1,2-dione-2-oxime (1.40 g, 5.83 mmol) in CHCl₃ (80 mL) was added PCl₅ (1.82 g, 8.75 mmol) and stirred at RT for 16 h, after which a further portion of PCl₅ (121 mg, 0.583 mmol) was added and the mixture was stirred for a further 1 h. The reaction mixture was concentrated in vacuo and the residue dissolved in 4 M HCl dioxane (100 mL). The resulting mixture was allowed to stir at RT for 16 h. The reaction mixture was concentrated in vacuo and diluted with EtOAc (50 mL), washed with water (25 mL), saturated NaHCO₃ solution (25 mL), brine solution (25 mL), dried (Na₂SO₄), filtered and concentrated in vacuo. The crude material was washed with diethyl ether (3×10 mL), n-pentane (3×10 mL) and was dried in vacuo to obtain 5-bromo-3-chloro-2H-isoquinolin-1-one as a pale yellow solid (681 mg, 45%).

¹H NMR (400 MHz, DMSO-d₆): δ12.64 (brs, 1H), 8.17 (d, J=8.1 Hz, 1H), 8.28 (dd, J=7.8, 1.0 Hz, 1H), 7.42 (t, J=7.8 Hz, 1H), 6.72 (s, 1H).

AnalpH2_MeOH_4min(2): Rt 3.21 min; m/z 258.8 [M+1]⁺

The following 2-(hydroxyimino)-2,3-dihydro-1H-inden-1-one derivatives 32 & 35 are prepared using analogous procedures.

TABLE 10

2-(Hydroxyimino-2,3-dihydro-1H-inden-1-one Derivatives of formula 32 & 35

| Compound | Reference | Analytical Data | Mass, % Yield, State |
|---|---|---|---|
| | | ¹H NMR (400 MHz, DMSO-d₆): δ 12.84 (br s, 1H), 8.43 (d, J = 8.1 Hz, 1H), 8.28 (dd, J = 7.3, 1.0 Hz, 1H), 7.64 (t, J = 7.8 Hz, 1H), 6.68 (s, 1H). AnalpH2_MeOH_4 min(2): Rt 2.50 min; m/z 205.1 [M + 1]⁺. | 130 mg, 58%, yellow solid. |
| 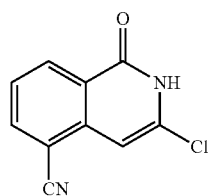 [SMILES: N#Cc1cccc2c(=O)[nH]c(Cl)cc12] | | ¹H NMR (300 MHz, DMSO-d₆): δ 13.05-12.60 (br. s, 1H), 8.40-8.37 (m, 1H), 8.18-8.15 (m, 1H), 6.70 (s, 1H). AnalpH2_MeOH_4 min(1): Rt 2.72 min; m/z 221.0 [M − 1]⁻. | 1.15 g, 73%, light brown solid. |

Scheme I, Step W: Alternative Synthesis of 5-nitrile-3-chloro-isoquinolin-1(2H)-one derivatives of formula 35

3-Chloro-1-oxo-1,2-dihydro-isoquinoline-5-carbonitrile

A mixture of 5-bromo-3-chloro-2H-isoquinolin-1-one (650 mg, 2.51 mmol), zinc cyanide (236 mg, 2.01 mmol) and tetrakis(triphenylphosphinepalladium (0) (172 mg, 0.149 mmol) in DMF (10 mL) was purged with N₂ for 10 mins and then heated in the microwave at 100° C.-110° C. for 3 h. A further aliquot of zinc cyanide (58.7 mg, 0.502 mmol) and tetrakis(triphenylphosphinepalladium (0) (146 mg, 0.126 mmol) in DMF (10 mL) was added to the reaction mixture and this was purged with N₂ for 10 mins and then heated in the microwave at 120° C.-130° C. for 2 h. The reaction mixture was then passed through a Si-thiol cartridge (2 g) and the column washed with MeOH (4×column volumes). The solvent was concentrated in vacuo and the crude solid was triturated with CH₂Cl₂ then purified by reverse phase preparative HPLC-MS to obtain 3-chloro-1-oxo-1,2-dihydroisoquinoline-5-carbonitrile as a yellow solid (129 mg, 25%).

$^1$H NMR (400 MHz, DMSO-d$_6$): δ12.84 (brs, 1H), 8.43 (d, J=8.1 Hz, 1H), 8.28 (dd, J=7.6, 1.0 Hz, 1H), 7.64 (t, J=8.1 Hz, 1H), 6.68 (s, 1H).

AnalpH2_MeOH_4min(2): Rt 2.54 min; m/z 205.3 [M+1]$^+$.

Synthesis of Boronic Acid/Ester Intermediates 25 (Required for Step Z, Scheme 1)

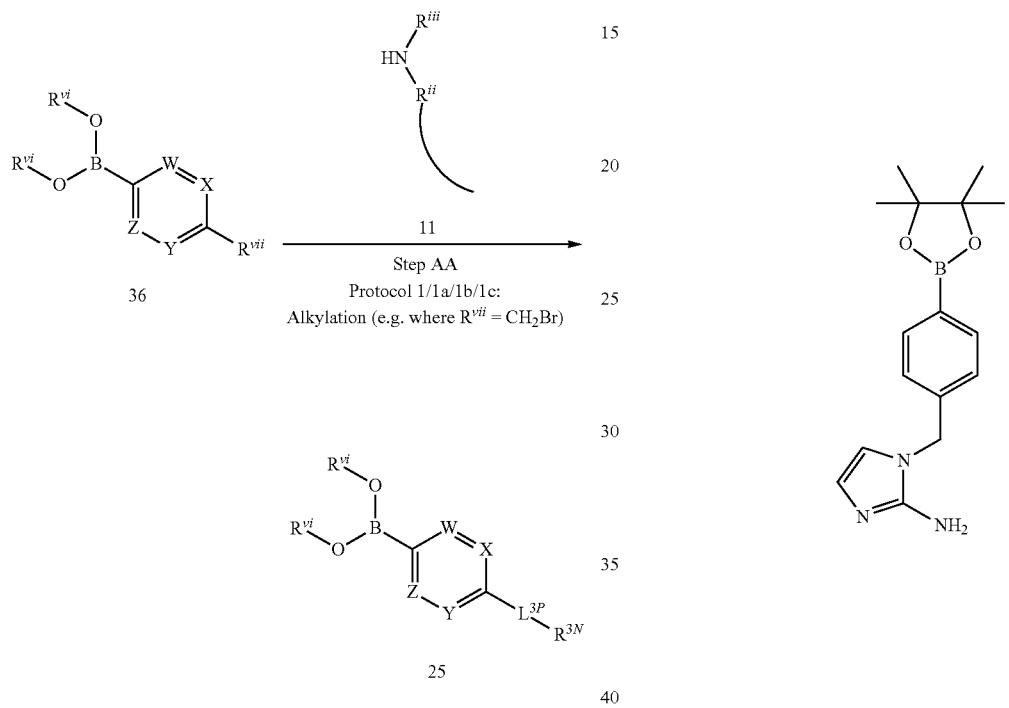

Synthesis of an Example of Amine of Formula 11 (Required for Step AA, Scheme J)

(1H-Imidazol-2-yl)-[1-phenyl-meth-(E)-ylidene]-amine

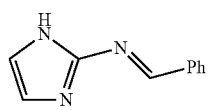 [SMILES: C(=N\c1ncc[nH]1)/c1ccccc1]

2-Aminoimidazole sulfate (1.0 g, 3.8 mmol) was dissolved in CH$_2$Cl$_2$ (4 mL) and benzaldehyde (0.5 mL, 4.9 mmol), Ti(OiPr)$_4$ (1.7 mL, 6.1 mmol) and triethylamine (0.11 mL, 0.76 mmol) were added sequentially and the reaction stirred at RT for 72 h. Solvent removed, EtOAc (50 mL) and water (50 mL) added, the mixture filtered and the phases separated. The organic layer was dried (MgSO$_4$) and solvent removed to afford (1H-imidazol-2-yl)-[1-phenyl-meth-(E)-ylidene]-amine as a yellow solid (476 mg, 73%) which was used in the next step without further purification.

Scheme J, Step AA (Protocol 1): Synthesis of Aryl Boronic Ester Derivatives of Formula 25 (Via Alkylation)

1-[4-(4,4,5,5-Tetramethyl-[1,3,2]dioxaborolan-2-yl)-benzyl]-1H-imidazol-2-ylamine 4-Bromomethyl phenyl boronic acid pinacol ester (511 mg, 1.86 mmol), (1H-imidazol-2-yl)-[1-phenyl-meth-(E)-ylidene]-amine (476 mg, 2.78 mmol), K$_2$CO$_3$ (384 mg, 2.78 mmol), KI (15 mg, 0.09 mmol) and acetone (17 mL) were combined and heated at reflux for 3 h. The reaction mixture was cooled, solvent removed and partitioned between water and EtOAc. The combined organics were dried (MgSO$_4$) and solvent removed. The residue was dissolved in EtOAc and stirred with 2M HCl (10 mL) for 90 minutes. After this time the reaction was neutralised with solid NaHCO$_3$ and extracted with EtOAc (2×50 mL). No product was recovered by extraction. The product was extracted from the aqueous using a Biotage Isolute 103 column to afford 1-[4-(4,4,5,5-tetramethyl-[1,3,2]dioxaborolan-2-yl)-benzyl]-1H-imidazol-2-ylamine as a brown oil (70 mg, 17%) which was used in the next step without further purification.

AnalpH2_MeOH_4min(2): Rt 1.99 min; m/z 300 [M+1]$^+$; Rt 0.40 min; m/z 218 [M+1]$^+$ (mixture of boronic ester and acid observed).

The following aryl boronic acid or boronic ester derivatives 25 are prepared using analogous procedures.

TABLE 11

Aryl boronic acid or boronic ester derivatives of Formula 25

| Compound | Analytical Data | Mass, % Yield, State |
|---|---|---|
| 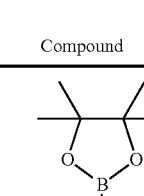 | AnalpH2_MeOH_ 4 min(2): Rt 1.89 min; m/z 315 [M + 1]$^+$; Rt 0.34 min; m/z 233 [M + 1]$^+$ (mixture of boronic ester and acid observed). | 435 mg, 82%, white powder |

Synthesis of Amines of Formula 11 (Required for Step AA, Scheme J)

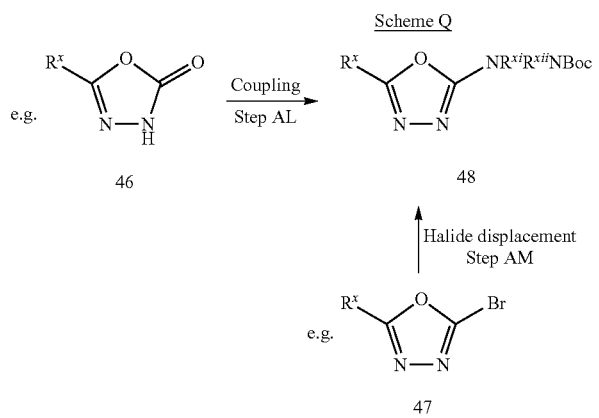

Synthesis of Amines of Formula 48 (Step AL, Via Coupling)

4-(5-Methyl[1,3,4]oxadiazol-2-yl)[1,4]diazepane-1-carboxylic acid tert-butyl ester

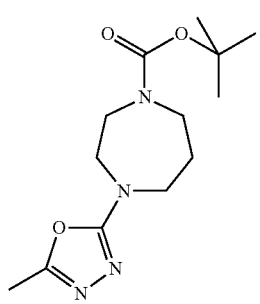 [SMILES: Cc1nnc(N2CCCN(C(=O)OC(C)(C)C)CC2)o1]

To a solution of tert-butyl-1-homopiperazine carboxylate (1.00 g, 5.00 mmol) and 5-methyl-1,3,4-oxadiazol-2[3H] one (250 mg, 2.50 mmol) in DMF (15 mL) under nitrogen was added DIPEA (871 µL, 5.00 mmol) and the reaction mixture was allowed to stir for 5 min. After this time, benzotriazol-1-yloxy)tris(dimethylamino)phosphonium hexafluorophosphate (1.22 g, 2.75 mmol) was added and the resulting mixture was stirred for 18 h. The reaction mixture was added to ice-water and extracted with EtOAc (3×50 mL). The combined organic layer was washed with brine (3×100 mL), dried (anhydrous Na$_2$SO$_4$), filtered and concentrated in vacuo. The crude compound was purified by silica gel chromatography eluting with 0-5% MeOH/DCM to obtain 4-(5-methyl[1,3,4]oxadiazol-2-yl)[1,4]diazepane-1-carboxylic acid tert-butyl ester (500 mg, 35%) as a yellow oil.

AnalpH2_MeOH_4min (1): Rt 2.59 min; m/z 283.3 [M+1]$^+$.

The following oxadiazole derivatives are prepared using analogous procedures.

| Compound | Analytical Data | Mass, % Yield, State |
|---|---|---|
| | AnalpH2_MeOH_ 4 min (1): Rt 2.80 min; m/z 283.3 [M + 1]$^+$ | 282 mg, quant., yellow oil |

| Compound | Analytical Data | Mass, % Yield, State |
|---|---|---|
| [Boc-azetidine-N(Me)-5-methyl-1,3,4-oxadiazole] | AnalpH2_MeOH_ 4 min (1): Rt 2.61 min; m/z 269.3 [M + 1]+ | 305 mg, 57%, yellow oil |
| [Boc-piperazine-5-ethyl-1,3,4-oxadiazole] | AnalpH2_MeOH_ 4 min (1): Rt 2.85 min; m/z 283.3 [M + 1]+ | 141 mg, quant., orange semi solid |

This method was also used to prepare aryl halides of formula 41 (using analogous procedures) via Scheme R.

Synthesis of Aryl Halides of Formula 41 (Required for Step AI)

Scheme R

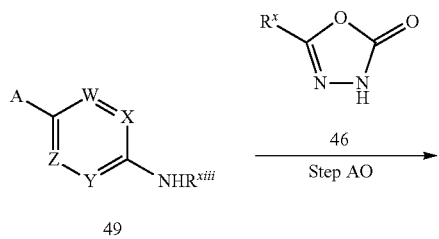

where $R^{xiii}$ = H or small alkyl

A = I, Br, Cl

| Compound | Analytical Data | Mass, % Yield, State |
|---|---|---|
| [4-bromo-phenyl-N(Me)-5-methyl-1,3,4-oxadiazole] | AnalpH2_MeOH_ 4 min (1): Rt 2.95 min; m/z 282.1, 284.1 [M + 1]+ | 112 mg, 66%, orange oil |

Synthesis of Amines of Formula 48 (Step AM, Via Halide Displacement)

3-Methyl-4-(5-methyl-[1,3,4]oxadiazol-2-yl)piperazine-1-carboxylic acid tert-butyl ester

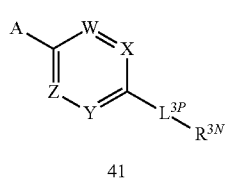

A mixture of 2-bromo-5-methyl-1,3,4-oxadiazole (81.5 mg, 0.50 mmol), 4-N-Boc-2-methylpiperazine (100 mg, 0.50 mmol) and sodium hydrogencarbonate (42.0 mg, 0.50 mmol) in DMF (2.5 mL) was heated at 90° C. for 18 h. The reaction mixture was concentrated to give a crude residue which was precipitated with 10% MeOH/DCM was added. The resulting suspension was filtered and washed with 10% MeOH/DCM. The filtrate was concentrated to afford 3-Methyl-4-(5-methyl-[1,3,4]oxadiazol-2-yl)piperazine-1-carboxylic acid tert-butyl ester (138 mg, 98%) as a light brown gum.

AnalpH2_MeOH_4min (1): Rt 2.78 min; m/z 283.3 [M+1]+.

The following oxadiazole derivatives are prepared using analogous procedures.

| Compound | Analytical Data | Mass, % Yield, State |
|---|---|---|
| 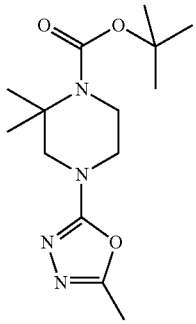 [SMILES: Cc1nnc(N2CCN(C(=O)OC(C)(C)C)C(C)(C)C2)o1] | AnalpH2_MeOH_4 min (1): Rt 2.90 min; m/z 297.3 [M + 1]+ | 143 mg, 97%, white solid |
| 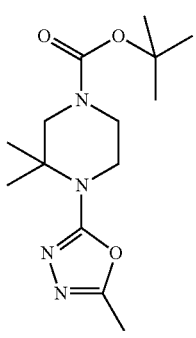 [SMILES: Cc1nnc(N2CCN(C(=O)OC(C)(C)C)CC2(C)C)o1] | AnalpH2_MeOH_4 min (1): Rt 2.93 min; m/z 297.3 [M + 1]+ | 207 mg, quant., orange gum |

4-(5-Methyl-[1,3,4]oxadiazol-2-yl)-piperidine-1-carboxylic acid tert-butyl ester

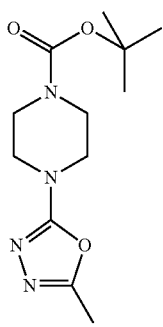 [SMILES: Cc1nnc(N2CCN(C(=O)OC(C)(C)C)CC2)o1]

To a solution of 1-(tert-butoxycarbonyl)piperidine-4-carbohydrazide (967 mg, 3.97 mmol) in THF (4.3 mL) was added N,N-dimethylacetamide dimethyl acetal (872 μL, 5.96 mmol) and the reaction mixture was heated at 50° C. for 4 h under nitrogen. The reaction mixture was concentrated in vacuo, the resulting residue dissolved in anhydrous toluene (4.3 mL) and para-toluene sulfonic acid (42 mg, 0.22 mmol) added. The resulting mixture was heated at 100° C. overnight (18 h). The reaction mixture was concentrated in vacuo, the resulting residue partitioned between $CH_2Cl_2$ (25 mL) and saturated $NaHCO_3$ (25 mL) and the mixture stirred vigorously followed by passing through a phase-separating cartridge. The organic layer was concentrated in vacuo. The crude residue was triturated with diethyl ether followed by isohexane to afford 4-(5-methyl-[1,3,4]oxadiazol-2-yl)-piperidine-1-carboxylic acid tert-butyl ester (924 mg, 87%) as a pale brown solid.

$^1$H NMR (400 MHz, CDCl$_3$) b 4.18-4.02 (br s, 2H), 3.06-2.87 (m, 3H), 2.50 (s, 3H), 2.04-2.01 (m, 2H), 1.83-1.73 (m, 2H), 1.46 (s, 9H).

AnalpH2_MeOH_4min (1): Rt 2.75 min; m/z 268.2 [M+1]+.

Synthesis of Amines of Formula 11 (Required for Step AA, Scheme J) Step AN, Via Boc Deprotection 4-(5-Methyl[1,3,4]oxadiazol-2-yl)[1,4]diazepane

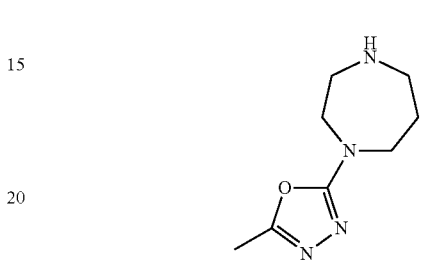

To a stirred solution of 4-(5-methyl[1,3,4]oxadiazol-2-yl)[1,4]diazepane-1-carboxylic acid tert-butyl ester (480 mg, 1.70 mmol) in $CH_2Cl_2$ was added TFA (2 mL, 26.1 mmol) and the resulting mixture was stirred for 2 h. The reaction mixture was concentrated in vacuo and further co-evaporated with MeOH (3×5 mL). The crude residue was passed through an SCX-2 cartridge (5 g) eluting with MeOH (4×column volumes). The product was eluted from the column using 0.5 M NH$_3$/MeOH (4×column volumes) and the solvent was removed in vacuo to afford 4-(5-methyl[1,3,4]oxadiazol-2-yl)[1,4]diazepane (260 mg, 84%) as an orange oil.

$^1$H NMR (400 MHz, DMSO-d$_6$) δ 3.54-3.51 (m, 2H), 3.49-3.46 (m, 2H), 2.89-2.86 (m, 2H), 2.77-2.74 (m, 2H), 2.31 (s, 3H), 1.78-1.73 (m, 2H).

AnalpH9_MeOH_4min (2): Rt 1.47 min; m/z 183.2 [M+1]+.

The following amines 11 are prepared using analogous procedures.

| Compound | Analytical Data | Mass, % Yield, State |
|---|---|---|
| 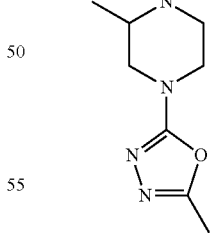 | AnalpH9_MeOH_4min (2): Rt 1.67 min; m/z 183.2 [M + 1]+ | 160 mg, 31%, yellow oil |
| 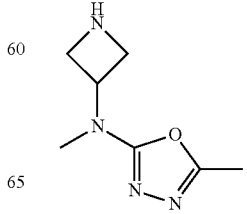 | AnalpH9_MeOH_4min (2): Rt 1.21 min; m/z 169.2 [M + 1]+ | 145 mg, 77%, orange oil |

-continued

| Compound | Analytical Data | Mass, % Yield, State |
|---|---|---|
| (piperidine-oxadiazole-methyl) | AnalpH2_MeOH_4min (1): Rt 0.26 min; m/z 168.2 [M + 1], Rt 0.31 min; m/z 168.2 [M + 1]$^+$ | 536 mg, 93%, off-white solid |
| (piperazine-oxadiazole-ethyl) | AnalpH9_MeOH_4min (2): Rt 1.75 min; m/z 183.3 [M + 1]$^+$ | 84.4 mg, 93%, light brown solid |
| (methylpiperazine-oxadiazole-methyl) | AnalpH9_MeOH_4min (2): Rt 1.61 min; m/z 183.3 [M + 1]$^+$ | 89.1 mg, quant., brown gum |
| (dimethylpiperazine-oxadiazole-methyl) | AnalpH9_MeOH_4min (2): Rt 1.82 min; m/z 197.3 [M + 1]$^+$ | 81.4 mg, quant., colourless oil |
| (dimethylpiperazine-oxadiazole-methyl) | AnalpH9_MeOH_4min (2): Rt 1.90 min; m/z 197.3 [M + 1]$^+$ | 239 mg, quant., yellow gum |

Scheme J, Step AA (Protocol 1a): Synthesis of Aryl Boronic Ester Derivatives of Formula 25 (Via Alkylation)

1-(5-Methyl-[1,3,4]oxadiazol-2-yl)-4-[4-(4,4,5,5-tetramethyl-[1,3,2]dioxaborolan-2-yl)-benzyl]-piperazine

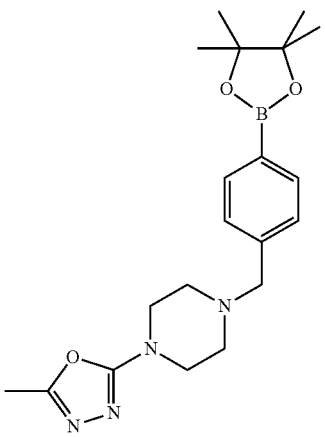

To 2-(4-bromomethyl-phenyl)-4,4,5,5-tetramethyl-[1,3,2]dioxaborolane (259 mg, 0.87 mmol) and 1-(5-methyl-[1,3,4]oxadiazol-2-yl)-piperazine hydrochloride (250 mg, 1.22 mmol) was added THF (6 mL), DMF (0.5 mL) and triethylamine (484 μL, 3.48 mmol). The reaction mixture was stirred at RT for 16 h. The reaction mixture was evaporated to dryness, suspended in $CH_2Cl_2/H_2O$ (1:1) and the mixture agitated. The organic layer was separated using a phase separation cartridge. The aq. layer was washed with a second portion of $CH_2Cl_2$, the organic layers combined, passed through a second phase separation cartridge and the solvent removed in vacuo to afford 1-(5-methyl-[1,3,4]oxadiazol-2-ylmethyl)-4-[4-(4,4,5,5-tetramethyl-[1,3,2]dioxaborolan-2-yl)-benzyl]-piperazine as a dark orange oil (298 mg, 89%) which was used in the next step without further purification.

AnalpH2_MeOH_4min(2): Rt 2.18 min; m/z 385.5 [M+1]$^+$; Rt 1.06 min; m/z 303 [M+1]$^+$ (mixture of boronic ester and acid observed).

The following aryl boronic acid or boronic ester derivatives 25 are prepared using analogous procedures.

TABLE 12

Aryl boronic acid or boronic ester derivatives of Formula 25

| Compound | Analytical Data | Mass, % Yield, State |
|---|---|---|
| (structure: 4-(pinacol boronate)benzyl-piperazine-(5-isopropyl-1,3,4-oxadiazol-2-yl)) | AnalpH2_MeOH_4 min (2): Rt 2.58 min; m/z 413 [M + 1]$^+$; Rt 1.42 min; m/z 331 [M + 1]$^+$ (mixture of boronic ester and acid observed). | 310 mg, 98%, yellow oil |
| (structure: 4-(pinacol boronate)benzyl-3-methylpiperazine-(5-methyl-1,3,4-oxadiazol-2-yl)) | AnalpH2_MeOH_4 min (1); Rt 2.23 min; m/z 399.3 [M + 1]$^+$; Rt: 2.00; m/z 317.3 [M + 1]$^+$ (mixture of boronic ester and acid observed). | 205 mg, 72%, dark orange oil |
| (structure: 4-(pinacol boronate)benzyl-azetidin-3-yl(methyl)amino-(5-methyl-1,3,4-oxadiazol-2-yl)) | AnalpH2_MeOH_4 min (1): Rt 1.95 min; m/z 385.3 [M + 1]$^+$; Rt: 1.05; m/z 303.3 [M + 1]$^+$ (mixture of boronic ester and acid observed). | 185 mg, 58%, orange oil |

TABLE 12-continued

Aryl boronic acid or boronic ester derivatives of Formula 25

| Compound | Analytical Data | Mass, % Yield, State |
|---|---|---|
| [structure: 4-methylhomopiperazinyl-CH2-C6H4-Bpin] | AnalpH2_MeOH_4 min (1): Rt 1.54 min; m/z 331.4 [M + 1]+, Rt; 0.38; m/z 249.4 [M + 1]+ (mixture of boronic ester and acid observed). | 353 mg, 54%, off-white solid |
| [structure: 4-(5-methyl-1,3,4-oxadiazol-2-yl)homopiperazinyl-CH2-C6H4-Bpin] | 1H NMR (400 MHz, CDCl3) δ 7.76 (d, J= 7.8 Hz, 2H), 7.32 (d, J = 7.8 Hz, 2H), 3.65 (s, 2H), 3.63-3.60 (m, 4H), 2.73-2.71 (m, 2H), 2.65-2.63 (m, 2H), 2.37 (s, 3H), 1.95-1.90 (m, 2H), 1.34 (s, 12H). AnalpH2_MeOH_4 min (1): Rt 1.94 min; m/z 399.3 [M + 1]+, Rt; 0.99; m/z 317.3 [M + 1]+ (mixture of boronic ester and acid observed). | 323 mg, 68%, pale yellow oil |
| [structure: 4-(5-methyl-1,3,4-oxadiazol-2-yl)piperidinyl-CH2-C6H4-Bpin] | AnalpH2_MeOH_4 min (1): Rt 1.92 min; m/z 384.2 [M + 1]+. | 215 mg, quant., orange gum |

TABLE 12-continued

Aryl boronic acid or boronic ester derivatives of Formula 25

| Compound | Analytical Data | Mass, % Yield, State |
|---|---|---|
| [structure: pinacol boronate-phenyl-CH2-piperazine-(5-ethyl-1,3,4-oxadiazol-2-yl)] | AnalpH9_MeOH_4 min (2): Rt 3.46 min; m/z 399.3 [M + 1]$^+$; Rt: 2.67; m/z 317.2 [M + 1]$^+$ (mixture of boronic ester and acid observed). | 184 mg, quant., off-white semi-solid |
| [structure: pinacol boronate-phenyl-CH2-piperazine-N-Boc] | AnalpH2_MeOH_4 min (1): Rt 2.56 min; m/z 403.2 [M + 1]$^+$; Rt: 1.57 m/z 321.2 [M + 1]$^+$ (mixture of boronic ester and acid observed). | 600 mg, 99%, white solid |
| [structure: pinacol boronate-phenyl-CH2-(2-methylpiperazine)-(5-methyl-1,3,4-oxadiazol-2-yl)] | AnalpH2_MeOH_4 min (1): Rt .262 min; m/z 399.3 [M + 1]$^+$; Rt: 2.00 m/z 317.3 [M + 1]$^+$ (mixture of boronic ester and acid observed). | 191 mg, 98%, light brown solid |

TABLE 12-continued

Aryl boronic acid or boronic ester derivatives of Formula 25

| Compound | Analytical Data | Mass, % Yield, State |
|---|---|---|
| (structure) | AnalpH2_MeOH_4 min (1): Rt 2.28 min; m/z 413.3 [M + 1]$^+$; Rt: 1.18 m/z 331.3 [M + 1]$^+$ (mixture of boronic ester and acid observed). | 171 mg, quant., light yellow solid |
| (structure) | AnalpH2_MeOH_4 min (1): Rt 3.00 min; m/z 413.3 [M + 1]$^+$; Rt: 1.47 m/z 331.3 [M + 1]$^+$ (mixture of boronic ester and acid observed). | 239 mg, quant., light yellow oil |

Scheme J, Step AA (Protocol 1 b): Synthesis of Aryl Boronic Ester Derivatives of Formula 25 Via Alkylation 1-[4-(4,4,5,5-Tetramethyl-[1,3,2]dioxaborolan-2-yl)-benzyl]-1H-pyrazole

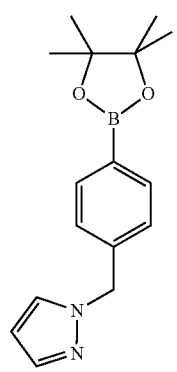 [SMILES: CC1(C)OB(c2ccc(Cn3cccn3)cc2)OC1(C)C]

Pyrazole (114 mg, 1.68 mmol) was added to a stirred suspension of potassium tert-butoxide (227 mg, 2.02 mmol) and 18-crown-6-ether (44.4 mg, 0.168 mmol) in diethyl ether (5 mL) and the mixture was stirred for 15 minutes. A solution of 4-bromomethylphenylboronic acid pinacol ester (500 mg, 1.68 mmol) in diethyl ether (5 mL) was added to the mixture followed by stirring for 24 h. The reaction mixture was quenched with water (10 mL) and extracted with ethyl acetate (10 mL). The organic layer was dried (anhydrous Na$_2$SO$_4$), filtered and concentrated in vacuo. The residue was purified by silica gel chromatography, eluting with 0-10% EtOAc/iso-hexane to afford 1-[4-(4,4,5,5-tetramethyl-[1,3,2]dioxaborolan-2-yl)benzyl]-1H-pyrazole as an off-white solid (437 mg, 36%).

AnalpH2_MeOH_4min(2): Rt 3.22 min; m/z 285.4 [M+1]$^+$.

Scheme J, Step AA (Protocol 1c): Synthesis of Aryl Boronic Ester Derivatives of Formula 25 (Via Alkylation)

4-[1,2,3]Triazol-2-ylmethyl-boronic acid pinacol ester

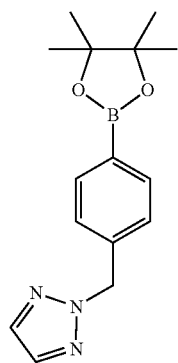 [SMILES: CC1(C)OB(c2ccc(Cn3nccn3)cc2)OC1(C)C]

2H-[1,2,3]Triazole (150 mg, 2.17 mmol) was dissolved in DMF (4 mL) under nitrogen and cooled in an ice bath. Sodium hydride (104 mg, 2.6 mmol) was added to the solution and the reaction was stirred at RT for 10 minutes. A solution of 2-(4-bromomethyl-phenyl)-4,4,5,5-tetramethyl-[1,3,2]dioxaborolane (774 mg, 2.6 mmol) in DMF (4 mL) was added dropwise to the reaction mixture. The reaction was heated at 80° C. for 2 hours and then allowed to cool to RT overnight. The reaction mixture was diluted with water (50 mL) and extracted with CHCl$_3$/$^i$PrOH (3:1, 3×20 mL). The combined extracts were filtered through a hydrophobic frit and concentrated in vacuo. The crude product was purified on a 10 g Si cartridge. Elution with 20% EtOAc/isohexane gave 2-[4-(4,4,5,5-tetramethyl-[1,3,2]dioxaborolan-2-yl)-benzyl]-2H-[1,2,3]triazole as an off white solid (156 mg, 25.2%).

AnalpH2_MeOH_4min(1): Rt 3.25 min; m/z 286.2 [M+1]$^+$.

The following aryl boronic acid or boronic ester derivatives 25 are prepared using analogous procedures.

TABLE 14

Aryl boronic acid or boronic ester derivatives of Formula 25

| Compound | Analytical Data | Mass, % Yield, State |
|---|---|---|
| (structure) | AnalpH2_MeOH_ 4 min(1): Rt 2.99 min; m/z 286.2 [M + 1]$^+$; Rt 1.65 min; m/z 204.2 [M + 1]$^+$ (mixture of boronic ester and acid observed). | 261.9 mg, 42.3%, off white solid. |

Synthesis of Boronic Acid/Ester Intermediates 25 of Formula 39 (Required for Step Z, Scheme I)

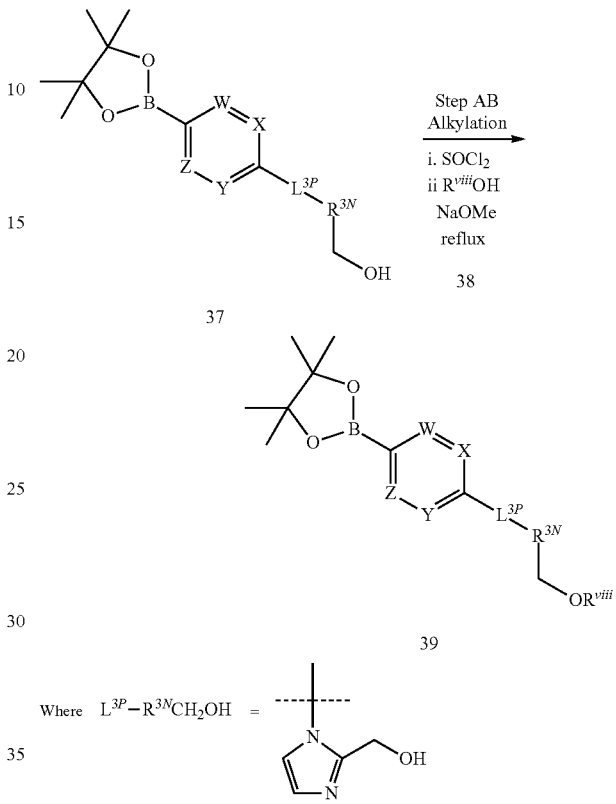

Scheme K Step AB: Ether formation from alcohol 37

2-Methoxymethyl-1-[4-(4,4,5,5-tetramethyl-[1,3,2]dioxaborolan-2-yl)-benzyl]-1H-imidazole

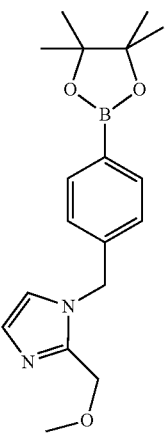 [SMILES: COCc1nccn1Cc1ccc(B2OC(C)(C)C(C)(C)O2)cc1]

{1-[4-(4,4,5,5-Tetramethyl-[1,3,2]dioxaborolan-2-yl)-benzyl]-1H-imidazol-2-yl}-methanol (130 mg, 0.41 mmol) was dissolved in SOCl$_2$ (2 mL) and the reaction stirred at RT for 3 h. The solvent was removed and the residue azeotroped with toluene. The residue was dissolved in MeOH (2 mL) and NaOMe (20 mg) and heated at reflux for 1 h. The reaction was cooled to RT, diluted with water and extracted with CH$_2$Cl$_2$. The combined organics were dried (MgSO$_4$), filtered and the solvent removed to afford 2-methoxymethyl-1-[4-(4,4,5,5-tetramethyl-[1,3,2]dioxaborolan-2-yl)-benzyl]-1H-imidazole (50 mg, 47%) as an off-white solid which was used in the next step without further purification.

AnalpH2_MeOH_4min(2): Rt 2.13 min; m/z 329 [M+1]$^+$; Rt 0.46 min; m/z 247 [M+1]$^+$ (mixture of boronic ester and acid observed).

Synthesis of Boronic Acid/Ester Intermediates 25 of Formula 40 (required for Step Z, Scheme I)

Scheme L

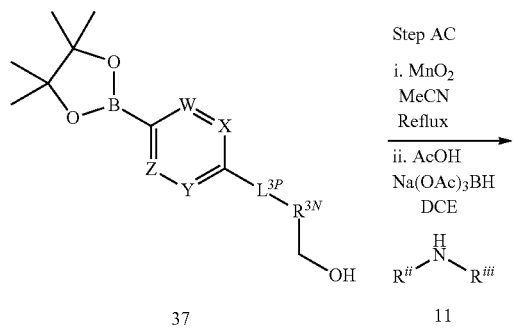

Scheme L Step AC: Oxidation of Alcohol 37 Followed by Reductive Amination

Dimethyl-{1-[4-(4,4,5,5-tetramethyl-[1,3,2]dioxaborolan-2-yl)-benzyl]-1H-imidazol-2-ylmethyl}-amine

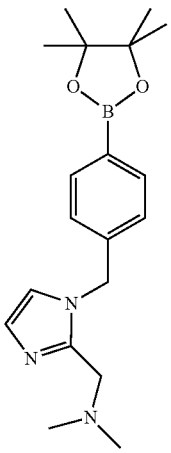 [SMILES: CN(C)Cc1nccn1Cc1ccc(B2OC(C)(C)C(C)(C)O2)cc1]

{1-[4-(4,4,5,5-Tetramethyl-[1,3,2]dioxaborolan-2-yl)-benzyl]-1H-imidazol-2-yl}-methanol (190 mg, 0.61 mmol) was dissolved in MeCN (5 mL), MnO$_2$ (263 mg, 3.03 mmol) was added and stirred at reflux for 3 h. The reaction mixture was cooled to RT and filtered through celite, washing with CH$_2$Cl$_2$. The solvent was removed, the residue dissolved in DCE and dimethylamine hydrochloride (99 mg, 1.22 mmol), AcOH (70 uL, 1.22 mmol) and NaBH(OAc)$_3$ (259 mg, 1.22 mmol) were added and the reaction stirred at RT overnight. The reaction mixture was purified by SCX-2 to afford dimethyl-{1-[4-(4,4,5,5-tetramethyl-[1,3,2]dioxaborolan-2-yl)-benzyl]-1H-imidazol-2-ylmethyl}-amine as (83 mg, 40%) as an off-white solid which was used in the next step without further purification. AnalpH2_MeOH_4min(2): Rt 0.78 min; m/z 260 [M+1]$^+$.

Synthesis of Boronic Acid/Ester Intermediates 25 (Required for Step Z, Scheme I)

Scheme M

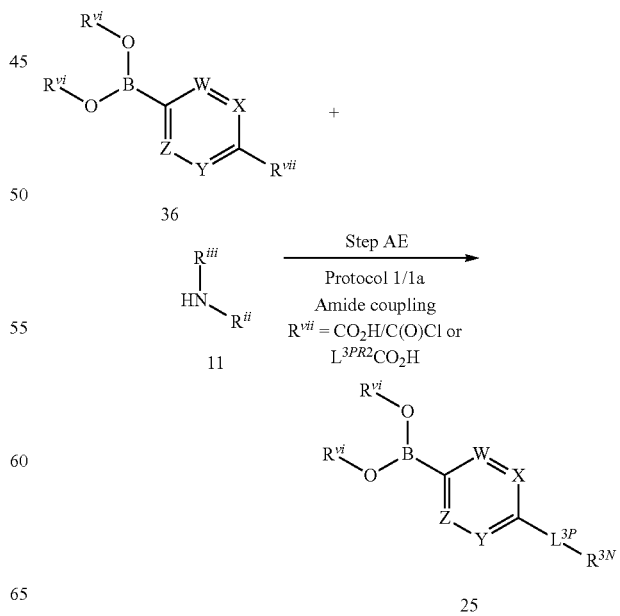

Scheme M, Step AE (Protocol 1): Synthesis of Boronic Acid/Ester Derivatives of Formula 25 (Via Amide Coupling)

[4-(2-Methoxy-ethyl)-piperazin-1-yl]-[4-(4,4,5,5-tetramethyl-[1,3,2]dioxaborolan-2-yl)-phenyl]-methanone

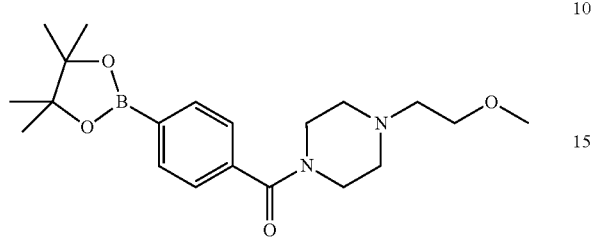

To a stirred suspension of 4-carboxylphenylboronic acid pinacol ester (1.5 g, 6.05 mmol) in acetonitrile (50 mL) was added DMAP (catalytic amount 10 mg) and EDCI.HCl (1.39 g, 7.26 mmol) at RT. After 5 minutes, 1-(2-methoxy-ethyl)-piperazine (1.12 mL, 7.56 mmol) was added and the mixture stirred at RT for 16 h. The reaction mixture was diluted with 10% MeOH/CH$_2$Cl$_2$ (100 mL), washed with water (50 mL) and brine solution. The organic layer was dried (Na$_2$SO$_4$) and concentrated in vacuo to afford the crude compound. The crude compound was purified by Florisil® column chromatography (100-200 mesh) and eluted with pet-ether to afford the desired compound as a gummy liquid. The obtained compound was further purified by trituration with n-pentane under cooling, the precipitated solid was collected by filtration and dried under vacuum to afford [4-(2-methoxy-ethyl)-piperazin-1-yl]-[4-(4,4,5,5-tetramethyl-[1,3,2]dioxaborolan-2-yl)-phenyl]-methanone as a white solid (1.1 g, 48%).

R$_f$: 0.7 (5% MeOH/CH$_2$Cl$_2$).

$^1$H NMR (400 MHz, CDCl$_3$): δ 7.83 (d, J=7.6 Hz, 2H), 7.38 (d, J=8.4 Hz, 2H), 3.74-3.88 (m, 2H), 3.51 (t, J=5.2 Hz, 2H), 3.38-3.46 (m, 2H), 3.35 (s, 3H), 2.61-2.52 (m, 4H), 2.37-2.48 (m, 2H), 1.34 (s, 12H).

AnalpH2_MeOH_4min(1): Rt 1.95 min; m/z 375.2 [M+1]$^+$.

The following aryl boronic acid or boronic ester derivatives 25 are prepared using analogous procedures.

Scheme M, Step AE (Protocol 1): Synthesis of Boronic Acid/Ester Intermediates of Formula 25 (Via Amide Coupling—Alternative Conditions)

4-[2-(4-Methyl-piperazin-1-yl)-2-oxo-ethyl]-boronic acid

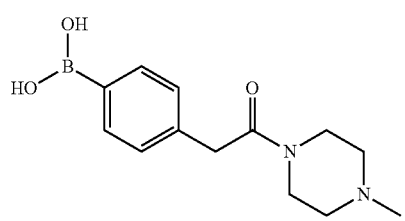 [SMILES: CN1CCN(C(=O)Cc2ccc(B(O)O)cc2)CC1]

To 4-(carboxymethyl)phenylboronic acid (200 mg, 1.11 mmol) and TBTU (357 mg, 1.11 mmol) in DMF (9 mL)/CH$_2$Cl$_2$ (3 mL) was added DIPEA (0.194 mL, 1.11 mmol) and the reaction mixture stirred at RT for ~45 min. N-Methyl-piperazine (134 mg, 1.33 mmol) in CH$_2$Cl$_2$/DMF 1:1 (2 mL) was added and the reaction mixture stirred at RT for 16 h. The reaction mixture was passed through a SCX-2 cartridge (10 g) eluting with MeOH (3×column volumes). The crude product was eluted from the column with 0.5M NH$_3$/MeOH (3×column volumes) and the solvent removed in vacuo to afford 4-[2-(4-methyl-piperazin-1-yl)-2-oxo-ethyl]-boronic acid as a dark orange oil (242 mg, 83%).

AnalpH9_MeOH_4min(2): Rt 1.61 min; m/z 263 [M+1]$^+$.

TABLE 15

Aryl boronic acid or boronic ester intermediates of Formula 25

| Compound | Analytical Data | Mass, % Yield, State |
|---|---|---|
|  | AnalpH2_MeOH_4 min(1): Rt 1.83 min; m/z 331.2 [M + 1]$^+$. $^1$H NMR (400 MHz, CDCl$_3$): δ 7.83 (d, J = 8.0 Hz, 2H), 7.38 (d, J = 8.0 Hz, 2H), 3.72-3.88 (m, 2H), 3.20-3.47 (m, 2H), 2.43-2.54 (m, 2H), 2.28-2.36 (m, 5H), 1.34 (s, 12H). | 1.06 g, 53% white solid. |

Synthesis of Bromo Intermediates 41 (Required for Step AI)

Scheme N

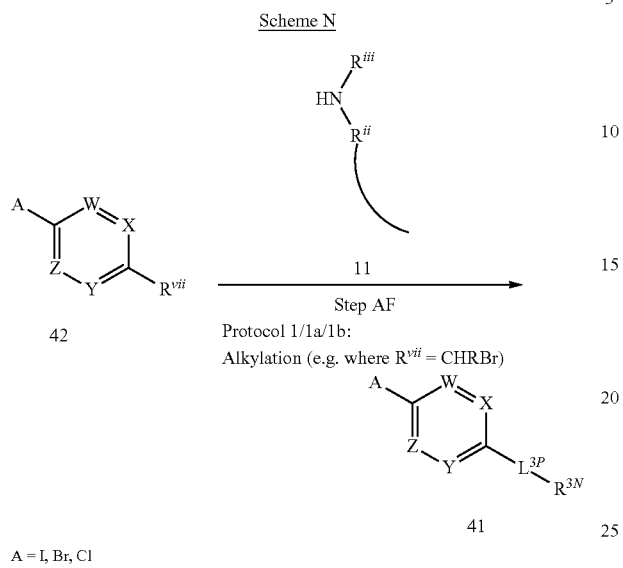

A = I, Br, Cl

Synthesis of Aromatic/Heteroaromatic Halide of Formula 42

5-Bromo-2-ethyl-pyridine

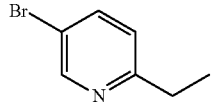

A suspension of 2,5-dibromo-pyridine (10 g, 42.21 mmol) and Pd(PPh$_3$)$_4$ (2.43 g, 2.11 mmol) in THF (100 mL) was added 1M Et$_2$Zn (42.2 mL, 42.21 mmol) at 0° C. The reaction mixture was stirred at 0° C. for 30 min and then allowed to stir at RT for 1 h. The reaction mixture was quenched with NaHCO$_3$ solution and extracted with EtOAc. The EtOAc layer was washed with water, brine, dried (Na$_2$SO$_4$), filtered and concentrated in vacuo. The crude compound was purified by silica gel column chromatography eluting with 4% EtOAc/pet-ether to obtain 5-bromo-2-ethyl-pyridine as a pale yellow liquid (3 g, 38%).

R$_f$: 0.6 (10% EtOAc/pet-ether).

$^1$H NMR (400 MHz, CDCl$_3$): δ 8.57 (d, J=2.4 Hz, 1H), 7.72-7.69 (m, 1H), 7.06 (d, J=8.0 Hz, 1H), 2.81-2.75 (m, 2H), 1.29 (t, J=8.0 Hz, 3H).

5-Bromo-2-(1-bromo-ethyl)-pyridine

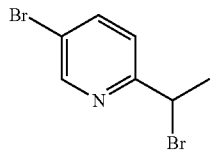

To a solution of 5-bromo-2-ethyl-pyridine (3 g, 16.21 mmol) in 1,2-dichloroethane (30 mL) and added NBS (2.88 g, 16.21 mmol) and AIBN (26 mg, 0.16 mmol) and the reaction mixture heated at 90° C. for 2 h. The reaction mixture was cooled to RT, water added and the organic layer separated. The organic layer was washed with water, brine, dried (Na$_2$SO$_4$) and concentrated in vacuo. The crude compound was purified by silica gel column chromatography eluting with 2% EtOAc/pet-ether to obtain 5-bromo-2-(1-bromoethyl)-pyridine as a pale yellow liquid (3 g, 71%).

R$_f$: 0.7 (10% EtOAc/pet-ether).

$^1$H NMR (400 MHz, CDCl$_3$): δ 8.62 (d, J=2.4 Hz, 1H), 7.83-7.80 (m, 1H), 7.36 (d, J=8.0 Hz, 1H), 5.22-5.16 (m, 1H), 2.05 (d, J=7.2 Hz, 3H).

1-Bromo-4-(1-bromo-ethyl)-benzene

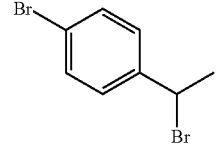

To a solution of compound 1-bromo-4-ethyl-benzene (5 g, 27.01 mmol) in CCl$_4$ (50 mL) was added NBS (5.04 g, 28.36 mmol) and AIBN (0.4 g, 2.70 mmol) at RT and the mixture was heated at 90° C. for 16 h. The reaction mixture was cooled to RT and filtered. The filtrate was washed with water (25 mL), brine (25 mL), and the organic layer was dried (Na$_2$SO$_4$) and concentrated. The crude compound was purified by silica gel column chromatography eluting with 1% EtOAc/pet-ether to obtain 1-bromo-4-(1-bromo-ethyl)-benzene as a pale yellow liquid (3.5 g, 50%).

R$_f$: 0.6 (5% EtOAc/pet-ether).

$^1$H NMR (400 MHz, CDCl$_3$): δ 7.48-7.43 (m, 2H), 7.32-7.25 (m, 2H), 5.17-5.12 (m, 1H), 2.01 (d, J=4.0 Hz, 3H).

Synthesis of Amine Intermediates of Formula 11

(1H-Imidazol-2-yl)-methanol

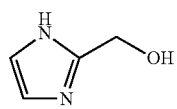

To a solution of compound 1H-imidazole-2-carbaldehyde (5 g, 52.08 mmol) in MeOH (50 mL) was added sodium borohydride (3.93 g, 104.16 mmol) portion-wise, at 5° C., and the reaction mixture was allowed to stir at RT for 3 h. The reaction mixture was quenched with brine (25 mL) and concentrated in vacuo. The crude compound was purified by silica gel column chromatography eluting with 10% MeOH/CHCl$_3$) to obtain (1H-imidazol-2-yl)-methanol as a pale yellow solid (4 g, 78%).

R$_f$: 0.1 (10% MeOH/CHCl$_3$).

$^1$H NMR (400 MHz, CD$_3$OD): δ 6.97 (s, 2H), 4.61 (s, 2H).

4-(5-Methyl-[1,3,4]oxadiazol-2-yl)-piperazine-1-carboxylic acid tert-butyl ester

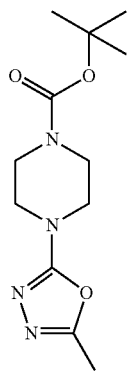 [SMILES: Cc1nnc(N2CCN(C(=O)OC(C)(C)C)CC2)o1]

To a stirred solution of 4-cyano-piperazine-1-carboxylic acid tert-butyl ester (5 g, 23.7 mmol) in toluene (125 mL) was added sodium azide (4.62 g, 71.09 mmol) and triethylamine hydrochloride (9.78 g, 71.09 mmol) and the resulting suspension was heated at 80° C. for 18 h. The reaction mixture was cooled to RT, 20% MeOH/EtOAc (300 mL) and water (200 mL) were added and the layers separated. The aqueous layer was acidified with 2M HCl (pH-4) and extracted with 10% MeOH/CH$_2$Cl$_2$ (2×200 mL). The combined organic extract was dried (Na$_2$SO$_4$) and concentrated in vacuo. The crude compound was triturated with pet-ether to afford an off-white solid. The above solid was dissolved in chloro benzene (65 mL), cooled to 0° C., and N, N-diisopropyl ethylamine (5.35 mL, 30.81 mmol) added. Acetic anhydride (2.01 mL, 21.33 mmol) was added drop-wise over a period of 10 minutes under N$_2$ and the reaction mixture was heated at 130° C. for 18 h. The reaction mixture was cooled to RT, diluted with EtOAc (200 mL), washed with water, saturated NaHCO$_3$ and brine. The organic layer was separated, dried (Na$_2$SO$_4$) and concentrated in vacuo. The crude compound was purified by trituration with pet-ether to afford 4-(5-methyl-[1,3,4]oxadiazol-2-yl)-piperazine-1-carboxylic acid tert-butyl ester as a white solid (3.0 g, 47%).

$R_f$: 0.3 (5% MeOH/CH$_2$Cl$_2$).

$^1$H NMR (400 MHz, CDCl$_3$): δ 3.54-3.51 (m, 4H), 3.47-3.43 (m, 4H), 2.39 (s, 3H), 1.48 (s, 9H).

AnalpH2_MeOH_4min(1): Rt 2.69 min; m/z 269 [M+1]$^+$.

1-(5-Methyl-[1,3,4]oxadiazol-2-yl)-piperazine

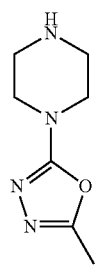

To a stirred solution of 4-(5-methyl-[1,3,4]oxadiazol-2-yl)-piperazine-1-carboxylic acid tert-butyl ester (7.56 g, 28.21 mmol) in CH$_2$Cl$_2$ (45 mL) was added TFA (27 mL, 282.09 mmol) at 0° C. and stirred at room temperature for 2 h. The reaction mixture was concentrated in vacuo, the residue dissolved in methanol (300 mL) and basified with Ambersep 900 (hydroxide) resin, filtered and washed with MeOH. The filtrate was concentrated under in vacuo and further dried under high vacuum to afford 1-(5-methyl-[1,3,4]oxadiazol-2-yl)-piperazine as an off-white semi-solid (3.5 g, 74%).

$^1$H NMR (400 MHz, DMSO-d$_6$): δ 3.26 (t, J=5.2 Hz, 4H), 2.76 (t, J=5.2 Hz, 4H), 2.31 (s, 3H).

AnalpH9_MeOH_4min(2): Rt 1.40 min; m/z 169 [M+1]$^+$.

Scheme N, Step AF (Protocol 1): Synthesis of Aryl Bromo Derivatives of Formula 41 (Via Alkylation)

{1-[1-(4-Bromo-phenyl)-ethyl]-1H-imidazol-2-yl}-methanol

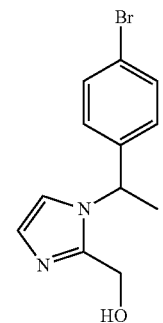 [SMILES: CC(c1ccc(Br)cc1)n1ccnc1CO]

To a solution of 1-bromo-4-(1-bromo-ethyl)-benzene (3.5 g, 13.36 mmol) and (1H-imidazol-2-yl)-methanol (1.96 g, 20.04 mmol) in acetone (35 mL) was added K$_2$CO$_3$ (2.76 g, 20.04 mmol) and KI (110 mg, 0.66 mmol). The reaction mixture was heated under reflux for 16 h. The reaction mixture was cooled to RT and concentrated in vacuo. The residue was dissolved in water, extracted with EtOAc, dried (Na$_2$SO$_4$) and concentrated in vacuo. The crude compound was purified by silica gel column chromatography eluting with 5% MeOH/CHCl$_3$ to obtain {1-[1-(4-Bromo-phenyl)-ethyl]-1H-imidazol-2-yl}-methanol as a white solid (1.5 g, 40%).

$R_f$:0.3 (10% MeOH/CHCl$_3$).

$^1$H NMR (400 MHz, DMSO-d$_6$): δ 7.53 (t, J=8.0 Hz, 2H), 7.28-7.20 (m, 3H), 6.84 (s, 1H), 5.73-5.67 (m, 1H), 5.36 (t, J=4.0 Hz, 1H), 4.51-4.37 (m, 2H), 1.73 (d, J=8.0 Hz, 3H).

AnalpH2_MeOH_4min(1): Rt 1.56 min; m/z 281.1 [M+1]$^+$.

The following bromo derivatives 41 are prepared using analogous procedures.

TABLE 16

Aryl bromo derivatives of Formula 41

| Compound | Analytical Data | Mass, % Yield, State |
|---|---|---|
| 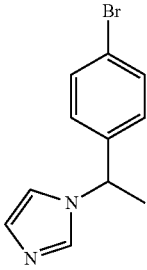 | ¹H NMR (400 MHz, CDCl₃): δ 7.60 (s, 1H), 7.49-7.45 (m, 2H), 7.09 (s, 1H), 7.01 (d, J = 8.0 Hz, 2H), 6.90 (s, 1H), 5.34-5.29 (m, 1H), 1.84 (d, J = 4.0 Hz, 3H). AnalpH2_MeOH_4 min(1): Rt 1.48 min; m/z 251.1 [M + 1]⁺. | 600 mg, 31%, brown liquid. |
| 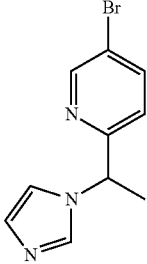 | ¹H NMR (400 MHz, CDCl₃): δ 8.64 (d, J = 2.0 Hz, 1H), 7.77-7.74 (m, 1H), 7.65 (s, 1H), 7.11 (s, 1H), 7.01 (s, 1H), 6.81 (d, J = 8.4 Hz, 1H), 5.42-5.37 (m, 1H), 1.9 (d, J = 7.2 Hz, 3H). AnalpH2_MeOH_4 min(1): Rt 1.28 min; m/z 252.2 [M + 1]⁺. | 600 mg, 31%, off-white solid. |

R_f: 0.7 (30% EtOAc/pet-ether).

¹H NMR (400 MHz, DMSO-d₆): δ 7.65 (d, J=2.0 Hz, 1H), 7.53-7.51 (d, J=8.4 Hz, 2H), 7.08-7.06 (d, J=8.0 Hz, 2H), 6.94 (d, J=2.0 Hz, 1H), 5.68 (s, 2H), 4.58 (q, J=7.2 Hz, 2H), 1.25 (t, J=7.2 Hz, 3H).

AnalpH2_MeOH_4min(1): Rt 3.44 min; m/z 309 [M+1]⁺.

The following bromo derivatives 41 are prepared using analogous procedures.

TABLE 17

Aryl bromo derivatives of Formula 41

| Compound | Analytical Data | Mass, % Yield, State |
|---|---|---|
| 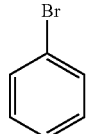 | ¹H NMR (400 MHz, DMSO-d₆): δ 7.99 (d, J = 2.4 Hz, 1H), 7.57 (d, J = 8.4 Hz, 2H), 7.20 (d, J = 8.4 Hz, 2H), 6.75 (d, J = 2.4 Hz, 1H), 5.41 (s, 2H), 4.25 (q, J = 7.4 Hz, 2H), 1.26 (t, J = 7.4 Hz, 3H). AnalpH2_MeOH_4 min(1): Rt 3.14 min; m/z 309 [M + 1]⁺. | 6.0 g, 54%, white solid. |

Scheme N, Step AF (Protocol 1a): Synthesis of Aryl Bromo Derivatives of Formula 41 (Via Alkylation)

2-(4-Bromo-benzyl)-2H-pyrazole-3-carboxylic acid ethyl ester

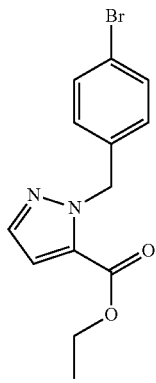 [SMILES: CCOC(=O)c1ccnn1Cc1ccc(Br)cc1]

To a suspension of 2H-pyrazole-3-carboxylic acid ethyl-ester (5 g, 35.68 mmol) and K₂CO₃ (14.79 g, 107.06 mmol) in DMF (10 mL) was added 4-bromobenzyl bromide (8.92 g, 35.68 mmol) at RT and stirred for 16 h. The reaction mixture was concentrated in vacuo, the residue was dissolved in EtOAc (150 mL), washed with H₂O (50 mL), brine (50 mL), dried (Na₂SO₄) and concentrated in vacuo. The crude compound was purified by silica gel column chromatography eluting with 10% EtOAc/pet-ether to afford 2-(4-bromo-benzyl)-2H-pyrazole-3-carboxylic acid ethyl ester as pale yellow liquid (4.0 g, 36%).

Scheme N, Step AF (Protocol 1b): Synthesis of Aryl Bromo Derivatives of Formula 41 (Via Alkylation)

1-[1-(4-Bromo-phenyl)-ethyl]-4-(5-methyl-[1,3,4]oxadiazol-2-yl)-piperazine

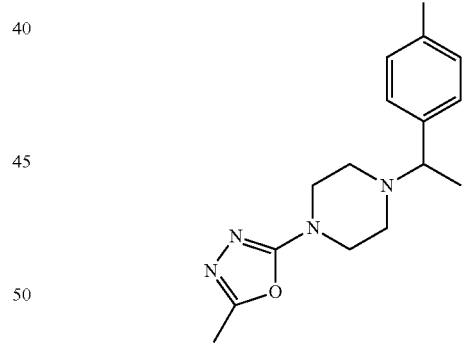

To a stirred suspension of 1-(5-methyl-[1,3,4]oxadiazol-2-yl)-piperazine (1 g, 5.95 mmol) and K₂CO₃ (1.14 g, 8.33 mmol) in 1,4-dioxane (20 mL) was added 1-bromo-4-(1-bromo-ethyl)-benzene (1.72 g, 12.44 mmol) and further stirred for 16 h at RT. Further K₂CO₃ was added (903 mg, 6.55 mmol) and the reaction mixture was heated at 100° C. for 3 h. The reaction mixture was cooled to RT, diluted with EtOAc, filtered and the filtrate washed with water. The organic layer was dried (Na₂SO₄) and concentrated in vacuo to obtain the crude compound. The crude compound was purified by silica gel chromatography and eluting with 0-2% MeOH/CH₂Cl₂ to afford 1-[1-(4-bromo-phenyl)-ethyl]-4-(5-methyl-[1,3,4]oxadiazol-2-yl)-piperazine as gummy liquid (1.02 g, 49%).

$R_f$: 0.35 (5% MeOH/CH$_2$Cl$_2$).

$^1$H NMR (400 MHz, CDCl$_3$): δ 7.44 (d, J=8.4 Hz, 2H), 7.20 (d, J=8.0 Hz, 2H), 3.45-3.36 (m, 5H), 2.58-2.53 (m, 2H), 2.47-2.42 (m, 2H), 2.37 (s, 3H), 1.34 (d, J=6.8 Hz, 3H).

Synthesis of Bromo Intermediates 41 of Formula 43 (Required for Step AE, Scheme I)

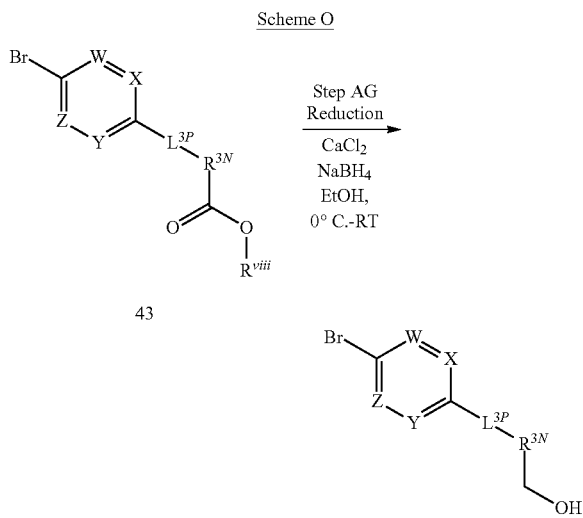

Scheme O, Step AG: Reduction of Ester 43 to Alcohol 44

[2-(4-Bromo-benzyl)-2H-pyrazol-3-yl]-methanol

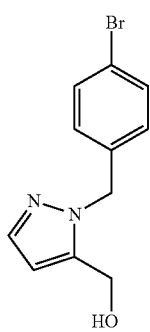 [SMILES: OCc1ccnn1Cc1ccc(Br)cc1]

To a solution of compound 2-(4-bromo-benzyl)-2H-pyrazole-3-carboxylic acid ethyl ester (4 g, 12.93 mmol) in EtOH (40 mL) was added NaBH$_4$ (1.95 g, 51.75 mmol) and CaCl$_2$ (2.87 g, 25.87 mmol) at 0° C. and stirred at RT for 3 h. The reaction mixture was quenched with ice and the solvent removed in vacuo. The residue was diluted with water (50 mL) and extracted with EtOAc (2×100 mL), the combined organic layers were dried over Na$_2$SO$_4$ and concentrated under reduced pressure to obtain [2-(4-bromo-benzyl)-2H-pyrazol-3-yl]-methanol as a white solid (3.1 g, 86%).

$R_f$: 0.2 (30% EtOAc/pet-ether).

$^1$H NMR (400 MHz, DMSO-d$_6$): δ 7.51 (d, J=8.4 Hz, 2H), 7.38 (d, J=2.0 Hz, 1H), 6.21 (d, J=1.6 Hz, 1H), 5.33 (t, J=5.6 Hz, 1H), 5.31 (s, 2H), 4.46-4.45 (d, J=5.6 Hz, 2H).

AnalpH2_MeOH_4min(1): Rt 2.73 min; m/z 267 [M+1]$^+$.

The following bromo derivatives 44 are prepared using analogous procedures.

TABLE 18

Aryl bromo derivatives of Formula 44

| Compound | Analytical Data | Mass, % Yield, State |
| --- | --- | --- |
|  | $^1$H NMR (400 MHz, DMSO-d$_6$): δ 7.74 (d, J = 2.0 Hz, 1H), 7.53 (d, J = 8.4 Hz, 2H), 7.16 (d, J = 8.4 Hz, 2H), 6.20 (d, J = 2.0 Hz, 1H), 5.23 (s, 2H), 4.96 (t, J = 6.0 Hz, 1H), 4.37 (d, J = 6.0 Hz, 2H). AnalpH2_MeOH_4 min(1): Rt 2.70 min; m/z 267 [M + 1]$^+$. | 4.4 g, 85%, white solid. |

Synthesis of Bromo Intermediates 41 of Formula 45 (Required for Step AI, Scheme I)

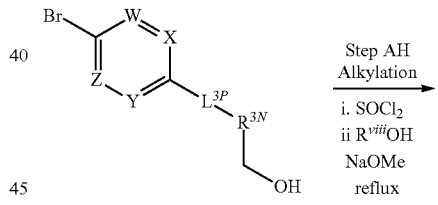

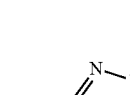

Where L$^{3P}$—R$^{3N}$CH$_2$OH = aryl/heteroaryl-CH$_2$OH

Scheme P Step AH: Ether Formation from Alcohol 44

1-f[1-(4-Bromo-phenyl)-ethyl]-2-methoxymethyl-1H-imidazole

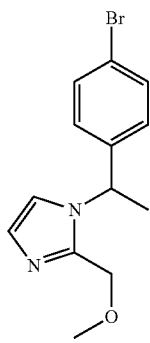 [SMILES: COCc1nccn1C(C)c1ccc(Br)cc1]

A mixture of {1-[1-(4-bromo-phenyl)-ethyl]-1H-imidazol-2-yl}-methanol (0.8 g, 2.85 mmol) and thionyl chloride (9.6 mL, 132 mmol) were stirred at RT for 3 h. The reaction mixture was concentrated in vacuo. The obtained residue was dissolved in MeOH (3 mL) and NaOMe added (105 mg, 1.95 mmol) at RT and the reaction mixture was heated under reflux for 1 h. The reaction mixture was cooled to RT, quenched with ice-cold water, extracted with $CH_2Cl_2$, dried ($Na_2SO_4$) and concentrated in vacuo. The crude compound was purified by silica gel column chromatography eluting with 5% MeOH/$CHCl_3$ to obtain 1-[1-(4-bromo-phenyl)-ethyl]-2-methoxymethyl-1H-imidazole as a pale yellow liquid (340 mg, 40%).

$R_f$:0.6 (10% MeOH/$CHCl_3$).

$^1$H NMR (400 MHz, $CDCl_3$): δ 7.46-7.43 (m, 2H), 7.02-6.99 (m, 4H), 5.65-5.60 (m, 1H), 4.51-4.40 (m, 2H), 3.28 (s, 3H), 1.78 (d, J=4.0 Hz, 3H).

AnalpH2_MeOH_4min(1): Rt 1.85 min; m/z 297.1 [M+1]$^+$.

The following bromo derivatives 45 are prepared using analogous procedures.

TABLE 19

Aryl bromo derivatives of Formula 45

| Compound | Analytical Data | Mass, % Yield, State |
|---|---|---|
| ![Br-pyrazole-OMe structure] | $^1$H NMR (400 MHz, DMSO-$d_6$): δ 7.51 (d, J = 9.2 Hz, 2H), 7.44 (d, J = 2.0 Hz, 1H), 7.09 (d, J = 8.4 Hz, 2H), 6.30 (d, J = 1.6 Hz, 1H), 5.29 (s, 2H), 4.42 (s, 2H), 3.20 (s, 3H). AnalpH2_MeOH_4 min(1): Rt 3.08 min; m/z 281 [M + 1]$^+$. | 2.3 g, 54%, pale yellow liquid. |

TABLE 19-continued

Aryl bromo derivatives of Formula 45

| Compound | Analytical Data | Mass, % Yield, State |
|---|---|---|
| ![Br-pyrazole-OMe structure] | $^1$H NMR (400 MHz, DMSO-$d_6$): δ 7.79 (d, J = 2.0 Hz, 1H), 7.53 (d, J = 8.8 Hz, 2H), 7.16 (d, J = 8.0 Hz, 2H), 6.24 (d, J = 2.4 Hz, 1H), 5.27 (s, 2H), 4.30 (s, 2H), 3.22 (s, 3H). AnalpH2_MeOH_4 min(1): Rt 2.99 min; m/z 281 [M + 1]$^+$. | 1.8 g, 71%, light yellow viscous liquid. |

Scheme IB, Step AI (Protocol 1): Synthesis of Aryl Boronic Ester/Acid Derivatives of Formula 25 (Via Boronic Ester/Acid Insertion, Required for Step Z, Scheme I)

1-(5-Methyl-[1,3,4]oxadiazol-2-yl)-4-{1-[4-(4,4,5,5-tetramethyl-[1,3,2]dioxaborolan-2-yl)-phenyl]-ethyl}-piperazine

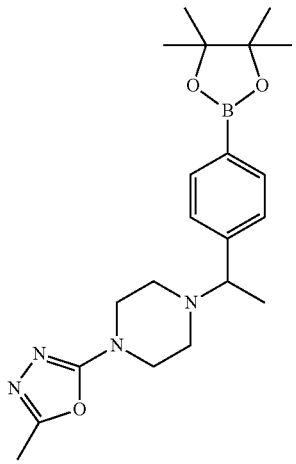 [SMILES: Cc1nnc(N2CCN(C(C)c3ccc(B4OC(C)(C)C(C)(C)O4)cc3)CC2)o1]

A stirred solution of 1-[1-(4-bromo-phenyl)-ethyl]-4-(5-methyl-[1,3,4]oxadiazol-2-yl)-piperazine (800 mg, 2.28 mmol) in 1,4-dioxane (25 mL) was degassed with nitrogen. Pd(dppf)$Cl_2$.DCM (1:1) (185 mg, 0.23 mmol), potassium acetate (669 mg, 6.83 mmol) and bis(pinacolato)diborane (635 mg, 2.50 mmol) was added to the above solution and again degassed for another 20 minutes and the reaction mixture was heated at 100° C. for 16 h. The reaction mixture was cooled to RT, diluted with EtOAc, filtered through a Celite bed and washed with EtOAc. The filtrate was concentrated in vacuo to obtain the crude compound. The crude compound was purified by Florisil® (100-200 mesh) column chromatography, eluting with pet-ether to afford 1-(5-methyl-[1,3,4]oxadiazol-2-yl)-4-{1-[4-(4,4,5,5-tetramethyl-[1,3,2]dioxaborolan-2-yl)-phenyl]-ethyl}-piperazine as a white solid (225 mg, 25%).

$R_f$: 0.3 (5% MeOH/CH$_2$Cl$_2$).

$^1$H NMR (400 MHz, CDCl$_3$): δ 7.77 (d, J=7.6 Hz, 2H), 7.32 (d, J=8.0 Hz, 2H), 3.45-3.33 (m, 5H), 2.59-2.53 (m, 2H), 2.48-2.42 (m, 2H), 2.26 (s, 3H), 1.37 (d, J=7.2 Hz, 3H), 1.34 (s, 12H).

AnalpH2_MeOH_4min(1): Rt 2.26 min; m/z 399.3 [M+1]$^+$.

The following boronic acid/ester derivatives are prepared using analogous procedures.

TABLE 20

Boronic acid/ester derivatives of Formula 25

| Compound | Analytical Data | Mass, % Yield, State |
|---|---|---|
| (structure) | $^1$H NMR (400 MHz, DMSO-d6): δ 7.61 (d, J = 8.0 Hz, 2H), 7.43 (d, J = 2.0 Hz, 1H), 7.12 (d, J = 8.0 Hz, 2H), 6.30 (d, J = 1.6 Hz, 1H), 5.34 (s, 2H), 4.39 (s, 2H), 3.19 (s, 3H), 1.27 (s, 12H). AnalpH2_MeOH_4 min(1): Rt 3.31 min; m/z 329.2 [M + 1]$^+$. | 1.2 g, 70%, oight yellow viscous liquid. |
| (structure) | $^1$H NMR (400 MHz, DMSO-d6): δ 7.77 (d, J = 2.0 Hz, 1H), 7.63 (d, J = 8.0 Hz, 2H), 7.20 (d, J = 8.0 Hz, 2H), 6.24 (d, J = 2.4 Hz, 1H), 5.31 (s, 2H), 4.30 (s, 2H), 3.21 (s, 3H), 1.27 (s, 12H). AnalpH2_MeOH_4 min(1): Rt 3.25 min; m/z 329.2 [M + 1]$^+$. | 1.4 g, 82%, light yellow viscous liquid. |
| (structure) | $^1$H NMR (400 MHz, DMSO-d6): δ 8.84 (s, 1H), 8.32 (s, 1H), 8.07 (dd, J = 1.2, 7.6 Hz, 1H), 7.79 (d, J = 3.2 Hz, 1H), 7.26 (s, 1H), 7.14 (dd, J = 7.6, 22 Hz, 1H), 6.90 (s, 1H), 5.59 (t, J = 7.6 Hz, 1H), 1.79 (d, J = 6.8 Hz, 3H). AnalpH9_MeOH_4 min(2): Rt 1.32 min; m/z 218.2 [M + 1]$^+$. | 70 mg, 32%, white solid |

TABLE 20-continued

Boronic acid/ester derivatives of Formula 25

| Compound | Analytical Data | Mass, % Yield, State |
|---|---|---|
| (structure) | AnalpH2_MeOH_4 min (1): Rt 3.19 min; m/z 330.3 [M + 1]$^+$; Rt: 2.16; m/z 248.3 [M + 1]$^+$ (mixture of boronic ester and acid observed); | 128 mg, quant., brown oil |

Scheme IB, Step AI (Protocol 2): Synthesis of Aryl Boronic Ester/Acid Derivatives of Formula 25 (Via Boronic Ester/Acid Insertion)

2-Methoxymethyl-1-{1-[4-(4,4,5,5-tetramethyl-[1,3,2]dioxaborolan-2-yl)-phenyl]-ethyl}-1H-imidazole 1-[1-(4-Bromo-phenyl)-ethyl]-2-methoxymethyl-1H-imidazole (155 mg, 0.53 mmol), bis(pinacolato)diborane (200 mg, 0.79 mmol), Pd(dppf)Cl$_2$:DCM (1:1) (43 mg, 0.053 mmol), potassium acetate (155 mg, 1.58 mmol) in 1,4-dioxane (2.5 mL) was de-gassed with N$_2$ bubbling. The reaction mixture was irradiated using a microwave reactor (300 W, 130° C., 1 h). The reaction mixture was filtered and the filtrate concentrated in vacuo. Aqueous HCl was added to the residue and the aqueous mixture was washed with iso-hexane and Et$_2$O. The aqueous layer was then basified with Na$_2$CO$_3$ and the product extracted into CH$_2$Cl$_2$. The CH$_2$Cl$_2$ layers were combined, passed through a phase separation cartridge and concentrated in vacuo to afford 2-methoxymethyl-1-{1-[4-(4,4,5,5-tetramethyl-[1,3,2]dioxaborolan-2-yl)-phenyl]-ethyl}-1H-imidazole as a dark brown semi-solid (161 mg, 89%).

AnalpH2_MeOH_4min(1): Rt 2.28 min; m/z 343.3 [M+1]⁺.

The following boronic acid/ester derivatives are prepared using analogous procedures.

TABLE 21

Boronic acid/ester derivatives of Formula 25

| Compound | Analytical Data | Mass, % Yield, State |
|---|---|---|
| (structure: pinacol boronate-phenyl-CH(CH₃)-imidazole) | AnalpH2_MeOH_4 min(1): Rt 2.11 min; m/z 299.3 [M + 1]⁺. | 97.4 mg, 82%, brown gum. |
| (structure: pinacol boronate-phenyl-CH(CH₃)-imidazole-CH₂OH) | AnalpH2_MeOH_4 min(1): Rt 2.05 min; m/z 329.2 [M + 1]⁺. | quantitative, brown solid. |

Scheme I, Step Z: Synthesis of 2H-Isoquinolin-1-One Derivatives of Formula 5 (Via Suzuki Cross-Coupling)

3-[4-(2-Hydroxymethyl-imidazol-1-ylmethyl)-phenyl]-1-oxo-1,2-dihydro-isoquinoline-5-carbonitrile (IQ-015)

3-Chloro-1-oxo-1,2-dihydro-isoquinoline-5-carbonitrile (50 mg, 0.24 mmol), {1-[4-(4,4,5,5-tetramethyl-[1,3,2]dioxaborolan-2-yl)-benzyl]-1H-imidazol-2-yl}-methanol (100 mg, 0.32 mmol), Pd(dppf)Cl₂ (20 mg, 0.024 mmol) and K₂CO₃ (66 mg, 0.48 mmol) were combined in a microwave vial with a solution of DME/H₂O/EtOH 8:2:1 (2 mL). The mixture was degassed with N₂ bubbling for 10 minutes and irradiated using a microwave reactor (300 W, 130° C., 2 h). After this time the reaction mixture was applied directly to a SCX-2 column (5 g), washed with MeOH (6×column volumes) followed by elution with 2M NH₃ in MeOH (6 column volumes). The crude material was purified by silica gel column chromatography, eluting with CH₂Cl₂ and increasing the polarity to 10% MeOH/CH₂Cl₂. The product was lyophilised from 1:1 MeCN/H₂O to afford 3-[4-(2-hydroxymethyl-imidazol-1-ylmethyl)-phenyl]-1-oxo-1,2-dihydro-isoquinoline-5-carbonitrile as a pale brown solid (35 mg, 41%).

$^1$H NMR (400 MHz, d₆-DMSO): δ 12.0 (s, 1H), 8.49 (d, J=7.8 Hz, 1H), 8.28 (dd, J=7.6, 1.3 Hz, 1H), 7.80 (d, J=8.6 Hz, 2H), 7.63 (t, J=8.0 Hz, 1H), 7.37 (d, J=8.3 Hz, 2H), 7.19 (d, J=1.3 Hz, 1H), 6.86 (d, J=1.3 Hz, 1H), 6.80 (s, 1H), 5.42 (t, J=5.6 Hz, 1H), 5.35 (s, 2H), 4.49 (d, J=6 Hz, 2H).

AnalpH2_MeOH_QC(3): Rt 4.63 min; m/z 357.4 [M+1]⁺.

The following 2H-isoquinolin-1-one derivatives are prepared using analogous procedures.

TABLE 13

2H-isoquinolin-1-one derivatives of Formula 5

| Compound | Code | Analytical Data | Mass, % Yield, State |
|---|---|---|---|
| | IQ-016 | AnalpH2_MeOH_QC(3): Rt 4.89 min; m/z 384.5 [M + 1]+ | 23 mg, 48%, off-white solid |
| | IQ-017 | 1H NMR (400 MHz, d6-DMSO): δ 12.0 (s, 1H), 8.49 (d, J = 7.8 Hz, 1H), 8.28 (d, J = 7.8 Hz, 1H), 7.81 (d, J = 8.3 Hz, 2H), 7.63 (t, J = 7.8 Hz, 1H), 7.35 (d, J = 8.1 Hz, 2H), 7.27 (s, 1H), 6.91 (s, 1H), 6.80 (s, 1H), 5.30 (s, 1H), 4.45 (s, 2H), 3.23 (s, 3H). AnalpH2_MeOH_QC(3): Rt 4.99 min; m/z 371.5 [M + 1]+ | 17.7 mg, 24%, grey solid |
| | IQ-018 | AnalpH2_MeOH_QC(3): Rt 4.70 min; m/z 342.4 [M + 1]+ | 1.7 mg, 14%, brown solid |

TABLE 13-continued 2H-isoquinolin-1-one derivatives of Formula 5

| Compound | Code | Analytical Data | Mass, % Yield, State |
|---|---|---|---|
| | IQ-019 | AnalpH2_MeOH_QC(3): Rt 5.81 min; m/z 455.5 [M + 1]+ | 44 mg, 41%, pale orange solid |
| | IQ-020 | $^1$H NMR (400 MHz, DMSO-d$_6$): δ 12.03-12.00 (br s, 1H), 8.49 (d, J = 7.8 Hz, 1H), 8.28 (dd, J = 7.6, 1.3 Hz, 1H), 7.80 (d, J = 8.3 Hz, 2H), 7.63 (t, J = 7.8 Hz, 1H), 7.50 (d, J = 8.3 Hz, 2H), 6.81 (s, 1H), 3.61 (s, 2H), 3.40-3.37 (m, 4H), 2.52-2.49 (m, 4H), 2.33 (s, 3H). AnalpH2_MeOH_QC(3): Rt 5.07 min; m/z 427.5 [M + 1]+ | 62.6 mg, 61%, off-white solid |
| | IQ-021 | $^1$H NMR (400 MHz, DMSO-d$_6$): δ 12.03 (br s, 1H), 8.48 (d, J = 7.8 Hz, 1H), 8.27 (dd, J = 7.3, 1.0 Hz, 1H), 7.89 (d, J = 2.3 Hz, 1H), 7.78 (d, J = 8.1 Hz, 2H), 7.62 (t, J = 7.8 Hz, 1H), 7.49 (d, J = 1.8 Hz, 1H), 7.35 (d, J = 8.3 Hz, 2H), 6.78 (s, 1H), 6.30 (t, J = 2.0 Hz, 1H), 5.43 (s, 2H). AnalpH2_MeOH_QC (3): Rt 7.33 min; m/z 327.4 [M + 1]+ | 12.3 mg, 15%, light brown solid |

TABLE 13-continued 2H-isoquinolin-1-one derivatives of Formula 5

| Compound | Code | Analytical Data | Mass, % Yield, State |
|---|---|---|---|
| | IQ-027 | AnalpH2_MeOH_QC (2): Rt 7.50 min; m/z 328.2 [M + 1]+ | 4.2 mg, 4%, white solid |
| | IQ-028 | AnalpH2_MeOH_QC (2): Rt 5.35 min; m/z 385.2 [M + 1]+ | 29.4 mg, 25%, off-white solid |
| | IQ-029 | $^1$H NMR (400 MHz, d$_6$-DMSO): δ 12.03 (s, 1H), 8.49 (d, J = 7.8 Hz, 1H), 8.28 (dd, J = 7.3, 1.0 Hz, 1H), 7.87 (s, 1H), 7.81 (d, J = 8.3 Hz, 2H), 7.63 (t, J = 7.8 Hz, 1H), 7.43 (d, J= 8.3 Hz, 2H), 7.34 (t, J = 1.0 Hz, 1H), 6.94 (t, J = 1.0 Hz, 1H), 6.80 (s, 1H), 5.64 (q, J = 7.1 Hz, 1H), 1.84 (d, J = 7.1 Hz, 3H). AnalpH2_MeOH_QC (2): Rt 5.00 min; m/z 341.2 [M + 1]+ | 21 mg, 28%, off-white solid |
| | IQ-030 | AnalpH2_MeOH_QC (2): Rt 6.92 min; m/z 328.1 [M + 1]+ | 9.2 mg, 9.6%, white solid |

TABLE 13-continued
2H-isoquinolin-1-one derivatives of Formula 5
| Compound | Code | Analytical Data | Mass, % Yield, State |
|---|---|---|---|
| 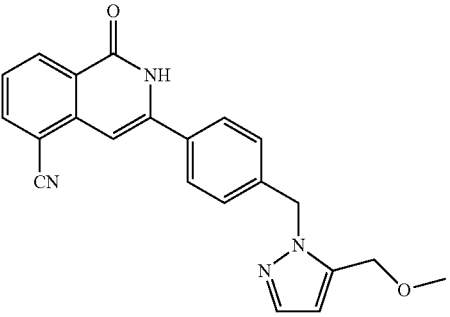 [SMILES: COCc1ccnn1Cc1ccc(-c2cc3c(C#N)cccc3c(=O)[nH]2)cc1] | IQ-031 | AnalpH2_MeOH_QC (2): Rt 7.66 min; m/z 371.2 [M + 1]+ | 26.7 mg, 24.6%, off-white solid |
| 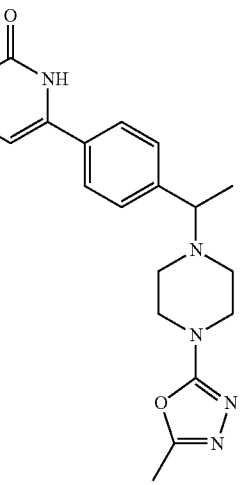 | IQ-032 | 1H NMR (400 MHz, CDCl3): δ 9.31 (s, 1H), 8.55 (d, J = 8.1 Hz, 1H), 7.96 (dd, J = 7.6, 1.3 Hz, 1H), 7.63 (d, J = 8.1 Hz, 2H), 7.48 (t, J = 8.6 Hz, 1H), 7.48 (d, J = 8.1 Hz, 2H), 7.03 (s, 1H), 3.46 (q, J = 6.9 Hz, 1H), 3.43 (t, J = 4.6 Hz, 4H), 2.56 (m, 2H), 2.44 (m, 2H), 2.32 (s, 3H), 1.36 (d, J = 6.9 Hz, 3H). AnalpH2_MeOH_QC (2): Rt 5.44 min; m/z 441.2 [M + 1]+ | 32.8 mg, 25.4%, off-white solid |
| 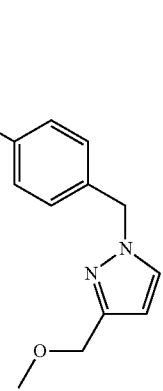 | IQ-033 | AnalpH2_MeOH_QC (2): Rt 7.49 min; m/z 371.2 [M + 1]+ | 54.2 mg, 49.7%, off-white solid |

TABLE 13-continued 2H-isoquinolin-1-one derivatives of Formula 5

| Compound | Code | Analytical Data | Mass, % Yield, State |
|---|---|---|---|
| (structure) | IQ-034 | AnalpH2_MeOH_QC (2): Rt 4.60 min; m/z 342.2 [M + 1]+ | 23.9 mg, 26.8%, light brown solid |
| (structure) | IQ-035 | $^1$H NMR (400 MHz, CDCl$_3$): δ 9.97 (br s, 1H), 8.62 (d, J = 8.1 Hz, 1H), 8.04 (dd, J = 7.6, 1.6 Hz, 1H), 7.81 (d, J = 8.3 Hz, 2H), 7.60 (d, J = 8.6 Hz, 2H), 7.56 (d, J = 7.8 Hz, 2H), 7.12 (s, 1H), 3.91-3.83 (m, 2H), 3.54 (t, J = 5.3 Hz, 2H), 3.53-3.46 (m, 2H), 3.37 (s, 3H), 2.64 (t, J = 5.3 Hz, 2H), 2.63-2.47 (m, 4H). AnalpH2_MeOH_QC (2): Rt 4.78 min; m/z 417.2 [M + 1]+ | 68.1 mg, 40.9%, pale yellow solid |
| (structure) | IQ-036 | $^1$H NMR (400 MHz, DMSO-d$_6$): δ 12.13 (br s, 1H), 8.38 (dd, J = 8.6, 3.0 Hz, 1H), 8.21 (dd, J = 8.2, 2.6 Hz, 1H), 7.75 (d, J = 8.8 Hz, 2H), 7.38 (d, J = 8.4 Hz, 2H), 6.79 (s, 1H), 3.80 (s, 2H), 3.52-3.45 (m, 4H), 2.27-2.23 (m, 4H), 2.16 (s, 3H). AnalpH2_MeOH_QC (2): Rt 5.19 min; m/z 380.2 [M + 1]+ | 35.8 mg, 32.8%, pale yellow solid |

TABLE 13-continued 2H-isoquinolin-1-one derivatives of Formula 5

| Compound | Code | Analytical Data | Mass, % Yield, State |
|---|---|---|---|
| (structure) | IQ-037 | $^1$H NMR (400 MHz, DMSO-d$_6$): δ 12.03 (br s, 1H), 8.48 (d, J= 8.0 Hz, 1H), 8.27 (dd, J = 7.6, 1.2 Hz, 1H), 7.76 (d, d, J = 8.4 Hz, 2H), 7.62 (t, J = 7.8 Hz, 1H), 7.38 (d, J = 8.4 Hz, 2H), 6.80 (s, 1H), 3.80 (s, 2H), 3.52-3.46 (m, 4H), 2.27-2.24 (m, 4H), 2.17 (s, 3H). AnalpH2_MeOH_QC (2): Rt 4.86 min; m/z 387.2 [M + 1]$^+$ | 29.7 mg, 24.1%, off-white solid |
| (structure) | IQ-038 | AnalpH2_MeOH_QC (2): Rt 4.98 min; m/z 371.2 [M + 1]$^+$ | 33.8 mg, 26.7%, light brown solid |
| (structure) | IQ-039 | $^1$H NMR (400 MHz, DMSO-d$_6$): δ 12.13 (br s, 1H), 8.39 (dd, J= 8.6, 2.6 Hz, 1H), 8.22 (dd, J = 8.8, 2.4 Hz, 1H), 7.75 (d, J = 8.0 Hz, 2H), 7.50 (d, J = 8.4 Hz, 2H), 6.80 (s, 1H), 3.61 (s, 2H), 3.40-3.34 (m, 4H), 2.51-2.48 (m, 4H), 2.33 (s, 3H). AnalpH2_MeOH_QC (2): Rt 5.48 min; m/z 445.2 [M + 1]$^+$ | 41.2 mg, 34.3%, pale yellow solid |

TABLE 13-continued 2H-isoquinolin-1-one derivatives of Formula 5

| Compound | Code | Analytical Data | Mass, % Yield, State |
|---|---|---|---|
| | IQ-040 | ¹H NMR (400 MHz, DMSO-d₆) δ 12.03 (br s, 1H), 8.51-8.47 (m, 1H), 8.28 (dd, J = 7.6, 1.3 Hz, 1H), 7.79 (d, J = 8.6 Hz, 2H), 7.63 (t, J = 7.7 Hz, 1H), 7.50 (d, J = 8.3 Hz, 2H), 6.81 (s, 1H), 4.04 (d, J = 14.0 Hz, 1H), 3.58 (dd, J = 12.6, 2.5 Hz, 1H), 3.51-3.47 (m, 1H), 3.34-3.30 (m, 1H), 3.20-3.14 (m, 1H), 2.98 (dd, J = 12.4, 8.6 Hz, 1H), 2.73-2.68 (m, 1H), 2.62-2.55 (m, 1H), 2.33 (s, 3H), 2.28-2.21 (m, 1H), 1.15 (d, J = 6.3 Hz, 3H). AnalpH2_MeOH_QC (2): Rt 5.33 min; m/z 441.2 [M + 1]⁺ | 44.8 mg, 20%, white solid |
| | IQ-041 | ¹H NMR (400 MHz, DMSO-d₆) δ 12.14-11.96 (br s, 1H), 8.49 (d, J = 8.1 Hz, 1H), 8.28 (dd, J = 7.3, 1.3 Hz, 1H), 7.79 (d, J = 8.3 Hz, 2H), 7.63 (t, J = 7.6 Hz, 1H), 7.49 (d, J = 8.3 Hz, 2H), 6.81 (s, 1H), 3.58 (s, J = 6.3 Hz, 2H), 3.01-2.79 (m, 3H), 2.46 (s, 3H), 2.16 (t, J = 10.8 Hz, 2H), 1.99 (d, J = 10.8 Hz, 2H), 1.79-1.67 (m, 2H). AnalpH2_MeOH_QC (2): Rt 4.78 min; m/z 426.2 [M + 1]⁺ | 20.9 mg, 11%, off-white solid |
| | IQ-042 | ¹H NMR (400 MHz, DMSO-d₆): δ 12.07-12.03 (br s, 1H), 8.49 (d, J= 7.8 Hz, 1H), 8.28 (dd, J = 7.6, 1.3 Hz, 1H), 7.82 (d, J = 8.3 Hz, 2H), 7.63 (t, J = 7.8 Hz, 1H), 7.46 (d, J = 8.1 Hz, 2H), 6.81 (s, 1H), 4.63 (s, 2H), 3.00 (s, 3H), 2.35 (s, 3H). | 51.4 mg, 35%, white solid |

TABLE 13-continued 2H-isoquinolin-1-one derivatives of Formula 5

| Compound | Code | Analytical Data | Mass, % Yield, State |
|---|---|---|---|
| | | AnalpH2_MeOH_QC (2): Rt 7.36 min; m/z 372.2 [M + 1]⁺ | |
| 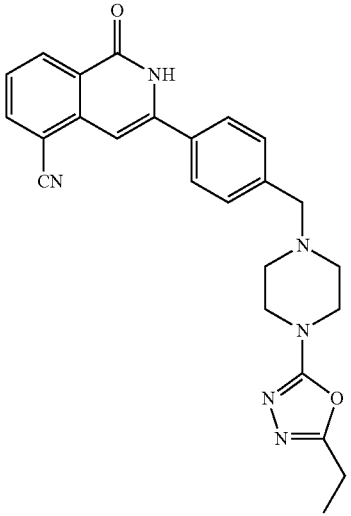 [SMILES: CCc1nnc(N2CCN(Cc3ccc(-c4cc5c(C#N)cccc5c(=O)[nH]4)cc3)CC2)o1] | IQ-044 | ¹H NMR (400 MHz, DMSO-d₆) δ 12.03 (br s, 1H), 8.50-8.47 (m, 1H), 8.28 (dd, J = 7.5, 1.4 Hz, 1H), 7.82-7.78 (m, 2H), 7.63 (dd, J = 8.0, 7.5 Hz, 1H), 7.50 (d, J = 8.4 Hz, 2H), 6.81 (s, 1H), 3.61 (s, 2H), 3.41-3.36 (m, 4H), 2.68 (q, J = 7.5 Hz, 2H), 2.52-2.49 (m, 4H), 1.19 (t, J = 7.5 Hz, 3H). AnalpH2_MeOH_QC (2): Rt 5.60 min; m/z 441.3 [M + 1]⁺ | 18.7 mg, 11%, white solid |
| 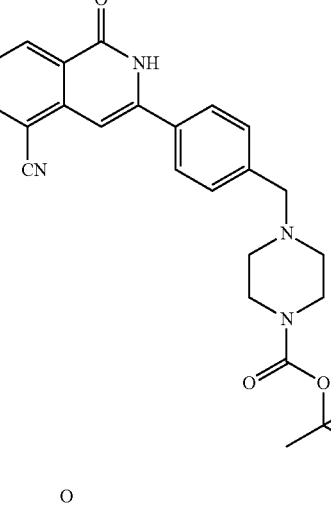 | IQ-046 | ¹H NMR (400 MHz, DMSO-d₆) δ 12.03 (br s, 1H), 8.51-8.47 (m, 1H), 8.28 (dd, J = 7.5, 1.3 Hz, 1H), 7.81-7.77 (m, 2H), 7.63 (dd, J = 8.1, 7.5 Hz, 1H), 7.50-7.46 (m, 2H), 6.81 (s, 1H), 3.57 (s, 2H), 3.35-3.31 (m, 4H), 2.37-2.32 (m, 4H), 1.40 (s, 9H). AnalpH2_MeOH_QC (2): Rt 5.90 min; m/z 445.3 [M + 1]⁺ | 15.4 mg, 43%, light brown solid |
| 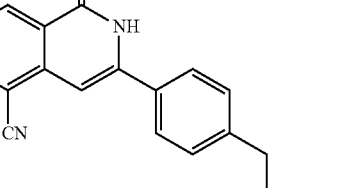 | IQ-047 | ¹H NMR (400 MHz, DMSO-d₆): δ 12.02 (s, 1H), 8.50-8.47 (m 1H), 8.27 (dd, J = 7.6, 1.3 Hz, 1H), 7.77 (d, J = 8.3 Hz, 1H), 7.62 (t, J = 7.8 Hz, 1H), 7.46 (d, J = 8.3 Hz, 1H), 6.80 (s, 1H), 4.33 (quint, J = 6.8 Hz, 1H), 3.70 (s, 2H), 3.57-3.52 (m, 2H), 3.21-3.16 (m, 2H), 2.98 (s, 3H), 2.32 (s, 3H). AnalpH2_MeOH_QC (2): Rt 4.90 | 43.6 mg, 44%, off-white solid |

TABLE 13-continued 2H-isoquinolin-1-one derivatives of Formula 5

| Compound | Code | Analytical Data | Mass, % Yield, State |
|---|---|---|---|
| | | min; m/z 427.2 [M + 1]⁺ | |
| (structure: 5-cyano-2H-isoquinolin-1-one with 3-(4-((4-methyl-1,4-diazepan-1-yl)methyl)phenyl) substituent) | IQ-048 | ¹H NMR (400 MHz, DMSO-d₆): δ 12.08-11.92 (br s, 1H), 8.48 (d, J = 7.8 Hz, 1H), 8.27 (d, J = 7.1 Hz, 1H), 7.78 (d, J = 8.1 Hz, 2H), 7.63 (t, J = 7.8 Hz, 1H), 7.48 (d, J = 8.1 Hz, 2H), 6.80 (s, 1H), 3.67 (s, 3H), 2.68-2.62 (m, 4H), 2.57 (t, J = 5.8 Hz, 2H), 2.53-2.50 (m, 2H), 2.25 (s, 3H), 1.76-1.70 (m, 2H). AnalpH2_MeOH_QC (2): Rt 3.98 min; m/z 373.3 [M + 1]⁺ | 10.9 mg, 10%, pale brown solid |
| (structure: 5-cyano-2H-isoquinolin-1-one with 3-(4-((4-(5-methyl-1,3,4-oxadiazol-2-yl)-1,4-diazepan-1-yl)methyl)phenyl) substituent) | IQ-049 | ¹H NMR (400 MHz, DMSO-d₆): δ 12.02 (s, 1H), 8.50-8.47 (m 1H), 8.28 (dd, J = 7.6, 1.3 Hz, 1H), 7.78 (d, J = 8.3 Hz, 2H), 7.35 (t, J = 8.3 Hz, 1H), 7.47 (d, J = 8.3 Hz, 2H), 6.81 (s, 1H), 3.71 (s, 2H), 3.57-3.53 (m, 4H), 2.75-2.72 (m, 2H), 2.64-2.61 (m, 2H), 2.32 (s, 3H), 1.89-1.83 (m, 2H). AnalpH2_MeOH_QC (2): Rt 4.83 min; m/z 441.3 [M + 1]⁺ | 85.1 mg, 27%, pale brown solid |
| (structure: 5-cyano-2H-isoquinolin-1-one with 3-(6-(4-(tert-butoxycarbonyl)piperazin-1-yl)pyridin-3-yl) substituent) | IQ-051 | ¹H NMR (400 MHz, DMSO-d₆) δ 12.00-11.97 (br s, 1H), 8.59 (s, 1H), 8.44 (d, J = 7.8 Hz, 1H), 8.24 (d, J = 7.8 Hz, 1H), 7.99 (d, J = 8.8 Hz, 1H), 7.58 (t, J = 7.8 Hz, 1H), 6.98 (d, J = 9.1 Hz, 1H), 6.73 (s, 1H), 3.66-3.60 (m, 4H), 3.48-3.42 (m, 4H), 1.43 (s, 9H). AnalpH2_MeOH_QC (2): Rt 8.36 min; m/z 432.2 [M + 1]⁺ | 430 mg, quant., green solid |

TABLE 13-continued 2H-isoquinolin-1-one derivatives of Formula 5

| Compound | Code | Analytical Data | Mass, % Yield, State |
|---|---|---|---|
| | IQ-053 | ¹H NMR (400 MHz, DMSO-d₆): δ 11.88 (s, 1H), 8.47-8.43 (m, 1H), 8.23 (dd, J = 7.6, 1.3 Hz, 1H), 7.72 (d, J = 9.1 Hz, 2H), 7.56 (t, J = 7.6 Hz, 1H), 7.08 (d, J = 8.8 Hz, 2H), 6.75 (s, 1H), 3.49-3.47 (m, 4H), 3.28-3.26 (m, 4H), 1.43 (s, 9H). AnalpH2_MeOH_QC (2): Rt 8.57 min; m/z 375.2 [M + 1]⁺ | 26.5 mg, 25%, bright yellow solid |
| | IQ-055 | ¹H NMR (400 MHz, DMSO-d₆): δ 11.89 (s, 1H), 8.47-8.43 (m, H), 8.24 (dd, J = 7.8, 1.3 Hz, 1H), 7.74 (d, J = 8.8 Hz, 2H), 7.56 (t, J = 7.8 Hz, 1H), 7.13 (d, J = 9.1 Hz, 2H), 6.75 (s, 1H), 3.54-3.51 (m, 4H), 3.43-3.41 (m, 4H), 2.36 (s, 3H). AnalpH2_MeOH_QC (2): Rt 7.68 min; m/z 413.2 [M + 1]⁺ | 35.2 mg, 28%, yellow solid |
| | IQ-056 | ¹H NMR (400 MHz, DMSO-d₆) δ 12.03 (br s, 1H), 8.49 (d, J = 7.8 Hz, 1H), 8.28 (dd, J = 7.6, 1.3 Hz, 1H), 7.81 (d, J = 8.3 Hz, 2H), 7.63 (t, J = 7.8 Hz, 1H), 7.52 (d, J = 8.1 Hz, 2H), 6.82 (s, 1H), 4.03-3.95 (m, 1H), 3.64 (d, J = 13.8 Hz, 1H), 3.58-3.52 (1H, m), 3.54 (d, J = 13.8 Hz, 1H), 3.29 (dd, J = 12.4, 3.0 Hz, 1H), 2.88-2.86 (m, 1H), 2.72-2.66 (m, 1H), 2.33 (s, 3H), 2.28 (dd, J = 11.4, 3.8 Hz, 1H), 2.17 (dt, J = 11.6, 3.5 Hz, 1H), 1.27 (d, J = 6.6 Hz, 3H | 280 mg, 17%, light brown solid |

TABLE 13-continued 2H-isoquinolin-1-one derivatives of Formula 5

| Compound | Code | Analytical Data | Mass, % Yield, State |
|---|---|---|---|
| | | AnalpH2_MeOH_QC (2): Rt 6.07 min; m/z 441.3 [M + 1]+ | |
| | IQ-057 | 1H NMR (400 MHz, DMSO-d6) δ 12.02 (br s, 1H), 8.49 (d, J = 7.7 Hz, 1H), 8.28 (dd, J = 7.7, 1.3 Hz, 1H), 7.78 (d, J = 8.3 Hz, 2H), 7.63 (t, J = 7.7 Hz, 1H), 7.52 (d, J = 8.1 Hz, 2H), 6.80 (s, 1H), 3.61 (s, 2H), 3.32 (t, J = 5.8 Hz, 2H), 3.21 (s, 2H), 2.48 (t, J = 5.8 Hz, 2H), 2.33 (s, 3H), 1.16 (s, 6H). AnalpH2_MeOH_QC (2): Rt 5.40 min; m/z 455.2 [M + 1]+ | 26.6 mg, 17%, light brown solid |
| | IQ-058 | 1H NMR (400 MHz, DMSO-d6) δ 12.02 (br s, 1H), 8.49 (d, J = 7.7 Hz, 1H), 8.28 (dd, J = 7.7, 1.3 Hz, 1H), 7.81 (d, J = 8.3 Hz, 2H), 7.63 (t, J = 7.7 Hz, 1H), 7.52 (d, J = 8.3 Hz, 2H), 6.82 (s, 1H), 3.59 (s, 2H), 3.38 (t, J = 4.8 Hz, 2H), 2.54 (t, J = 4.8 Hz, 2H), 2.35 (s, 3H), 2.31 (s, 2H), 1.38 (s, 6H). AnalpH2_MeOH_QC (2): Rt 6.64 min; m/z 455.3 [M + 1]+ | 36.1 mg, 20%, light brown solid |
| | IQ-060 | AnalpH2_MeOH_4min (1): Rt 1.66 min; m/z 276.2 [M + 1]+ | 111.5 mg, 35% off-white solid |

Scheme I, Step AJ: Synthesis of 2H-Isoquinolin-1-One Derivatives of Formula 5b (Via Boc Deprotection)

1-Oxo-3-(4-piperazin-1-ylmethyl-phenyl)-1,2-dihydro-isoquinoline-5-carbonitrile (IQ-050)

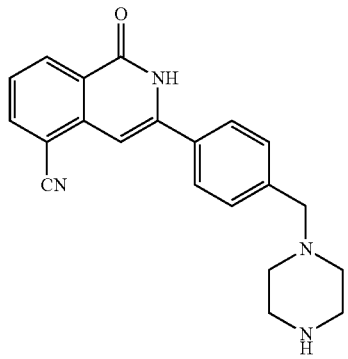 [SMILES: N#Cc1cccc2c(=O)[nH]c(-c3ccc(CN4CCNCC4)cc3)cc12]

To a stirred solution of 4-[4-(5-cyano-1-oxo-1,2-dihydro-isoquinolin-3-yl)-benzyl]-piperazine-1-carboxylic acid tert-butyl ester (213 mg, 0.48 mmol) in $CH_2Cl_2$ (2.5 mL) was added TFA (0.37 mL, 4.79 mmol) and the resulting mixture was stirred at RT for 3 h. The reaction was concentrated in vacuo, $CH_2Cl_2$ added and the mixture passed through an SCX-2 cartridge (2 g) eluting with $CH_2Cl_2$ (3×column volumes) followed by MeOH (3×column volumes). The desired product was eluted from the column with 7M $NH_3$/MeOH (3×column volumes) and the solvent removed in vacuo to afford 1-oxo-3-(4-piperazin-1-ylmethyl-phenyl)-1,2-dihydro-isoquinoline-5-carbonitrile as a light brown solid (133 mg, 81%).

$^1$H NMR (400 MHz, DMSO-$d_6$) 8.51-8.48 (m, 1H), 8.29 (dd, J=7.5, 1.3 Hz, 1H), 7.81 (d, J=7.5 Hz, 2H), 7.64 (t, J=7.6 Hz, 1H), 7.49 (d, J=8.3 Hz, 2H), 6.81 (s, 1H), 3.61 (s, 2H), 3.07-3.02 (m, 4H), 2.58-2.52 (m, 4H).

AnalpH2_MeOH_QC (2): Rt 4.78 min; m/z 345.2 [M+1]$^+$.

The following 2H-isoquinolin-1-one derivatives are prepared using analogous procedures.

| Compound | Reference | Analytical Data | Mass, % Yield, State |
|---|---|---|---|
| (5-cyano-isoquinolin-1(2H)-one with 4-(aminomethyl)phenyl at 3-position) | IQ-043 | AnalpH2_MeOH_QC (2): Rt 4.58 min; m/z 276.2 [M + 1]$^+$ | 26.5 mg, 25%, pale yellow solid |
| (5-cyano-isoquinolin-1(2H)-one with 6-(piperazin-1-yl)pyridin-3-yl at 3-position) | IQ-052 | $^1$H NMR (400 MHz, DMSO-$d_6$) δ 8.56 (d, J = 2.4, 1H), 8.45 (d, J = 7.9 Hz, 1H), 8.24, (dd, J = 7.5, 1.4 Hz, 1H), 7.95 (dd, J = 9.1, 2.6 Hz, 1H), 7.57 (t, J = 7.6 Hz, 1H), 6.93 (d, J = 9.1 Hz, 1H), 6.72 (d, J = 0.6 Hz 1H), 3.57-3.53 (m, 4H), 2.82-2.78 (m, 4H). AnalpH2_MeOH_QC (2): Rt 4.77 min; m/z 332.2 [M + 1]$^+$ | 94 mg, 29%, green solid |

| Compound | Reference | Analytical Data | Mass, % Yield, State |
|---|---|---|---|
| (structure shown) | IQ-054 | $^1$H NMR (400 MHz, DMSO-$d_6$): δ 11.92 (s, 1H), 8.84-8.75 (br s, 2H), 8.48-8.44 (m, 1H), 8.25 (dd, J = 7.6, 1.3 Hz, 1H), 7.75 (d, J = 8.8 Hz, 2H), 7.58 (t, J = 7.8 Hz, 1H), 7.14 (d, J = 9.1 Hz, 2H), 6.75 (s, 1H), 3.51-3.49 (m, 4H), 3.30-3.22 (m, 4H). AnalpH2_MeOH_QC (2): Rt 5.05 min; m/z 331.2 [M + 1]$^+$ | 401 mg, 78%, dark yellow solid |

Scheme I, Step AK: Synthesis of 2H-isoquinolin-1-one derivatives of formula 5c (N-heteroarylation via Protocol 1: halide displacement)

3-{4-[4-(5-Methyl-[1,3,4]oxadiazol-2-yl)piperazin-1-yl]phenyl}-1-oxo-1,2-dihydroisoquinoline-5-carbonitrile (IQ-055)

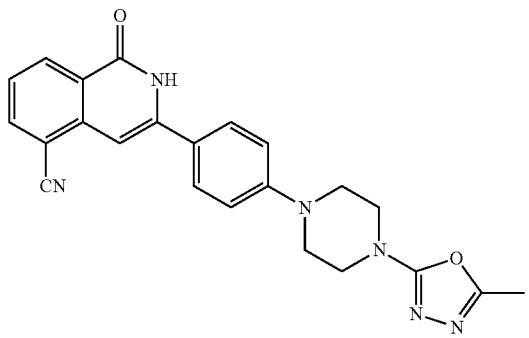 [SMILES: Cc1nnc(N2CCN(c3ccc(-c4cc5c(C#N)cccc5c(=O)[nH]4)cc3)CC2)o1]

A mixture of amine (100 mg, 0.303 mmol), 2-bromo-5-methyl-1,3,4-oxadiazole (54.3 mg, 0.33 mmol), potassium carbonate (167 mg, 1.21 mmol) in DMF (5 mL) was stirred at rt for 20 min then heated in the microwave at 90° C. for 70 min. The reaction mixture was concentrated in vacuo, the resulting solid diluted with water and filtered. The crude solid was further triturated with EtOAc then heated in ethanol at 60° C. for 10 mins. The mixture was filtered to afford the 3-{4-[4-(5-methyl-[1,3,4]oxadiazol-2-yl)piperazin-1-yl]phenyl}-1-oxo-1,2-dihydroisoquinoline-5-carbonitrile (35.2 mg, 28%) as a yellow solid which was further dried in vacuo.

$^1$H NMR (400 MHz, DMSO-$d_6$): δ 11.89 (s, 1H), 8.47-8.43 (m, 1H), 8.24 (dd, J=7.8, 1.3 Hz, 1H), 7.74 (d, J=8.8 Hz, 2H), 7.56 (t, J=7.8 Hz, 1H), 7.13 (d, J=9.1 Hz, 2H), 6.75 (s, 1H), 3.54-3.51 (m, 4H), 3.43-3.41 (m, 4H), 2.36 (s, 3H). AnalpH2_MeOH_QC (2): Rt 7.68 min; m/z 413.2 [M+1]$^+$.

Scheme I, Step AK: Synthesis of 2H-isoquinolin-1-one derivatives of formula 5c (N-heteroarylation via Protocol 2: coupling)

3-{4-[5-Methyl-[1,3,4]-oxadiazol-2-ylamino)methyl]phenyl}-1-oxo-1,2-dihydroisoquinoline-5-carbonitrile (IQ-045)

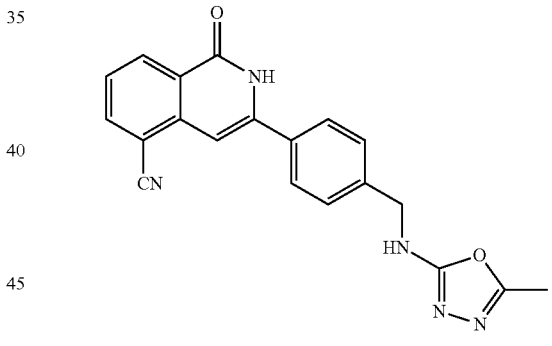

To a solution of 3-(4-aminomethylphenyl)-1-oxo-1,2-dihydroisoquinoline-5-carbonitrile (36 mg, 0.131 mmol) and 5-methyl-1,3,4-oxadiazol-2[3H]one (13.1 mg, 0.131 mmol) in DMF (4 mL) under nitrogen was added DIPEA (45.6 μL, 0.262 mmol) and the reaction mixture was allowed to stir for 5 min. After this time, benzotriazol-1-yloxy)tris(dimethylamino)phosphonium hexafluorophosphate (63.7 mg, 0.144 mmol) was added and the resulting mixture was heated at 50° C. for 2 h. The reaction mixture was added to ice-water and extracted with EtOAc (3×50 mL). The combined organic layer was washed with brine (3×100 mL), dried (anhydrous $Na_2SO_4$), filtered and concentrated in vacuo. The crude compound was purified by silica gel chromatography eluting with $CH_2Cl_2$ and increasing the polarity to 5% MeOH/$CH_2Cl_2$ followed by reverse phase preparative HPLC-MS. The product was lyophilised from 1:1 MeCN/$H_2O$ to obtain 3-{4-[5-methyl-[1,3,4]oxadiazol-2-ylamino)methyl]phenyl}-1-oxo-1,2-dihydroisoquinoline-5-carbonitrile (11.2 mg, 13%) as an off-white solid.

$^1$H NMR (400 MHz, DMSO-d$_6$): δ 12.05 (s, 1H), 8.49 (d, J=8.1 Hz, 1H), 8.28 (dd, J=7.6 Hz, 1.3 Hz, 1H), 8.06 (t, J=6.3 Hz, 1H), 7.79 (d, J=8.3 Hz, 1H), 7.63 (t, J=7.8 Hz, 1H), 7.50 (d, J=8.3 Hz, 2H), 4.43 (d, J=6.1 Hz, 2H), 6.80 (s, 1H), 2.30 (s, 3H).

AnalpH2_MeOH_QC (2): Rt 7.04 min; m/z 358.2 [M+1]$^+$.

Synthesis of 2H-isoquinolin-1-ones of Formula 5
(Route 2b)

130° C. for 2 h in a microwave. The reaction mixture was passed through a Si-thiol cartridge and washed with MeOH. A solid precipitate from the top of the column was combined with the filtrate and the mixture was concentrated in vacuo to give 3-(4-hydroxy-phenyl)-1-oxo-1,2-dihydro-isoquinoline-5-carbonitrile as a brown solid (used without further purification).

AnalpH2_MeOH_4min (1): Rt 2.74 min; m/z 263.2 [M+1]$^+$.

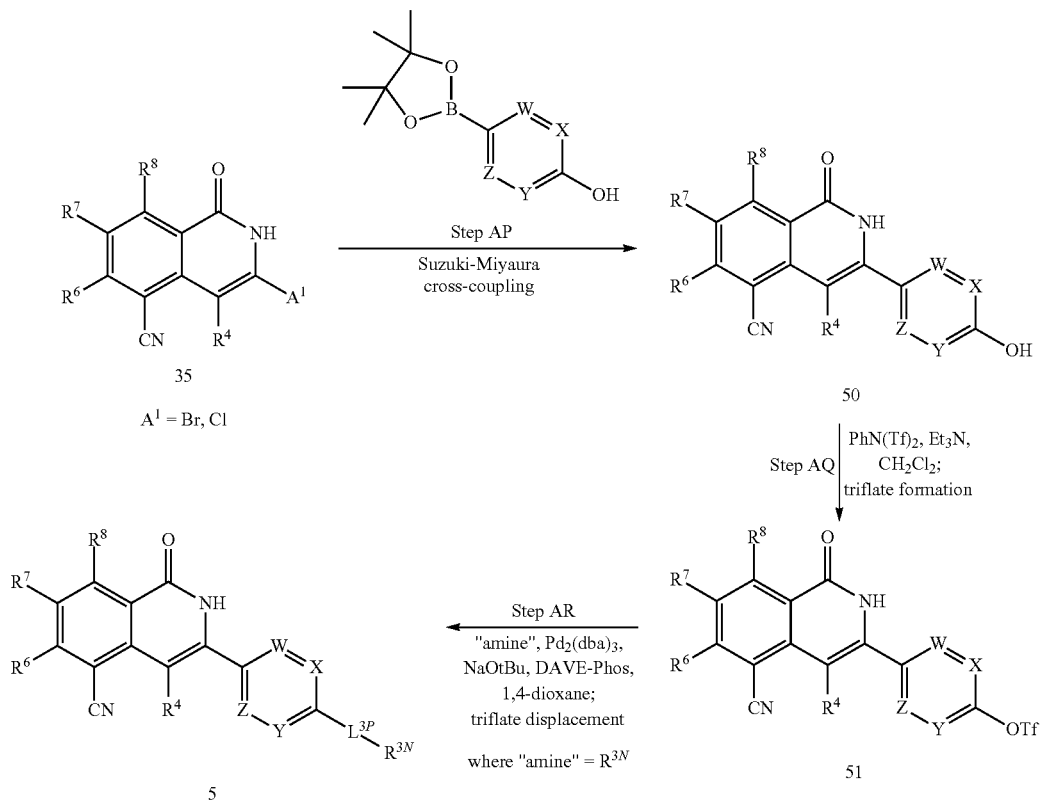

Scheme S

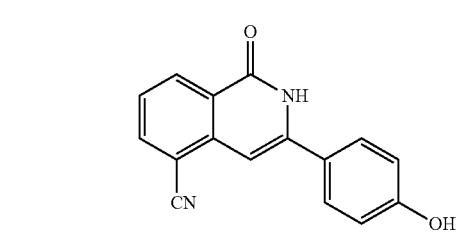 [SMILES: N#Cc1cccc2c(=O)[nH]c(-c3ccc(O)cc3)cc12]

3-(4-Hydroxy-phenyl)-1-oxo-1,2-dihydro-isoquinoline-5-carbonitrile

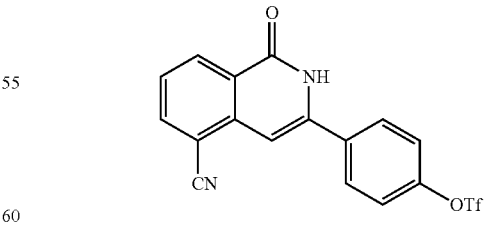

Trifluoro-methanesulfonic acid 4-(5-cyano-1-oxo-1,2-dihydro-isoquinolin-3-yl)-phenyl ester 3-Chloro-1-oxo-1,2-dihydro-isoquinoline-5-carbonitrile (100 mg, 0.49 mmol), 4-hydroxybenzene boronic acid pinacol ester (129 mg, 0.59 mmol), Pd(dppf)Cl$_2$ (40 mg, 0.049 mmol) and K$_2$CO$_3$ (135 mg, 0.98 mmol) were combined and suspended in DME/H$_2$O/EtOH (8:2:1, 4 mL). The mixture was degassed for 10 min with N$_2$ bubbling then heated at Crude 3-(4-hydroxy-phenyl)-1-oxo-1,2-dihydro-isoquinoline-5-carbonitrile was suspended in CH$_2$Cl$_2$ (5 mL) and N-phenyl-bis(trifluoromethanesulfonimide) (350 mg, 0.98 mmol), Et$_3$N (170 μL, 1.23 mmol) were added. The reaction was heated at reflux for 1 h, followed by addition of DMF (5 mL), N-phenyl-bis(trifluoromethanesulfonimide) (350 mg, 0.98 mmol) and Et₃N (170 μL, 1.23 mmol). The reaction was heated at 50° C. for a further 2 h, followed by cooling to room temperature. Water was added and the crude product extracted with 20% MeOH in CH₂Cl₂. The organic layer was passed through a hydrophobic frit and concentrated in vacuo. The residue was purified by silica gel column chromatography, eluting with isohexane and increasing the polarity to 100% EtOAc/iso-hexane to give trifluoro-methanesulfonic acid 4-(5-cyano-1-oxo-1,2-dihydro-isoquinolin-3-yl)-phenyl ester as a pale yellow solid (210 mg, quant.).

AnalpH2_MeOH_4min (1): Rt 3.33 min; m/z 395.2 $[M+1]^+$.

3-{4-[4-(5-Methyl-[1,3,4]oxadiazol-2-yl)-[1,4]diazepan-1-yl]-phenyl}-1-oxo-1,2-dihydro-isoquinoline-5-carbonitrile (IQ-059)

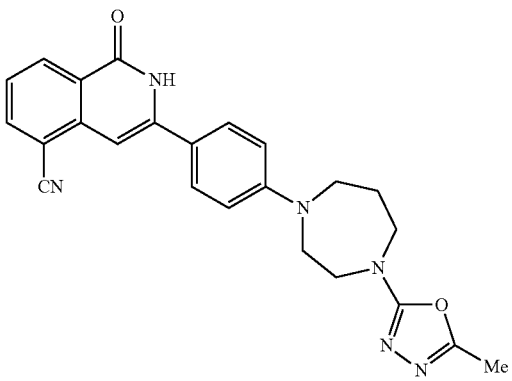 [SMILES: Cc1nnc(N2CCCN(c3ccc(-c4cc5c(C#N)cccc5c(=O)[nH]4)cc3)CC2)o1]

Trifluoro-methanesulfonic acid 4-(5-cyano-1-oxo-1,2-dihydro-isoquinolin-3-yl)-phenyl ester (100 mg, 0.25 mmol), 4-(5-Methyl[1,3,4]oxadiazol-2-yl)[1,4]diazepane (59 mg, 0.33 mmol), DAVE-phos (10 mg, 0.025 mmol), Pd₂(dba)₃ (11 mg, 0.0125 mmol) and NaOtBu (36 mg, 0.38 mmol) were combined in 1,4-dioxane (2 mL) and degassed for 10 minutes with N₂ bubbling. The reaction was heated for 20 min at 120° C. in a microwave, then for 60 min at 130° C. The reaction mixture was passed through a Si-thiol cartridge and washed with MeOH. The mixture was concentrated in vacuo and the resulting residue purified by silica gelcolumn chromatography, eluting with CH₂Cl₂ and increasing the polarity to 5% MeOH/CH₂Cl₂ to give a yellow solid. This was further purified by reverse phase preparative HPLC-MS to give 3-{4-[4-(5-methyl-[1,3,4]oxadiazol-2-yl)-[1,4]diazepan-1-yl]-phenyl}-1-oxo-1,2-dihydro-isoquinoline-5-carbonitrile as a yellow solid (8 mg, 7%).

AnalpH2_MeOH_QC (2): Rt 7.65 min; m/z 427.2 $[M+1]^+$.

¹H NMR (400 MHz, DMSO-d₆) b 11.78 (s, 1H), 8.44-8.41 (m, 1H), 8.20 (dd, J=7.3, 1.3 Hz, 1H), 7.67, (br d, J=9.1 Hz, 2H), 7.52 (t, J=7.8 Hz, 1H), 6.90 (d, J=8.8 Hz, 2H), 6.69 (s, 1H), 3.81-3.76 (m, 2H), 3.69-3.64 (m, 2H), 3.64-3.58 (m, 2H), 3.48-3.43 (m, 2H), 2.26 (s, 3H), 1.97-1.91 (m, 2H).

Biological Methods
Biochemical Assay 1:
TNKS1/PARP Biochemical Assay

Tankyrase activity was assayed using a 96-well format HT Universal Chemiluminescent PARP Assay Kit (Trevigen, Inc, cat. no. 4676-096-K) according to the manufacturer's instructions. In short, tankyrase/PARP activity is quantified by the incorporation of biotinylated nicotinamide adenine dinucleotide (biotin-NAD⁺) onto the immobilised pseudo substrate, Histone. The extent of poly(Biotin-ADP) ribosylation (PARylation) in the presence of increasing dose of inhibitor is then quantified by binding of streptavidin conjugated horse radish peroxidase (strep-HRP) followed by chemiluminescent detection.

Prior to assay initiation, inhibitor stocks were prepared in aqueous DMSO (10% (v/v)) from 5 millimolar (mM) stock in 100% DMSO (Sigma Aldrich, cat. no. 265855) as 10× concentrations. For the primary assay (i.e., single dose at 1 micromolar (μM) final concentration) this corresponded to 10 μM in 10% DMSO. For IC₅₀ determination, this corresponded to 100 μM, 30 μM, 10 μM, 3.0 μM, 1.0 μM, 0.30 μM, 0.10 μM and 0 μM in 10% DMSO for final concentrations of 10 μM, 3.0 μM, 1.0 μM, 0.30 μM, 0.10 μM, 0.030 μM, 0.010 μM, and 0 μM with 1% (v/v) final DMSO. The assay was initiated by the addition of 10× inhibitor (5 microliters (μL)) or 10% aqueous DMSO (5 μL) to triplicate wells. Twenty microliters of diluted TNKS1 protein (200 nanomolar (nM) final conc.) in PARP buffer (Trevigen, Inc, cat. no. 4671-096-02) was added to each histone coated well, which was previously hydrated with PARP buffer. Triplicate wells with 1% DMSO/buffer alone (no enzyme) were also added as a measure of assay 'noise'. Positive control for PARP inhibition included the addition of 4-amino-1,8-naphthalimide (Sigma Aldrich, cat. no A0966) in corresponding doses.

The mixture was incubated for 10 minutes at room temperature and the PARylation reaction initiated by the addition of PARP cocktail (25 μL, Trevigen, Inc) containing biotin-NAD⁺ (Trevigen, Inc, cat. no. 4670-500-01), activated DNA (Trevigen, Inc, cat. no. 4671-096-06) and PARP buffer. The reaction was incubated for 1.5 hours (for TNKS1) or 1 hour (for PARP1) at room temperature. The reaction mixture was then removed by aspiration and the wells washed (3×200 μL) with phosphate buffered saline containing Triton X-100 (0.1% (v/v), Sigma Aldrich cat. no. T8787). The wells were then washed (3×200 μL) with phosphate buffered saline and then incubated with strep-HRP (50 μL, Trevigen, Inc, cat. no. 4800-30-06) in strep-diluent (1:500 dilution, Trevigen Inc, cat. no. 4671-096-04) for 1 hour at room temperature. The Strep-HRP mixture was then aspirated and the wells washed (3×200 μL) with phosphate buffered saline containing Triton X-100 (0.1% (v/v)) followed by phosphate buffered saline (3×200 μL) and then incubated with PeroxyGlow™ reagent (100 μL, Trevigen, Inc, cat. nos. 4675-096-01, 4675-096-02, room temperature, mixed 1:1).

The amount of light emitted as a result of the peroxidase-chemiluminescent reagent reaction was in proportion to the extent of poly(Biotin-ADP)ribosylation and was immediately measured with a Victor² plate reader (Perkin Elmer, luminescence detection assay, luminescent units described as 'Counts Per Second' (CPS)). The data were normalised to the DMSO control after subtraction of 'noise' and was expressed as % PARP activity as a function of inhibitor dose. Inhibition was expressed as 100%−(% PARP activity). Dose response curves used to determine IC₅₀ values were Log transformed and analysed by non-linear regression analysis (variable slope) using Prism (GraphPad Software, Inc) and were presented as IC₅₀ with 95% confidence interval to determine relative potency.

Preparation of Recombinant Proteins:
Tankyrase1 (pNIC-Bsa4-TNKS1$^{PARP}$) expression construct was obtained from the Structural Genomics Consortium (SGC) and expresses the active PARP domain of TNKS1 as a polyhistidine tagged protein. The expression and purification of TNKS1 protein was carried out according to the SGC protocol provided at http://www.thesgc.org/structures/materials_methods/2RF5/, which is summarised in the following table.

| | |
|---|---|
| Structure | TNKS1 |
| PDB Code | 2RF5 |
| Entry clone accession | BC098394 |
| Entry clone source | Mammalian Gene Collection |
| Tag | N-terminal hexahistidine tag with integrated TEV protease cleavage site: mhhhhhhssgvdlgtenlyfq*s(m) |
| Construct sequence | mhhhhhhssgvdlgtenlyfq*sMQGTNPYLTFHCVNQGTILLDLAPEDKEYQSVEEEMQSTIREHRDGGNAGSFF NRYNVIRIQKVVNKKLRERFCHRQKEVSEENHNHHNERMLFHGSPFINAIIHKGFDERHAYIGGMFGASFYFAENS SKSNQYVYSFGGGTGCPTHKDRSCYICHRQMLFCRVTLGKSFLQFSTIKMAHAPPGHHSVIGRPSVNGLAYAEYVI YRGEQAYPEYLITYQIMKPEAPSQTATAAEQ |
| Vector | pNIC-Bsa4 |
| Expression host | E.coli Rosetta2(DE3) (Novagen) |
| Growth method | Cells from a glycerol stock were streaked onto LB-agar plates. 5-10 colonies were used to inoculate 20 mL TB supplemented with 8 g/L glycerol, 100 μg/mL kanamycin and 34 μg/mL chloramphenicol. The cells were grown at 30° C. overnight. The overnight culture (20 mL) was used to inoculate 1.5 L TB supplemented with 8 g/L glycerol, 50 μg/mL kanamycin and approximately 200 μL PPG P2,000 81380 anti-foam solution (Fluka). The culture was grown in a LEX bioreactor system (Harbinger Biotechnology) at 37° C. until $OD_{600}$ reached ~2. The culture was down-tempered to 18° C. over a period of 1 hour before target expression was induced by addition of 0.5 mM IPTG. Expression was allowed to continue overnight and cells were harvested the following morning by centrifugation (5,500 × g, 10 min, 4° C.). The resulting cell pellet (38.2 g wet cell weight) was resuspended in lysis buffer (2 mL/g cell pellet), supplemented with one tablet of Complete EDTA-free protease inhibitor (Roche Applied Science). The cell suspension was stored at −80° C. |
| Extraction buffers | Lysis buffer: 50 mM HEPES, 300 mM NaCl, 10% glycerol, 10 mM imidazole, 0.5 mM TCEP, pH 7.8 |
| Extraction procedure | The cell suspension was quickly thawed in water and 2500 U Benzonase (Merck) was added. Cells were disrupted by sonication (Vibra-Cell, Sonics) at 80% amplitude for 3 min effective time (pulsed 4 s on, 4 s off) and cell debris was removed by centrifugation (49,100 × g, 20 min, 4° C.). The supernatant was decanted and filtered through a 0.45 μm flask filter. |
| Purification buffers | IMAC wash1 buffer: 30 mM HEPES, 500 mM NaCl, 10% glycerol, 10 mM imidazole, 0.5 mM TCEP, pH 7.5. IMAC wash2 buffer: 30 mM HEPES, 500 mM NaCl, 10% glycerol, 25 mM imidazole, 0.5 mM TCEP, pH 7.5. IMAC elution buffer: 30 mM HEPES, 500 mM NaCl, 10% glycerol, 500 mM imidazole, 0.5 mM TCEP, pH 7.5. Gel filtration (GF) buffer: 30 mM HEPES, 300 mM NaCl, 10% glycerol, 0.5 mM TCEP, pH 7.5 |
| Purification procedure | Columns: IMAC: Ni-charged 1 mL HiTrap Chelating HP (GE Healthcare). Gel filtration column: HiLoad 16/60 Superdex 75 Prep Grade (GE Healthcare). Procedure: Purification of the protein was performed as a two step process on an ÄKTAxpress system (GE Healthcare). Prior to purification, columns were equilibrated with IMAC wash1 buffer and gel filtration buffer, respectively. The filtered lysate was loaded onto the Ni-charged HiTrap Chelating column and washed with IMAC wash1 buffer followed by IMAC wash2 buffer. Bound protein was eluted from the IMAC column with IMAC elution buffer and automatically loaded onto the gel filtration column. Fractions containing the target protein were pooled and fresh TCEP was added to a final concentration of 2 mM. The protein was subsequently concentrated using a Amicon Ultra-15 centrifugal filter device, 10,000 NMWL (Millipore) to 22.8 mg/mL in a volume of 0.28 mL. The identity of the protein was confirmed by mass spectrometry. |

Tankyrase2(pNIC-Bsa4-TNKS2$^{PARP}$) expression construct was also obtained from the Structural Genomics Consortium (SGC) and prepared in an analogous method to TNKS1.
PARP1 protein was commercially available and was obtained from Trevigen, Inc (PARP-HSA 'High Specific Activity', cat. no. 4668-50-010).

Cell-Based Assay 1:
Wnt-Luciferase Reporter Assay
Generation of Reporter Cell Lines:
A Wnt dependent cell line (i.e., DLD1 colorectal adenocarcinoma cell line) was transduced with replication incompetent VSV-g pseudotyped lentiviral particles expressing the firefly luciferase gene under the control of minimal cytomegalovirus (mCMV) promoter and tandem repeats of the TCF/LEF transcriptional response element. Post-transduction selection using puromycin (Sigma Aldrich, cat. no. P8833, 1.5 micrograms per milliliter (μg/mL)) for one week resulted in an enriched polyclonal cell population (DLD1-Wnt-Luc cells) that was expanded and collected for minimal passage and stored in liquid nitrogen.

Wnt-Reporter Assay:
DLD1-Wnt-Luc cells were seeded (5000 cells/well) in a 96-well plate (Greiner Bio-One, cat. no. 655098) in Dubelco's Modified Eagle Medium (DMEM, SFBCO/Invitrogen, cat no. 41965-039) supplemented with Fetal Bovine Serum (FBS, 10%, SFBCO/Invitrogen, cat no. 10108-165). After overnight incubation, the media was replaced with OptiMEM (SFBCO/Invitrogen, cat no. 11058-021) supplemented with FBS (0.5%) and non-essential amino acids (1%, SFBCO/Invitrogen, cat no. 11140-035) and the appropriate putative TNKS inhibitor at a final concentration of 10 μM, 3 μM, 1 μM, 0.30 μM, 0.10 μM, 0.030 μM, 0.010 μM and 0 μM with 1% (v/v) final DMSO in double-triplicate wells. Positive control includes the use of XAV-939 (Maybridge, FisherScientific, 3,5,7,8-tetrahydro-2-[4-(trifluoromethyl)phenyl]-4H-thiopyrano[4,3-d]pyrimidin-4-one, cat. no. RF03920, see: Huang et al., Nature, 2009, Vol. 461, pp. 614-620). Cells were incubated for 20-22 hours before assaying for luciferase (first set of triplicates: Wnt activation) and viability (second set of triplicates: cell survival for data normalisation vs Wnt-activation) using ONE-Glo (Promega, cat. no. E6110) and CellTiter-Glo (Promega, cat. no. G7570) reagents consecutively. The assay was measured using a Victor$^2$ plate reader. The data were normalised to the DMSO control and were expressed as % Wnt activity as a function of inhibitor dose. Dose response curves used to determine $IC_{50}$ values were Log transformed and analysed by non-linear regression analysis (variable slope) using Prism (GraphPad Software, Inc).

Cell-Based Assay 2:
Tumour Cell Inhibition in Colorectal Tumour Cells
In order to determine the efficacy of acute dosing of putative TNKS inhibitors, five day exposure cell viability assays were carried out. This included the sparse seeding of cells in a 96-well plate followed by continuous dosing of cells over a five day period.

Appropriate cell lines (HT55, COLO320DM and SW620) were seeded at 500 cells/well in a 96-well plate in MEM (HT55), RPMI (COLO320DM) or DMEM (SW620) supplemented with FBS. After overnight incubation, cells were treated with the appropriate putative TNKS inhibitor in 6 or 10 concentrations ranging from 0 μM to 10 μM at 0.2% final DMSO concentration in appropriate media supplemented with 10% or 0.5% FBS. Dosages were carried out in triplicate. Termination of the assay and measurement of cell viability was achieved by the use of Cell Titre Glo reagent and luminescence measurement on an appropriate plate reader.

Dose response curves used to determine $SF_{50}$ values were Log transformed and analysed by non-linear regression analysis (variable slope) using Prism (GraphPad Software, Inc).

Cell-Based Assay 3:
Clonogenic Inhibition in DLD1 or HT55 Cells
In order to determine the efficacy of chronic dosing of putative TNKS inhibitors, long term clonogenic or 'colony formation' assays were carried out. This included the sparse seeding of cells in a 6-well dish followed by continuous dosing of cells over 12-14 days (depending on relative cell growth). Appropriate cell lines (DLD1 or HT55) were seeded at 500 cells/well in a 6-well dish in DMEM supplemented with FBS. After overnight incubation, cells were treated with the appropriate putative TNKS inhibitor at 10 μM, 3 μM, 1 μM, 0.30 μM, 0.1 μM and 0 μM at 0.2-1% final DMSO concentration (cell line dependent) in DMEM supplemented with 10% FBS (DLD1 cells were dosed in DMEM supplemented with 0.5% FBS). Dosages were carried out in triplicate. Cell media containing compound or DMSO only was replenished every 48 hours. On termination of the assay, plates were read with Cell Titre Glo reagent and luminescence measured on an appropriate plate reader.

The data was normalised to the DMSO control and was expressed as surviving fraction as a function of inhibitor dose. Dose response curves used to determine $SF_{50}$ values were Log transformed and analysed by non-linear regression analysis (variable slope) using Prism (GraphPad Software, Inc).

Biological Data
The following compounds were tested in the TNKS1/PARP Biochemical Assay described above:
IQ-001, IQ-002, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-022, IQ-023, IQ-024, IQ-025, IQ-026, IQ-027, IQ-028, IQ-029, IQ-030, IQ-031, IQ-032, IQ-033, IQ-034, IQ-035, IQ-036, IQ-037, IQ-038, IQ-039, IQ-040, IQ-041, IQ-042, IQ-043, IQ-044, IQ-045, IQ-046, IQ-047, IQ-048, IQ-049, IQ-050, IQ-051, IQ-052, IQ-053, IQ-054, IQ-055, IQ-056, IQ-057, IQ-058, IQ-059.

All of the compounds tested have a TNKS1 $IC_{50}$ of less than 1 μM.

The following compounds have a TNKS1 $IC_{50}$ of less than 0.1 μM:
IQ-002, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-022, IQ-023, IQ-027, IQ-028, IQ-029, IQ-030, IQ-031, IQ-032, IQ-033, IQ-034, IQ-035, IQ-036, IQ-037, IQ-038, IQ-039, IQ-040, IQ-041, IQ-042, IQ-043, IQ-044, IQ-045, IQ-047, IQ-048, IQ-049, IQ-052, IQ-054, IQ-055, IQ-056, IQ-057, IQ-058, IQ-059.

The following compounds have a TNKS1 $IC_{50}$ of less than 0.05 μM:
IQ-002, IQ-004, IQ-005, IQ-006, IQ-007, IQ-009, IQ-010, IQ-012, IQ-013, IQ-015, IQ-016, IQ-017, IQ-018, IQ-019, IQ-020, IQ-021, IQ-022, IQ-023, IQ-028, IQ-029, IQ-030, IQ-032, IQ-033, IQ-034, IQ-035, IQ-036, IQ-037, IQ-038, IQ-039, IQ-041, IQ-042, IQ-044, IQ-045, IQ-047, IQ-048, IQ-049, IQ-054, IQ-055, IQ-056, IQ-057, IQ-059.

For example, IQ-013 has a TNKS1 $IC_{50}$ of 0.018 μM.

The following compounds were tested in the Wnt-Luciferase Reporter Assay described above:
IQ-001, IQ-002, IQ-003, IQ-004, IQ-005, IQ-006, IQ-007, IQ-008, IQ-009, IQ-011, IQ-012, IQ-013, IQ-014, IQ-015, IQ-016, IQ-017, IQ-018, IQ-019, IQ-020, IQ-021, IQ-027, IQ-028, IQ-029, IQ-030, IQ-031, IQ-032, IQ-033, IQ-034, IQ-035, IQ-036, IQ-037, IQ-038, IQ-039, IQ-040, IQ-041, IQ-042, IQ-043, IQ-044, IQ-045, IQ-046, IQ-047, IQ-048, IQ-049, IQ-050, IQ-051, IQ-052, IQ-053, IQ-054, IQ-055, IQ-056, IQ-057, IQ-058, IQ-059.

All of the compounds have a Wnt $IC_{50}$ of less than 1 µM.

The following compounds have a Wnt $IC_{50}$ of less than 0.3 µM:

IQ-002, IQ-003, IQ-005, IQ-006, IQ-007, IQ-009, IQ-011, IQ-012, IQ-013, IQ-014, IQ-015, IQ-016, IQ-017, IQ-018, IQ-019, IQ-020, IQ-021, IQ-027, IQ-028, IQ-029, IQ-030, IQ-031, IQ-032, IQ-033, IQ-035, IQ-036, IQ-037, IQ-038, IQ-039, IQ-040, IQ-041, IQ-042, IQ-044, IQ-045, IQ-046, IQ-047, IQ-048, IQ-049, IQ-050, IQ-051, IQ-052, IQ-053, IQ-054, IQ-055, IQ-056, IQ-057, IQ-058, IQ-059.

The following compounds have a Wnt $IC_{50}$ of less than 0.1 µM:

IQ-006, IQ-009, IQ-013, IQ-015, IQ-016, IQ-017, IQ-019, IQ-020, IQ-028, IQ-029, IQ-030, IQ-031, IQ-032, IQ-033, IQ-038, IQ-039, IQ-040, IQ-042, IQ-044, IQ-046, IQ-047, IQ-048, IQ-049, IQ-051, IQ-053, IQ-054, IQ-055, IQ-056, IQ-057, IQ-058, IQ-059.

For example, IQ-013 has a Wnt $IC_{50}$ of 0.045 µM.

The following compounds were tested in the Tumour Cell Inhibition Assay described above (COLO320DM cells):

IQ-001, IQ-002, IQ-003, IQ-004, IQ-005, IQ-006, IQ-007, IQ-008, IQ-009, IQ-011, IQ-012, IQ-013, IQ-014, IQ-015, IQ-016, IQ-017, IQ-018, IQ-019, IQ-020, IQ-021, IQ-024, IQ-025, IQ-027, IQ-028, IQ-029, IQ-030, IQ-031, IQ-032, IQ-033, IQ-034, IQ-035, IQ-036, IQ-037, IQ-038, IQ-039, IQ-040, IQ-041, IQ-042, IQ-044, IQ-045, IQ-046, IQ-047, IQ-048, IQ-049, IQ-050, IQ-051, IQ-052, IQ-053, IQ-054, IQ-055, IQ-056, IQ-057, IQ-058, IQ-059.

All of the compounds have a cell inhibitory $SF_{50}$ (COLO320DM) of less than 10 µM.

The following compounds have a cell inhibitory $SF_{50}$ (COLO320DM) of less than 5 µM:

IQ-002, IQ-003, IQ-005, IQ-006, IQ-009, IQ-011, IQ-012, IQ-013, IQ-014, IQ-015, IQ-016, IQ-017, IQ-018, IQ-019, IQ-020, IQ-021, IQ-024, IQ-027, IQ-028, IQ-029, IQ-030, IQ-031, IQ-032, IQ-033, IQ-035, IQ-036, IQ-037, IQ-038, IQ-039, IQ-040, IQ-042, IQ-044, IQ-045, IQ-046, IQ-047, IQ-048, IQ-049, IQ-051, IQ-052, IQ-053, IQ-054, IQ-055, IQ-056, IQ-057, IQ-059.

The following compounds have a cell inhibitory $SF_{50}$ (COLO320DM) of less than 1 µM:

IQ-009, IQ-013, IQ-017, IQ-019, IQ-021, IQ-029, IQ-031, IQ-032, IQ-044, IQ-053, IQ-054, IQ-055.

For example, IQ-013 has a cell inhibitory $SF_{50}$ (COLO320DM) of 0.98 µM (replicate 1.12 µM).

The following compounds were tested in the Tumour Cell Inhibition Assay described above (HT55 cells):

IQ-002, IQ-004, IQ-011, IQ-012, IQ-013, IQ-015, IQ-018, IQ-041, IQ-048, IQ-054, IQ-059.

All of the compounds have a cell inhibitory $SF_{50}$ (HT55) of less than 10 µM.

The following compounds have a cell inhibitory $SF_{50}$ (HT55) of less than 5 µM:

IQ-004, IQ-011, IQ-012, IQ-015, IQ-018, IQ-041, IQ-048, IQ-054.

For example, IQ-012 has a cell inhibitory $SF_{50}$ (HT55) of 1.7 µM (replicate 1.8 µM).

The following compounds were tested in the Tumour Cell Inhibition Assay described above (SW620 cells):

IQ-011, IQ-012.

All of the compounds have a cell inhibitory $SF_{50}$ (SW620) of less than 10 µM.

For example, IQ-012 has a cell inhibitory $SF_{50}$ (SW620) of 3.0 µM (replicate 1.7 µM).

The following compounds were tested in the Long-Term Clonogenic Assay described above (HT55 cells):

IQ-002, IQ-004, IQ-011, IQ-012, IQ-013, IQ-014.

All of the compounds have a cell inhibitory $SF_{50}$ (HT55) of less than 10 µM.

The following compounds have a cell inhibitory $SF_{50}$ (HT55) of less than 5 µM:

IQ-002, IQ-011, IQ-012, IQ-013, IQ-014.

For example, IQ-013 has a cell inhibitory $SF_{50}$ (HT55) of 1.6 µM.

The following compounds were tested in the Long-Term Clonogenic Assay described above (DLD1 cells):

IQ-002.

IQ-002 has a cell inhibitory $SF_{50}$ (DLD1) of 2.3 µM.

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Adaimy et al., 2007 "Mutation in WNT10A is associated with an autosomal recessive ectodermal dysplasia: the odonto-onycho-dermal dysplasia", *Am. J. Hum. Genet.*, Vol. 81, pp. 821-828.

Ashworth et al., 2013, "3-aryl-5-substituted-isoquinolin-1-one compounds and their therapeutic use", international patent application publication number WO 2013/132253 A1 published 12 Sep. 2013.

Balemans et al., 2001, "Increased bone density in sclerosteosis is due to the deficiency of a novel secreted protein (SOST)", *Hum. Mol. Genet.*, Vol. 10, pp. 537-543.

Balemans et al., 2002, "Identification of a 52 kb deletion downstream of the SOST gene in patients with van Buchem disease", *J. Med. Genet.*, Vol. 39, pp. 91-97.

Bao et al., 2012, "Inhibition of tankyrases induces Axin stabilization and blocks Wnt signalling in breast cancer cells", *PLoS One*, Vol. 7, No. 11, e48670.

Bergmann et al., 2006, "Mutations in the gene encoding the Wnt-signaling component R-spondin 4 (RSPO4) cause autosomal recessive anonychia", *Am. J. Hum. Genet.*, Vol. 79, pp. 1105-1109.

Blaydon et al., 2006, "The gene encoding R-spondin 4 (RSPO4), a secreted protein implicated in Wnt signaling, is mutated in inherited anonychia", *Nat. Genet.*, Vol. 38, pp. 1245-1247.

Caricasole et al., 2003, "The Wnt pathway, cell-cycle activation and beta-amyloid: novel therapeutic strategies in Alzheimer's disease?", *Trends Pharmacol. Sci.*, Vol. 24, pp. 233-238.

Casás-Selves et al., 2012, "Tankyrase and the canonical Wnt pathway protect lung cancer cells from EGFR inhibition", *Cancer Research*, Vol. 72, No. 16, pp. 4154-4164.

Chang et al., 2005, "Tankyrase-1 polymerization of poly(ADP-ribose) is required for spindle structure and function", *Nat. Cell Biol.*, Vol. 7, No. 11, pp. 1133-1139.

Cho-Park et al., 2013, "Proteasome regulation by ADP-ribosylation", *Cell*, Vol. 153, No. 3, pp. 614-627.

Christodoulides et al., "WNT10B mutations in human obesity", *Diabetologia*, Vol. 49, pp. 678-684.

Daniels, 2004, "Abnormal cytokinesis in cells deficient in the breast cancer susceptibility protein BRCA2", *Science*, Vol. 306, No 5697, pp. 876-879.

Deng et al., 2002, "Telomeric proteins regulate episomal maintenance of Epstein-Barr virus origin of plasmid replication", *Mol. Cell*, Vol. 9, pp. 493-503.

Distler et al., 2012, "Inactivation of tankyrases reduces experimental fibrosis by inhibiting canonical Wnt signalling", *Ann. Rheum. Dis.*, 12 Nov. 2012, e-publication ahead of print.

Dorsch et al., 2014, "(Aza-)isoquinolinone derivatives", international patent application publication number WO 2014/023390 A2 published 13 Feb. 2014.

Fancy et al., 2011, "Axin2 as regulatory and therapeutic target in newborn brain injury and remyelination", *Nat. Neurosci.*, Vol. 14, pp. 1009-1016.

Fujio et al., 2004, "Fused heterocyclic compound and medicinal use thereof", European patent application publication number EP 1 396 488 A1 published 10 Mar. 2004.

Fujio et al., 2004, "Fused heterocyclic compound and medicinal use thereof", international patent application publication number WO 02/094790 A1 published 28 Nov. 2002.

Fujio et al., 2005, "Isoquinoline compounds and pharmaceutical use thereof", international patent application publication number WO 2005/113540 A1 published 1 Dec. 2005.

Gong et al., 2001, "LDL receptor-related protein 5 (LRP5) affects bone accrual and eye development", *Cell*, Vol. 107, pp. 513-523.

Grzeschik et al., 2007, "Deficiency of PORCN, a regulator of Wnt signaling, is associated with focal dermal hypoplasia", *Nat. Genet.*, Vol. 39, pp. 833-835.

Harley, 2008, "Telomerase and cancer therapeutics", *Nat. Rev. Cancer*, Vol. 8, No. 3, pp. 167-169.

Hattori et al., 2005, "1-(2H)-isoquinolone derivatives and use thereof as anticancer agents", international patent publication number WO 2005/075432 A1 published 18 Aug. 2005.

Hattori et al., 2006, "1-(2H)-Isoquinolone derivative", European patent publication number EP 1 724 262 A1, published 22 Nov. 2006.

Hsiao et al., 2008, "Tankyrase function at telomeres, spindle poles, and beyond", *Biochimie*, Vol. 90, No. 1, pp. 83-92.

Hsiao et al., 2009, "Sister telomeres rendered dysfunctional by persistent cohesion are fused by NHEJ", *J. Cell. Biol.*, Vol. 184, No. 4, pp. 515-526.

Huang et al., 2009, "Tankyrase inhibition stabilizes axin and antagonizes Wnt signalling", *Nature*, Vol. 461, No. 7264, pp. 614-620.

James et al., 2012, "WIKI4, a novel inhibitor of tankyrase and Wnt/β-catenin signaling", *PLoS One*, Vol. 7, No. 12, e50457.

Johnson et al., 2004, "Isoquinolinone derivatives and their use as therapeutic agents", international patent application publication number WO 2004/058717 A1 published 15 Jul. 2004.

Kaelin, 2009, "Synthetic lethality: a framework for the development of wiser cancer therapeutics", *Genome Med.*, Vol. 1, No. 10, p. 99.

Kozlovsky et al., 2002, "GSK-3 and the neurodevelopmental hypothesis of schizophrenia", *Eur. Neuropsychopharmacol.*, Vol. 12, pp. 13-25.

Krishnakumar et al., 2010, "The PARP side of the nucleus: molecular actions, physiological outcomes, and clinical targets", *Mol. Cell.*, Vol. 39, No. 1, pp. 8-24.

Lammi et al., 2004, "Mutations in AXIN2 cause familial tooth agenesis and predispose to colorectal cancer", *Am. J. Hum. Genet.*, Vol. 74, pp. 1043-1050.

Le et al., 2004, "A versatile total synthesis of benzo[c]phenanthridine and protoberberine alkaloids using lithiated toluamide-benzonitrile cycloaddition", *J. Org. Chem.*, Vol. 69, pp. 2768-2772.

Li et al., 2010, "Platinum(II)-catalyzed intramolecular cyclization of alkynylbenzonitriles: synthesis of 1-alkoxyisoquinolines and isoquinolones", *Tetrahedron Letters*, Vol. 51, pp. 6422-6425.

Li et al., 2011, "Herpes Simplex Virus Requires PARP Activity for Efficient Replication and Induces ERK-dependent Phosphorylation and ICP0-dependent Nuclear Localization of Tankyrase 1", *J. Virol.*, Vol. 86, pp. 492-503.

Lord et al., 2008, "Targeted therapy for cancer using PARP inhibitors", *Curr. Opin. Pharmacol.*, Vol. 8, No. 4, pp. 363-369.

Loughlin et al., 2004, "Functional variants within the secreted frizzled-related protein 3 gene are associated with hip osteoarthritis in females," *Proc. Natl. Acad. Sci. USA*, Vol. 101, pp. 9757-9762.

McCabe et al., 2009a, "Materials and methods for exploiting synthetic lethality in BRCA-associated cancers", international patent publication number WO 2009/027650 A1 published 5 Mar. 2009.

McCabe, 2009b, "Targeting Tankyrase 1 as a therapeutic strategy for BRCA-associated cancer", *Oncogene*, Vol. 28, No. 11, pp. 1465-1470.

McLure et al., 2013, "Treatment of diseases by epigenetic regulation", US patent application publication number US 2013/0281397 A1 published 24 Oct. 2013.

Merchant et al., 1984, "Synthesis of Heterocyclic Compounds involving Reactions of Indan-1-ones", Indian Journal of Chemistry, Section B: Organic Chemistry including Medicinal Chemistry, Vol. 23, pp. 863-865.

Miyaoka et al., 1999, "Increased expression of Wnt-1 in schizophrenic brains", *Schizophr. Res.*, Vol. 38, pp. 1-6.

Moon et al., 2004, "WNT and beta-catenin signalling: diseases and therapies", Nat. Rev. Genet., Vol. 5, pp. 691-701.

Mudher et al., 2002, "Alzheimer's disease-do tauists and baptists finally shake hands?", *Trends Neurosci.*, Vol. 25, pp. 22-26.

Musso et al., 2003, "Indanylidenes. 1. Design and synthesis of (E)-2-(4,6-difluoro-1-indanylidene)acetamide, a potent, centrally acting muscle relaxant with anti-inflammatory and analgesic activity, Vol. 46, pp. 399-408.

Papeo et al., 2013, "3-Phenyl-isoquinolin-1(2H)-one derivatives as PARP-1 inhibitors", international patent application publication number WO 2013/076090 A1 published 30 May 2013.

Parma et al., 2006, "R-spondin1 is essential in sex determination, skin differentiation and malignancy", *Nat. Genet.*, Vol. 38, pp. 1304-1309.

Riffell et al., 2012, "Tankyrase-targeted therapeutics: expanding opportunities in the PARP family", *Nat. Rev. Drug Discovery*, Vol. 11, No. 12, pp. 923-936.

Robitaille et al., 2002, "Mutant frizzled-4 disrupts retinal angiogenesis in familial exudative vitreoretinopathy", *Nat. Genet.*, Vol. 32, pp. 326-330.

Shkreli et al., 2011, "Reversible cell-cycle entry in adult kidney podocytes through regulated control of telomerase and Wnt signaling", *Nat. Med.*, submitted for publication.

Threadgill et al., 2014, "Tankyrase inhibitors", international patent application publication number WO 2014/087165 A1 published 12 Jun. 2014.

Turner et al., 2004, "Hallmarks of 'BRCAness' in sporadic cancers", Nat. Rev. Cancer, Vol. 4, No. 10, pp. 814-819.

Varallo et al., 2003, "Beta-catenin expression in Dupuytren's disease: potential role for cell-matrix interactions in modulating beta-catenin levels in vivo and in vitro", *Oncogene*, Vol. 22, pp. 3680-3684.

Waaler et al., 2012, "A novel tankyrase inhibitor decreases canonical Wnt signaling in colon carcinoma cells and reduces tumor growth in conditional APC mutant mice", *Cancer Research*, Vol. 72, No. 11, pp. 2822-2832.

Wang et al., 2011, "Cardiac induction of embryonic stem cells by a small molecule inhibitor of Wnt/beta-catenin signaling", *ACS Chem. Biol.*, Vol. 6, pp. 192-197.

Wong et al., 2008, "Compounds for the prevention and treatment of cardiovascular diseases", US patent application publication number US 2008/0188467 A1 published 7 Aug. 2008.

Woods et al., 2006, "Mutations in WNT7A cause a range of limb malformations, including Fuhrmann syndrome and Al-Awadi/Raas-Rothschild/Schinzel phocomelia syndrome", *Am. J. Hum. Genet.*, Vol. 79, pp. 402-408.

Xu et al., 2004, "Vascular development in the retina and inner ear: control by Norrin and Frizzled-4, a high-affinity ligand-receptor pair", *Cell*, Vol. 116, pp. 883-895.

Yeh et al., 2007, "Insulin-stimulated exocytosis of GLUT4 is enhanced by IRAP and its partner tankyrase", *Biochem. J.*, Vol. 402, pp. 279-290.

The invention claimed is:

1. A compound selected from compounds of the following formula, and pharmaceutically acceptable salts and, N-oxides thereof:

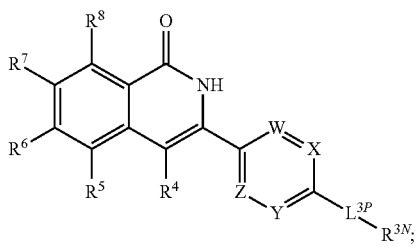

wherein:
W is $CR^W$, X is $CR^X$, Y is $CR^Y$, and Z is $CR^Z$ ("phenyl"); or
W is N, X is $CR^X$, Y is $CR^Y$, and Z is $CR^Z$ ("pyrid-2-yl"); or
W is $CR^W$, X is N, Y is $CR^Y$, and Z is $CR^Z$ ("pyrid-3-yl"); or
W is N, X is $CR^X$, Y is $CR^Y$, and Z is N ("pyrimidin-2-yl"); or
W is $CR^W$, X is N, Y is N, and Z is $CR^Z$ ("pyrimidin-5-yl"); or
W is N, X is $CR^X$, Y is N, and Z is $CR^Z$ ("pyrazin-2-yl"); or
W is N, X is N, Y is $CR^Y$, and Z is $CR^Z$ ("pyridazin-3-yl");

wherein:
—$R^W$ is independently —H or —F;
—$R^X$ is independently —H or —F;
—$R^Y$ is independently —H or —F; and
—$R^Z$ is independently —H or —F;

and wherein:
-$L^{3P}$- is independently a single covalent bond or -$L^{3PL}$-;

wherein:
-$L^{3PL}$- is independently -$L^{3PR1}$-, —C(=O)—, -$L^{3PR2}$-C(=O)—, —S(=O)$_2$—, -$L^{3PR3}$-S(=O)$_2$—, or —O-$L^{3PR4}$-;

wherein:
each -$L^{3PR1}$- is linear or branched saturated $C_{1-4}$alkylene;
each -$L^{3PR2}$- is linear or branched saturated $C_{1-4}$alkylene;
each -$L^{3PR3}$- is linear or branched saturated $C_{1-4}$alkylene;
each -$L^{3PR4}$- is linear or branched saturated $C_{1-4}$alkylene;

and wherein:
—$R^{3N}$ is independently —NH$_2$, —NHR$^A$, —NR$^A$R$^B$, or —NR$^C$R$^D$;

wherein:
each —$R^A$ is independently:
—$R^{A1}$, —$R^{A2}$, —$R^{A3}$, —$R^{A4}$, —$R^{A5}$, -$L^A$-$R^{A2}$, -$L^A$-$R^{A3}$, -$L^A$-$R^{A4}$, or -$L^A$-$R^{A5}$;
each —$R^{A1}$ is linear or branched saturated $C_{1-6}$alkyl,
and is optionally substituted with one or more groups —$R^{S1}$;
each —$R^{A2}$ is saturated $C_{3-6}$cycloalkyl,
and is optionally substituted with one or more groups —$R^{S2C}$;
each —$R^{A3}$ is non-aromatic $C_{3-7}$heterocyclyl,
and is optionally substituted on carbon with one or more groups —$R^{S2C}$,
and is optionally substituted on secondary nitrogen, if present, with a group —$R^{SN}$;
each —$R^{A4}$ is independently phenyl or naphthyl,
and is optionally substituted with one or more groups —$R^{S3C}$;
each —$R^{A5}$ is $C_{5-10}$heteroaryl,
and is optionally substituted on carbon with one or more groups —$R^{S3C}$,
and is optionally substituted on secondary nitrogen, if present, with a group —$R^{SN}$;
each -$L^A$- is linear or branched saturated $C_{1-4}$alkylene;

and wherein:
each —$R^{S1}$ is independently:
—F, —Cl, —Br, —I,
—OH, —OR$^{TT}$,
—OCF$_3$,
—NH$_2$, —NHR$^{TT}$, —NR$^{TT}_2$, R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$,
C(=O)R$^{TM}$,
—NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, —NHC(=O)R$^{TM}$,
—NR$^{TN}$C(=O)NH$_2$, —NR$^{TN}$C(=O)NHR$^{TT}$, —NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$, —S(=O)$_2$NH$_2$, —S(=O)$_2$NHR$^{TT}$, —S(=O)$_2$NR$^{TT}_2$,
—S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, —SR$^{TT}$, or =O;
each —R$^{S2C}$ is independently:
—R$^{TT}$,
—F, —Cl, —Br, —I,
—OH, —OR$^{TT}$,
-L$^T$-OH, -L$^T$-OR$^{TT}$,
—CF$_3$, —OCF$_3$,
—NH$_2$, —NHR$^{TT}$, —NR$^{TT}_2$, R$^{TM}$,
-L$^T$-NH$_2$, -L$^T$-NHR$^{TT}$, -L$^T$-NR$^{TT}_2$, -L$^T$-R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$,
—C(=O)R$^{TM}$,
—NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, —NHC(=O)R$^{TM}$,
—NR$^{TN}$C(=O)NH$_2$, —NR$^{TN}$C(=O)NHR$^{TT}$,
—NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$,
—S(=O)$_2$NH$_2$, —S(=O)$_2$NHR$^{TT}$, —S(=O)$_2$NR$^{TT}_2$,
—S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, —SR$^{TT}$, or =O;
each —R$^{S3C}$ is independently:
—R$^{TT}$,
—F, —Cl, —Br, —I,
—OH, —OR$^{TT}$,
-L$^T$—OH, -L$^T$-OR$^{TT}$,
—CF$_3$, —OCF$_3$,
—NH$_2$, —NHR$^{TT}$, —NR$^{TT}_2$, R$^{TM}$,
-L$^T$-NH$_2$, -L$^T$-NHR$^{TT}$, -L$^T$-NR$^{TT}_2$, -L$^T$-R$^{TM}$,
—C(=O)OH, —C(=O)OR$^{TT}$, —OC(=O)R$^{TT}$,
—C(=O)NH$_2$, —C(=O)NHR$^{TT}$, —C(=O)NR$^{TT}_2$,
—C(=O)R$^{TM}$,
—NHC(=O)R$^{TT}$, —NR$^{TN}$C(=O)R$^{TT}$,
—NHC(=O)NH$_2$, —NHC(=O)NHR$^{TT}$, —NHC(=O)NR$^{TT}_2$, NHC(=O)R$^{TM}$,
—NR$^{TN}$C(=O)NH$_2$, —NR$^{TN}$C(=O)NHR$^{TT}$,
—NR$^{TN}$C(=O)NR$^{TT}_2$, —NR$^{TN}$C(=O)R$^{TM}$,
—NHC(=O)OR$^{TT}$, —NR$^{TN}$C(=O)OR$^{TT}$,
—OC(=O)NH$_2$, —OC(=O)NHR$^{TT}$, —OC(=O)NR$^{TT}_2$, —OC(=O)R$^{TM}$,
—C(=O)R$^{TT}$,
—S(=O)$_2$NH$_2$, —S(=O)$_2$NHR$^{TT}$, —S(=O)$_2$NR$^{TT}_2$,
—S(=O)$_2$R$^{TM}$,
—NHS(=O)$_2$R$^{TT}$, —NR$^{TN}$S(=O)$_2$R$^{TT}$,
—S(=O)$_2$R$^{TT}$,
—CN, —NO$_2$, or —SR$^{TT}$;
and additionally, two adjacent groups —R$^{S3C}$, if present, may together form:
—O—CH$_2$—O— or —O—CH$_2$CH$_2$—O—;
each —R$^{SN}$ is independently:
—R$^{TT}$,
-L$^T$-OH, -L$^T$-OR$^{TT}$,
-L$^T$-NH$_2$, -L$^T$-NHR$^{TT}$, -L$^T$-NR$^{TT}_2$, -L$^T$-R$^{TM}$,
—C(=O)R$^{TT}$,
—C(=O)OR$^{TT}$,
—C(=O)NH$_2$, —C(=O)NHR$^{TT}$, —C(=O)NR$^{TT}_2$,
—C(=O)R$^{TM}$, or
—S(=O)$_2$R$^{TT}$;

wherein:
each -L$^T$- is linear or branched saturated C$_{1-4}$alkylene;
each —R$^{TT}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{TTT}$, wherein —R$^{TTT}$ is linear or branched saturated C$_{1-4}$alkyl;
each —R$^{TN}$ is linear or branched saturated C$_{1-4}$alkyl;
each —R$^{TM}$ is independently azetidino, pyrrolidino, piperidino, piperazino, morpholino, azepano, or diazepano, and is:
optionally substituted on carbon with one or more groups selected
from: —R$^{TMM}$, —C(=O)R$^{TMM}$, —S(=O)$_2$R$^{TMM}$, —F, —NH$_2$, —NHR$^{TMM}$, —NR$^{TMM}_2$, —OH, and —OR$^{TMM}$; and
optionally substituted on secondary nitrogen, if present, with a group selected
from: —R$^{TMM}$, —C(=O)R$^{TMM}$, —C(=O)OR$^{TMM}$, and —S(=O)$_2$R$^{TMM}$;
wherein each —R$^{TMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—R$^B$ is independently —R$^{B1}$, —R$^{B2}$, or -L$^B$-R$^{B2}$;
—R$^{B1}$ is linear or branched saturated C$_{1-6}$alkyl, and is optionally substituted with —OH or —OR$^{BB}$,
wherein —R$^{BB}$ is linear or branched saturated C$_{1-4}$alkyl;
—R$^{B2}$ is saturated C$_{3-6}$cycloalkyl; and
-L$^B$- is linear or branched saturated C$_{1-4}$alkylene;
and wherein:
—NR$^C$R$^D$ is independently —NR$^{C1}$R$^{D1}$, —NR$^{C2}$R$^{D2}$, —NR$^{C3}$R$^{D3}$, —NR$^{C4}$R$^{D4}$, or —NR$^{C5}$R$^{D5}$;
wherein:
—NR$^{C1}$R$^{D1}$ is a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;
and wherein said monocyclic non-aromatic heterocyclyl group is:
optionally substituted on carbon with one or more groups —R$^{NC}$, and
optionally substituted on secondary nitrogen, if present, with a group —R$^{NN}$;
—NR$^{C2}$R$^{D2}$ is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;
and wherein said fused bicyclic non-aromatic heterocyclyl group is:
optionally substituted on carbon with one or more groups —R$^{NC}$, and optionally substituted on secondary nitrogen, if present, with a group —$R^{NN}$;

—$NR^{C3}R^{D3}$ is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;

and wherein said bridged non-aromatic heterocyclyl group is:

optionally substituted on carbon with one or more groups —$R^{NC}$, and optionally substituted on secondary nitrogen, if present, with a group —$R^{NN}$;

—$NR^{C4}R^{D4}$ is a spiro non-aromatic heterocyclyl group having from 6 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, wherein said S is optionally in the form of S(=O) or S(=O)$_2$;

and wherein said spiro non-aromatic heterocyclyl group is:

optionally substituted on carbon with one or more groups —$R^{NC}$, and optionally substituted on secondary nitrogen, if present, with a group —$R^{NN}$;

wherein:

each —$R^{NC}$ is independently:
—$R^{QQ}$,
—F, —Cl, —Br, —I,
—OH, —$OR^{QQ}$,
-$L^Q$-OH, -$L^Q$-$OR^{QQ}$,
—$CF_3$, —$OCF_3$,
—$NH_2$, —$NHR^{QQ}$, —$NR^{QQ}_2$, —$R^{QM}$,
-$L^Q$-$NH_2$, -$L^Q$-$NHR^{QQ}$, -$L^Q$-$NR^{QQ}_2$, -$L^Q$-$R^{QM}$,
—C(=O)OH, —C(=O)$OR^{QQ}$, —OC(=O)$R^{QQ}$,
—C(=O)$NH_2$, —C(=O)$NHR^{QQ}$, —C(=O)$NR^{QQ}_2$,
—C(=O)$R^{QM}$,
—NHC(=O)$R^{QQ}$, —$NR^{QN}$C(=O)$R^{QQ}$,
—NHC(=O)$NH_2$, —NHC(=O)$NHR^{QQ}$, —NHC(=O)$NR^{QQ}_2$, —NHC(=O)$R^{QM}$,
—$NR^{QN}$C(=O)$NH_2$, —$NR^{QN}$C(=O)$NHR^{QQ}$,
—$NR^{QN}$C(=O)$NR^{QQ}_2$, —$NR^{QN}$C(=O)$R^{QM}$,
—NHC(=O)$OR^{QQ}$, —$NR^{QN}$C(=O)$OR^{QQ}$,
—OC(=O)$NH_2$, —OC(=O)$NHR^{QQ}$, —OC(=O)$NR^{QQ}_2$, —OC(=O)$R^{QM}$,
—C(=O)$R^{QQ}$,
—S(=O)$_2NH_2$, —S(=O)$_2NHR^{QQ}$, —S(=O)$_2NR^{QQ}_2$, —S(=O)$_2R^{QM}$,
—NHS(=O)$_2R^{QQ}$, —$NR^{QN}$S(=O)$_2R^{QQ}$,
—S(=O)$_2R^{QQ}$,
—CN, —$NO_2$, —$SR^{QQ}$, or =O;

each —$R^{NN}$ is independently:
—$R^{QQ}$,
-$L^Q$-OH, -$L^Q$-$OR^{QQ}$,
-$L^Q$-$NH_2$, -$L^Q$-$NHR^{QQ}$, -$L^Q$-$NR^{QQ}_2$, -$L^Q$-$R^{QM}$,
—C(=O)$R^{QQ}$,
—C(=O)$OR^{QQ}$,
—C(=O)$NH_2$, —C(=O)$NHR^{QQ}$, —C(=O)$NR^{QQ}_2$,
—C(=O)$R^{QM}$, or
—S(=O)$_2R^{QQ}$;

wherein:

each -$L^Q$- is linear or branched saturated $C_{1-4}$alkylene;
each —$R^{QQ}$ is independently —$R^{QQ1}$, —$R^{QQ2}$, or —$R^{QQ3}$;
each —$R^{QQ1}$ is independently linear or branched saturated $C_{1-4}$alkyl, saturated $C_{3-6}$cycloalkyl,
or saturated $C_{3-6}$cycloalkyl-methyl; and is optionally substituted with —OH or —$OR^{QQQ}$;
each —$R^{QQ2}$ is independently phenyl or benzyl; and is optionally substituted with —$R^{QQQ}$;
each —$R^{QQ3}$ is independently $C_{5-6}$heteroaryl; and is optionally substituted with —$R^{QQQ}$;
each —$R^{QQQ}$ is linear or branched saturated $C_{1-4}$alkyl or saturated $C_{3-6}$cycloalkyl;
each —$R^{QN}$ is linear or branched saturated $C_{1-4}$alkyl;
each —$R^{QM}$ is independently azetidino, pyrrolidino, piperidino, piperazino, morpholino, azepano, or diazepano, and is:
optionally substituted on carbon with one or more groups selected
from: —$R^{QMM}$, —C(=O)$R^{QMM}$, —S(=O)$_2R^{QMM}$, —F, —$NH_2$, —$NHR^{QMM}$, —$NR^{QMM}_2$, —OH, and —$OR^{QMM}$; and
optionally substituted on secondary nitrogen, if present, with a group selected
from: —$R^{QMM}$, —C(=O)$R^{QMM}$, —C(=O)$OR^{QMM}$, and —S(=O)$_2R^{QMM}$;
wherein each —$R^{QMM}$ is independently linear or branched saturated $C_{1-4}$alkyl, saturated $C_{3-6}$cycloalkyl, saturated $C_{3-6}$cycloalkyl-methyl, phenyl, or benzyl;

and wherein:

—$NR^{C5}R^{D5}$ is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 2H-[1,2,3]triazol-2-yl; 1H-[1,2,4]triazol-1-yl; 1H-benzotriazol-1-yl; or 1H-tetrazol-1-yl; and is optionally substituted with one or more groups —$R^H$;

wherein each —$R^H$ is independently:
—$R^{HH}$,
—F, —Cl, —Br, —I,
—OH, —$OR^{HH}$,
-$L^H$-OH, -$L^H$-$OR^{HH}$,
—$CF_3$, —$OCF_3$,
—$NH_2$, —$NHR^{HH}$, —$NR^{HH}_2$, —$R^{HM}$,
-$L^H$-$NH_2$, -$L^H$-$NHR^{HH}$, -$L^H$-$NR^{HH}_2$, -$L^H$-$R^{HM}$,
—C(=O)OH, —C(=O)$OR^{HH}$, —OC(=O)$R^{HH}$,
—C(=O)$NH_2$, —C(=O)$NHR^{HH}$, —C(=O)$NR^{HH}_2$,
—C(=O)$R^{HM}$,
—NHC(=O)$R^{HH}$, —$NR^{HN}$C(=O)$R^{HH}$,
—NHC(=O)$NH_2$, —NHC(=O)$NHR^{HH}$, —NHC(=O)$NR^{HH}_2$, —NHC(=O)$R^{HM}$,
—$NR^{HN}$C(=O)$NH_2$, —$NR^{HN}$C(=O)$NHR^{HH}$,
—$NR^{HN}$C(=O)$NR^{HH}_2$, —$NR^{HN}$C(=O)$R^{HM}$,
—NHC(=O)$OR^{HH}$, —$NR^{HN}$C(=O)$OR^{HH}$,
—OC(=O)$NH_2$, —OC(=O)$NHR^{HH}$, —OC(=O)$NR^{HH}_2$, —OC(=O)$R^{HM}$,
—C(=O)$R^{HH}$, —S(=O)₂NH₂, —S(=O)₂NHR$^{HH}$, —S(=O)₂NR$^{HH}$₂, —S(=O)₂R$^{HM}$,
—NHS(=O)₂R$^{HH}$, —NR$^{HN}$S(=O)₂R$^{HH}$,
—S(=O)₂R$^{HH}$,
—CN, —NO₂, or —SR$^{HH}$;
wherein:
each -L$^H$- is linear or branched saturated C$_{1-4}$alkylene;
each —R$^{HH}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{HHH}$, wherein —R$^{HHH}$ is linear or branched saturated C$_{1-4}$alkyl;
each —R$^{HN}$ is linear or branched saturated C$_{1-4}$alkyl;
each —R$^{HM}$ is independently azetidino, pyrrolidino, piperidino, piperazino, morpholino, azepano, or diazepano, and is:
optionally substituted on carbon with one or more groups selected
from: —R$^{HMM}$, —C(=O)R$^{HMM}$, —S(=O)₂R$^{HMM}$, —F, —NH₂, —NHR$^{HMM}$, —NR$^{HMM}$₂, —OH, and —OR$^{HMM}$; and
optionally substituted on secondary nitrogen, if present, with a group selected
from: —R$^{HMM}$, —C(=O)R$^{HMM}$, —C(=O)OR$^{HMM}$, and —S(=O)₂R$^{HMM}$;
wherein each —R$^{HMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—R⁵ is independently —R$^{5A}$, —R$^{5B}$, —R$^{5C}$, or —R$^{5D}$;
—R$^{5A}$ is —CN;
—R$^{5B}$ is independently —CH₂NH₂, —CH₂NHR$^{5B1}$, or —CH₂NR$^{5B1}$R$^{5B2}$;
—R$^{5C}$ is independently —CH₂NHC(=O)R$^{5C1}$ or —CH₂NR$^{5C2}$C(=O)R$^{5C1}$; and
—R$^{5D}$ is independently —CH₂NHS(=O)₂R$^{5D1}$ or —CH₂NR$^{5D2}$S(=O)₂R$^{5D1}$;
wherein:
each —R$^{5B1}$ is independently linear or branched saturated C$_{1-4}$alkyl;
each —R$^{5B2}$ is independently linear or branched saturated C$_{1-4}$alkyl;
each —R$^{5C1}$ is independently linear or branched saturated C$_{1-4}$alkyl;
each —R$^{5C2}$ is independently linear or branched saturated C$_{1-4}$alkyl;
each —R$^{5D1}$ is independently linear or branched saturated C$_{1-4}$alkyl; and
each —R$^{5D2}$ is independently linear or branched saturated C$_{1-4}$alkyl;
and wherein:
—R⁴ is —H;
—R⁶ is independently —H or —F; and
—R⁷ is independently —H or —F; and
—R⁸ is independently —H or —F.

2. A compound according to claim 1, wherein:
W is CR$^W$, X is CR$^X$, Y is CR$^Y$, and Z is CR$^Z$.

3. A compound according to claim 1, wherein:
W is CR$^W$, X is N, Y is CR$^Y$, and Z is CR$^Z$.

4. A compound according to claim 1, wherein:
—R$^W$, if present, is —H;
—R$^X$, if present, is —H;
—R$^Y$, if present, is —H; and
—R$^Z$, if present, is —H.

5. A compound according to claim 1, wherein -L$^{3P}$- is a single covalent bond.

6. A compound according to claim 1, wherein -L$^{3P}$- is -L$^{3PL}$-.

7. A compound according to claim 1, wherein if present, is -L$^{3PR1}$-.

8. A compound according to claim 1, wherein -L$^{3PL}$-, if present, is —C(=O)—.

9. A compound according to claim 1, wherein -L$^{3PL}$-, if present, is -L$^{3PR2}$-C(=O)—.

10. A compound according to claim 1, wherein:
each -L$^{3PR1}$-, if present, is independently —CH₂—, —CH(Me)-, or —C(Me)₂-; and
each -L$^{3PR2}$-, if present, is —CH₂—.

11. A compound according to claim 1, wherein —R$^{3N}$ is —NR$^A$R$^B$.

12. A compound according to claim 1, wherein —R$^{3N}$ is —NR$^C$R$^D$.

13. A compound according to claim 1, wherein each —R$^A$, if present, is independently: —R$^{A1}$, R$^{A3}$, or R$^{A5}$.

14. A compound according to claim 1, wherein:
each —R$^{A1}$, if present, is independently linear or branched saturated C$_{1-4}$alkyl, and is optionally substituted with one or more groups —R$^{S1}$; and
each —R$^{A3}$, if present, is piperidinyl,
and is optionally substituted on carbon with one or more groups —R$^{S2C}$,
and is optionally substituted on secondary nitrogen with a group —R$^{SN}$.

15. A compound according to claim 1, wherein each —R$^{TT}$, if present, is independently linear or branched saturated C$_{1-4}$alkyl, saturated C$_{3-6}$cycloalkyl, or saturated C$_{3-6}$cycloalkyl-methyl.

16. A compound according to claim 1, wherein each —R$^{TT}$, if present, is -Me.

17. A compound according to claim 1, wherein —NR$^C$R$^D$, if present, is —NR$^{C1}$R$^{D1}$,
wherein, —NR$^{C1}$R$^{D1}$ is independently selected from the following groups, and is:
optionally substituted on carbon with one or more groups —R$^{NC}$, and
optionally substituted on secondary nitrogen, if present, with a group —R$^{NN}$:

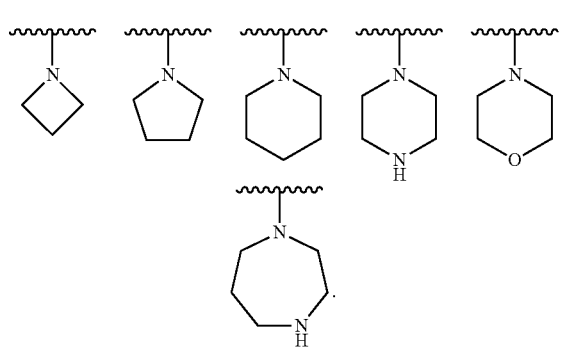

18. A compound according to claim 1, wherein:
each —R$^{NC}$, if present, is independently:
—R$^{QQ}$,
—OH, —OR$^{QQ}$,
—NH₂, —NHR$^{QQ}$, —NR$^{QQ}$₂, —R$^{QM}$, or
=O;

each —$R^{NN}$, if present, is independently:
—$R^{QQ}$,
$L^Q$-OH, -$L^Q$-OR$^{QQ}$,
$L^Q$-NH$_2$, -$L^Q$-NHR$^{QQ}$, -$L^Q$-NR$^{QQ}{}_2$, $L^Q R^{QM}$,
—C(=O)R$^{QQ}$, or
—C(=O)OR$^{QQ}$; and
each —$R^{QQ}$, if present, is independently —$R^{QQ1}$ or —$R^{QQ3}$.

19. A compound according to claim 1, wherein each —$R^{QQ1}$, if present, is independently -Me or cyclopropylmethyl.

20. A compound according to claim 1, wherein each —$R^{QQ3}$, if present, is independently [1,3,4]oxadiazol-2-yl; and is optionally substituted with —$R^{QQ}$.

21. A compound according to claim 1, wherein each —$R^{QQ}$, if present, is independently -Me, -Et, or -iPr.

22. A compound according to claim 1, wherein —NR$^C$R$^D$, if present, is —NR$^{C5}$R$^{D5}$, wherein —NR$^{D5}$R$^{D5}$ is independently: 1H-pyrrol-1-yl; 1H-pyrazol-1-yl; 1H-imidazol-1-yl; 4H-[1,2,4]triazol-4-yl; 1H-[1,2,3]triazol-1-yl; 2H-[1,2,3]triazol-2-yl; 1H-[1,2,4]triazol-1-yl; or 1H-tetrazol-1-yl; and is optionally substituted with one or more groups —$R^H$.

23. A compound according to claim 1, wherein each —$R^H$, if present, is independently:
-$L^H$-OH, -$L^{HH}$-OR$^{HH}$,
—NH$_2$, —NHR$^{HH}$, —NR$^{HH}{}_2$, —$R^{HM}$,
-$L^H$-NH$_2$, -$L^H$-NHR$^{HH}$, -$L^H$-NR$^{HH}{}_2$, or -$L^H$-R$^{HM}$.

24. A compound according to claim 1, wherein each —$R^H$, if present, is independently —$R^{HH}$.

25. A compound according to claim 1, wherein —$R^5$ is —$R^{5A}$.

26. A compound according to claim 1, wherein —$R^5$ is —$R^{5B}$.

27. A compound according to claim 1, wherein —$R^5$ is —$R^{5C}$.

28. A compound according to claim 1, wherein —$R^5$ is —$R^{5D}$.

29. A compound according to claim 1, wherein:
each —$R^{5B1}$, if present, is -Me;
each —$R^{5B2}$, if present, is -Me;
each —$R^{5C1}$, if present, is -Me;
each —$R^{5C2}$, if present, is -Me;
each —$R^{5D1}$, if present, is -Me; and
each —$R^{5D2}$, if present, is -Me.

30. A compound according to claim 1, selected from compounds of the following formulae and pharmaceutically acceptable salts and N-oxides thereof: IQ-001 through IQ-060.

31. A pharmaceutical composition comprising a compound according to claim 1, and a pharmaceutically acceptable carrier or diluent.

32. A method of preparing a pharmaceutical composition comprising the step of mixing a compound according to claim 1, and a pharmaceutically acceptable carrier or diluent.

33. A method of inhibiting PARP function, TNKS1 and/or TNKS2 function, or Wnt signalling in a cell, in vitro or in vivo, comprising contacting the cell with an effective amount of a compound according to claim 1.

* * * * *